(12) United States Patent
Bailey, Sr. et al.

(10) Patent No.: US 6,865,825 B2
(45) Date of Patent: Mar. 15, 2005

(54) ERGONOMIC SYSTEMS AND METHODS PROVIDING INTELLIGENT ADAPTIVE SURFACES AND TEMPERATURE CONTROL

(75) Inventors: Richard F. Bailey, Sr., Pennington, NJ (US); Ronald A. Fisher, New Haven, CT (US); Steven M. Hoffberg, West Harrison, NY (US)

(73) Assignee: ProMDX Technology, Inc., New Haven, CT (US)

( * ) Notice: Subject to any disclaimer, the term of this patent is extended or adjusted under 35 U.S.C. 154(b) by 341 days.

(21) Appl. No.: 09/853,097

(22) Filed: May 10, 2001

(65) Prior Publication Data

US 2001/0045104 A1 Nov. 29, 2001

Related U.S. Application Data

(63) Continuation of application No. 09/303,585, filed on May 3, 1999, now Pat. No. 6,230,501, which is a continuation-in-part of application No. 08/911,261, filed on Aug. 14, 1997, now abandoned, and a continuation-in-part of application No. 08/349,509, filed on Dec. 2, 1994, now abandoned, which is a continuation-in-part of application No. 08/227,634, filed on Apr. 14, 1994, now Pat. No. 5,658,324.

(51) Int. Cl.[7] ............................................. A43B 7/14
(52) U.S. Cl. ........................................... 36/88; 36/29
(58) Field of Search ................... 36/28, 29, 88, 36/93, 3 R

(56) References Cited

U.S. PATENT DOCUMENTS 1,506,282 A  8/1924  Barbieri
3,273,264 A  9/1966  Farinello
4,674,199 A  6/1987  Lakic
4,691,762 A  9/1987  Elkins et al.
4,736,530 A  4/1988  Lakic et al.
4,782,602 A  11/1988 Lakic (List continued on next page.)

OTHER PUBLICATIONS

Kahney, "Intel Chips in on Future Devices", http://www.wired.com/news/print/0,1294,34951,00.html.
"Cool comfort in footwear"; just–style.com; http://www.google.com/search?q=cache:just–style.com/features_detail.asp%3Fast%3D252+footv.
Dynamic Athletic Footwear Technology; http://www.sneakers.pair.com/draft.htm.
VectraSenseCorporate; http://www.vectrasense.com/corp.html.
How Does It Work?; http://www.vectrasense.com/how.html.
Technology; http://www.vectrasense.com/tech.html.
Press Release; http://www.vectrasense.com/prl.html (Vectrasense Computerized Shoes teaches Cust).
Press Release; http://www.vectrasense.com/prz.html (Vectrasense Launches Multi–city Promotional Tour Featuring Thinkshoe and Motorola Digitaldna).

Primary Examiner—Marie Patterson
(74) Attorney, Agent, or Firm—Milde & Hoffberg LLP

(57) ABSTRACT

Ergonomic systems which provide medical therapy, comfort and enhanced function are provided. Surfaces are provided with adjustable contour, transient force damping and temperature. The technologies are applied to footwear, seating surfaces an cryotherapy devices. The cooling and cryotherapy system employ an evaporator in close proximity to skin, and therefore employ methods to reduce risk of frostbite. Advanced control and power supply options are disclosed.

56 Claims, 35 Drawing Sheets

U.S. PATENT DOCUMENTS

| | | | |
|---|---|---|---|
| 4,823,482 A | | 4/1989 | Lakic |
| 4,845,338 A | | 7/1989 | Lakic |
| 5,098,119 A | | 3/1992 | Williams et al. |
| 5,121,962 A | | 6/1992 | Weber et al. |
| 5,179,792 A | * | 1/1993 | Brantingham .................. 251/4 |
| 5,230,249 A | * | 7/1993 | Sasaki et al. ................. 36/132 |
| 5,330,249 A | | 7/1994 | Weber et al. |
| 5,348,270 A | | 9/1994 | Dinh |
| 5,367,788 A | * | 11/1994 | Chen ........................... 36/2.6 |
| 5,384,977 A | | 1/1995 | Chee |
| 5,392,535 A | | 2/1995 | Van Noy et al. |
| 5,427,347 A | | 6/1995 | Swanson et al. |
| 5,443,521 A | | 8/1995 | Knoth et al. |
| 5,444,881 A | | 8/1995 | Landi et al. |
| 5,460,012 A | | 10/1995 | Kwok |
| 5,495,682 A | * | 3/1996 | Chen .......................... 219/211 |
| 5,586,067 A | * | 12/1996 | Gross et al. ............. 297/284.1 |
| 5,652,484 A | | 7/1997 | Shafer et al. |
| 5,652,985 A | | 8/1997 | Wilkinson et al. |
| 5,658,050 A | | 8/1997 | Lorbiecki |
| 5,669,597 A | | 9/1997 | Rittstieg et al. |
| 5,671,964 A | | 9/1997 | DeRees et al. |
| 5,673,498 A | * | 10/1997 | Amir et al. ..................... 36/28 |
| 5,794,361 A | * | 8/1998 | Sadler ........................... 36/29 |
| 5,813,142 A | * | 9/1998 | Demon .......................... 36/28 |
| 5,903,941 A | | 5/1999 | Shafer et al. |
| 5,904,628 A | | 5/1999 | MacKay et al. |
| 5,932,975 A | | 8/1999 | Wut |
| 5,964,455 A | | 10/1999 | Catanzarite et al. |
| 5,975,508 A | | 11/1999 | Beard |
| 6,013,011 A | | 1/2000 | Moore et al. |
| 6,036,271 A | | 3/2000 | Wilkinson et al. |
| 6,037,723 A | | 3/2000 | Shafer et al. |
| 6,182,378 B1 | | 2/2001 | Sendaula |
| 6,201,314 B1 | | 3/2001 | Landry |
| 6,239,501 B1 | | 5/2001 | Komarechka |
| 6,255,799 B1 | | 7/2001 | Le et al. |
| 6,281,594 B1 | | 8/2001 | Sarich |

* cited by examiner

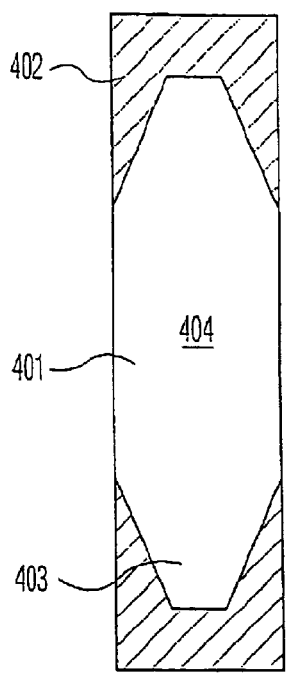
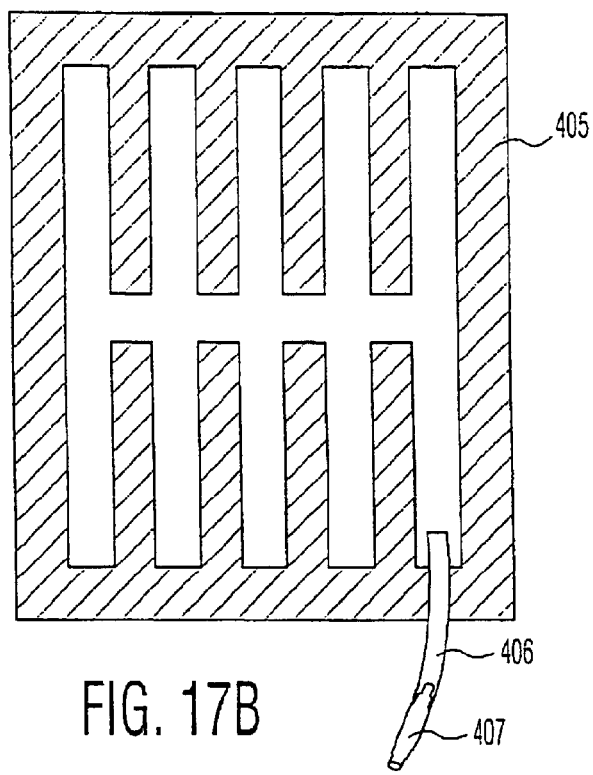
FIG. 17A  FIG. 17B
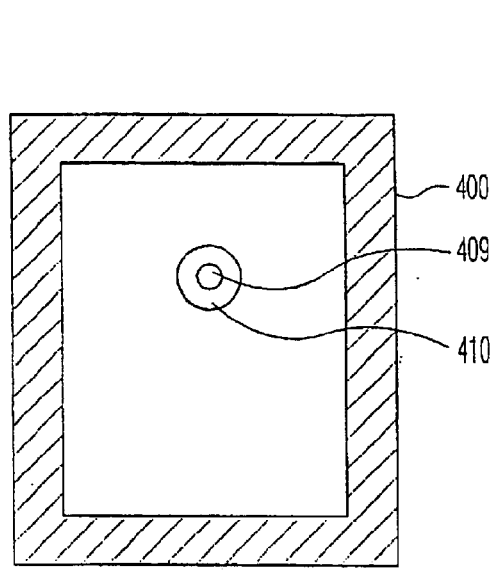
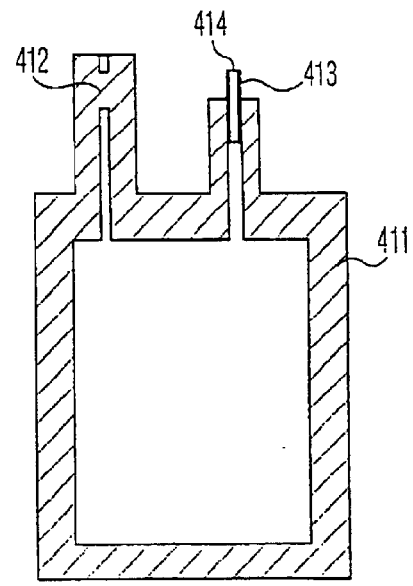
FIG. 17C  FIG. 17D

ERGONOMIC SYSTEMS AND METHODS PROVIDING INTELLIGENT ADAPTIVE SURFACES AND TEMPERATURE CONTROL

CONTINUING DATA

This application is a continuation of U.S. patent application Ser. No. 09/303,585, filed May 3, 1999, now U.S. Pat. No. 6,230,501, issued May 15, 2001, which is a continuation-in-part of copending U.S. patent application Ser. No. 08/911,261, filed Aug. 14, 1997 now abandoned, and a continuation-in-part of copending U.S. patent application Ser. No. 08/349,509, filed Dec. 2, 1994, now abandoned which is a continuation-in-part of U.S. patent application Ser. No. 08/227,634, filed Apr. 14, 1994, now U.S. Pat. No. 5,658,324, issued Aug. 19, 1997, all of which are expressly incorporated herein in their entirety.

FIELD OF THE INVENTION

The present invention relates to the field of ergonomic systems, having intelligent adaptive surfaces and temperature control, for providing comfort and cryotherapy, and apparatus and methods therefore.

BACKGROUND OF THE INVENTION

The advantages and general design of intelligent adaptive surfaces are well known, as are various methods for implementation in particular articles, such as seating surfaces, mattresses, and the like. However, miniaturization and ruggedization of these systems remains an issue.

Likewise, cryotherapy systems are also known, which facilitate healing and reduce inflammation. The combination of cryotherapy to about 4° C. and controlled external pressure of about 0.4–0.8 psi has been clearly documented.

In various types of athletic footwear, it is recognized that the comfort and fit of the footwear can affect the athletic performance. In order to increase both the comfort and fit of footwear, manufacturers have incorporated inflatable bladders of various designs into the construction of the footwear. The development, incorporation, and use of inflatable air bladders within athletic footwear was and is particularly appropriate for ski boots used for downhill skiing. Thus, a number of patents relate to the field of ski boots which incorporate inflatable air bladders, for example, German Patent No. 2,162,619, and U.S. Pat. No. 4,662,087. While the original designs for ski boots having air bladders incorporated the use of an external pressurizing device such as a hand pump, more recent designs incorporate the design of the pump into the article of footwear, such as for example the ski boot of U.S. Pat. No. 4,702,022. Various footwear designs also provide an compressor which is actuated by user activity, providing a supply of compressed air while the footwear is in vigorous use.

The demands for comfort and snugness of fit in other athletic events has resulted in the use of the inflatable bladders originally developed for ski boots in various types of athletic footwear, including athletic shoes used for basketball and other sports. There are presently available athletic shoes incorporating an air pump, such as depicted within U.S. Pat. No. 5,074,765, to inflate air bladders located within the sole of the shoe, or alternatively, bladders located in portions of the upper or the tongue of the athletic shoe. The advantages of these types of shoes is manifested primarily by their increased comfort and the secure positioning or fit of the foot within the shoe. Another benefit derived from the use of air bladders is the potential for reduction of forces transmitted through the shoe to the foot and ankle of the wearer during performance of the athletic endeavor. Thus, current athletic shoes having incorporated air bladders provide enhanced comfort and fit, while also reducing the occurrence of various types of injuries.

For typical athletic shoes currently commercially available which incorporate both the inflatable air bladders and a pump inflation means, the comfort and fit of the article of footwear is adjusted by inflating the air bladder by use of the pump after securing the footwear about the foot. The wearer simply inflates the air bladder until a particular pressure level, or fit, is felt by the foot. However, due to the rigors of various athletic events, and because the human foot tends to swell and contract with varying levels of activity, it is very difficult for the individual to obtain a consistent fit from one use to the next, or to recognize the difference in their performance, based upon a pressure setting for the air bladders that is merely sensed by the foot. Therefore, designs have been proposed which include a pressure sensor, for example, see U.S. Pat. No. 5,588,227, expressly incorporated herein by reference.

Heat transfer systems are desirable under many circumstances. Heating is generally easily accomplished, by dissipating power Cooling, however, generally requires coupling an endothermic reaction with an exothermic reaction of equal or greater magnitude, although in a different environment. Thus, heat may be transferred without violating the laws of thermodynamics. Many different types of cooling systems are known. However, efficient active miniature (<300 W thermal transfer capacity) cooling systems pose many design compromises, and few optimal designs are available.

Cooling is generally provided in a number of ways. First, heat in an object to be cooled may be lost by transferring heat energy from a hotter mass to a cooler mass, which may be an active, facilitated or conduction process. Second, an artificial gradient may be created to allow heat to be moved effectively from a hotter to a colder mass. This process includes; e.g., compressing a gas to increase its temperature, then shedding the heat resulting from the compression to the environment, followed by decompressing the cooled gas in a different location to a net colder state than prior to compression. Various phase change, e.g., vaporization, solidification, adsorption, dissolution, etc., and irreversible processes may also be used to provide cooling. Thermoelectric junctions may also be used to cool, although their power efficiency is low.

"Cryotherapy" is defined as the treatment of injury using the benefits derived by application of cold, optionally with external applied pressure Such therapy has been shown to be particularly effective in treating musculoskeletal trauma resulting from an injury or by the application of a wrenching force to the body, e.g., lacerations, sprains, strains, fractures, contusions or fractures. This type of injury may be accompanied by a tearing of tendons, ligaments or other tissue, and triggers the body's own natural healing process. See Sloan et al., "Effects of Cold and Compression on Edema", *The Physician and Sports Medicine*, 16(8) (1988); Bailey, "Cryotherapy", *Emergency*, 40–43 (August, 1984); Cryomed Brochures.

In order to minimize secondary trauma subsequent to a primary musculoskeletal insult, prompt treatment is required. Secondary trauma results from the body's own healing process which acts by first degrading injured tissue and then rebuilding, typically with scar tissue. This treatment should immobilize the trauma site, ease pain and minimize the risk of secondary tissue damage which usually accompanies breaks, sprains and strains.

An injury will almost immediately produce pain and will be followed rapidly by an accumulation of blood, interstitial fluids and lymphatic fluids. In addition, injured cells will release histamine, cytokines and other substances which act to perpetuate the inflammation process and increase the permeability of the vasculature. For a number of reasons, a free radical process ensues. The inflammatory process also causes the release of chemicals and causes conditions under which damaged collagen dissolves or degrades. The extent of this collagen damage depends on a number of factors, including the extent of the inflammatory process.

The collagen removal process forms a part of the normal healing process, and under certain circumstances, is desirable in that it allows reconstruction of the tissue by collagen regrowth. Unfortunately, in most circumstances, the damaged collagen is replaced by a random regrowth, forming a scar. While scar formation may be necessary to replace the lost tissue matrix, in many circumstances the scar impairs a return to normal functioning. Thus, scar formation in a joint, where uninjured collagen is linearly dispersed, tends to proceed after the injury by randomly-fashioned replacement, which may interfere with joint mobility and produce chronic pain.

The body's healing response is natural and necessary for restoring the functioning of the damaged tissue and the body as a whole. This natural process may produce detrimental side effects that, if not properly controlled, can exacerbate patient discomfort, impede recovery and result in long term or permanent impairment of the injured area.

Damage to the tissue may allow the formed blood components to leave the vasculature in the area of the injury (called a "hematoma"). Enhanced permeability of the blood vessels may lead to an accumulation of fluids in the extra-cellular space (called "edema"). This excess or accumulated fluid causes swelling, which may form part of a self-perpetuating process of inflammation. Further, in circumstances when the pressure in the tissue exceeds the perfusion pressure in the capillary microcirculation, the flow of oxygenated blood in that tissue becomes insufficient and the tissue becomes hypoxic, eventually leading to hypoxic necrosis. Thus, leakage of fluids at or near arterial blood pressures will impede circulation in the tissue. This process, called a "compartment syndrome", may occur when an external pressure is applied to tissues which exceeds the perfusion pressure, or when an inflammatory process in a tissue compartment causes the buildup of interstitial fluid with an increase in pressure in the compartment.

Secondary trauma is a process by which a primary injury causes inflammation, edema and/or hematoma, which secondarily is responsible for further tissue damage. If the secondary process is treated, slowed or its course modified, the extent of this secondary injury may be reduced. Thus, after a musculoskeletal injury, edema and/or hematoma may result, causing tissue compression and other effects. This compression can result in further injury while the swelling lasts, and prevent other treatments from being effectively applied. Under normal circumstances, secondary trauma lasts approximately one to three days after a primary musculoskeletal insult, and during this period, further definitive treatment, including surgery, may have to be postponed.

While the natural healing process is often sufficient and yields acceptable results, the fields of medicine and surgery have developed to overcome its shortcomings. Thus, there are a number of circumstances where it is desirable to circumvent or preempt the body's natural healing process and provide an external treatment.

It is known that the immediate application of compression and cold will slow down tissue metabolism and response to injury so that a slower and more controlled process may ensue. With the application of cold and pressure, this secondary trauma response may be blunted. Thus, the art teaches the use of ice pack compresses or other cooling devices, which may involve ice or ice-cooled water, endothermic reactions (blue ice), primary cooling with a volatile refrigerant (Roslonski, Cryomed), or secondary cooling with a refrigeration system and circulating antifreeze solution (Seabrook).

Besides injuries, there are other applications for cryotherapy. For example, normal tissues, such as hair follicles, may be spared the effects of cancer chemotherapy by the topical application of pressure and cold around the time of chemotherapeutic treatments. See, e.g., Dean, J. O. et al., 'Prevention of Doxorubicin-Induced Scalp Hair Loss," New England Journal of Medicine, Dec. 27, 1979, 301(26): 1427–29; H. F. P. Hillen, et al., "Scalp Cooling By Cold Air for the Prevention of Chemotherapy-Induced Alopecia," Netherlands Journal of Medicine, 37 (1990) 231–235; Cline, B. W., "Prevention of Chemotherapy-Induced Alopecia: a Review of the Literature,' Cancer Nursing, 1984, 7:221–228: Dean, J. O., et al. "Scalp Hypothermia: A Comparison of Ice Packs and the Kold Kap in the Prevention of Doxorubicin-Induced Alopecia," J. Clin. Oncol., 1983, 1:33–37; Bulow J., et al., "Frontal Subcutaneous Blood Flow, and Epi- and Subcutaneous Temperatures During Scalp Cooling in Normal Man," Scand. J. Clin. Lab Invest., 1985, 45:505–508; Parbhoo, S. P., et al., "An Improved Technique of Scalp Hypothermia to Prevent Adriamycin/Mitozantrone Induced Alopecia in Patients with Advanced Breast Cancer," Clinical Oncology and Cancer Nursing, Stockholm, 1986, 232 (Abstract); Gregory, R. P., et al., "Prevention of Doxorubicin-Induced Alopecia by Scalp Hypothermia: Relation to Degree of Cooling," Br. Med. J., 1982, 284:1674. Chemotherapeutic agents which cause alopecia which may be reduced by cryotherapy include anthracycline antibiotics, e.g. doxorubicin or epirubicin, nucleoside analogs, e.g. 6-fluorouracil, folate antagonists, e.g. methotrexate and alkylating agents, e.g. cyclophosphamide.

In addition, cryotherapy may also be employed for other medical purposes, where control of metabolic rate is desired.

For example, U.S. Pat. No. 3,871,381 to Roslonski teaches a cryotherapy device which applies both cold and pressure to an extremity which involves the introduction of a pressurized volatile refrigerant liquid, e.g., Freon® (a chlorofluorocarbon or "CFC"), through a controlled flow rate valve, which cools a maze passage in a flexible device. A pressure relief valve maintains a back-pressure in the system. It is also known to circulate a cooled fluid through a conduit in a bandage. Cold and pressure are therefore known treatments for traumatic injuries, as well as inflammatory pathologic processes which involve externally accessible organs.

The device disclosed in Roslonski, U.S. Pat. No. 3,871, 381, however, presents a number of drawbacks. First, the design of Roslonskis flow path allows refrigerant liquid to pool in some areas, while other areas do not receive sufficient liquid refrigerant, thus causing uneven tissue cooling. Further, a crimp in one portion of the device may block a flow of coolant liquid to other portions of the device, likewise causing uneven cooling and additionally causing noise due to turbulent flow and focal refrigerant vaporization. The temperature of these known CFC-based systems depend in large part on the composition of the refrigerant fluid employed, which usually have an effective boiling plateau slightly above the freezing point of water (0° C.). These systems therefore provide a relatively uncontrolled temperature, seeking to maintain a desired temperature by providing an excess of refrigerant having a boiling point of about the desired final temperature. In these systems, the only way to control the temperature, other than starving the cooling device (to achieve a non-equilibrium condition), is to vary the allow refrigerant composition. The known systems do not provide a uniform response to refrigerant starving, producing temperature non-uniformities and unpredictability. These known systems also have an operating temperature which depends in lesser part on the rate at which heat is removed by the refrigerant, which in turn depends on the rate of volatilization of the refrigerant. For example, a greater volume of refrigerant will withdraw more heat than a lesser volume, thus producing a lower temperature. Other performance factors include the ambient temperature, ambient humidity, body temperature, atmospheric pressure, pressure within the device, refrigerant composition and flow rate of the refrigerant. The rate of volatilization of a refrigerant also relates to flow turbulence and nucleation centers.

Chlorofluorocarbon refrigerants are known to be available and to be used alone or in mixtures. Some mixtures have boiling characteristics with a plurality of plateaus. Known refrigerants (Freon®) such as R-11, R-12 and R-114 have boiling points of approximately 24° C. (75° F.), −30° C. (−22° F.) and 3.8° C. (39° F.) respectively, and these may be mixed to form a refrigerant composition having boiling plateaus at approximately the boiling points of the individual components. See Freon Product information, Du Pont (1973). In a Roslonski-type system, the lowest boiling component of such a refrigerant mixture acts to propel the refrigerant from the canister and precool the remaining refrigerant liquid as it enters the cooling matrix. The mid temperature boiling refrigerant acts to cool the tissue by boiling in the cooling matrix at a temperature approximately the same as the desired tissue temperature. Lastly, the highest boiling component acts as a heat transfer agent to improve the effectiveness of the device, by stabilizing the operation over a range of environmental conditions and helping to distribute the vaporizing refrigerant. The highest boiling component generally vaporizes before it reaches the end of the cooling matrix. Thus, the lowest temperature in the heat transfer portion of the cryotherapy device, using the known CFC refrigerants, will be around 0–4° C., thereby posing only a small risk of tissue freezing (frostbite), unless too much refrigerant mixture is injected from the canister to the cooling matrix so that the lowest boiling component is present in substantial quantities, or if the tissue is poorly vascularized. These mixtures, therefore, may be used in open-loop cryotherapy systems, with minimal or imprecise flow regulation. In practice, these devices pose low risk of tissue freezing and are effective. However, these systems are environmentally unfriendly, venting chlorofluorocarbons into the atmosphere These CFC's are known ozone depleting chemicals and greenhouse gasses. Known refrigerant compositions which are more acceptable do not completely emulate CFCs, and typically are themselves greenhouse gasses and therefore should not be indiscriminately released into the environment.

CFC substitutes, which are generally fluorinated hydrocarbon molecules (HFC's), fluorocarbons (FC's), hydrochlorofluorocarbons (HCFC's) or hydrocarbons, are or are becoming available. Because each composition is distinct, there is no correspondence or equivalency between the prior employed CFC gasses and these other gasses, each gas having its own unique properties and compatibilities with mechanical components. Therefore, prior teachings as to how to provide a portable refrigeration arrangement using specific CFC's do not provide specific teachings as to how to design a system employing non-CFC refrigerants.

Certain available known second generation (HCFC) mid-boiling refrigerants, including R-124 and R-142B, have much lower boiling points than the corresponding mid-boiling CFC components, e.g. −11° C. and −9° C. respectively and therefore pose a substantial risk of tissue freezing when substantial quantities of refrigerant liquid (at about atmospheric pressure) vaporize in proximity to an aqueous liquid or biological tissue to be cooled, in contrast to Freon R-114 (BP around 3.8° C.) which poses low risk of frostbite. The major penalty excess flow rate in an R-114 based system is the premature exhaustion of the CFC supply and a high flow rate of gas (and/or liquid in extreme cases) exhausted from the system.

A particular difficulty results from a difference in boiling points of the normally available non-CFC refrigerants as compared to the traditionally used CFC counterparts. Lower boiling point substitutes create a risk of spot freezing or frostbite, even if the heat of vaporization of the amount of fluid supplied is insufficient to freeze the bulk of the tissue or fluid to be cooled. The prior art teaches against the use of such low boiling refrigerants at atmospheric pressure in close potential proximity to skin or aqueous liquids, which are not desired to be frozen. If the boiling point is too high, it will be difficult to reach a desired final temperature.

Many systems have been proposed for cooling beverages outside of traditional refrigeration systems, which may be large or clumsy. These past proposals have employed thermoelectric cooling modules (TEMs, employing Peltier junctions), compressed gasses, CFC refrigerants, and endothermic reactions (absorption refrigeration, typically with one solid phase component, such as a zeolite).

A range of refrigerant compositions (both pure refrigerant and combinations of refrigerants) considered useful for cooling of aqueous fluids below atmospheric temperatures are known, typically having a boiling point of about −65 to +40° C. at approximately atmospheric pressure, and a heat of vaporization of in excess of about 10 cal/gm. These compositions are permitted to vaporize in an expansion chamber (evaporator), resulting in a cooling effect.

While refrigeration systems may operate in a single phase, i.e., expansion of a compressed gas, high efficiency at environmental temperatures may often be advantageously obtained when a fluid boils or evaporates, carrying the heat of vaporization with the gas phase from the site of cooling. Thus, the area in proximity to the phase change will be cooled, and the gas is expelled to the atmosphere or to a recycling (reliquification) system. This phase change generally allows substantial heat energy transfer with comparatively lower temperature gradients than single phase systems, i.e., gas expansion systems. These smaller temperature gradients allow temperature buffering around a desired temperature range, thus allowing a degree of self regulation. The fluid also typically withdraws more heat per mass and volume unit than a gas. Thus, a system employing a liquid phase may also allow a more compact system, due to the higher heat energy capacity of liquids than gasses.

Temperature buffering at a temperature around 0° C. is preferred because it limits freezing of an object to be cooled and minimizes the danger of frostbite and freezing of biological tissues.

Hadtke, U.S. Pat. No. 5,449,379, expressly incorporated herein by reference, relates to an improvement on the system of Roslonski. This system uses Dymel® or Freon refrigerants, and is fabricated of polyvinyl chloride or polypropylene coated woven nylon. An aluminized Mylar® thermal transfer patch, not in contact with the refrigerant, may be employed to direct heat transfer to an area of interest.

The following patents relate to known refrigerant systems: Lodes, U.S. Pat. No. 2,529,092; Senning, U.S. Pat. No. 2,641,579; Ashkenaz, U.S. Pat. No. 2,987,438; Munro, U.S. Pat. No. 3,733,273: Borchardt, U.S. Pat. No. 3,812,040; Hutchinson. U.S. Pat. No. 3,940,342; Murphy, U.S. Pat. No. 4,055,054; Orfeo, U.S. Pat. No. 4,533,536; Nikolsky, U.S. Pat. No. 4,495,776; Ermack, U.S. Pat. No. 4,510,064; and Nikolsky U.S. Pat. No. 4,603,002.

Brown, U.S. Pat. No. 2,696,395 relates to a pneumatic pressure garment for application of therapeutic pressure.

Gottfried, U.S. Pat. No. 3,153,413 relates to a pressurized bandage with splint functions.

Towle, et al., U.S. Pat. No. 3,171,410 relates to a pneumatic wound dressing.

Gardner, U.S. Pat. No. 3,186,404 relates to a pressure device for therapeutic treatment of body extremities.

Romano, U.S. Pat. No. 4,135,503 relates to an orthopedic device having a pressurized bladder for spinal treatment.

Curlee, U.S. Pat. No. 4,622,957 relates to a therapeutic corset for applying pressure to a portion of the back.

Cronin, U.S. Pat. No. 4,706,658 relates to a gloved splint, providing a shock absorbing treatment and possible heat removal from the hand.

Johnson, Jr. et al., U.S. Pat. No. 5,230,335, and Johnson Jr. et al., U.S. Pat. No. 5,314,455, both relate to a leg treatment system having a cold thermal fluid and having means for applying pressure.

Smith, U.S. Pat. No. 5,324,318, relates to a cryotherapy apparatus having a cold compress and a gravity fed cold liquid. Smith, U.S. Pat. No. 5,170,783, relates to a cryotherapy procedure employing a gravity pressurized cold liquid.

French et al., U.S. Pat. No. 4,844,072, relates to a heated or cooled liquid thermal therapy system.

Wright, U.S. Pat. No. 5,172,689, relates to a cryotherapy sleeve for therapeutic compression.

Meserlian, U.S. Pat. No. 5,167,227, relates to an apparatus for massaging or supporting the legs of a horse.

Gammons et al., U.S. Pat. No. 4,149,541, relates to a flexible circulating pad which ensures fluid flow to all areas.

Sauder, U.S. Pat. No. 4,170,998, and Sauder, U.S. Pat. No. 4,184,537, both relate to a limb refrigeration device for cryotherapy.

Kolstedt, U.S. Pat. No. 4,335,716, relates to a device for circulating pressurized cold fluid in a sleeve for cryotherapy.

Arkans, U.S. Pat. No. 4,338,944, relates to a cooled liquid cryotherapy device

Larsen, U.S. Pat. No. 4,998,415, relates to a body cooling apparatus including a compressor and a condenser Tucker, et al., U.S. Pat. No. 4,442,834, relates to a pneumatic splint device Robbins et a., U.S. Pat. No. 4,175,297 relates to an inflatable pillow support having automated cycling inflation and deflation of various portions thereof.

Artemenko et al., U.S. Pat. No. 3,683,902 relates to a medical splint apparatus, having an inflatable splint body and a circulated cooling agent, cooled by solid carbonic acid $CO_2$.

Davis et al., U.S. Pat. No. 3,548,819 relates to a pressurized splint adapted to apply a thermal treatment to a human extremity.

Nicholson, U.S. Pat. No. 3,561,435 relates to on inflatable splint having a coolant chamber to apply pressure and cool to a human extremity.

Berndt et al., U.S. Pat. No. 3,623,537 relates to a self-retaining cold wrap which treats an injury with cold and pressure.

Baron, U.S. Pat. No. 4,300,542 and Baron, U.S. Pat. No. 4,393,867 both relate to a self-inflating compression device for use as a splint.

Golden, U.S. Pat. No. 4,108,146 relates to a cooling thermal pack with circulating fluid which conforms to body surfaces to apply a cooling treatment.

Moore et al., U.S. Pat. No. 4,114,620 and Gammons et al., U.S. Pat. No. 4,149,541 relate to treatment pads with circulating fluid for providing a hot or cold treatment to a patient.

Brannigan et al., U.S. Pat. No. 4,575,097 relates to a thermally capacitive compress for applying hot or cold treatments to the body.

Arkans, U.S. Pat. No. 4,331,133 relates to a pressure measurement apparatus for measuring the pressure applied by a pressure cuff to a human extremity Kiser et al., U.S. Pat. No. 4,502,470 relates to a device for assisting in pumping tissue fluids from a foot and ankle up the leg.

Stark, U.S. Pat. No. 3,000,190 relates to an apparatus providing body refrigeration, for use in high ambient temperature environments by workers.

FR 2,133.680 relates to a system for cooling objects, including beverage cans, using fluorocarbons, e.g. Freon.

Nelson, U.S. Pat. No. 2,051,100, Burkhardt, U.S. Pat. No. 2,463,516 and Richards, U.S. Pat. No. 4,103,704 relate to pressure relief valves. Ninomiya et al., U.S. Pat. No. 4,286,622 relates to a check valve assembly.

Martin et al., U.S. Pat. No. 2,550,840, Both et al., U.S. Pat. No. 2,757,964, Galeazzi et al., U.S. Pat. No. 2,835,534, Mura, U.S. Pat. No. 3,314,587, White, U.S. Pat. No. 3,976,110 and Turner, U.S. Pat. No. 4,281,775 relate to pressurized container dispensing valves and systems containing same. Frost, U.S. Pat. No. 3,273,610 relates to a pressurized container valve and detachable dispensing attachment device.

Nakano, et al., U.S. Pat. No. 4,958,501, relates to a refrigerant charging apparatus for charging a refrigerant, including a refrigerant can, an upper can-opening part, a conduit having two inner passages for indication and charging, respectively, a lower can-opening part, and a level indicator communicating with the refrigerant can via both can-opening parts, for indicating a remaining quantity of the refrigerant in the can.

Chruniak, U.S. Pat. No. 5,181,555, relates to a climate controlled food and beverage container which operates off an automotive climate control system. Howell, U.S. Pat. No. 5,203,833, also relates to a food storage container operating off an automotive air conditioning system. Fujiwara, et al., U.S. Pat. No. 4,637,222, relates to an automobile refrigerator detachably connected to the air conditioner of a vehicle.

Maier, et al., U.S. Pat. No. 5,007,248, relates to an automobile air conditioner driven beverage cooling system.

Kitayama, U.S. Pat. No. 5,189,890, relates to a portable chiller for chilling an ophthalmic solution, cosmetic preparation, beverage or the like. This portable chiller consists generally of a cylinder filled with a liquefied refrigerant gas and a chiller case.

Ramos, U.S. Pat. No. 5,201,183, relates to a cooling device for beverage cans which cools by releasing liquid nitrogen or liquid air from a containment "bubble".

Sundhar, et al, U.S. Pat. No. 5,201,193, relates to a cooling device for beverages which cool by releasing liquid carbon dioxide. Saia, et al., U.S. Pat. No. 5,337,579, also relates to a liquid carbon dioxide cooling system. Fischer, et al., U.S. Pat. No. 4,669,273, relates to a coiled tube insert releasing a liquid refrigerant for cooling a beverage.

Aitchison, et al., U.S. Pat. No. 5,214,933, relates to a liquid pressurized refrigerant system for cooling a fluid container. Beck, U.S. Pat. No. 3,919,856, relates to a liquid refrigerant beverage cooling device. Willis, U.S. Pat. No. 3,987,643, relates to a beverage cooling system employing compressed gas or liquid refrigerant with an improved heat exchanger system. Barnett, U.S. Pat. No. 4,584,484, relates to a liquid refrigerant system for cooling a can. Johnson, U.S. Pat. No. 4,640,101, relates to a liquid refrigerant beverage chilling mechanism. Tenebaum, et al., U.S. Pat. No. 4,640,102, also relates to a liquid refrigerant beverage cooling mechanism.

Dodd, U.S. Pat. No. 4,319,464, relates to a container which is cooled by the release of a pressurized refrigerant. Kim, U.S. Pat. No. 4,628,703, and Kim, et al., U.S. Pat. No. 4,679,407, both relate to a refrigerant cooled can mechanism. Shen, U.S. Pat. No. 4,656,838, relates to a pressurized coolant for a beverage can. Chou, U.S. Pat. No. 4,925,470, relates to a self cooling can having a pressurized refrigerant.

Ladany, U.S. Pat. No. 3,862,548, relates to a beverage cooling device which employs compressed gas. Nof, U.S. Pat. No. 4,597,271, relates to a pressurized gas method for cooling a container and liquid contained therein. Riley, U.S. Pat. No. 3,881,321, also relates to a beverage cooling device which preferably carbonates the beverage on release of the gas.

Rhyne Jr., et al., U.S. Pat. No. 4,054,037, relates to a beverage cooler for sequentially cooling a plurality of beverage containers.

Holcomb, U.S. Pat. No. 4,668,395, relates to a food container cooling system having a pressurized refrigerant fluid which is released into an expansion chamber.

Campbell, U.S. Pat. No. 4,434,158, relates to an insulin cooling device including a refrigerating agent. Ehmann, U.S. Pat. No. 4,429,793, also relates to an insulating container with a refrigerant.

Manz, et al., U.S. Pat. No. 5,497,625, relates to a Thermoelectric refrigerant handling system.

Merritt-Munson, et al., U.S. Pat. No. 5,237,838, relates to a refrigerant cooled cosmetic bag. Martello, et al., U.S. Pat. No. 4,584,847, relates to a liquid refrigerant system for cosmetics Merritt, et al, U.S. Pat. No. 5,353,600, relates to a solar powered thermoelectric cooler for a cosmetic bag which seeks to employ heat produced by the thermoelectric cooling element to recharge a rechargeable power source.

Collard, U.S. Pat. No. 5,247,798, relates to a thermoelectric refrigeration device. Rudick, U.S. Pat. No. 4,671,070, relates to a thermoelectric beverage can cooler.

Harris, et al., U.S. Pat. No. 4,280,330, relates to a thermoelectric vehicle cooling system.

Kitayama, U.S. Pat. No. 5,287,707, relates to a portable vaporizing liquid refrigerant chiller device.

Isaacson, et al., U.S. Pat. No. 5,313,809, relates to an insulating wrap having a eutectic solution in a film barrier container.

Baroso-Lujan, et al., U.S. Pat. No. 5,325,680, relates to a Freon-22 cooled beverage container which flashes liquid Freon into an evacuated space.

Goble, U.S. Pat. No. 5,214,929, relates to a non-CFC substitute refrigerant for R-12, including 2–20% isobutane (R-600a), 41–71% chlorodifluoromethane (R-22) and 21–51% chlorodifluoroethane (R-142b).

Murphy, U.S. Pat. No. 3,901,817, relates to a low boiling azeotropic or essentially azeotropic mixtures containing monochlorotrifluoromethane and methyl fluoride.

Murphy, et al., U.S. Pat. No. 4,054,036, relates to constant boiling mixtures of 1,1,2 trichorotrifluoroethane and cis-1, 1,2,2-tetrafluorocyclobutane.

Murphy, et al., U.S. Pat. No. 4,055,049, relates to constant boiling mixtures of 1,2 difluoroethane and 1,1,2-tricloro-1, 2,2-trifluoroethane.

Murphy, et al., U.S. Pat. No. 4,055,054, relates to constant boiling mixtures of dichloromonofluoromethane and 1-chloro-2,2,2-trifluoroethane.

Murphy, et al., U.S. Pat. No. 4,057,973, relates to constant boiling mixtures of 1-chloro-2,2,2-trifluoroethane and 2-chloroheptafluoropropane.

Murphy, et al., U.S. Pat. No. 4,057,974, relates to constant boiling mixtures of 1-chloro-2,2,2-trifluoroethane and octafluorocyclobutane.

Murphy, et al., U.S. Pat. No. 4,101,436, relates to constant boiling mixtures of 1-chloro-2,2,2-trifluoroethane and hydrocarbons.

Ostrozynski, et al., U.S. Pat. No. 4,155,865, relates to constant boiling mixtures of 1,1,2,2-tetrafluoroethane and 1,1,1,2-tetrafluorochloroethane.

Ostrozynski, et al., U.S. Pat. No. 4,157,976, relates to constant boiling mixtures of 1,1,1,2-tetrafluorochloroethane and chlorofluoromethane.

Zuber, U.S. Pat. No. 4,169,807 describes an azeotropic composition containing water, isopropanol, and either perfluoro-2-butyltetrahydrofuran or perfluoro-1,4-dimethylcyclohexane. The inventor states that the composition is useful as a vapor phase drying agent.

Van der Puy, U.S. Pat. No. 5,091,104, describes an "azeotropic-like" composition containing t-butyl-2,2,2-trifluoroethyl ether and perfluoromethylcyclohexane. The inventor states that the composition is useful for cleaning and degreasing applications.

Fozzard, U.S. Pat. No. 4,092,257 describes an azeotrope containing perfluoro-n-heptane and toluene.

Batt et al., U.S. Pat. No. 4,971,716 describes an "azeotrope-like" composition containing perfluorocyclobutane and ethylene oxide. The inventor states that the composition is useful as a sterilizing gas.

Shottle et al., U.S. Pat. No. 5,129,997 describes an azeotrope containing perfluorocyclobutane and chlorotetrafluorethane.

Merchant, U.S. Pat. No. 4,994,202 describes an azeotrope containing perfluoro-1,2-dimethylcyclobutane and either 1,1-dichloro-1-fluoroethane or dichlorotrifluoroethane. The inventor states that the azeotrope is useful in solvent cleaning applications and as blowing agents. The inventor also notes that "as is recognized in the art, it is not possible to predict the formation of azeotropes. This fact obviously complicates the search for new azeotrope compositions" (col. 3, lines 9–13).

Azeotropes including perfluorohexane and hexane, perfluoropentane and pentane, and perfluoroheptane and heptane are also known.

Flynn et al., U.S. Pat. No. 5,494,601, provides an azeotropic composition, including a non-cyclic perfluorinated alkane and a hydrochlorofluorocarbon (HCFC) solvent, for example, perfluoropentane and perfluorohexane, and 1,1,1-trifluoro-2,2-dichloroethane and 1,1-dichloro-1-fluoroethane.

A hydrofluorocarbon composition, R-236fa, having a boiling point of −1° C. is known. Another known composition is $c\text{-}(CF_2)_4O$, also having a boiling point of about −1° C.

Known aerosol-type cans have a stem which protrudes upwardly, and which is depressed to release the contents of the can. The nozzle is generally secured to the stem by friction. A cap is generally provided to prevent inadvertent release of the contents of the can.

Known volatile refrigerant-supply cans are generally sealed with and release their contents only after a metal diaphragm is punctured. Thus, Vos, U.S. Pat. No. 3,756,472 relates to a system for use with a pressurized canister to produce a desired stream characteristic during ejection of the pressurized contents. This system may be mounted atop an aerosol container.

SUMMARY AND OBJECTS OF THE INVENTION

The present invention provides a number of different ergonomic intelligent adaptive surface and thermal control embodiments, providing comfort, cooling and/or heating functions. These include cryotherapy, garments, footwear, seating surfaces or the like The technologies may also be applied to inanimate objects, for example the cooling technologies may be employed for the cooling of objects and beverage containers.

Seating Surfaces

The theory of intelligent adaptive surfaces provides that too high a pressure applied to an area of skin may cause discomfort or produce medical problems. By adjusting the pressure LOQ, applied to an area of skin, a more ergonomic support is provided. See, U.S. Pat. Nos. 5,745,937; 5,713,631; 5,658,050; 5,558,398; 5,129,704; 4,949,412; 4,833,614; 4,467,252; 4,542,547; 3,879,776, expressly incorporated herein by reference. Using a first approximation, the goal of an intelligent support surface is to equalize the pressure applied to the skin along the entirety of the contact area, and to increase the contact area. See, U.S. Pat. No. 4,797,962, incorporated herein by reference. Using sensors, the pressure applied to the skin is measured. Actuators, provided under the surface, deform the surface to adjust the applied pressure and potentially increase the contact patch. See, U.S. Pat. Nos. 5,687,099; 5,587,933; 5,586,557; 5,586,067; 5,283,735; 5,240,308; 5,170,364; 5,060,174; 5,018,786, and 4,944,554, expressly incorporated herein by reference. See also U.S. Pat. Nos. 5,174,424; 5,022,385; A more sophisticated system models the anatomical portion being supported and provides a force distribution map, thereby selectively applying forces over the contact surface. Thus, more sensitive areas are subject to less pressure than less sensitive areas. An even more sophisticated algorithm takes into consideration the time of pressure application, and will adjust the contact force dynamically to, for example, promote circulation.

In particular contexts, the system may be even more sophisticated. For example, in a seating surface, the pressure along the back should not equal the pressure along the seat. However, the optimal conformation of the surface may be more related to the compliance of the surface at any controlled area than on the pressure per se Thus, a highly compliant region is likely not in contact with flesh Repositioning the surface will have little effect. A somewhat compliant region may be proximate to an identifiable anatomical feature, such as the scapula in the back. In this case, the actuator associated with that region may be adjusted to a desired compliance, rather than pressure per se. This provides even support, comparatively relieving other regions. Low compliance regions, such as the buttocks, are adjusted to achieve an equalized pressure, and to conform to the contour of the body to provide an increased contact patch. This is achieved by deforming the edges of the contact region upwardly until contact is detected. The thigh region employs a hybrid algorithm, based on both compliance and pressure.

An adaptive intelligent surface need not be limited to the control of surface contour. Thus, the surface contour, local compliance and local damping may all be controlled. Thus, for example, the dynamic aspects of the control may all be subject to closed loop electronic control; however, for a large number of actuators, this may be expensive and/or difficult. Alternately, the contour may be set with a hydraulic actuator, having a relatively low update frequency. The compliance may be adjusted, for example, by providing a controlled ratio of air and fluid in a hydraulic system feeding the actuator; the damping factor may controlled by an additional proportional valve which adjusts a bleed rate. Therefore, a dynamically adjustable surface may be constructed.

As discussed below in more detail, the seating surface may be cooled, for example by the flow of cool air, or a heat exchanger beneath the seating surface. The heat exchanger may be primary, i.e., absorb heat in a primary refrigeration cycle, or secondary, i.e., transfer heat through a heat exchange medium to a primary heat exchanger. Advantageously, common elements of the system for cooling the seating surface are also used to heat the surface, as appropriate. Thus, hot or cold air may be directed to the seating surface, which is, for example, a cloth or other open surface. Where a heat exchanger is provided, the heat exchange fluid may be heated or cooled, as appropriate, to control the seating surface temperature. This is readily implemented easier with a secondary heat exchange system, wherein the secondary heat exchange fluid is either heated or cooled, for example by taps from a vehicular heating and air conditioning system In a primary heat exchange system, refrigeration proceeds by a normal cycle, in which a volatile refrigerant evaporates within the heat exchanger to cool the surface. To heat the surface, a refrigerant-compatible oil is circulated through the same heat exchanger, with the refrigerant gas stored compressed in a reservoir. The refrigerant may be drawn from a vehicular air conditioning system or a separate system, while the heating may be electrical or derive from a heat source within the vehicle. It is noted that a seating surface according to the present invention need not be associated with a vehicle, and therefore the control system, heating and/or cooling may be independent. Where a volatile refrigerant gas is present in the seat, the actuators for an intelligent surface may employ this gas, which is pressurized, for displacing the actuators.

The seating surface may include, for example, a thermally conductive gel layer, e.g., HeatPath thermally conductive gel CTQ 3000 from Raychem, Menlo Park, Calif. This gel provides both thermal conductivity and compliance.

Footwear

These same principles may be applied to other skin contact systems. In particular, footwear presents significant ergonomic issues. Footwear is typically designed for low weight, comfort and function. Fashion and style may also be significant considerations Embedding significant control systems within footwear must therefore justify the cost, complexity, weight and size, especially in view of the adequate functioning of existing available footwear designs.

Thus, the air bladder fit systems for footwear are well known and accepted. These systems have good performance, are low mass and size, acceptable cost and a simple user interface. See, U.S. Pat. Nos. 5,756,298; 5,480,287; 5,430,961; 5,416,988; 5,343,638; 5,257,470; 5,230,249; 5,146,988; 5,113,599; 4,999,932; 4,995,173; 4,823,482; 4,730,403; 4,662,087; and 4,502,470, each of which is expressly incorporated herein by reference, showing designs and construction methods for adjustable footwear upper and methods and means for adjustment thereof. The present invention therefore provides an improvement over the existing air bladder system by providing an array of bladder segments, each separately controlled, with an automated control system within the shoe See U.S. Pat. No 4,374,518, expressly incorporated herein by reference. While complete manual control over each segment is possible, this creates a complex user interface Therefore, an automated control system is provided This control system may operate in an open loop manner, i.e., without feedback control, or may have a sensing system to provide feedback.

According to the present invention, a high tensile flexible strength polymer film is preferably employed in fabricating bladder structures. These films, which are, for example, polyester (Polyethylene Phthalate polymer), although other films may be employed. The preferred polyester films have a modulus per ASTM D882 of about 550 kpsi, making them relatively stiff. Therefore, when heat sealed to form a bladder structure or fluid (gas or liquid) flow path, the walls are relatively non-compliant, even with relatively thin films, for example 50 gauge, of course, the selected film thickness will depend on the desired mechanical properties and vapor diffusion limits. Thus, in contrast to prior designs which employ polyurethane or poly vinyl chloride films to form bladder structures, the preferred polyester films according to the present invention may be pressurized to relatively higher levels to allow a finer degree of control over the contour of the shoe. Of course, if the bladder pressure is relatively high, padding should be separately provided. This high pressure containment capability also allows the bladder structure to withstand greater transient pressures without failure or requiring a relief valve, even where inflated or pressurized to a lower pressure. Suitable films are readily heat sealed, to with a strength of, for example, greater than 400 g/in. Thus, the bladder structures need not be molded into the shoe, and therefore may be provided as a separately manufactured subassembly.

A number of technologies are known for improving the function and comfort of footwear soles. These include adjustments for size and foot shape, as well as cushioning, energy recovery, pumps and compressors for providing a source of compressed air, and improved stability. See, U.S. Pat. Nos. 5,771,606, 5,704,137; 5,701,687; 5,598,645; 5,575,088; 5,537,762; 5,384,977; 5,353,525; 5,325,614; 5,313,717; 5,224,278; 5,224,277; 5,222,312; 5,199,191; 5,179,792; 5,086,574; 5,046,267; 5,095,575; 4,999,932; 4,991,317, 4,936,030; 4,934,072; 4,894,932; 4,888,887; 4,845,863; 4,772,131; 4,763,426; 4,756,096; 4,670,995, 4,610,099; 4,458,430; 4,446,634; 4,414,760; 4,319,412; 4,305,212; 4,229,889, 4,187,690; 4,129,951, 4,016,662, 4,008,530; and 3,758,964, expressly incorporated herein by reference.

A number of known footwear designs seek to generate a flow of air through the footwear to promote evaporation of perspiration and cool the foot. See, U.S. Pat. Nos. 5,697,171; 5,697,170; 5,655,314; 5,515,622; 5,505,010; 5,408,760; 5,400,526; 5,341,581; 5,303,397; 5,295,313; 5,068,981; 4,974,342; 4,888,887; 4,860,463; 4,813,160; 4,776,110; 4,679,335; 4,602,441; 4,499,672; 4,438,573; 4,373,275, 4,364,186; 4,078,321; and 3,973,336, expressly incorporated herein by reference, for their disclosure of designs and methods for cooling footwear, the implementation of locomotion actuated air compressors, and integration within footwear designs.

According to one aspect of the invention, an array of sensors is situated inside the shoe. Foot and shoe sensor arrangements are disclosed in U.S. Pat. Nos. D365,999; 5,775,332; 5,720,200; 5,678,448; 5,673,500; 5,662,123; 5,659,395; 5,655,316; 5,642,096; 5,619,186; 5,608,599; 5,566,479; 5,541,570; 5,511,561; 5,500,635; 5,471,405; 5,456,027; 5,449,002; 5,437,289; 5,408,873; 5,361,133; 5,357,696; 5,323,650; 5,302,936; 5,296,837; 5,269,081; 5,253,656; 5,253,654; 5,107,854; 5,079,949; 5,042,504; 5,033,291; 5,010,772; 4,996,511; 4,956,628; 4,862,743; 4,858,621; 4,852,443; 4,827,763; 4,814,661; 4,771,394; 4,745,930; 4,745,301; 4,703,445; 4,651,446; 4,649,918; 4,649,552; 4,644,801; 4,604,807; 4,578,769; 4,554,930; 4,503,705; 4,489,302; 4,437,138; 4,426,884; 4,152,304; 4,054,540; 3,974,491; and 3,791,375, all of which are expressly incorporated herein by reference, which may be suitable in various embodiments of the invention, and also disclose various electronic interfaces which may also be applicable to the present invention. Thus array is preferably either integral to each actuator zone, i.e., a pressure or displacement sensor associated with each actuator, or a separate array of sensors disposed around the foot.

In footwear, the upper and sole present different problems. The upper is typically designed as a thin, relatively non-compliant shell, which form-fits the foot. The sole, on the other hand, preferably provides cushioning, traction (see, U.S. Pat. No. 5,471,768) and stability. Since the sole is subject to relatively high static pressures, i.e., potentially over 300 psi, and is non-porous, the ergonomic factors differ markedly from the upper, which is typically porous and thus allows evaporation of water vapor, and is subject to much lower static forces, and typically lower dynamic forces as well, depending on shoe construction. Therefore, solutions designed to improve the ergonomics of shoes will also propose different solutions for the upper and the sole. Thus, low pressure air (e.g., less than about 3 psi unloaded) in the sole will feel squishy and potentially result in instability. The dynamic range of pressures will also pose materials issues for the bladder construction, of the air pressure is to dominate the effect. Therefore, sole constructions typically employ higher pressure gas or gels, in addition to bladder wall films, polymers, and polymer foams. In classic footwear construction, the sole may also be leather with organic material padding.

The upper is typically leather, nylon, canvas, or other low compliance sheet. The upper has an opening for the foot, which is closed after foot insertion by laces, Velcro straps, buckles, or to the like. Known systems for improving fit include pumpable air bladders, which may be in the tongue, ankle collar, or other areas.

The present invention provides improvements over known designs in a number of areas. An intelligent adaptive conformation system may be provided to provide a good static fit. This may be established by equalizing static pressure on significant contact areas, e.g., in the sole of footwear over the entire sole of foot, or separately the heel, toe area, instep, lateral edge of foot, upper, etc., or in the upper over the whole foot or selected regions, the toe, medial aspect, lateral aspect, Achilles tendon region, ankle, etc. In this way, a single passive valve may be provided to redistribute and equalize pressure over the region. After the static pressure is equalized, it is maintained until reset.

However, greater control is provided by having a compressor with a selectively operable valve for each region, allowing direct control over the shoe conformation. With such a system, if the foot changes size or shape, a may happen during protracted exercise, the system may properly adapt. Further, the optimal applied pressure may differ for different regions of the foot, and may change over time, making passive control difficult In the upper, the fit is preferably adjusted by air bladders having a relatively low void volume. In the sole, as discussed above, a high pressure pneumatic or hydraulic system may be provided. Since these have different operational characteristics, it may be preferable to separate these functions.

Since fit is typically achievable without automated control, this aspect of the adaptive footwear design may, in many instances be avoided. Cases where fit control may be important include rigid boots, such as ski and skating (ice, roller blade, etc.). The energy source for active fit control may be a compressed gas cylinder, spring or other mechanical energy storage component, electric motor or other actuator, combustor, compressor based on foot activity, or other type.

In many types of footwear, active fit control is not necessary, such as a property fitted sneaker. In this case, modulation over dynamic aspects of the system may be more important. These dynamic aspects include compliance and damping. The compliance of various controlled elements may be controlled by adjusting a gas void volume upon which a force acts, the greater the gas volume, the greater the compliance. Polymer walls also have compliant properties. The compliance of an actuator segment may therefore be adjusted by varying a fluid/gas ratio within a fixed volume, or by expanding an available gas space available for a force Typically, the compliance of a region will not be adjusted rapidly. The control may be, therefore, a microvalve associated with a tube selectively extending to a gas space. The microvalve may be provided in an array, thereby allowing consolidated control over all zones. In order to control damping, an energy loss element is provided. This energy loss element acts directly or indirectly on forces within the shoe. For example, in some circumstances, efficient energy recovery from locomotive forces is desirable, and the damping should be low. On the other hand, often, a motion is not repetitive, and therefore rebound will lead to instability and excess force transmission to the joints. Therefore, control over damping is desirable. Similar considerations apply to automobiles, and therefore similar, though larger, systems are found in that field In order to control damping, a fluid is passed between two chambers, with a restriction therebetween energy is lost as the fluid passes the restriction The restriction may be asymmetric, providing a different degree of restriction as the fluid passes in either direction. Control over the damping is excited by controlling the degree of restriction As with a controllable damping system, the damping may be controlled with a microvalve, more particularly a proportionally controllable valve Such proportional control may be provided by a single valve structure with partial response, a valve structure capable of pulse modulating the flow, or a set of microvalves which in combination set the flow restriction In fact, the compliance and damping may be integrally controlled, or controlled through a single array or microvalves.

In order to control the microvalves, a microprocessor is provided. The microprocessor is powered by an electrical source, for example a primary or rechargeable battery, super-capacitor (e.g., Ultracapacitor PC223 by Maxwell Energy Products, San Diego Calif.), or generator. Preferably, an electrical generator activated by locomotion charges a super-capacitor, which powers the microprocessor and microvalves. See, U.S. Pat. No. 5,167,082, expressly incorporated herein by reference. The electrical generator preferably is activated by sole dorsiflexion, asymmetrically on flexion.

Where a hydraulic compressor is required, it preferably is actuated by sole flexion, for example by the elongation of the sole during dorsiflexion of the foot Where a pneumatic compressor is required, it preferably is actuated by a bladder near the toe or heel of the sole. Preferably, such compressors are themselves controlled in terms of release of compressed air or fluid, to control the compliance and damping of the shoe.

In further refining shoes for comfort and ergonomic factors, temperature control is important. Known systems provide a flow of air through the shoe to facilitate perspiration evaporation. However, these systems generate "squish", and may be subject to clogging, etc. According to the present invention, a facilitated heat transport or active refrigeration system is provided, especially under non-porous surfaces, such as bladders and below the foot.

The present invention thus provides an intelligent and adaptive fit function for footwear. Traditionally, means have been propose to measure the fit and dynamic forces present in footwear. Limited means were available to alter the fit of footwear, typically not simultaneously with strenuous exercise. Thus, while a poor static or dynamic fit could be detected, it was not possible to correct the condition during use.

This inability to implement a closed loop feedback control has been because the required actuators were bulky, expensive and inefficient; the control system required significant computing resources; an active actuator system is power hungry; and the theory of operation was not well defined.

The present invention addresses these issues by providing a system which is miniature and low cost, manufacturable, utilizes available power, and employs a low power control system having a well defined control algorithm.

The first step in providing an adaptive control system is to provide appropriate sensors to detect the status of the condition to be sensed. There are typically two control strategies; first, actuators and sensors are paired, with the sensor measuring very nearly the variable altered by the actuator, allowing simplified closed loop control over the operation of each actuator, and a distributed sensor network with no one-to-one relationship with the actuators. According to the present invention, both strategies are employed in various portions of the system.

In order to sense the plantar surface of the foot, a pressure sensing matrix is provided within the uppermost layer of padding within the shoe. This may be a pressure sensitive resistor or a pressure responsive capacitor array, with the later being preferred. In the upper, on the other hand, the preferred sensor array provides a sensor associated with each actuator. Preferable, the actuators in the upper are relatively orthogonal, while in the sole it is likely that adjustments will be interactive.

A microprocessor with an integral analog data acquisition system is provided within the structure of the sole. This microprocessor has both volatile and nonvolatile memory, and an interface for controlling the various actuators. A lithium battery, for example, provides a continuous power source, while a "generator" within the shoe provides power during vigorous use, for example to drive the actuators.

While the device is active, a compressor network driven off use of the shoe is the motive force for altering the fit; the microprocessor merely controls a set of valves and regulators, rather than the compressor itself.

The system provides two distinct systems for adjusting the fit of the shoe. First, a hydraulic system is used to fill bladders for contour and piston actuators for tensioning. Second, a pneumatic system is used to fill bladders and reactive energy chambers within the sole for control over dynamic properties and pressure around the foot. The hydraulic pump is a piston structure driven off flexion of the sole. As the toes flex upwards (dorsiflexes), a strap in the sole acts to cause a cylinder to pressurize a working fluid in the mid-sole of the shoe. The natural recoil of the shoe (and/or assisted by a spring) extends the cylinder for a subsequent operation. With respect to the pneumatic compressor, a pancake shaped bladder is formed near the heel of the shoe. As weight is applied to the heel, the bladder pressurizes. A set of check valves controls flow direction. Rebound of the pump bladder is by way of a proximate gas pressurized toroidal ring.

The hydraulic system is capable of operating at up to 300 psi operating pressure at the pump, while the pneumatic system has a typical peak operating pressure of 15–25 psi. Transient pressure peaks due to activity may exceed 1000 psi in both instances.

The sole of the shoe, below the pressure sensing pad, includes a set of hydraulic bladders. For example, four anatomical zones are defined, each having a bladder space. A set of pneumatic structures is also provided within the sole; however, these are preferably static, as is conventional. If desired, one or two pneumatic structures within the sole may be dynamically controlled during use, for example to balance energy recovery and stability. The upper preferably has a set of hydraulic actuators which tension the upper material to assist in achieving a desired fit. Each tensioner is preferably associated with a sensor, which may be a mechanical sensor near the points of action or a hydraulic pressure sensor at any location within the hydraulic circuit to that tensioner. For example, three to six tensioners may be provided on the upper.

The upper may also include static or dynamic air bladder structures Each air bladder structure in the upper is associated with a respective relief valve. These relief valves may be automatically or manually set. Preferably, these relief valves include a dynamic suppression so that transient pressure increases do not deflate the bladder. The bladders may therefore be filled to relief pressure by compression of the pneumatic compressor and thus maintained in a desired state.

The preferred control for both hydraulic and pneumatic systems is a piezoelectric valve system, similar to that employed in an ink jet printer. See U.S. Pat. Nos. 5,767,878; 5,767,877; and 4,536,097, expressly incorporated herein by reference. In order to generate drive voltages, a piezoelectric element, e.g., PVDF or ceramic, may be excited by movement of the shoe.

In order to provide individual control over the various actuators and bladders, a rotary valve system may be provided in the mid-sole area. See, e.g., U.S. Pat. No. 5,345,968. Flexion of the sole not only pressurizes the hydraulic fluid, it may also be employed to generate an electric current and changes the position of the rotary valve. Alternately, the rotary valve may be electrically controlled, separate from the flexion. Thus, each step allows a different zone of the shoe to be adjusted. Since the hydraulic and pneumatic systems are separate, each position of the rotary valve allows separate actuation of a respective hydraulic and pneumatic zone.

Since the hydraulic pump and pneumatic compressor are not subject to direct control, the microprocessor provides a regulator function to control a zone pressure and a controllable check valve function to maintain a desired pressure.

Certain zones may be interactive, i.e., the controlled parameter is sensitive to a plurality of actuators (bladders, pistons, etc.), and each actuator will have effects outside its local context. Therefore, in order to achieve a desired conformation, the actuators must be controlled in synchrony. While it may be possible to sequentially adjust each actuator without a priori determining the interaction, this may result in oscillation and prolonged settling time, discomfort, and waste of energy. Therefore, the microcontroller executes a predictive algorithm which estimates the interaction, and precompensates all affected actuators essentially simultaneously. As discussed herein, a preferred embodiment employs a sequential multiplexed valve and compressor structure. Therefore, as each valve position is sequentially achieved, an appropriate compensation applied. The predictive algorithm need not be perfect, as the effect of each compensation step may be measured using the sensor array, and thus the actuator controls may be successively refined to achieve an optimal configuration.

In a first order approximation, at least, the effects of actuators will be superposable. Further, each actuator will typically have a control function which approximates the function $f(x)=\cos(\omega x)e^{-bx}$, where x is the absolute distance from the actuator center, $\omega$ is a periodic spatial constant and b is a decay constant. The resulting function therefore provides a long range effect of each actuator, which is periodic over distance. The interactivity of actuators may be analyzed using a Fourier type analysis or wavelet analysis.

The actuators are intentionally made interactive; if there were no interactivity, there would necessarily be a sharp cutoff between actuator zones, which would likely cause discomfort and shifting of the foot, or the zones would be spaced too far apart to exert continuous control. By spatially blending the actuator effects, spatially smooth control is possible.

In one embodiment, the pneumatic compressor system is also employed to cool the foot. This cooling may be effected directly by air flow, or by developing a refrigeration cycle, using heat exchangers within the shoe and external to it.

Under some circumstances, it may be advantageous to employ a refrigerant gas, such as an HFC, within the pneumatic chambers, pressurized such that under load, the gas enters a nonlinear range. Thus, in this nonlinear range, the properties of the refrigerant do not approximate the ideal gas law, providing a cushioning option not available with air or gels The generator within the shoe comprises a magnet which spins in response to a flexion of the sole. In one embodiment, a gear arrangement is provided with a unidirectional clutch, allowing the magnet to retain its inertia over a series of actuations. The magnet interacts with a coil or set of coils, the output of which is rectified and the electrical energy stored in a high capacity, low voltage capacitor. Alternately, a linearly moving magnet generates a varying magnetic field within a coil.

The rotary valve is preferably actuated mechanically by the flexion of the sole. However, a "pancake" stepping motor or shape memory allow actuator (see, U.S. Pat. Nos. 5,127,228 and 4,965,545, expressly incorporated herein by reference) may also be employed to rotate the valve body, potentially allowing random access to any desired zone. The stepping motor is actuated and controlled by the microcontroller.

As an alternate to a rotary valve, an array of electromagnetic or micromachined valves may be provided, selectively controlling individual zones. Preferably, such valves have low static power dissipation.

Present micromachining and photolithographic fabrication techniques make possible miniature, low cost pneumatic and hydraulic control structures. Therefore, in accordance with one aspect of the present invention, micromachined structures are used to control flows. Some valve types are capable of both low leakage and wide dynamic range operation. Others suffer from either excessive leakage or non-linear response. Therefore, it is possible to employ two valve types in series, one to block leakage and the other to provide proportional control over flow. Further, micromachined valve structures typically are limited in maximum flow capacity and flow impedance. Both thermal (see U.S. Pat. Nos. 5,681,024; 5,659,171; 5,344,117; 5,182,910; and 5,069,419, expressly incorporated herein by reference) and piezoelectric (see U.S. Pat. No. 5,445,185, expressly incorporated herein by reference) microvalves are known, with other physical effects, such as magnetic, electrostatic (see, U.S. Pat. Nos. 5,441,597; 5,417,235; 5,244,537; 5,216,273; 5,180,623; 5,178,190; 5,082,242; and 5,054,522, expressly incorporated herein by reference), electrochemical (see, U.S. Pat. No. 5,671,905, expressly incorporated herein by reference) and pure mechanical devices also possible. See, U.S. Pat. Nos. 5,647,574; 5,640,995; 5,593,134; 5,566,703; 5,544,276; 5,429,713; 5,400,824; 5,333,831; 5,323,999; 5,310,111; 5,271,431; 5,238,223; 5,161,774; 5,142,781, expressly incorporated herein by reference.

A preferred microvalve structure employs a nickel titanium alloy "shape memory alloy" ("SMA") actuator to control flows. See U.S. Pat. Nos. 5,659,171; 5,619,177; 5,410,290; 5,335,498; 5,325,880; 5,309,717; 5,226,619; 5,211,371; 5,172,551; 5,127,228; 5,092,901; 5,061,914; 4,932,210; 4,864,824; 4,736,587; 4,716,731; 4,553,393; 4,551,974; 3,974,844, expressly incorporated herein by reference. Such a device is available from TiNi Alloy Co. (San Leandro, Calif.). See "Tini Alloy Company Home Page", http://www.sma-mems.com/nistpapr.htm; "Thin-film TI-NI Alloy Powers Silicon Microvalve", Design News, Jul. 19, 1993, pp. 67–68; see also "Micromechanical Investigations of silicon and Ni—Ti—Cu Thin Films", Ph. D. Thesis by Peter Allen Krulevitch, University of California at Berkley (1994); MicroFlow, Inc. (CA) PV-100 Series Silicon Micromachined Proportional Valve. In these systems, an electric current is controlled to selectively heat an actuator element, which non-linearly deforms as it passes through a critical temperature range, which is typically between 50°–100° C. Thus actuator unseats a valve body, controlling flow. The memory metal actuator is formed by a vapor phase deposition process and then etched to its desired conformation. The actuator has relatively low power requirements, e.g., 100 mW per element, and is capable of linear flow modulation. The response time is about 1 mS to heat, and 1–10 mS to cool, depending on the ambient temperature and heat capacity, e.g., whether the environment is liquid or gas. The system may be readily formed into microarrays. Importantly, the system readily operates at logic switching voltage levels, facilitating direct interface with electronic control circuitry.

Therefore, for example, if the microvalve array has an active duty cycle of 25%, with two elements active during each cycle, and the system has an operating voltage of 3V, the average current draw will be about 2×100 mW/4=50 mW, with less than 20 mA draw. A 1350 mAH rechargeable lithium battery will therefore have a life of about 70 hours. Of course, there may be other demands on the power supply, but there may also be a real-time recharger. Thus, the system is not untenable to operate from available power.

Depending on cost and other architecture factors, an array of selectively operable microvalves may be present in place of the rotary valve mentioned above. In this case, it is possible to have one or more microvalves open at any time As discussed in more detail below, a second valve function controls the dynamic response of the system In this case, the dynamic functions may be controlled by the same valve as the setpoint (static operating condition), or preferably by a second valve structure. This second valve structure facilitates separate control over the static and dynamic parameters of the system.

An array of microvalves may be provided in a single integrated structure. The microvalve structure may act alone or in concert with another valve structure, such as the aforementioned rotary valve.

The hydraulic system within the sneaker may also be operated by an electrical pump. Both traditional and subminiature designs may be employed. See, U.S. Pat. Nos. 5,362,213; and 4,938,742, expressly incorporated herein by reference. In this case, the system is capable of adjusting actuators even in the absence of foot movement. A preferred pump is a gear pump (or variant thereof), which provides a small number of moving parts, relative ease of hermetic sealing, no reciprocating movement, high pressure differential capability, and may be adapted to the torque/speed characteristics of an electrical motor. The preferred electrical motor is a brushless DC design, preferably with a moving magnet (rotor) integrated with the gear pump, allowing a hermetic seal. The coils (stator) are located outside the fluid space, and are controlled by the microprocessor. The position of the rotor may be sensed with a hall-effect transducer, optical sensor through a transparent wall of the pump, or other known means.

Where the pump is electrically driven, a generator within the shoe is advisable, in order to maintain operation over extended periods. If the pump is electrically driven, the generator system may then absorb all available energy from the shoe, i.e., from flexion of the sole and/or compression of the sole portions. The sole flexion comprises a reciprocating motion, and thus may be used to drive various types of electrical generation systems. On the other hand, the compression of the sole may also be directly used to derive energy. For example, piezoelectric or electret elements may be used to draw electrical power, although typically these types of elements generate high voltages. Many types of athletic footwear have air cushions in the sole Often, these are employed to store and release energy, thus absorbing shocks while returning energy to the user. However, it is often useful to provide a degree of damping of these pneumatic elements, in order to increase stability and reduce overshoot. Therefore, an amount of air may be drawn from the pneumatic element and used to drive an electric generator, such as a gear pump or other device. Therefore, at least two distinct sources of electric power may be used. Preferably, the system employs synchronous rectification of AC signals, especially those induced in a coil by a cyclically varying magnetic field. While an intrinsic control system may be employed, the microcontroller may also be used to generate switching signals. The microcontroller derives the timing for the switching based, e.g., on sensing the voltages or pressure signals (from pressure sensors in the sole, etc.).

The high voltages generated by piezoelectric or electret elements may be used, for example, to drive high voltage devices, such as piezoelectric or electrostatic valve elements or actuators, electroluminescent devices, fluorescent devices, or the like.

Typically, during use, the adjustments made to hydraulic devices will be small, and changes acceptable if made over period on the order of minutes. Therefore, a microvalve structure may be useful without assistance under these circumstances. However, during startup, the compensation volumes will be larger and the acceptable timeframe for adjustment shorter. This suggests that a separate system be available for initial adjustment, with dynamic control maintained by the microvalves.

As stated above, in order to miniaturize the actuators, and provide tolerance for strenuous activity and sudden shocks, the working pressures of the hydraulic actuators may be, for example, 300 psi, with the operating pressure of the pump and proof pressure of the actuators significantly higher. However, materials are readily available which will support such stresses. It is important that the actuators have low leakage and sufficient lifetimes. This may be assured by using "exotic" materials, such as ceramics (e.g., silicon nitride, alumina, zirconia) and diamond-like coatings. However, these "exotic" materials are becoming more commonplace, and are used in relatively small amounts in a shoe, making their use commercially acceptable. Of course, known high performance polymers and materials formulated therefrom may provide acceptable performance without the use of exotics In principle, each actuator serves as a tensioner. In fact, the actuator may be mounted resiliently, increasing user comfort and reducing stresses on the device. By providing carefully controlled resiliency, which may be provided by a well defined spring, elastic element, pneumatic element, gel, and/or dashpot, the remaining elements may be relatively noncompliant, providing the designer with increased control over the dynamic response by adjusting the mounting system. Likewise, the actuator and mounting may also be non-compliant, with the dynamic response controlled through the hydraulic system, e g., a compliant accumulator or variable rate leakage. Therefore, using microvalves, both the operating point and dynamic response of the system may be controlled. It is noted that, unless a pressure reservoir is maintained, typically the dynamic response is limited to a "leakage" of fluid from the hydraulic line. Since it is unlikely that the integral pump in the sole can maintain a supply of pressurized fluid sufficient for heavy activity, it is important that the shoe employ a dynamic energy recovery system so that after a transient, the system naturally returns to its setpoint without addition of energy to the system.

Because of the inherent compliance of gas, it is far more difficult to independently control the setpoint and dynamic response of an air-filled bladder. Thus, the control strategy for these elements is different than the hydraulic elements. Likewise, because of the incompliance of hydraulic elements, the dynamic response of the system incorporating these elements must be specifically addressed.

Air bladders are typically used to cushion and ensure fit. Because of the interactivity of the fit adjustment and cushioning, it is difficult to control both simultaneously, and further, once a decision is made to use air to control fit, it is difficult for a designer to specify and control the cushioning. On the other hand, despite these shortcomings, air bladders are accepted and are considered comfortable and useful. According to the present invention, the comfort achieved by using an air bladder may be maintained while adjusting fit, by controlling fit primarily with a separate actuator, rather than by the volume of air within the bladder Therefore, in a shoe upper, an air bladder may be relatively fixed in volume, and therefore a pump, if present, may be used to adjust the pneumatic cushioning, independent of fit.

In various parts of the shoe, air bladders may be used to control fit. For example, in the Achilles tendon area, the use of fluid may incur significant weight, and the use of actuators might be cumbersome. Therefore, air bladders are an acceptable solution.

According to one embodiment of the present invention, heat is drawn out of the shoe. A number of passive and active means are available for this purpose. Typically, the upper of a shoe is relatively efficient at shedding heat to the environment passively, although the presence of pneumatic bladders interferes with this function. On the other hand, the sole of the shoe is a good insulator, and thus can sustain a significant temperature differentials. Therefore, any cooling system typically addresses the sole.

Various known cooling systems for footwear typically provide a pump driven by user activity to generate air flow within the shoe. This, however, generates a perceptible to difficult to control squish, thus reducing the utility of a sneaker as a high performance athletic tool, and potentially introducing instability. The present invention provides an active or facilitated heat transport mechanism preferably employing liquids of phase change media. See, U.S. Pat. Nos. 5,658,324; 5,460,012; and 5,449,379, expressly incorporated herein by reference. For example, a refrigeration cycle may be established using a compressor within the sole of the shoe. See U.S. Pat. Nos. 5,375,430; 4,953,309; 4,823,482; and 4,736,530, expressly incorporated herein by reference. See also, U.S. Pat. Nos. 4,800,867; and 4,005, 531, expressly incorporated herein by reference. Other cooling methods are also known, e.g., thermoelectric. See, U.S. Pat. Nos. 5,367,788 and 4,470,263. Since this compressor operates at relatively high pressure, squish will be less noticeable, and may provide an advantageous damping effect. Excess heat is shed in an external radiator, while heat is absorbed in a heat exchanger in the sole. Footwear heating devices are also known; see U.S. Pat. Nos. 5,722,185, 5,086,573; 5,075,983; 5,062,222; 4,823,482; 4,782,602; and 3,935,856.

In contrast, where air bladders are provided, the heat transfer is preferably passive facilitated, employing heat pipe structures, to circumvent the barrier provided by the air bladder.

Where both control over the shoe and control over temperature are exerted, a common control system is preferably employed, and preferably further structures are shared. For example, the working gaseous fluid may be a refrigerant, such that the refrigerant provides both cooling and compression. Therefore, a single compressor may be employed for both functions.

Advantageously, the air bladder in this case is formed as a three layer structure; a pair of layers proximate to the foot defining a serpentine flow passage, and an outer layer forming an overpocket with the middle layer. The overpocket preferably has a pressure relief valve to control the back pressure and allow continuous flow of gas.

The user interface for the adaptive footwear is preferably minimal, i.e., the user has basically no control over operational parameters. However, in some circumstances, it may be desirable to allow the user to control parameters. Preferably, the user interface in that case is hand-free, for example using a voice input device, such as available from Sensory, Inc., Sunnyvale, Calif.

Cryotherapy

One aspect of the present invention therefore provides a cooling system, principally for direct cooling of objects or mammalian flesh, by proximity of a refrigerant evaporator device. The evaporator thus is cooled by refrigerant to a temperature at or somewhat below the desired temperature of the object or therapeutic temperature. This temperature is achieved by equilibrium at the boiling point of the refrigerant (under the conditions in the evaporator) in a properly sized evaporator, or in steady state above the boiling point of the refrigerant, in an oversized (starved) evaporator. In the later case, it is preferred to distribute the cooling over the entire evaporator, to avoid temperature variances, for example, by providing a tapered evaporator having an increasing cross section with increasing distance from the inlet, to accommodate the increasing volumes of gas generated by progressive refrigerant evaporation as it passes through the evaporator. Advantageously, the pressure of the refrigerant vapor is used to compress the evaporator against the object to be cooled.

One set of embodiments of the cryotherapy device according to the present invention is used to treat human or equine injuries. While a variety of human injuries are addressed herein, the present system also is useful for the treatment of newly-acquired and preexisting limb injuries in horses, both prior and subsequent to competition, and may even be used to condition limbs prior to exertion in anticipation of stress injury. It is noted that, statistically, about one in four horses suffers limb injuries during a race, and subsequent racing is limited by the healing rates of the injuries. Therefore, any method which reduces the amount of injury and promotes healing of existing injuries is desirable. The present cryotherapy system, because of its portability and ease of storage, may be immediately available at race tracks to thereby minimize secondary trauma through the rapid and simultaneous application of pressure and cold to the injuries which will thereby promote more rapid healing.

The present invention also finds application in the pre-exercise conditioning of muscles in order to decrease the likelihood and extent of injuries that occur during exercise. Likewise, after exercise, the application of the cryotherapy device will decrease the effects of any microinjury that has occurred during exercise. With respect to horses, it is known that equine lower leg vasculature and circulation are generally inadequate for the stresses that man applies while racing the horses, and therefore competitive and noncompetitive exercise, even without overt injury, may produce significant microtrauma to these animals, a condition generally treatable by use of cryotherapy.

The cryotherapy system according to the present invention includes a number of technologies, typically comprising entire systems of specially designed components which work together. These systems are environmentally friendly, and use refrigerant compositions which are free of chlorofluorocarbons (CFC's). Preferably, the devices have low emissions of refrigerant vapors, but are not necessarily designed for zero emissions. The refrigerant compositions employed preferably have low toxicity and low flammability. The system is therefore adapted to effectively make use of non-CFC refrigerants, in a reliable, portable, efficient, safe and effective system.

In one embodiment, the present invention relates to a self contained, portable secondary trauma reduction system that simultaneously surrounds sprains, strains, twists, pulls and painful sites with deep-penetrating, controlled, therapeutic cold having the additional characteristic of consistent controlled pressure. The cryotherapy system according to the present invention includes a reusable, pressurized, cold therapeutic device employing canisters of pressurized refrigerant for the treatment of secondary trauma. The present invention applies cold and pressure for preexercise and post-exercise muscular conditioning, the immediate treatment of musculoskeletal injuries and inflammatory conditions, therapeutic reduction of tissue metabolism and the reduction of chemotherapeutically-induced hair loss.

The applicator is designed in a number of configurations, for human and veterinary use, to address the major accidental injuries encountered by providing an anatomically conforming applicator with appropriate heat transfer characteristics. Configurations are also provided for body cooling, as is required in certain protective garb, e.g. Hazmat (hazardous material handling) suits. In addition, the system provides a muscular conditioning system which allows improved performance and reduced musculoskeletal microtrauma. A scalp cooling system, designed to prevent cancer-chemotherapy induced hair loss is also provided. The cryotherapy system is also used in conjunction with medical monitoring and medical therapeutic devices, providing a combination therapy for both acute and chronic musculoskeletal injuries. The system may also include sequential pressurization of compartments to form a peristaltic pump, to provide for circulation assistance.

The present pressurized cryotherapy devices may be preferably adapted to fit various parts of the human or animal body, including the head (e.g. a headband), shoulder, forearm, elbow, wrist, hand, lower back, thigh, knee, patella, calf, ankle and foot for humans. The pressurized cryotherapy devices according to the present invention may be further adapted for use as a tri-dimensional skull cap (pre and post-cancer chemotherapy treatment and migraine headaches), cervical collar, facial compress (pre and post-cosmetic surgery treatment), full arm extension, hip joint applicator, and hill leg device The cryotherapy device is designed so that the surface closely approximates the anatomical surface to which it is applied, for a proper fit, and such that an increased pressure is evenly applied to the tissue.

The intelligent adaptive surface technologies discussed elsewhere herein may also be applied to ensure a good fit and assist in applying an appropriate pressure, pressure profile and/or time-pressure profile to an anatomical region.

In a preferred embodiment of a full leg cryotherapy device, an elongated cooling pad is lo provided with a straight line closure, having a patella relief. Likewise, a full arm cryotherapy device is provided with a straight line closure having an elbow relief. A shoulder-chest embodiment covers the body from the sternum to spine and from the top of the shoulder to well below the shoulder blade and down the arm to the elbow. A vest system preferably covers the chest and upper back. The shoulder-chest embodiment is preferred for sports-related injuries, such as throwing arm injuries, while the vest is preferred for pre- and postoperative cryotherapy, especially using a recirculating refrigerant system. The portable vest and/or pants (leg) system may be used in conjunction with Hazmat protective clothing, without a pressurized bladder being operative.

The cryotherapy method and apparatus according to the present invention is tolerant of volatile refrigerant liquids having a boiling point below the target cooling temperature, while providing a safe and effective treatment regimen. Thus, in this instance, the system is specially designed to distribute the coolant and the cooling effect so that freezing and frostbite are prevented. The cooling system therefore operates in a non-equilibrium steady state.

The refrigerant may be supplied in a standard aerosol-type canister which is self pressurized by the refrigerant. This canister is preferably topped by an adapter, which allows detachable quick-connect coupling of the cryotherapy device, with minimal leakage. The canister is disposable or recyclable after use. In this embodiment, the coolant flow is controlled by an inject valve which connects to the canister adapter, and provides a predictable, controlled refrigerant flow to the cryotherapy system. The inject valve preferably also allows rapid initiation of the cryotherapy by providing a "fast fill" feature. The inject valve also includes an integral check valve, to prevent backflow from the cryotherapy system toward the canister adapter.

The refrigerant flows from the inject valve to the cryotherapy applicator through a tube. The tube, through a connector, enters into the applicator at the beginning of a serpentine flow path, specially designed to prevent pooling of refrigerant and to provide an even cooling distribution throughout the device, even under adverse conditions. The tube is specially sealed to the applicator to prevent leakage and to provide mechanical strength.

As the refrigerant vaporizes, it forms a gas, which exits the serpentine maze and inflates a bladder which surrounds the cooling portion of the applicator, providing a controlled, constant pressure to the tissue under treatment. Preferably, the bladder has a common wall with the serpentine maze, and is formed as a three layer structure. The pressure in the bladder is controlled by a combination pressure control and bladder vent valve. This valve may be a fixed pressure relief valve, e.g., 21 mm Hg, 30 mm Hg or 35 mm Hg, or a variable pressure relief valve, which may be adjusted over a range of safe and effective pressures. The pressure is preferably manually controlled, although automated controls are possible. As discussed elsewhere herein, a segmented bladder arrangement may be provided, with separate controls over the segments. The segments may also be adaptively controlled to achieve a desired or optimum configuration and treatment profile. The preferred simple combination valve sits in a custom fabricated flanged tube valve seat which has superior resistance to failure and compatibility with the materials of the applicator for heat sealing. In other words, the valve seat is readily heat sealable to the wall of the bladder, and has sufficient strength and durability.

The cryotherapy system according to the present invention may also used in conjunction with medical monitoring and medical therapeutic devices, providing a combination therapy for both acute and chronic musculoskeletal injuries.

A peristaltic pump embodiment, activated by a sequential compression of portions of a subdivided bladder and controlled by a gas-driven sequencing valve, provides a system for circulation assistance. The peristaltic pump embodiment preferably provides cryotherapy, although is operable with compressed air without substantial cooling.

One embodiment of the cryotherapy apparatus according to the present invention comprises a refrigerant-canister having an integral valve with a valve stem and a lip; a dome, mating with said refrigerant canister at said lip, having an aperture into which said valve stem protrudes; an inject valve, having means for mounting on said dome, means for activating said integral valve when mounted on said dome, a selectively activated passage having a high flow rate and flow-restricted passage allowing a low flow rate; a tube, mounted to said inject valve by a nipple inserted into said tube and locked by an external constrictor around said tube and said nipple; a maze, having a passage formed between two sheets sealed into a pattern having a plurality of blind ends in a plurality of orientations, said maze having at least one wall having a textured surface and receiving said tube at one end, and having an apparent cross-sectional area which increases with increasing distance from said tube; an expansion space, formed by a layer of material on one side of said maze, being parallel to said maze, into which an end of said maze distal from said tube empties; a flange, formed in a wall of said expansion space opposite said maze; and a pressure regulating discharge valve having a pressure regulating function and a selectively activated gas discharging function, mounted at said flange.

The use of a cryotherapy device in accordance with the present invention is effective in providing cryotherapy for secondary trauma treatment for humans and animals, is useful for reducing an individuals actual recovery time and related medical costs, and limits or prevents subsequent and often costly future complications in the case of serious injury. Additionally, the instantly disclosed cryotherapy device has the ability, when applied promptly, to reduce lost productivity time of workers who have suffered mild to severe sprains, strains and fractures.

In some instances, this reduction in lost employee productivity time is even greater. For example, in cases where early surgical intervention is indicated, the use of the inventive cryotherapy device can facilitate immediate treatment, rather than the typical delays of one or more days due to tissue swelling, thereby reducing the overall recovery time and expense while improving tissue survival.

The present invention provides particular advantages over a number of other known cryotherapy systems. In the present cryotherapy system, controlled temperature and controlled compression are applied to prevent or treat secondary trauma. For example, the mere use of ice is ineffective since ice melts, thereby causing a buildup of water and requiring leak-proof systems or the reluctant acceptance of a system that leaks. Further, ice from a food freezer usually starts at a temperature well below 0° C., a temperature that may cause ice burns (frostbite). Traditional bandages, administered to provide pressure, may slip or can be applied too tightly, thereby resulting in negative therapeutic efficacy. Various cryotherapy devices heretofore available typically fail to provide controlled cooling, controlled compression or require significant capital equipment to operate.

The cryotherapy system according to the present invention employs ergonomic custom-designed cryotherapy devices, adapted for various body parts. The preferred embodiment includes a rugged, highly durable and reusable compression device that surrounds an injured body part. A refrigerant is released into the compression device, which then absorbs heat as it vaporizes, causing an inflation of the device so that pressure (e.g., up to about 0.4 psi) and cold (e.g., about 2° C.) is applied to the injury. This therapy may be continued as long as is required, with possible replacement of the refrigerant canister if required.

In accordance with the invention, maximum pressure is applied in a manner that does not create a substantial risk of compartment syndrome, onset of which is generally considered to begin at an interstitial tissue pressure above 40 mm Hg. Therefore, the preferred pressure is between 21–35 mm Hg. The pressure is applied so that an extravasation of fluid from capillaries in the area of the injury is retarded or blocked, and to help ensure that interstitial fluids are returned to the lymphatic drainage system. Thus, the pressure is often an integral part of the treatment in accordance with the invention. The simultaneous application of pressure and cold may also reduce the incidence of pain According to a further embodiment, a known pulse oximeter system may be used in conjunction with the present cryotherapy system to assist in determining whether the tissue under treatment is receiving adequate blood circulation. Inadequate blood circulation typically results from too high an applied pressure or as a result of injury or pathological process. Since oximeters generally measure the capillary circulation, they may provide an early indication of the onset of compartment syndrome (although skin perfusion may not correlate well with deeper tissues). Since the cryotherapy device according to the present invention is applied to injuries, and sometimes severe injuries, and the applicator portion of the device may obscure view of the tissues, the pulse oximeter may further be useful in determining tissue status and the severity of the injury.

In a preferred embodiment, the pulse oximeter sensor may include a phototransistor and LED pair which illuminate the skin below the cuff which determines blood oxygenation by differential light absorption at a plurality of wavelengths. Other known types of pulse oximeters may also be employed. The signals from the phototransistor are conveyed to a control system, which can, among other things, display oxygen saturation level or provide an alarm. A closed circuit feedback system may also be provided to reduce cuff pressure if tissue perfusion falls to an insufficient level. An external alarm, e.g., an audible or visible indication, or signal to another system, may also be provided.

Of course, other types of tissue perfusion indicators are available, including ultrasonic, electromyographic, and other types. These known tissue perfusion indicators may be integrated with the present cryotherapy system to provide clinical data or sensor information for a control system, which may vary operating parameters of the cryotherapy device or other therapeutic devices. The cryotherapy system according to the present invention may be situated beneath a cast or splint, to provide cooling and/or cryotherapy to the affected area. The pressure within the bladder helps immobilize the extremity, and may be selectively depressurized for access and exercise.

The present cryotherapy system may also be employed in conjunction with invasive and non-invasive, electric or electromagnetic stimulation devices. These stimulators may be used in the treatment of recalcitrant bone fractures (nonunions). Electric or electromagnetic stimulation may also be used to assist in the healing of fresh bone fractures. In addition, stimulators may be used as an adjunct to surgical spinal fusion procedures. Controlled cold and pressure aid in the reduction of postoperative pain, edema and blood loss.

The attenuation of the inflammatory process may also improve healing. One available stimulation device, the EBI Bone Healing System (Biomet Inc.), is a preferred device to be used in conjunction with the present cryotherapy system. This system is non-invasive, and produces low-energy pulsed electromagnetic field signals that induce weak pulsing currents in living tissues, including bone, when such tissue is exposed to the signals. These signals are reportedly optimized by amplitude, repetition rate and duration to induce bone healing. The Biomet system further includes a control unit, which generates appropriate signals, and which may be powered by batteries (e.g. EBI Model 1020) or line current, and a treatment head which may be used proximate to the skin or displaced, such as through a cast or the present cryotherapy device. Treatment coils may also be incorporated in the cryotherapy device, especially flexible coils (e.g., EBI FLX Flexible treatment Coils). This treatment head emits electromagnetic pulses which induce pulsed currents around a bone fracture site. Of course, other types of therapeutic devices may be integrated with the cryotherapy system. Thus, the present cryotherapy system may be used in conjunction with an electrical stimulation device such as the Biomet device in order to assist in healing, and is compatible with various other types of electrical stimulation, which may be applied through the device, to the skin under the device, or fabricated as an integral part of the device.

The present cryotherapy device may be employed as part of a diagnostic system to determine, in a controlled manner, the effect of cold on tissues. For example, various disorders may alter a cold-induced variation in response, such as muscular irritability.

The maze in the subject cryotherapy device is preferably cooled to about 2° C., a temperature which does not create a substantial risk of tissue freezing The lowest temperature at any point at the surface of the bladder in contact with the tissue should be above 0° C., preferably above 2° C. The maximum temperature of the bladder in contact with the tissue is below ambient temperature, preferably at least 10° C. below ambient temperature, within the above constraints. The tissue cooling lowers the tissue metabolic rate, reduces inflammations, and reduces secondary inflammatory processes. Related to the lowering of the tissue metabolic rate, the oxygen demand of the peripheral tissue generally drops by a factor of two for each 10° C. drop in temperature (assuming that a shivering response is not evoked), thus lengthening the time for which oxygen-starved tissue may survive until the circulatory flow is restored. Thus, injured tissues which are treated with cryotherapy and localized controlled compression tend to be subjected to less tissue destruction secondary to trauma. The pressurized bladder may also help to stabilize musculoskeletal injuries and prevent additional accidental trauma to the injured site.

Cooling Device Evaporators

The materials used for fabrication of the cooling device evaporator are preferably selected to be compatible with each other and with the refrigerants. Therefore, according to one embodiment, polyurethanes and nylons are preferred. According to another embodiment of the present invention, a laminated structure of high tensile strength polymer film is employed as a containment vessel, vaporization matrix and/or conduit for the refrigerant mixtures. The high tensile strength polymer is preferably low compliance, and heat sealable to form a high strength dimensionally stable system. The materials, especially in locations subject to heat sealing or bonding should not have any coating or residues on the surface which are incompatible with the chemistry of the process of administration of cryotherapy or the sealing process Likewise, coatings may be applied which improve the surface properties of the materials for the joining process.

Suitable high tensile strength polymers include polyesters (e.g., Mylar®), PVDF, and other non-woven polymer films having sufficient tensile strength, in a thin film, to contain the refrigerant under vaporization conditions without substantial elastic or inelastic distortion of configuration These films tend to be non-compliant and stiff Woven or regular matrix fibers or composites may also be employed. A principle difference between a woven reinforced polymer sheet and a high tensile strength polymer sheet itself is that the high tensile strength polymer sheet withstands the rigors of serving as an evaporator of a refrigeration system without requiring a laminated supporting structure. Thus, a simple polyurethane sheet would tend to balloon and fail under such stresses. Likewise, when ballooning, the heat-sealed seams would tend to fail.

Typical 48–50 gauge polymer films, du Pont Mylar 500L2 and Mylar LB, have tensile strengths of at least 20 kpsi, MD per ASTM D883, with an ultimate tensile strength of at least 25 kpsi TD. Tear strength is, for example, greater than 0.5 lb. The stiffness modulus is, for example, 550 kpsi per ASTM D882. Another characteristic of these films, in 48–50 gauge thickness, is an elongation at break of about 100–150 MD, 70–125% TD per ASTM D882.

The Fluorinert "Liquid Heat Sink" (3M, St. Paul, Minn.) is an example of a fluorocarbon heat transfer medium (perfluorocarbon) which is encased in multilayer film bag. The liquid within the bag is not intended to volatilize, and has a boiling point above 85° C.

One embodiment according to the present cryotherapy device is a heavy duty, long-lasting, structure. In the event that the device is expected to be subject to or at risk of contamination, a disposable liner may be supplied which surrounds the device. The liner is constructed so as have an insubstantial effect on the heat transfer from tissue to the maze, and to allow venting of refrigerant gas from the exhaust valve. The outer liner may be formed of flexible plastic or elastomeric film. The liner preferably has a seal, such as a "ziplock" seal, or is sealable, in a manner which provides for entrance of the umbilical tube through the sealed portion and a vent aligned with the exhaust valve which diverts released gas out of the liner.

Under certain circumstances, a disposable device, with or without a liner, is preferred. For example, where the unit is likely to become covered with blood or other contaminant, is expected to be abused or risks puncture (while not being used in a critical procedure), a disposable device is preferred. A disposable device may also be preferred if there is a risk of pilferage or return of the device after use is impractical. The disposable unit differs from the heavy duty unit by being made by a cheaper, less durable process, designed for a shorter life cycle of a limited number of treatments Thus, while a preferred, heavy duty embodiment consists of layers of polyurethane covered nylon, a disposable embodiment might be fabricated from polyurethane sheet, reinforced polyurethane sheet or polyester film. The preferred polyester film is a high tensile strength film which shows minimal stretch when subjected to 5 psi in a thickness having a burst strength of a heat sealed structure of in excess of 50 psi Thus, for a disposable embodiment, the polymer films may be provided as quite thin layers, as compared to polyurethane. For example, a tensile strength ratio of 3–10:1 would be expected, allowing corresponding reductions in size and weight, and being amenable to low cost fabrication methods.

Likewise, the heavy duty embodiment includes a fast-fill function in the inject valve to rapidly cool the maze of the heat transfer portion of the device and to fill the bladder to operating pressure, while a disposable unit might forego this feature with a delayed achievement of steady state conditions. A heavy duty embodiment includes a replaceable discharge valve, with a variety of available pressures, while a disposable embodiment might have a permanently-installed discharge valve with a fixed relief pressure.

The device according to the present invention is preferably sterilizable, especially where the device is applied in emergency situations where blood contamination may occur or where the device is to be applied in proximity to an open wound. Likewise, disposable devices are preferably shipped sterile, to avoid contamination or infection of a user.

The refrigerant passage containing device of a durable embodiment of the present system is formed of a urethane coated nylon cloth (1000 denier, for example) which is formed into a maze, having a plurality of blind pockets that form traps of varying orientation, by the use of radio frequency sealing, into specific patterns that allow for contour placement of the device over and/or around the injury sites. The Nylon cloth is preferably between 100–1000 denier. The nylon is most preferably 200 denier, with a water repellent outer finish. The radio-frequency sealing process joins two or more sheets in parallel planes by passing a radio-frequency or microwave signal through the layers, causing localized heating in the layers in a pattern conforming to the antenna-applicators, also referred to as RF sealing dies. If materials other than urethane are used, then other known sealing or fusing the layers may be applicable. These methods include heat sealing, laser sealing, adhesives, pressure sealing, sewing and the like. This localized, patterned heating from an RF sealing process causes the polyurethane coating of the nylon mesh to fuse with adjacent layers. On cooling, the fused portions form a hermetic-type seal, which is adequate to contain the refrigerant as a liquid and as a pressurized gas. The polyurethane coated nylon material has a low compliance, so that once the device is filled with refrigerant, further input of refrigerant will expel substantially the same amount of refrigerant through the pressure relief valve.

After the heat transfer portion of the device is placed proximate to the injury site, refrigerant is injected to rapidly to cool the maze to operating temperature, e.g., about 2° C. The injected refrigerant fluid vaporizes in the maze, to rapidly cool the device and tissue. Thereafter, the rapid injection of refrigerant is stopped and fluid slowly flows into the maze, wherein it vaporizes, absorbing heat in the process, to maintain the desired cool temperature. The maze terminates in a port which empties into a bladder, which allows the vaporized refrigerant to fill a space distal from the maze with respect to the tissue. A pressure regulating valve allows the gas to escape from the bladder, maintaining a predetermined positive pressure in the bladder. The temperature preferably achieved when the device is in use is around 2° C., and the predetermined pressure is preferably around 0.41 psi or 21 mm Hg. Alternatively, a pressure relief valve can be provided which allows pressures of about 0.58 psi or 30 mm Hg and 0.67 psi or 35 mm Hg. Of course, a pressure relief valve may be provided having any desired relief pressure, the preferred maximum for biological tissues being 300 mm Hg, being effective for arterial occlusion. The 21 mm Hg pressure is preferred for over-the-counter available devices, while 30 and 35 mm Hg pressure relief valves are preferably available for use under medical supervision.

With the exception of the canister and valve components, it is preferred that the various components of the cryotherapy system be formed of non-metallic components so that the device need not be removed for high quality X-ray images. Thus, the device may be applied immediately after an injury (first aid), and maintained in place until other therapy is begun. Thus, the cryotherapy system according to the present invention may be incorporated in fixation devices for chronic therapy, and may be used in conjunction with other diagnostic or therapeutic modalities. In the case of a cast device, the maze portion is applied proximate to the skin, optionally with a thin absorbent pad between the maze and skin to facilitate evaporation of sweat. The cast is applied with the bladder empty or partially or fully inflated, to allow use of the device without inappropriate pressure buildup and to allow proper functioning. The cryotherapy device should be situated avoid interference with the fixation function of the cast. Further, the exhaust valve is placed accessible through the cast, without substantial flow restriction. The exhaust valve is preferably mounted on a flange fixed to the cast, or may be ported, using a flow tube, to an edge of the cast.

The change in inflation pressure is preferably delivered by changing the exhaust valve itself, which has a fixed, calibrated relief pressure. Of course, the pressure relief valve function of the exhaust valve could be a variable pressure type, possibly with an electronic control system. A variable pressure relief function may be obtained by providing a helical thread and follower to alter a spring tension applied to a ball in a valve seat. A turning of the follower with respect to the helical thread will therefore alter the relief pressure, and the relief pressure may be calibrated to the rotational angle of the thread.

An electronic pressure relief valve may employ, for example, a solenoid valve, thermally activated microvalve, piezoelectric valve, or the like, which is activated by a control, based on a pressure sensor. The pressure sensor need not be located at the relief valve location, thereby allowing the system to compensate for various intervening structures which might alter the pressure seen at the valve as compared to the pressure seen by the tissue. The tissue pressure is presumed to be the relevant factor, and thus a sensor may be provided immediately adjacent to the skin. The pressure sensor may be, for example, an air pressure sensor reading the pressure of a bulb, a force sensing resistor, a pressure responsive capacitive sensor, or other known type. A force sensing resistor may be constructed, for example by providing a compressible polymer loaded with tin oxide, available commercially from Interlink Electronics, Inc. A force sensing capacitor may be constructed by forming conductive electrodes on the surface of a compressible dielectric, for example a polyurethane foam. The electronic control may also be used to provide an alarm indication if the relief valve malfunctions, or if the tissue pressure is high despite a relief of pressure in the bladder. It is also noted that if a single electronic control may be used for the entire device, and therefore all aspects of the operation of the device may be integrated and controlled together. An electronic control is especially preferred for chronic treatments where portions of the cryotherapy system may be obscured from view and unsupervised operation is desired. The electronic control system is also preferred where the device is used under medical supervision to provide aggressive therapy, i.e., therapy which, unless carefully monitored, might be hazardous. Thus, the control system may carefully control temperature, pressure and treatment cycle, and may further allow programmed mid-treatment variations in temperature and/or pressure. Further, the use of condition feedback sensors and biofeedback sensors may also allow customization of the treatment for the patient, while ensuring safety. It is also noted that the cryotherapy and/or cooling systems may also include adaptive and intelligent surface controls, to effect control over pressure, in the case of a static therapy for an injury, but also over dynamic system parameters, in the case of a cooling device which is worn by an active subject.

Control of Closed Systems

In order to control the resulting temperature in the cooling device, a number of possibilities are available:

1. First, in the case of cooling, the refrigerant composition may be specifically selected for appropriate volatilization characteristics. For example, the boiling point temperature at the containment pressure, which will normally be superatmospheric, may be selected so that the boiling temperature is approximately the same as the desired temperature. If cooling alone is desired, the boiling temperature should be somewhat below the desired temperature. If heating is desired, then the boiling temperature should be above the desired temperature. Thus, in the case of heating, it is desired that the heat transfer liquid not be volatile or substantially evaporate at the working temperatures and pressures, while in the case of cooling, it is desired that the refrigerant volatilize to withdraw heat. Stated in terms of material properties, for heating, it is desirable that the heat transfer fluid have a vapor pressure below the containment pressure in the heat transfer device, while for cooling, it is desirable that a phase within the heat transfer device have a vapor pressure above the containment pressure. The refrigerant may therefore be used for both heating and cooling if the operating conditions change so that the refrigerant volatilizes during cooling and does not volatilize during heating, by, e.g., increasing the operating pressure or by temporarily altering the composition of the refrigerant (heat transfer medium). Of course, if the refrigerant volatilizes at the desired temperature, it will tend to buffer the cooling matrix around this desired temperature, assuming the heat exchanger is controlled to supply or withdraw heat appropriately.

2. Second, the containment pressure in the cooling matrix may be altered to control the boiling temperature.

3. Third, the rate of supply of refrigerant to the evaporation zone in a cooling system may be tightly controlled to regulate the heat absorption to such a level that localized cooling capacity does not exceed localized heat production for extended periods.

4. Fourth, heat may be provided, i.e., through a generator or transfer mechanism, to counterbalance the heat transfer to the refrigerant, especially at a localized cold spot, so that surrounding areas achieve a desired temperature.

5. Finally, a combination of measures may be employed in a control system, which may be, e.g., active or passive, mechanical, hydraulic, pneumatic or electronic systems or methods.

Obviously, if an optimal flow rate of a particular refrigerant may be determined, a system for providing this optimal flow rate provides a simple solution for controlling the system. However, the effect of the evaporation of the refrigerant on the system as a whole is very dependent on environmental factors, so that maximum efficiency cannot be guaranteed in an unregulated control system, i.e., one which has a constant flow of refrigerant or is otherwise not controlled for alteration in environmental factors.

A cooling vest or garment may be provided for environments unsuitable for air conditioning, such as mobile applications or where the air on the environment is not contained.

In this case, the cooling device of the present invention is configured as a vest, pants, suit or large pad. The cooling medium in the cooling device is preferably a refrigerant, to provide high efficiency heat transfer. In this case, the target temperature is higher than cryotherapy applications, e.g., 15–30° C. This temperature is achieved in one of two ways; providing a refrigerant having a higher boiling point, which may result in thermodynamic inefficiency due to low differential between high and low temperature parts of refrigeration cycle, or propelling the refrigerant through the cooling device without allowing it to achieve equilibrium temperatures. The heat load in such an application will typically be about 100–500W, depending on the ambient conditions and activity level. The garment may also be cooled with a circulating aqueous solution with a secondary refrigeration loop. In a primary-secondary system, the refrigeration system may employ more traditional refrigerants, such as R-134a. The power source is preferably a 12 VDC power supply, which may be derived from a battery system or vehicle alternator.

The present invention may also include an absorption refrigeration system, such as the endothermic reaction exhibited by the absorption of ammonia gas by water or a zeolite and water. The power for these absorption refrigeration systems is typically provided by a heat source, which, while relatively inefficient, provides significant flexibility, especially where excess energy is available and heat transfer to the environment is efficient.

The present invention provides various options for elimination of the refrigerant vapor efflux from the evaporator. In the case of refrigerants which are environmentally benign, or in cases where the environmental effects are not unacceptable, the refrigerant may be vented or otherwise disposed of. Otherwise, the refrigerant is recycled by removing the heat of vaporization and returned to its original state, i.e., a liquid refrigerant in the case of an evaporation refrigeration system, or separation of states in the case of an absorption refrigeration system. The system preferably employs a single loop system, i.e., the refrigerant in the evaporator is the same component which is processed to shed heat to the environment; however, dual loop systems, wherein the refrigerant in the evaporator is cooled by a secondary cooling system to remove the added heat is also encompassed by the invention.

The refrigerant fed to the evaporator is preferably carefully metered, maintaining a flow necessary to achieve a desired temperature at or above its boiling point, while avoiding waste. This metering system may be fixed at a desired optimum or compromise flow rate, or adaptively controlled. It is note that, in a closed loop refrigeration cycle, certain error conditions may exist. In those cases, the metering valve is preferably shut off, to help avoid divergent system response or catastrophic failure or erroneous operation. Typically, while high evaporator temperatures are undesirable during operation, this represents a most acceptable failure mode.

In some embodiments of the invention, unlike in many common evaporation refrigeration systems, during non-operation states, the evaporator is depressurized, and thus isolated from the condenser and receiver.

Because the refrigerant selection is primarily determined by its boiling point, the possibilities for refrigeration cycle optimization are limited. The refrigerant is preferably also non-toxic, non-flammable and environmentally benign, e.g., low ozone depleting potential and low greenhouse gas effect. The refrigeration cycle thermodynamic efficiency will typically be somewhat lower than refrigeration systems employing traditional refrigerants, such as R-134a.

In a closed loop system, the efflux of refrigerant vapor from the evaporator must equal the influx to the compressor, or a vapor buildup or vacuum will result. Thus, the volume or speed of the compressor is preferably regulated. While the influx and efflux to the evaporator are also equal over time, the influx is preferably regulated to define the evaporator temperature. Thus, a flow or pressure gauge on the efflux of the evaporator controls the compressor, while the temperature of the evaporator controls the metering valve, where regulatable.

In a typical cycle, a refrigerant having a boiling point of about –1–0° C. at 14.7 psia (760 mm Hg) is provided in a receiver. The refrigerant is metered through a metering valve from a dip tube in a receiver, to provide a coldest temperature in the evaporator of about 0°–1° C. The back pressure in the evaporator exit is held at about 0.3–0 8 psig, to provide a positive pressure and compression The efflux gas is compressed by a compressor to about 80–120 psig, and accompanying heating to 50°14 75° C. The compressed refrigerant is cooled, for example to below 30°–40° C., with a degree of condensation, which accumulates in the receiver In this system, a number of potential errors may exist, including disconnect of evaporator during operation, blockage of connection, buildup of non-condensables, high condenser pressure, low temperature in evaporator, or the like. A control system is preferably provided, which initially stops flow from the metering valve, which will hopefully allow a return to normal operation. As the compressor continues to operate, the refrigerant in the evaporator is exhausted, and eventually the positive pressure begins to drop. At that point, the compressor is also stopped, to avoid vacuum and potential draw of air into the system. A relief valve is provided near the receiver, which allows the venting of gas from the condenser, which will include both non-condensables and some refrigerant vapor, also allowing correction of an abnormal condition. The refrigerant in the receiver is provided in excess, to accommodate losses over time. The receiver may also be recharged.

In an embodiment of the present invention, the back pressure from the cuff, e.g., 0.4 psig, is important, and must be tightly regulated, more so than the refrigerant flow into the device. Therefore, the primary control to the compressor must be the inlet flow of refrigerant vapors, maintaining a pressure in the return hose of between 0 to 0.35 psig. Since the compressor is not a variable volume device, it cannot also control the output pressure or flow. Thus, if the compressor outlet pressure rises too high, the only option is to shut off the metering valve (to block further flow to the device) and vent refrigerant from the condenser. The conditions which would typically lead to increased pressures in the compressor are buildup of non-condensables, abnormal heat load, or transients. In the former two cases, venting is an appropriate response, while for the third, some compliance in the system is preferred.

Therefore, if the operating conditions at the compressor outlet are normally 100 psi, a pressure relief valve set at 110–130 psi might be appropriate. Note that this would vent non-condensables only after startup. A sensor is preferably provided to detect relief, for example to initiate a shutdown if the condition is not corrected quickly.

In order to control the compressor speed, a motor control is preferably provided, such as a PWM controller (pulse on/pulse off with varying duty cycle). Given the high current loads of the compressor motor, such as a 12 VDC motor, which draws up to about 16 amps at stall, a high efficiency system should be employed, for example using low loss power semiconductors. A preferred compressor is based on designs from Thomas Industries, Sheboygan Wis., which may employ a wobble piston and Teflon® cup seal.

The metering valve preferably includes an automated shutoff for shutdown and "emergency" regulation. A piezoelectric or electromagnetic device may be employed which pulses quantities, e.g., 50–100 microliters, of refrigerant. This metering valve, may use cooling device temperature as a primary control variable, subject to override by the compressor inlet pressure.

To shut down the system, the metering valve is closed. The compressor then operates to draw refrigerant from the cuff and device, until about 0 psig is achieved in the accumulator. A control is provided to draw the cuff pressure to the desired level, which will avoid vacuum and therefore possible influx of non-condensables, at which time the compressor is shut off. The check valve in the compressor head may be sufficient to prevent back-leakage. Otherwise, a secondary shutoff valve may be provided.

The hoses to and from the device are provided with interlock activated valve connectors, are available from, e.g., Colder Products Corp., St. Paul, Minn. ("Two way Shutoff Valves") and Qosina Corp., Edgewood, N.Y. The refrigerant supply tube is, for example, a ⅛' ID tube, and the vapor return tube a ½' flexible hose. An electrical continuity connector may also be provided to sense disconnect, which may also carry another sensor signal. In case of disconnect, the metering valve closes and the compressor stops immediately, to avoid draw of non-condensables. A pressure relief valve is provided on the cuff to prevent inflation (due to evaporating refrigerant) over 0.4–0.45 psig. This relief valve is also present during normal device usage, to prevent overpressure. A sensor preferably detects relief valve operation to shut down the metering valve. The electrical connections to this sensor may also sense connector disengagement.

The temperature controller for the metering valve may be a simple semiconductor temperature sensor having a low and high setpoint, low being 1° C. and high being 6° C., such as a three wire temperature controller available from Dallas Semiconductors. The sensor for the relief valve may be an electrical continuity sensor which detects relief valve ball unseating.

The compressor is preferably driven from a 12 VDC motor, driven by a motor control. The motor control of the prototype may be a PWM modulated MOSFET, IGBT or bipolar device, controlled to maintain the back pressure in the accumulator at less than 0.4 psig. The accumulator preferably includes a compliant bag, capable of handling up to about 2 psig. The refrigerant is drawn into the compressor, and compressed to about 85–100 psig, and is expelled through a check valve. The compressed refrigerant is cooled in a condenser with a cooling fan blowing ambient air. The main relief valve, by the receiver, is set at about 120 psi, and has a sensor to detect relief. The condenser leads to a receiver, in which liquid refrigerant sits. A dip tube draws refrigerant from the receiver to a metering valve, which is solenoid operated, or possibly a micro-machined device valve. The metering valve meters refrigerant to the supply tube to the cooling device. A solenoid operated metering valve may be a standard type, with a 12 VDC control signal. A micromachined valve device may be a thermally-activated valve, for example employing a shape memory alloy element.

The controller controls the following actions of the device:
(a) normal operation: (i) compressor drawing refrigerant vapor to keep accumulator less than 0.4 psig; (ii) metering valve to supply sufficient refrigerant to keep device at between +1° and +6° C.
(b) overpressure in condenser: (i) shut down metering valve; (ii) vent gas until pressure less than 110–120 psig; (iii) if venting too often, initiate shutdown procedure.
(c) overpressure in cuff: (i) shut down metering valve; (ii) increase motor speed; (iii) if persistent, run compressor until accumulator reaches about 0 psig.
(d) Coupling disconnect during operation; (i) shut down metering valve; (ii) immediately stop compressor;
(e) Normal shutdown: (i) shut down metering valve; (ii) run compressor until accumulator reaches about 0 psig.

The control system logic is thus as follows:

| condition | motor | metering valve |
| --- | --- | --- |
| cuff pressure high/accumulator normal (kink in hose) | normal | off |
| accumulator pressure high/cuff normal flow too high | normal (max) | off |
| cuff temp too low | normal | off |
| 120 psi relief valve active | normal | off |
| low accumulator pressure (shutdown) | normal (off) | off (manual override) |
| cuff disconnect | off | off |

As can be seen, in each case of an error condition, the metering valve shuts down. The motor maintains its normal operation (keeping accumulator pressure between 0–0.4 psig) under all conditions except cuff disconnect. In the case of controlled shutdown, the metering valve is forced off, and the motor operates until the accumulator reaches zero positive pressure. Thus, the logic may be a simple "OR" of the various error conditions. If error conditions persist or recur, then an override may be implemented to shutdown instead of restarting when the error condition abates. Obviously, more sophisticated control and error handling protocols may be implemented.

A compressor which may be suitable, depending on requirements, is a Thomas Industries model 315 (12 VDC, 130 psi max, ~16 Amp stall current, Teflon seal). Such a pump would be able to compress about 0.2 SCCFM of refrigerant at 100 psig. A preferred refrigerant, octafluorotetrahydrofuran, has the following properties: 14.7 psia vapor pressure at −1° C., 50 psia vapor pressure at 20° C., 100 psia vapor pressure at 65° C., making it suitable for use with this type of pump.

Refrigerant

In order to control the resulting temperature of an object to be cooled, the relevant factors are the selection of the refrigerant, the efficiency of the system in selectively cooling the liquid rather than the environment, and the desire to prevent localized freezing of the liquid. The refrigerant composition may be specifically selected to ensure that the boiling temperature, at the containment pressure, which will normally be superatmospheric, be somewhat below the desired temperature. Alternatively, a heat dissipation system is employed to ensure even cooling of the liquid and to prevent localized freezing. Efficiency may be improved by insulating the outside of the system, such as with a foam or spun fabric.

The cooling process may be prolonged, thus allowing a better opportunity for temperature equilibration, if the refrigerant is held at a superatmospheric pressure while it volatilizes. This slows the vaporization and elevates the boiling point slightly. Further prolongation of the cooling process may be obtained by allowing only a portion of the refrigerant to effectively contact the liquid container at any time, and feeding the liquid into a cooling zone over a period of time. Of course, these methods may be applied simultaneously.

The refrigerants employed in the present invention preferably do not include conventional chlorofluorocarbons (CFC's), which are believed to destroy the ozone layer, and are therefore the subject of an international ban, with limited exceptions. Rather, the refrigerants include second or later generation fluorocarbon, hydrofluorocarbon, hydrochlorofluorocarbon and hydrocarbon refrigerant fluids such as the mid-boiling components R-142B (BP around −9° C.) and R-124 (having a boiling point around −11° C.), the low boiling components R-152A (BP around −24° C.), R-143A, R-125, R-23, OZ-12 and R-134A and the high boiling component R-123 (BP around 28° C.), in a compatible mixture. See Du Pont Fluorochemicals, AG-2 ENG (10/92). The refrigerants alone and in combination are preferably selected so that they are relatively nontoxic Of course, any gas (other than oxygen) poses the risk of asphyxiation or adverse toxicology. Devices according to the present invention preferably include an accidental refrigerant release prevention system.

The known mid-boiling Freon refrigerant fluid R-114 has a boiling point around 3.8° C. (39° F.), while otherwise comparable second generation mid-boiling fluids generally have lower boiling points. The present refrigerant mixture preferably contains about equal proportions of R-152A, R-142B and R-123, although each may range from about 15–40% of the total, preferably with between 33–40% of the high boiling component, which acts as a heat transfer agent in the cooling matrix.

The refrigerant may also be a volatile liquid comprising a mixture of second generation non-CFC refrigerants consisting of 50–90% R-123 (having a boiling point around 28° C.) and 10–50% R-124 (having a boiling point around −11° C.). Such a mixture of components provide a number of advantageous characteristics in the present system. These refrigerants are miscible, and may form, at least in part, an azeotropic mixture. The low boiling component R-124 ensures a high vapor pressure at room temperature, which facilitates transfer of the refrigerant from a storage container and generally ensures a state of active vaporization. The high boiling component 123 promotes heat transfer through the walls of the evaporation system, and has a sufficient heat of vaporization to provide effective additional cooling.

Therefore, in contrast to prior systems relying on relatively high boiling point fluids, the absorption of heat of vaporization of the present fluids must be spread over a large area of the bladder to prevent tissue freezing. In addition, assuming that the cryotherapy system is in steady state at the desired 2° C., the known CFC refrigerants will tend to self-regulate at the desired temperature, while the new non-CFC refrigerants will have no such stability. While it is preferred that the refrigerant directly absorb heat from the tissue and through the wails of the maze, the systems according to the present invention may also include the use of a highly thermally-conductive heat sink structure which is in turn cooled by the refrigerant.

It is preferred that the refrigerant mixture in the disposable canister should not appreciably fractionate, so that through the expenditure of the contents of the canister, the refrigerant mixture remains such that the low-boiling component expels the mid- and high-boiling components and precools the mixture. Thus, the low-boiling component should not be reduced during use to such an extent that an insufficient amount of refrigerant flows from the canister due to insufficient self-pressurization. This allows the flow control system to operate without change over the course of a treatment. Of course, an external propulsion system, such as a compressed gas in a bladder within the canister, could be used to reduce the need for the low boiling component, thereby increasing the amount of mid-boiling component which may be provided, and possibly the refrigerant efficiency of the system.

The refrigerant is preferably a fluorocarbon-based coolant mixture. The mixture is may be, for example, a ternary mixture of components, with the mid-boiling component as least prevalent and the highest boiling component equal or greater in quantity than the lowest boiling component. However, any refrigerant or refrigerant mixture may be used which, under the circumstances of use, is relatively non-toxic, has low flammability, has a high specific heat of vaporization, is environmentally acceptable, does not adversely affect the materials of the device, and has a characteristic which allows the maze to be cooled to a stable 2° C. The choice of refrigerant will also be dictated by the availability of a recycling system for the refrigerant, and cost sensitivity.

The disposable canisters preferably contain a mixture of R-124, R-153 and R-142B refrigerants, provided for portable human emergency use preferably in a 4, 8. 17 or 25 oz. canister, respectively yielding a number of treatments dependent upon the circumstances of use. For other applications, the size of the canister may vary, up to about 35 lbs., where portability is less important than economy, and many treatments will be conducted with the device.

The canister may be provided with a quantity remaining indicator. This indicator may be a liquid crystal strip, applied axially to the wall of the canister, responsive to a change in temperature in the wall of the canister due to the presence or absence of refrigerant fluid on the other side of the wall This strip preferably displays differential temperatures over a broad range of temperatures, as may occur when the canister is venting, producing low temperatures, and when the canister is being stored, where high temperatures may occur. This latitude may be provided by providing longitudinally spaced strips of liquid crystal thermometric material, each strip having a different temperature band, The quantity remaining function may also be provided by a mass sensor, acoustic or resonant frequency sensor, dipstick, or other known type of sensing system.

The cryotherapy device according to the present invention may be used for veterinary, especially equine applications. The cryotherapy applicator is designed for application to either the ankle, hock or cannon bone, or the entire leg of the horse. The preferred canisters for use in veterinary applications are 25 oz. and between 3–5 lbs. in some veterinary applications and in fixed clinical applications, larger containers of refrigerant may be employed. When large containers are employed, it is preferred that a timer or automatic cutoff system be provided in order to prevent accidental over-treatment of a patient or waste of refrigerant. Further, large containers pose an increased risk of asphyxiation, and therefore the system must prevent unintended leakage and the canister must provide resistance to failure during adverse conditions, e.g., dropping, small fires, etc.

Components

Various components of the system may also be used separately from the cryotherapy applicator:

1. The canister adapter may be employed on any aerosol-type canister which must be quick-connected to a continuous flow system, e.g., insect repellent.
2. The inject valve provides a precisely controlled flow for low viscosity fluids with a rapid flow bypass and an integral check valve.
3. The flanged tubular valve seat will find application in diverse instances where traditional molded flanged tubes have inferior properties, especially where the flanged tube is heat sealed.
4. The refrigerant in the canister, with the adapter and controlled flow inject valve, may be used to provide pressurized gas flow and/or spot cooling, for electronics uses, cleaning, degreasing, cryogenic topical anesthesia, and other purposes.

The present invention preferably employs a standard aerosol-type canister, which is used in conjunction with a special adapter. As applied to the present cryotherapy device, however, the refrigerant is not applied as a propellant, but rather uniquely as a working constituent. The adapter prevents inadvertent access to the valve stern, provides secure affixation of the inject valve, and allows interruption of the treatment without significant loss of refrigerant. Thus, in a specific embodiment, the adapter, having an annular rib, snaps over an annular lip of the can, while providing an interrupted ½ turn lockable screw thread mount for the inject valve, which depresses the valve stem when mounted in such an embodiment, the valve stem is recessed below the top of the dome.

The adapter according to the present invention may also be used in any application (cryotherapeutic and non-cryotherapeutic) where a secure attachment of a secondary control or valve is desired to be affixed to a standard aerosol-type canister For example, it may be used to emit a bug spray as a fog, or to supply a lubricant or coolant to mechanical member, such as a machined part.

Portable Cooling

The system according to the present invention is also applicable for portable refrigeration applications, such as for storage or transport of pharmaceutical solutions, beverages, or other liquids which are to be refrigerated but not frozen. Portable freezers are also provided. In this case, it may be less critical to avoid sub-freezing temperatures in the evaporator, although efficient cooling of aqueous liquids and dehumidification may be obtained in this manner.

The present invention also provides a system and method for providing effective portable cooling and pressure for various purposes These include drug storage and hazardous material transport For example, insulin dependent diabetics often travel with insulin. This insulin should be cooled to between 4° and 22° C., in order to prevent degradation and ensure potency. Other macromolecular pharmaceuticals are also heat sensitive. However, under hot conditions, the ambient temperature is higher than the recommended storage temperature. While it is known to use a freezer-activated cooling device to cool pharmaceuticals, this requires that periodically a freezer be available. The present system, when adapted by miniaturization and the provision of external insulation, may provide a long term cooling system which does not require access to a freezer or employ CFC's. Likewise, where hazardous, heat sensitive materials are to be stored or transported, the present system allows for cooling for a prolonged period. Further, the present system may also be used to cool beverage cans, foods and other comestibles. In these examples, the controlled pressure is not necessary; however, such external pressures ensures firm contact and assures good heat transfer from the object(s) to be cooled and the cooling matrix. In these instances, the exhaust valve may be replaced with a restrictive aperture, because a controlled relief pressure is not necessary. Likewise, the fast fill feature provided in a medical or veterinary therapy embodiment according to the present invention to rapidly establish normal operating conditions in the device by allowing a rapid flow of refrigerant from the inject valve into the heat transfer portion of the cryotherapy device may be unnecessary. The refrigerant composition and maze system, though adapted in shape and form, may be essentially identical. It is noted that in many instances, it is important that a refrigeration system not cool to temperatures below freezing. The present system provides a simple, reliable and portable solution to this problem, which does not require electrical power, batteries or a secondary refrigeration system with a heat accumulator.

Since the quantity of a drug to be stored is generally small, and efficient insulation may be applied around the system, a miniature efficient system is possible. A further application of the present system for transport of hazardous materials and other goods which are perishable or require cooling. Such a system must have a refrigerant reserve which allows extended safe usage.

Beverage Container Cooling

A system for cooling foods and/or beverages, such as consumer and institutional beverage, including soda and beer cans, wine bottles, and other potable liquids, e g., water, milk, baby formula, may also be constructed according to the present principles The system preferably cools by at least 10° C., to a temperature above 0° C. For example, a beverage can may be inserted in a sleeve, which includes a refrigerant maze or a coolant matrix, through which the refrigerant passes. The sleeve preferably inflates, causing close contract between the sleeve and the can. The refrigerant canister preferably includes enough contents to cool a number of cans, e.g., each of six cans from 30° C.–4° C., and cools each can in about 1–5 minutes. The present invention also provides an active cooling system for potable liquids, which reduces a temperature of the liquid below the ambient temperature, by allowing a volatile refrigerant to vaporize in proximity to the liquid or container thereof Beverage containers may be generally mass produced, and therefore, their production is cost sensitive. Thus, it is an object of the present invention to provide a beverage cooling system an active cooling function having a simple design and low manufacturing cost, which may be optionally integrated into the beverage container manufacturing process. However, more complex designs still fall within the scope of the invention. The cooling system may have a modular design, adapted to cool a variety of beverage containers.

The cooling system takes one of two forms: First, an open refrigeration system is provided in which a liquid refrigerant is supplied to an evaporation matrix and allowed to vaporize, withdrawing heat, with the gaseous refrigerant vented to the atmosphere; Second, an endothermic reaction may be employed, which may be reversible or irreversible (one time use). For example, the dissolution of a salt in a solvent, such as sodium thiosulfate in water, is endothermic It is noted that unrefrigerated beverages are normally stored at temperatures of about 15°–35° C. A desired temperature for drinking a cool beverage is in the range of about 0°–12° C.

When used in accordance with a beverage cooling embodiment of the present invention, a refrigerant mixture is unlikely to cause freezing of a beverage, because the cooling rate is sufficiently low to allow substantial temperature equilibration between the cooled surface and the bulk fluid. Further, the amount of coolant provided is generally insufficient to freeze the bulk of an aqueous fluid. Accidental frostbite of a person holding the device is avoided by providing a gas pocket or insulating layer outside the volatilizing refrigerant which has a low heat capacity, and therefore a diminished heat transfer out of the system.

For a beverage cooling application, a local reservoir preferably contains or releases for use an amount of refrigerant insufficient to cause bulk freezing of the beverage. For example, a 12 ounce beverage can is preferably cooled by 3–6 ounces of refrigerant.

In use, the refrigerant is distributed over a large area for vaporization, further reducing the possibility of localized freezing. As the temperature drops, the vapor pressure of the refrigerant also drops, reducing the heat removed through vaporization per unit time, thus self-regulating the temperature, to some extent.

BRIEF DESCRIPTION OF THE DRAWINGS

The invention is shown by way of example in the drawings, in which

FIGS. 17A, 17B, 17C and 17D are plan views of laminated containers for liquid refrigerant according to the present invention;

DETAILED DESCRIPTION OF THE PREFERRED EMBODIMENTS

EXAMPLE 1

Cryotherapy System External Canister

Figure 1C:
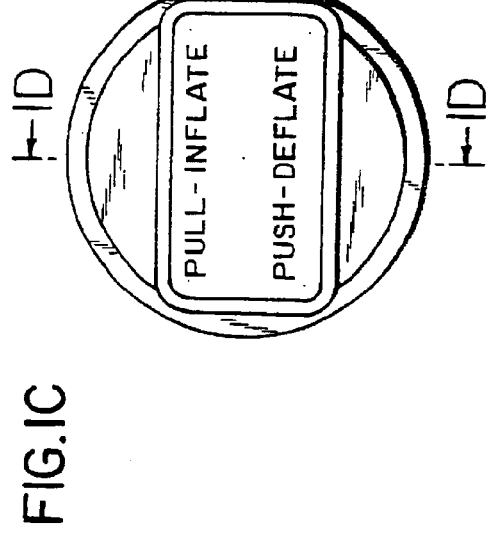
FIGS. 1C and 1D are top and cross sectional views of a pull to inflate exhaust valve.

A disposable canister 1 is provided with an adapter 2, which is designed to operate in conjunction with the inject valve 3. The adapter 2 fits atop a standard-type aerosol can, providing access to the standard valve stem 4 via a deep narrow recess 5 to prevent accidental or intentional misuse. The adapter 2 also allows stacking of the canisters The canister adapter 2 has an undercut lip 6 to hold on to the edge of the coolant canister dispensing valve The adapter 2 is designed for one time use, or it may be reused on a new or recharged canister 1. When the undercut lip 6 snaps over a portion of the valve cap 8, it is distorted into a positive lock through a full revolution. Thus, after mounting on the canister 1, the adapter 2 is rotationally stable with respect to the axis of the canister 1, while remaining securely in place. On the outside of the adapter 2 is a ½ turn interrupted helical thread 9 that provides a positive lock when the inject valve 3 is attached. The inject valve 3 is attached by aligning a female helical thread 10 on the bottom of the inject valve 3 with the male helical thread 9 on the top of the adapter 2. The inject valve 3 is then rotated with respect to the adapter 2, thus engaging the mating threads. The inject valve 3 female thread 10 includes a locking nub 11 for each thread 10 portion, so that when the threads are fully engaged, the locking nub 11 engages the bottom-most portion of the thread 9 of adapter 2, locking the two together. The central post 12 of the inject valve 3, when mated to the adapter 2, depresses a stem 4 of the canister valve, allowing flow of refrigerant 13 from the canister 1 to the inject valve 3. The central post 12 of the inject valve 3 is provided with snug enough fit so that there is no leakage around the central post 12. Sealing may be improved by use of an O-ring 14, which fits between the central post 12 and the canister valve stem 4. The inject valve body and the discharge valve body may both be using Nylon O-rings or buna-n rubber The inject valve 3 is removed from the canister adapter 2 by applying a torque to the inject valve 3 with respect to the adapter 2 in the opposite direction from the insertion twisting, which causes the locking nub 11 to disengage the bottom-most portion of the thread 9 of the adapter 2. The inject valve 3 is then rotated with respect to the adapter 2 to disengage the two. Upon axial displacement of the inject valve 3 from the canister adapter 2, the canister valve 15 is allowed to close, thereby preventing venting of refrigerant 13, if any remains in the canister 1.

Figure 1A:
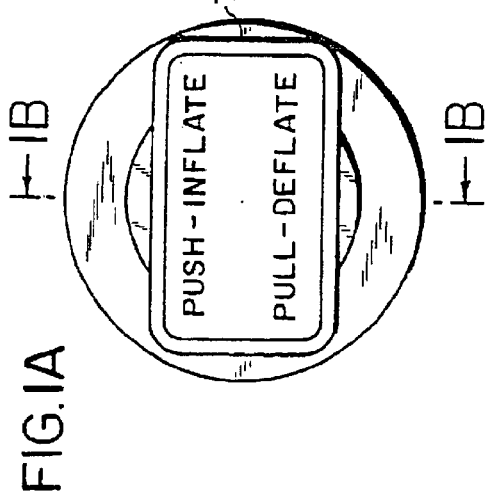
FIGS. 1A and 1B are top and cross sectional views of a push to inflate exhaust valve.
Figure 1D:
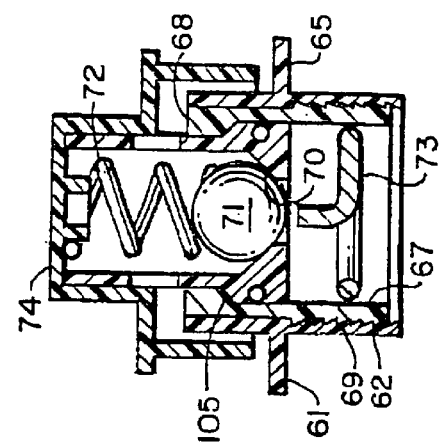

The inject valve 3 preferably also includes a check valve function to prevent back-flow from the heat transfer portion of the cryotherapy device 16, as shown in FIGS. 1C and 1D, and to allow mid-treatment replacement of the refrigerant canister 1 without substantial interruption of therapy. This function may be advantageously be provided by use of the same ball 17 used in conjunction with the fast fill feature, which seals, under conditions of reverse pressure, against an opposingly placed second conically tapered orifice 19 from the first conically tapered orifice 18 employed by the fast fill feature. Thus, in its resting position, the ball 17 blocks the fast fill passage 20, being pressed against the first conical orifice 18 by the pressure of the refrigerant 13, which exceeds a spring tension of a retaining spring 21, A manually operable push button 22, having an extension 23, displaces the ball 17 from proper seating against the first conically tapered orifice 18 to provide the fast fill feature. When depressed, the extension 23 pushes against the ball 17, allowing refrigerant 13 from the canister 1 to flow into the umbilical tube 24 and then to the maze 25. Under normal operating conditions, if the pressure in the tube 24 leading to the cryotherapy device 16 is greater than the pressure seen by the ball 17 from the direction of the canister 1, such as when the canister 1 is removed during therapy, the ball 17 will assume a position against the second conically tapered orifice 19 and prevent backflow. The normal flow rate of refrigerant 13 in the cryotherapy device 16 is established by one or more drilled orifices 26 in parallel with the first conically tapered orifice 18. These drilled orifices 26 preferably do not bypass the second conically tapered orifice 19, so that the check valve function operates on this bypass flow path as well.

The adapter 2 has a dome shape 27 on its upper surface 28, and has an annular rib or lip 6 on its lower surface 29 which snaps over a corresponding annular lip 7 of the refrigerant canister 1. The adapter 2 has a central elongated orifice 30, which when mounted on the canister 1, extends above a valve stem 4 protruding from the top of the canister 1, to prevent accidental activation and to facilitate stacking and shipping of the canisters.

EXAMPLE 2

Cryotherapy System Inject Valve

The inject valve 3 according to the present invention mates to the canister adapter 2, providing a sealed path from the canister valve 15, through the inject valve 3, to a piece of tube 24 which connects the inject valve 3 to the heat transfer portion of the cryotherapy device 16. Thus, the inject valve body 31 mates to the ½ turn interrupted screw thread 9, and connects easily. The ½ turn thread 9 causes the inject valve 3 to move axially toward the canister 1, and locks in place. The inject valve 3 includes a hollow cylindrical central post 12 which protrudes downward, concentric and outside the valve stem 4 of the canister 1. The stem or central cylindrical post 12 of the inject valve 3 depresses the valve stem 4 of the canister 1, releasing its contents, the refrigerant 13. An O-ring 14 provides a seal so that the refrigerant 13 does not leak around the inject valve 3.

The inject valve 3 comprises two flow paths. A first flow path provides a predetermined steady flow rate of coolant, which is sufficient to provide steady state cooling of the cryotherapy device 16. This first flow path is preferably formed by one or more narrow orifices 26 in a plate, although other configurations may be acceptable. The orifices 26 may be formed by laser drilling, electron beam drilling, insertion of a calibrated-orifice containing member in the plate (e.g. jeweled orifice), a glass capillary tube, or other known means in the present embodiment, the preferred orifice is about 1–6 mm in length and 0.006" in diameter, the diameter being precisely controlled, but the diameter of the orifice 26 is defined by the refrigerant 13 mixture, and the desired flow rate. The second flow path, part of the fast fill feature, is selectively activated by an external button, called the fast fill button, which is the inject valve pushbutton 22, to provide an immediate injection of a large amount of refrigerant 13 to quickly initiate the therapy and cool and inflate the cryotherapy device 16. This second flow path is preferably formed by a ball 17, resting in the first conical tapered orifice 18. The ball 17 is normally pressed against the tapered wall of the orifice 18 to seal the orifice 18 by the internal pressure of the refrigerant in the can. The externally accessible inject valve pushbutton 22 has an extension 23 which displaces the ball 17, thereby allowing a flow of refrigerant 13 to pass. Spring 21 returns the pushbutton 22 to its upright, non-functioning position The first and second flow paths are parallel, thus the net flow of refrigerant 13 is the sum of the constant flow through the first path and the selective flow through the second path.

Alternatively, the first flow path may comprise a system for ensuring a predetermined amount of leakage around the ball 17 of the second flow path, although this is not preferred due to the difficulty of controlling the static flow rate and possible difficulties in quality control.

An electronically controlled embodiment may include a solenoid, piezoelectric or micromachined valve 33 which acts in pulsatile or proportional fashion to establish the steady state flow condition. The pulsatile flow may be purely time based, or may be regulated by a sensor 34 to assist in temperature regulation in the maze 25. Such a temperature regulated device provides a temperature sensor 34 near the entrance of the umbilical tube 24 to the maze 25, which is presumed to the coldest portion of the maze 25. The coldest portion of the maze 25 preferably remains at about 2° C.

EXAMPLE 3

Cryotherapy System Overcap

An overcap 35 is preferably provided to prevent the inject valve pushbutton 22 from becoming lost. The overcap 35 is sealed to the inject valve body 31 by means of ultrasonic welding. The overcap 35 also includes a "V" type clip 36 which fits over the umbilical tube 24 which carries the refrigerant 13 from the inject valve 3 to the cryotherapy device 16, thereby preventing accidental disconnection of the tube 24. The retaining structure including the "V" type clip 36 also prevents catastrophic results from a kink in the tube 24 by ensuring that the flow path does not fail if the flow is temporarily blocked. The tube 24 is preferably a ⅛" ID Tygon® or polyurethane tube, which is inserted around a hollow stem 37 protruding from the side of the inject valve body 31.

EXAMPLE 4

Cryotherapy System Inject Valve Body

The inject valve 3 valve body 31 includes a ball seat 38. The ball seat 38 has a number of functions. First, it retains the ball 17 which is displaced to provide the fast fill feature. Second, it holds a rubber O-ring 39 which prevents leakage when the ball 17 is seated and the fast fill feature is not activated. Third, the ball seat 38 has one or more narrow orifices 26 drilled vertically through it to provide a normal, e.g., steady state, flow path. These orifices 26 are each about 0.006" diameter, although this will vary with the refrigerant 13 mixture used and the desired flow rate. The diameter of these orifices 26 is precisely determined to control the steady state flow rate and provide a constant temperature in the maze 25. The normal flow rate is generally predetermined, and devices which require differing steady state flow rates are modified by varying the number of orifices 26 bypassing the fast fill valve ball seat 38. It is also possible to vary the flow rate by varying the diameter of the orifices 26, although this is not preferred. The number of orifices 26 is therefore determined by the size of the heat transfer portion of the cryotherapy device 16 and the expected cooling capacity which will be necessary to maintain the proper temperature.

A retaining ring 40 is provided to hold the O-ring 44 in the ball seat 38 cavity, and preloads it. The retaining ring 40 reduces wear and seals around the canister valve 15.

A stem-like extension 23 is provided projecting from the inject valve pushbutton 22 which displaces the ball 17 from the ball seat 38 when the inject valve pushbutton 22 is depressed. The force of the stem-like extension 23 acts against the pressure of the refrigerant and a return spring 21, provided on the other side of the ball 17, returns the pushbutton to its original, upright position.

A diaphragm 41 is formed in conjunction with the ball seat 38. The diaphragm 41 prevents leakage of refrigerant 13 around the stem-like extension 23 and out of the inject valve 3 when the inject valve pushbutton 22 is depressed The diaphragm 41 is held in place by a retaining ring 42, which is a star washer pressed into the cavity 43 of the inject valve body 31 to retain the diaphragm 41.

The backflow prevention function, as stated above, is provided in the inject valve 3 and employs the same ball 17 as the fast fill function. When the pressure in the inject valve 3 distal to the ball 17 exceeds the pressure proximal to the ball 12, i.e., the pressure on the canister 1 side of the inject valve 3, less the pressure applied by the return spring 21, is less than the pressure in the umbilical tube 24, then the ball 17 is displaced in the opposite direction to occlude a second conically tapered orifice 19

EXAMPLE 5

Cryotherapy System Cooling Device

The refrigerant fluid is transmitted through an umbilical tube 24 from the inject valve 3 to an inject port 46 of the heat transfer portion of the cryotherapy device 16. From the inject port 46, the refrigerant 13 follows a maze 25 pattern formed by three sheets, two polyurethane sheets 47, 48 and a polyurethane impregnated nylon cloth sheet 49. Of course, the two polyurethane sheets 47, 48 may be replaced by one thicker sheet, or a larger number of thinner sheets. The maze 25 pattern is fabricated by placing the sheets 47, 48, 49 parallel to each other and RF sealing them together by means of a die having a pattern corresponding to the desired maze 25 pattern, which heats the polyurethane material above a fusion temperature to cause adhesion of the layers. The heat thus causes a partial liquefaction of the polyurethane of the sheets 47, 48, 49 which results in fusion and sealing upon cooling. The maze 25 pattern provides blind pockets 51 in varying orientations, so that any refrigerant 13 liquid is distributed over the entire maze 25, both under static conditions and when the cryotherapy device 16 is shifted. Thus, any particular orientation of the cryotherapy device 16 or any random tilting or vibration of the cryotherapy device 16 will not result in substantial pooling of refrigerant 13 in any portion of the cryotherapy device 16.

The inner surface 52 of the polyurethane sheet 48 which faces the polyurethane coated nylon sheet 49 has small cylindrical protrusions, ribs or an interrupted spline longitudinally placed, i.e., with a long dimension parallel to the expected flow with respect to the maze 25, which protrude into the refrigerant 13 flow path. These surface features 53 may be formed by heating the sheet while it is placed under pressure in a die, having a corresponding pattern formed on its face. The second polyurethane sheet 47 is sealed parallel to the polyurethane sheet 48 with the surface features 53, and outside the refrigerant 13 flow path, for added wall strength.

The surface features 53 are herein referred to as turbulators. While these turbulators are not necessary in all circumstances, and indeed their function may be accomplished by the convolutions of the walls 54 of the maze pattern, where the maze 25 is large and the maze pattern includes relatively long runs, the inclusion of turbulators is preferred As stated above, the turbulators are preferably provided on the polyurethane sheet 48 wall of the maze 25, and serve to decrease laminar flow and increase turbulent flow in the maze 25. Turbulent flow promotes vaporization, and by providing dispersed turbulators throughout the flow path, temperature variations in the maze 25 are minimized. In addition, these surface features 53 have a second function, that of maintaining a flow passage in the maze 25 even if the cryotherapy device 16 is flexed or folded, thereby preventing a backpressure buildup and possible device failure.

The protrusions, ribs or interrupted spline provided as the surface features 53 are provided such that flow will be maintained even if the maze 25 is bent 90 degrees over a 1 cm diameter rod. The protrusions of the surface features 53 should protrude about one quarter to about one half the apparent diameter of the lumen of the maze 25. Ribs, if provided, preferably run parallel to the maze 25 pattern, and are about 3 mm long with an interruption of about 15 mm.

The turbulator elements are preferably located no further apart than about the apparent diameter of the lumen of the maze 25 at that point. Sharp turns, e.g. about 90 degrees or greater, may be used or applied instead of protrusions as the turbulators for generating turbulence. The longest straight path of the maze 25 should be no longer than about ten times the apparent diameter. The path layout is designed to be such that the maze 25 will allows removal of about 2 cal/min per 10 square centimeters of maze 25. The optimal heat removal rate, however, will depend on a number of factors, such as ambient temperature, external insulation, tissue temperature, heat production and heat capacity, humidity, and other factors.

The refrigerant 13 path is thus defined by the maze 25, with the walls maintained separated by the protrusions or ribs to help maintain patency of the lumen. The maze 25 has a cross sectional area which increases in tapered fashion as the refrigerant 13 progresses through the maze 25. The velocity of the refrigerant 13 will tend to remain constant or increase slightly due to vaporization of the refrigerant 13 and the pressure necessarily decrease, thus causing or allowing flow through the maze 25. The maze 25 is preferably formed by a flow path having a width of about 1.0 to 1.6 cm minimum between sealed portions 58, with a gradually enlarging taper along the flow path to a size having an inflated cross section about one and one-half times larger than that of the inlet portion cross section. The maze 25 has a series of pockets, blocking any straight path, which serves to distribute the volatilizing refrigerant throughout the maze 25 and prevent liquid refrigerant 13 from discharging directly to the exit of the maze 25, by means of s gravity (orientation), vibration, or by means of a sudden increase in pressure.

The maze 25 includes a single flow path which leads from the umbilical tube 24 to the bladder 55. The maze 25 follows a serpentine path which provides a plurality of spaces, the blind pockets 51, for the accumulation of refrigerant 13 fluid, having orientations so that fluid will be trapped no matter which orientation the cryotherapy device 16 obtains. The sealed portions 58 of the walls of the maze 25 preferably have a width of about from 0.12–0.16 inches, with any ends having a curved edge and a diameter of about 0.18 inches. The path is designed so that the coolest path, that near the inlet to the maze 25, is proximate to the warmest path, that near the exit of the maze 25, and that the inlet path is in the middle of the cryotherapy device 16.

The paths in the maze 25 are preferably oriented so as to be 45 degrees from a fold line or the longitudinal axis, e.g., the limb axis, of the cryotherapy device 16, thereby minimizing the risk that the maze 25 will be bent or crimped along a natural fold of the cryotherapy device 16 to occlude flow.

The maze 25 terminates in an expansion space, e.g., a bladder 55, which is preferably substantially coterminous with the area of the maze 25, but having a larger lumen size and less defined flow path. The bladder 55 is formed by a fourth sheet, consisting of polyurethane coated nylon cloth 50, which is RF sealed to the maze 25 in a second operation. The fourth sheet 50 is preferably sealed to the maze 25 only about its periphery, but may also be subdivided into smaller bladders, preferably sealed to the maze 25 at points aligning with the maze 25 pattern. Thus, the expansion space of the bladder 55 may be a single pocket, or be subdivided. The bladder 55 provides a reservoir of gas to apply the desired pressure to the injury. This bladder 55 is preferably on the outer surface of the cryotherapy device 16, e.g., away from the tissue, and provides insulation of the refrigerant 13 in the maze 25 from the external environment, helping to ensure that the cooling action is directed primarily to the injury. The bladder 55 is pressurized to about 0.4 psi, which is controlled by the exhaust valve 56, having a pressure relief function.

The tube 24 which supplies refrigerant 13 to the maze 25 is sealed to the maze 25 by means of a plastic sealing band 57, disposed between the two layers 48, 49 forming the walls of the maze 25, e.g., the polyurethane coated nylon cloth 49 and the polyurethane sheet 48 having the surface features 53, facing the polyurethane-coated nylon cloth 49.

EXAMPLE 6

Cryotherapy System Pressure Cuff

At a portion of the expansion space, somewhat displaced from the terminus 59 of the maze 25, an exhaust port 60 is located. This exhaust port 60 is displaced in order to limit a direct flow. The exhaust port 60 includes a flange 61 which is formed of a material which is compatible with the polyurethane coating on the nylon sheet 50. This compatibility includes compatibility with the RF heat sealing operation to attach the flange 61 to the polyurethane-coated nylon cloth 50. The flange 61 is RF sealed to the inner side of the fourth sheet, on the polyurethane coated portion of the nylon cloth 50.

This flange 61 is preferably formed of Tygon® or polyurethane. Of course, any tube material may be employed which is compatible with the material the device is made from, softens and flows under heating and pressure. The most preferred composition is polyurethane. The flange 61 is formed by cutting a preformed tube 62 of polyurethane, having a desired diameter and wall thickness, to a predetermined length. A portion of the tube 62, preferably displaced from the ends of the tube 62, is heated and axially compressed in a die 63 having a desired flange shape, and which supports the tube 62 on its inner and outer surfaces at least in the area of heating 64. The wall of the tube 62 in the area of heating 64 is extruded into the die 63, forming a flange 61, with the ends of the tube protruding axially from both sides.

The amount of pressure necessary to deform the walls of the tube 62 into the flange 61 shape depends on the materials, dimensions, heating temperature and heating rate. Using a ¾" urethane tube with a ¹⁄₁₆" wall thickness, approximately 80 lbs. of axially applied force is necessary, while a force of 160 lbs. significantly shortens the time necessary to form the flange 61.

The flange 61 produced according to the present method does not have any undesirable mold release compound, is stable to the refrigerant compositions, and has no mold partition marks that may induce cracking or failure due to stress and temperature cycling. Thus, while the die 63 must have a parting plane, any surface irregularities formed thereby will be reflected only in the flanged portion, not in the tubular portion. Since the flange 61 does not see particular stresses, and serves mainly to hold the tubular structure in place, the quality of the flange 61 is less important than the quality of the tube 62. The present method creates a high quality tubular structure with a flange portion of equal or better quality than a fully molded part. Further, fabrication defects are reduced because the tube 62 may be inspected prior to flanging, and therefore the incidence of wall defects will be reduced. Further, the normal processes for fabricating polyurethane or Tygon tubes create a tube having superior mechanical properties. These properties are substantially retained in the tubular portions of the present flange 61. A molded flange is normally fabricated of a different composition and does not possess these superior properties and tends to form a weaker tube which is more easily subject to stress failure.

Because the flange 61 is formed through heating in an RF die 63, it is possible to form the flange 61 in situ, i.e., while the formed flange is being sealed to the wall 50 of the bladder 55. This eliminates a fabrication step and reduces the reheating of the flange 61 material. In addition, the flange 61 may be formed with added material in the flanged region 65 by providing a disk of material in the die 63. The flanged tube 62 is therefore RF sealed to the outer polyurethane coated nylon cloth sheet 50 of the cryotherapy device 16, at the outer flange portion thereof As stated above, the flange 61 may be formed and sealed simultaneously, or formed and then RF sealed to the cryotherapy device 16 in separate steps.

The flanged tube 62 for use as an exhaust valve seat is preferably ¾" O.D. with a ¹⁄₁₆" wall. The resulting flanged tube is approximately 0.6" long, with a flange thickness of approximately ¹⁄₃₂", a protrusion out of the cryotherapy device 16 of about 0.30" and a protrusion into the cryotherapy device 16 of about 0.25". The flange 61 itself has a 1.50" diameter. The flange 61 is located ¼" from one end of the tube 62, but may be moved to the end for certain device configurations.

A flanged tube 62 fabrication method according to the present invention may also be employed to fabricate the inject valve diaphragm 41 from a polyurethane tube An exhaust valve 66, for discharging vaporized refrigerant 13, having a pressure relief of 21, 30 or 35 mm Hg is inserted into the flanged tube 62 The exhaust valve 66 has a tubular protrusion 67 from its base 68 with ridges 69, so that it holds firmly in the flanged tube 62, yet can be removed and replaced if desired. The composition of the exhaust valve 66 has a high stiction to the flange material, thereby holding it in place at and above the inflation pressure.

EXAMPLE 7

Cryotherapy System Exhaust Pressure Relief Valve

The discharge or exhaust valve 66 regulates the pressure in the cryotherapy device 16, thereby regulating the pressure that the cryotherapy device 16 exerts on the injury. The exhaust valve 66 also provides a purge function the selectively allows the contents of the bladder 55 to vent to the atmosphere. It is believed that the maximum pressure that can safely be exerted on tissue for any extended length of time is about 40 mm Hg. This number varies with the hydrostatic pressure in the vasculature, but is generally close to this range, but may be reduced in poorly vascularized tissues. The maximum time at a pressure above this limit is dependent on tissue temperature, tissue type, injuries or aberrations in the tissue and the like. Therefore, for safety reasons, the pressure in normal use is limited to about 35 mm Hg maximum, and for most purposes the refrigerant canister 1 will not last longer than about an hour. Of course, for emergency use, for medically supervised applications, and where otherwise required, larger canisters are available.

Under certain circumstances, it is desirable to block blood flow, especially for limited periods, until medical intervention is available. For example, certain poisons or toxins may or should be contained in an affected appendage by the application of peripheral pressure, even at the risk of tissue damage. The application of cold lengthens the time before irreversible damage occurs. Therefore, the present system may find application in the treatment of certain conditions, such as snake or insect bites.

The exhaust valve 56 is preferably a two position valve. In an open condition, the exhaust valve 56 provides a free flow, thereby allowing gas in the cryotherapy device 16 to escape to the environment. This is provided for deflation of the cryotherapy device 16 after use, and to allow shipping where residual refrigerant 13 may produce internal pressure and cause ballooning under certain circumstances, e.g., transport by airplane. The discharge position is preferably one which is unlikely to be accidentally achieved during therapy, such as being activated by pulling or lifting out a portion of the valve. The second position provides a predetermined relief pressure in the cryotherapy device 16, which as stated above is below 35 mm Hg, preferably fixed at one of 21 mm, 30 mm and 35 mm Hg. This exhaust valve 56 should also have a low operating hysteresis, e.g., not have any substantial overpressure for initial activation, so that during initial inflation the cryotherapy device 16 should regulate the pressure accurately and without oscillation or fluctuation. These fluctuations may cause pain, disruption of the injury, and possible secondary trauma, in addition to potentially creating an undesirable tourniquet effect.

The exhaust valve 56 pressure regulating mechanism includes a ball seat 70, a ball 71 and a calibrated spring 72. Below the predetermined pressure, the force of the gas in the cryotherapy device 16 is insufficient to unseat the ball 71 against the predetermined spring 72 pressure, so no venting occurs. When the pressure exceeds the predetermined pressure, the ball 71 becomes unseated from the ball seat 70 and the gas will flow around the ball 71. In normal operation, the ball 71 will be slightly unseated from the ball seat 70 continuously to allow release of the gas which is replaced by the injected refrigerant 13, without oscillation and probable consequent noise. A steady state is thus achieved. It is noted that a relatively high frequency oscillation will not adversely affect the function of the cryotherapy device 16, save possibly the production of audible noise, and indeed modulated venting is a preferred method of electronically regulating the cryotherapy device 16 pressure. If the pressure in the cryotherapy device 16 falls below the predetermined pressure, the ball 71 will reseat in the ball seat 70, and gas escape will cease, until proper pressure is restored.

Figure 1B:
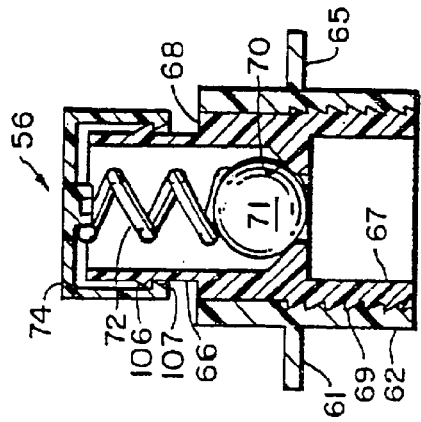
Figure 2A:
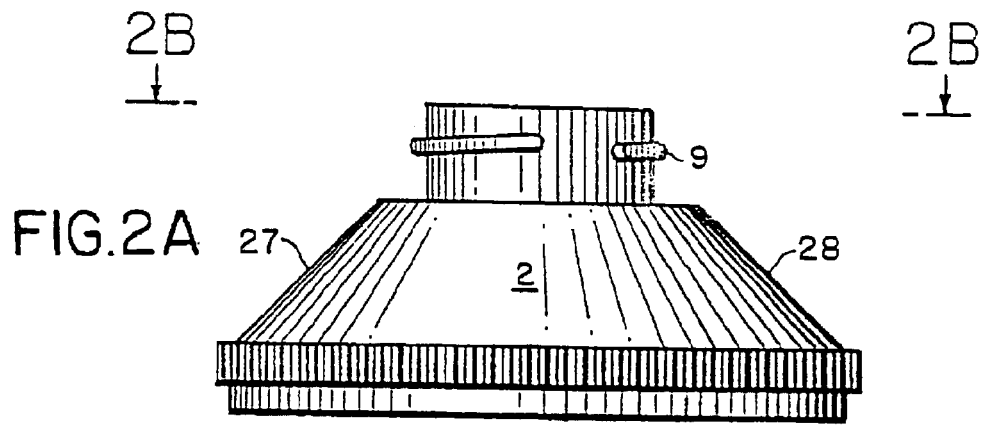
FIG. 2A is a top view of the adapter in accordance with the present invention.
Figure 2B:
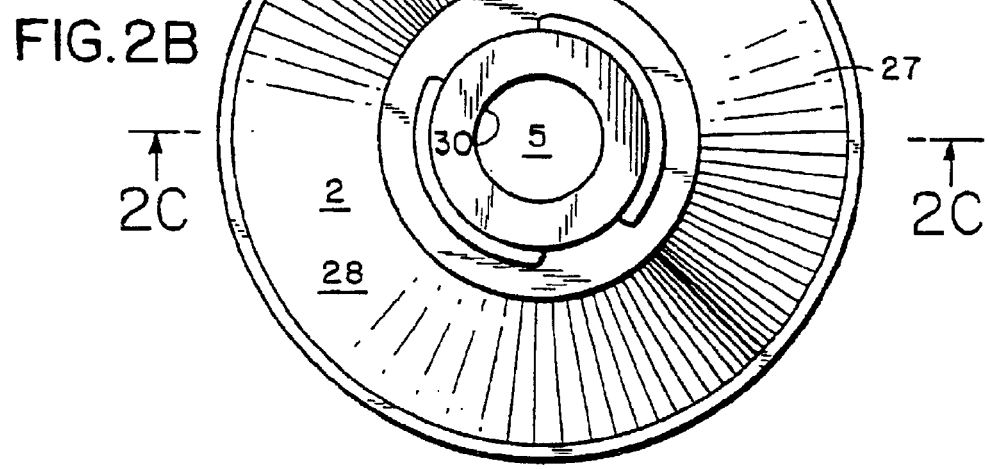
FIG. 2B is a side view of said adapter along line 2B—2B of FIG. 2A.
Figure 2C:
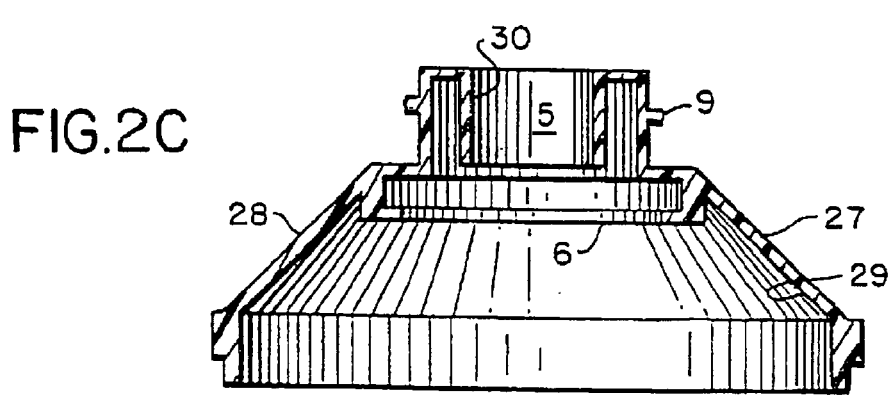
FIG. 2C is a cross-sectional view of said adapter along line 2C—2C of FIG. 2A.
Figure 3A:
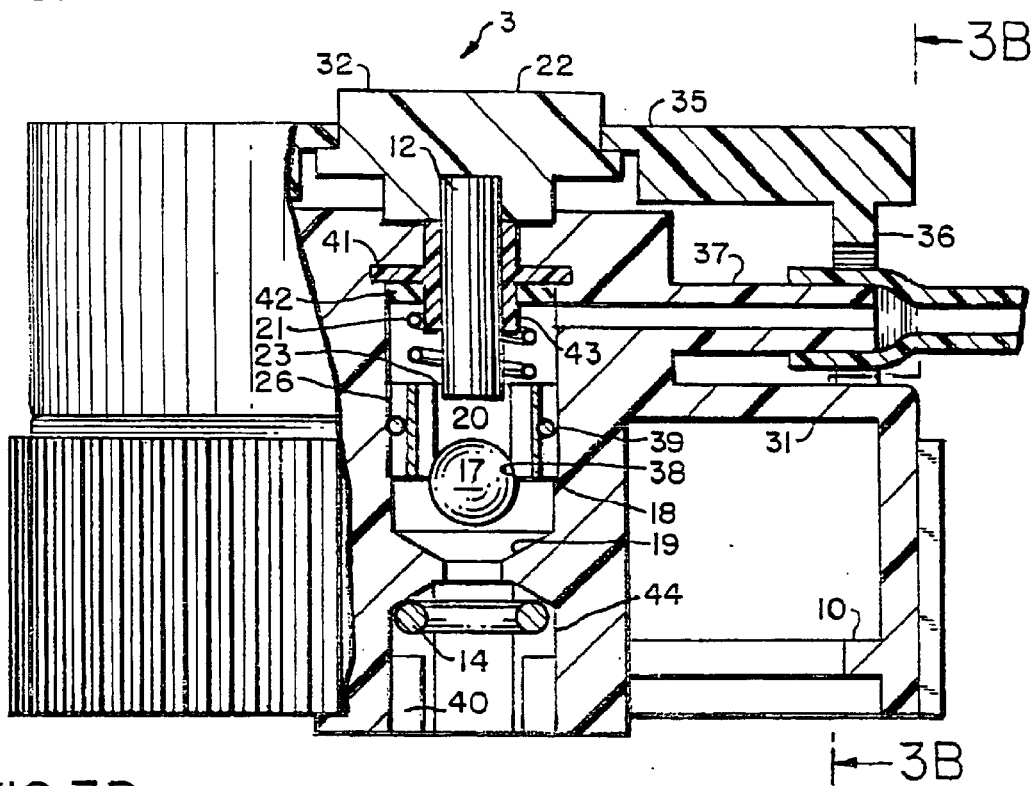
FIG. 3A is a side, partial-section view of an inject valve according to the present invention.
Figure 3B:
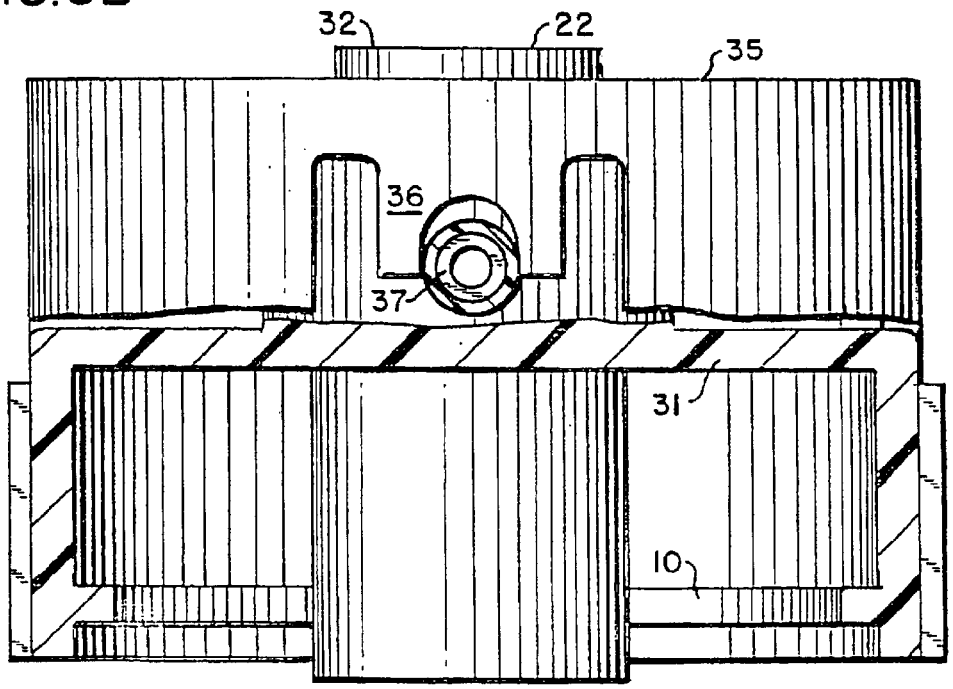
FIG. 3B is an end view of a tube-retaining mechanism shown in FIG. 3A along line 3B—3B.
Figure 4A:
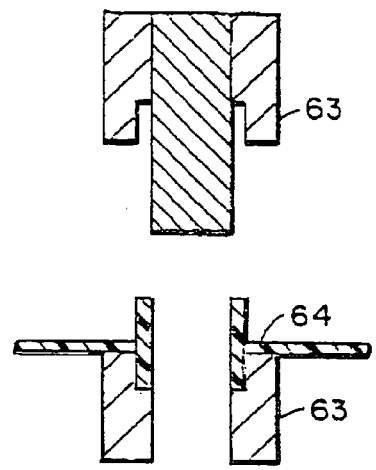
FIGS. 4A and 4B are, respectively cross-sectional views of a die for making the tube flange and for sealing the flanged valve seat to the side wall of a device, in open and closed configuration.
Figure 4B:
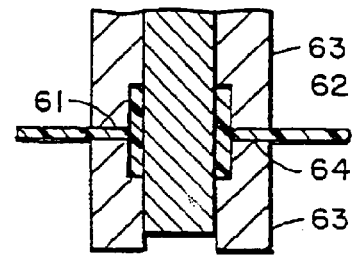
Figure 5A:
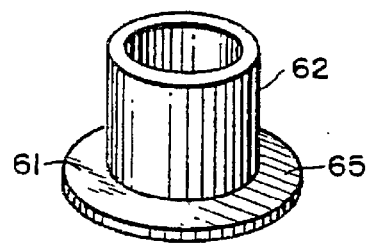
FIGS. 5A and 5B are perspective views of flanged tubes in accordance with FIGS. 4A and B, respectively.
Figure 5B:
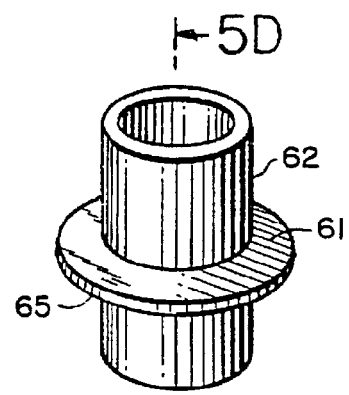
Figure 5C:
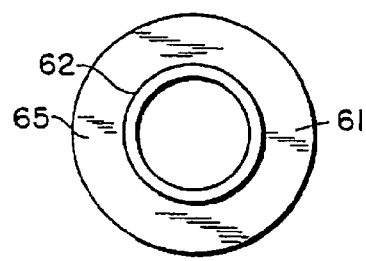
FIG. 5C is a top view of a flanged tube in accordance with the invention.
Figure 5D:
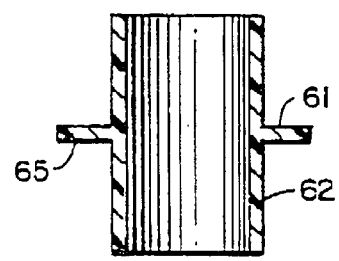
FIG. 5D is a cross-sectional view of the flanged tube of FIG. 5B along line 5D—5D.

In an preferred embodiment according to the present invention, shown in FIGS. 1A and 1B, the exhaust valve button 74 is linked to the exhaust valve spring 72, so that a lifting of the button 74 causes a reduction in the spring tension, thereby allowing venting to occur. The button 74 is locked in the pressure relief position by a notch 106 which engages a ridge 107 of the button 74. Alternatively, the venting function may be provided by a displacement member 73 which displaces the ball 71 from the valve ball seat 70, thereby allowing the gas to flow unimpeded out of the bladder 55 of the cryotherapy device 16. This displacement member 73 is linked to an externally accessible button 74, which is preferably operated by pulling or lifting, in order to avoid accidental deflation. Of course, the venting function may also be engaged by a pushbutton arrangement, with appropriate modifications of the exhaust valve.

EXAMPLE 8

Cryotherapy System Peristaltic Pump

Under certain circumstances, it is preferred that the cryotherapy device 16 be modified to function as a peristaltic pump to assist in tissue circulation. This peristaltic pumping function may also be performed without substantial cooling of the underlying tissue. Thus, a reduction in the amounts of mid and high boiling refrigerants in the mixture, thereby reducing the amount of effective cooling and the heat transfer from the tissue. The peristaltic pumping action may also be accompanied by cryotherapy, where appropriate.

For example, if the cryotherapy device 16 according to the present invention forms a cuff around an arm or leg, with a more distal portion uncovered, then the pressure of the cryotherapy device 16 may cause edema of the distal portion. Further, where long term treatments are indicated or the circulation is fragile, external circulation assistance for venous return may be helpful in this case, the cryotherapy device 16, formed as a cuff, is divided into at least three pressure bladders, arranged as distal 75, middle 76 and proximal 77 bladders. Of course, a greater number of bladders may be used, up to a number that is limited by practical limitations. In an arm cuff, up to about 9 bladders may be present. In a leg cuff, up to about 21 bladders may be present. A timing mechanism then causes a periodic wave wherein one of the bladders 76 has a reduced pressure, e.g. <15 mm Hg, as compared to the inflated bladders 75, 77 which have a pressure of between about 21 and 35 mm Hg for a few seconds. Of course, with a greater number of bladders, a number of simultaneous peristaltic waves may be present, each having a different phase, but with the same frequency. The sequence of decompression is from distal to proximal, with a continuously repeating cycle. Because of this action, fluid in the tissue, in the veins, lymphatic vessels and interstitial space, is pumped proximally, toward the torso. This system therefore allows the effective treatment of tissue with compromised circulatory drainage.

The timing mechanism may be of any type, but it is preferred that this operate from the flow of refrigerant 13. Therefore, a multi-position discharge valve 78 may be provided in which the flow of refrigerant 13 causes a cycling, sequentially draining and filling the various bladders 75, 76, 77. For this purpose, a simple turbine 79 with a reducing gear 80 may be provided to switch the position of the valve 78. A positive displacement pump or gear pump may also be provided. This valve 78 must also ensure that the pressure within any bladder 75, 76, 77 of the cryotherapy device 16 does not exceed 40 mm Hg, and preferable a predetermined pressure between 21 and 35 mm Hg. Thus, it is preferred that a single maze 25 be provided within the cryotherapy device 16 which ensures proper temperature control of the tissue. This maze 25 empties into the bladders 75, 77, with the exception of the discharging bladder 76. Thus, the same valve 78 which discharges the gas from one bladder 76 to the environment may also in a separate portion prevent flow of refrigerant into that bladder 76. The pressure relief portion 81 of the discharge valve 78 then vents gas as the pressure increases above the predetermined pressure. Prior to discharging a bladder 77, it is preferred that a valve 82 be actuated which equalizes the pressure in the bladder 77 to be discharged with the newly inflating bladder 76, so that the cuff more easily maintains proper pressure without wasted gas. Further, the discharging bladder 77 may have a second regulated pressure, lower than the predetermined pressure, e.g., about 15 mm Hg.

The sequence of the proposed valve 78 for a three bladder system is as follows initially, two bladders 75, 77 are inflated to 30 mm Hg, while a third is at 15 mm Hg. All three bladders 75, 76, 77 have check valves 83, which may be a simple flap 84 of sealing material in a conduit 85 to prevent backflow, and are shunted together through a pressure relief discharge valve 86 which exhausts at 30 mm Hg. The bladder 76 inflated to 15 mm Hg is selectively ported to a separate 15 mm Hg pressure relief valve 87, or may bleed to the atmosphere The gas exiting the maze 25 drives a turbine wheel 79. A reducing gear 80, driven by the turbine wheel 79 drives a rotary valve body 88 of the discharge valve 78. Because this valve body 88 is internal to the cryotherapy device 16, small amounts of gas leakage around the valve body 88 are not hazardous, and may even be desirable to reduce rotating friction. The gas exiting the turbine 79 enters a separate valve 89, ported to the bladders 75, 77 inflated to 30 mm Hg, but not to the bladder 76 inflated to 15 mm Hg. Therefore, the valve body 88 may be provided with sufficient clearance and configuration to have low friction. When the valve body 88 moves to a new position, it may make a smooth transition or be provided with a snap action detent to minimize intermediate states. As the valve body 88 moves, the flow of gas to the bladder 77 to be emptied ceases, and the gas is ported from the emptying bladder 76 to the bladder 77 which is to be filled, to provide a smooth transition. The 15 mm Hg relief valve 87 connection to the filling bladder 76 is then blocked by a second portion of the valve body 88. Thus, the two bladders 76, 77 which are changing state rapidly equalize to about 22.5 mm Hg. After a short period, the valve body 88 again moves so that the 15 mm Hg relief valve 87 is connected to the deflating bladder 77 and the port of the equalizing valve 82 between the two equalizing bladders 76, 77 is occluded. This sequence is then repeated for each of the possible combinations, to form a peristaltic pump powered by the gas flow.

It is noted that the check valves 83 will have a natural leakage, especially when the gas flow ceases, and therefore a rapid deflation valve is not necessary. If desired, this function may be provided by any of a number of means, including a triple vent valve to vent each bladder without intercommunication when not activated, a mechanical deformation of the check valve 83 structure to allow leakage, a valve system associated with the rotary valve body which selectively shunts the bladders together and allows venting, and other known systems In a preferred embodiment, with three bladders, the entire cycle takes between 30 and 60 seconds for all bladders The speed will depend on the rate of gas flow, the pressure in the bladders, the characteristics of the tissue to be pumped and the size of the bladders. The peristaltic embodiment is not preferred where continuous pressure should be applied over the entire area of the cryotherapy, where the fluids pooled in the extremity might be contaminated, or where secondary trauma might result as a result of tissue disruption or manipulation. Further, the peristaltic pumping adds complexity to the cryotherapy device 16, and is preferably not be employed where ruggedness and simplicity of operation are necessary. Thus, the peristaltic embodiment is preferable for application a series of medically supervised treatments of injuries or illness which each extend for a long period of time, or are to be applied to en extremity with impaired return circulation.

While the turbine 79 driven valve body 88 is preferred, an electrical or electronic system, employing a motor driven valve or an array of solenoid valves may also be used, especially in conjunction with other electrically powered functionality in the cryotherapy device 16.

The rotating valve body 88 thus has two functions. A first allows gas exiting from the maze 25 to inflate one or two bladders, and the second shunts the remaining bladders together. There is preferably no overlap between the two functions. The inflation phase is preferably about 205 degrees, while the shunting phase is preferably about 145 degrees. The non-overlap is preferably about 5 degrees. Thus, through about 30 degrees of the cycle (1/12 of the total cycle) two bladders are shunted together. Likewise, for about this same period, two bladders are inflated to 30 mm Hg.

The 15 mm Hg pressure relief valve 87 may be controlled using the same rotating valve body 88 as controls inflation of the bladders 75, 76, 77. This function is preferably provided through a separate flow path. A fluidic valve control system may also be employed. In addition, a gas flow control system based on pressure accumulation and volume redistribution may also be constructed.

While the above description describes a three bladder system, a system having more than three bladders may also be constructed according to the same principles. A two bladder system may also be constructed, which, though generally less effective as a peristaltic pump, intermittently relieves pressure in the underlying tissue, and allows a simplified control system.

EXAMPLE 9

Cryotherapy System Thermal Control System

The control system for the device according to the present invention may include a thermostat as the temperature sensor 34, for controlling the temperature of the tissue. The temperature should preferably be measured at the inject port 46 of the maze 25, which will most likely be the lowest temperature portion. This temperature is regulated so that it remains above 2° C., so that the risk of tissue freezing or frostbite is minimized. The temperature sensor 34 may include a bimetallic element, an expandable fluid, an electronic thermometer or other known temperature sensing device.

A bimetallic element is preferred for its simplicity and because the mechanical motion created by the temperature change can be transmitted directly to control the refrigerant 13 flow. In this case, a secondary valve 90 is formed near the inject port 46 of the maze 25, which is proportionally or thermostatically controlled. This secondary valve 90 slows or stops the refrigerant 13 flow into the maze 25 if the temperature drops too low, and likewise increases the flow if the temperature rises. It is noted however, that with a secondary valve 90 at in the cryotherapy device 16, the pressure in the umbilical tube 24 may be increased to high levels. Therefore, the attachment system must accommodate such pressures without risk of failure.

Alternatively, the bimetallic element may exert a pressure on a fluid (e.g. alcohol, antifreeze, e.g. polyethylene glycol solution or mineral oil), which force is transmitted from the cryotherapy device 16 to the inject valve 3 through a second tube 91, which runs parallel to the umbilical refrigerant tube 24. The fluid in the second tube 91, in turn, controls a flow rate of the refrigerant 13 in the inject valve 3, positively related to the temperature. Thus, if the temperature in the cryotherapy device 16 is too low, the flow rate is decreased, and likewise, if the temperature is too high the flow rate is increased. This regulation may be proportional or thermostatic The minimum flow rate is preferably established by a bypass aperture, so that some refrigerant always flows, in order to avoid deflation of the bladder 55 and to provide a fail-safe mechanism in case of failure of the temperature regulating mechanism. The maximum flow rate is preferably limited to a predetermined safe rate. The pressure in the second tube 91 may control the flow rate by moving an occluding member 92 in relation to a refrigerant flow aperture 93, applying a compensating force to a pressure relief valve, or other known methods. In the present system employing narrow bypass orifices 26, a cross member may be used as the occluding member 92, which may be displaced according to the temperature to interrupt a flow through one or more orifices 26, thereby modulating refrigerant 13 flow.

In another embodiment, a temperature sensor in the cryotherapy device 16 may produce a detectable pressure pulsation which is transmitted in retrograde fashion up the tube 24. This pulsation, when detected, may be deciphered as a temperature control signal. Thus, if the temperature drops too low, a thermostat may allow a member to vibrate from the flow of refrigerant, while when the temperature is too high, the member is outside the flow path and therefore does not vibrate, in the inject valve, a vibration sensor tuned to the vibrational frequency of the thermostatic controlled member near the inject port 46 monitors the refrigerant tube 24. When no vibration is detected, a normal flow of refrigerant is allowed. When vibration is detected, the vibration sensor variably occludes an orifice for the refrigerant flow. Therefore, when the temperature drops too low, a thermostatic sensor detects the condition and causes the member to vibrate. The vibration is transmitted up the refrigerant flow tube and is detected by a vibration sensor, which reduces the flow rate during the period of vibration.

An electronic thermometer may also be provided as the temperature sensor 34, which detects a temperature near the inject portion 46 of the maze 25. The electronic thermometer is a device which employs a sensor having an electrical output corresponding to temperature. An electrical thermostat, preset to detect conditions above or below 2° C. may also be used. The electrical output signal may then be displayed as an analog or numeric display, or be employed as an input to an electronic control device for regulating a characteristic of the operation of the cryotherapy device 16, such as temperature or time of treatment. In such a control system, the electrical output signal is preferably transmitted by means of a pair of wires to the inject valve 3, which regulates the refrigerant 13 flow by means of an electrically operated valve. The valve may be of any suitable known type, although a preferred type is a piezoelectric valve. A piezoelectric valve may operate to selectively occlude a narrow orifice 26 by applying a voltage to a piezoelectric material. The applied voltage causes a change in a dimension of the piezoelectric material, thereby allowing a mechanical control function. These piezoelectric materials may be stacked to increase a resulting amount of movement. The piezoelectric material may therefore be used to block or allow flow through the small bypass aperture. While a high voltage is generally necessary for operation of these devices, they generally require low power so they may be battery operated with a voltage multiplier. Alternatively, a solenoid valve or micromachined valve may be used to modulate refrigerant 13 flow through the orifice 26.

An electronic thermometer embodiment is preferred, however, where a very large area with widely varying characteristics is to be covered. For example, in a full leg cryotherapy device or full upper body cryotherapy device, the tissue heat production may vary widely, along with the local environmental conditions (e.g., exposed to air or resting on a bed). In this case, multiple thermostatically or thermometrically (e.g. binary or proportional) controlled inject valves with multiple maze flow paths provide the advantage of a tighter degree of control over local temperature, and lower spatial variation, over the entire area to be treated. In this case, the inject valve system includes a plurality of orifices, each controlled by a separate electronic valve and a separate temperature sensor, and each orifice feeding a separate umbilical tube 24 to the cryotherapy device 16. Alternatively, a single high pressure tube may feed the entire heat transfer portion of the cryotherapy device 16, which contains the control system internally, thereby minimizing the necessary external cabling and tubing. It is noted that the temperature sensors need not correspond in a one-to-one fashion to the valve actuators, and an electronic control may integrate a sensor array and control the actuators as an interrelated system Therefore, the number of temperature sensors may be less than or greater than the number of valise actuators In such a case it is preferred that a control include a model-based or fuzzy logic control, possibly with adaptive characteristics. This control may be implemented in a standard 8-bit microprocessor, such as a Motorola 68HC08, Intel 80C51 derivative, or Microchip PIC series microcontroller.

EXAMPLE 10

Cryotherapy System Cooling Device Fabrication

The cryotherapy device 16 may be formed as follows. A piece of polyurethane coated nylon cloth sheet 49 is placed polyurethane side up an a die table 94. A textured polyurethane sheet 48, having surface features 53, which are protrusions, ribs, an interrupted spline, or other texturing. The sheet 48 is placed texturing down on top of the inlet tube 24, with a smooth polyurethane sheet 47 placed on top of the textured sheet 48. The two polyurethane sheets 47, 48 have aligned holes 95, providing a vent from the maze 25. An RF heating die 96 then is placed over the aligned sheets 47, 48, with care to align a notch 97 in the die 96 with the location for the inlet tube 24, and the die 96 is heated and pressed against the die table 94, causing fusion of the polyurethane in the pattern of the die 96 and sealing of the inlet tube 24 to fix it in place and prevent leakage. These steps can, of course, be performed separately and need not be done simultaneously.

The inlet tube 24 may be sealed directly to the maze 25 in an initial formation process. The inlet tube 24 is positioned in place, leading from an edge of the sheets 47, 48, 49, with a plastic sealing band 98 made of polyurethane placed under the tube 24 in the direction of the tube 24. Preferably, however, the tube 24 is added in a separate later operation. A short length of tube 99, with a ground rod 100 inserted therein, is placed in the opening for the tube 99 in the cryotherapy device 16. The polyurethane plastic sealing band 98 is placed next to the tube 99 to provide added material for fusion and sealing. A first RF sealing operation with a first sealing die 101 seals the maze material to the tube 99 from one side, followed immediately by a second RF sealing operation with a second RF sealing die 102 from the opposite side. Both RF sealing operations use the ground rod 100 in the tube 99. The ground rod 100 is then removed and a tube connector 103 affixed to the short length of tube 99, to attach the umbilical tube 24.

A dimpling may be provided as the surface features 53 on an inner surface of the maze 25, which helps to create turbulence, maintain the patency of the maze 25 lumen, and increase the surface area of the maze 25. The dimpled surface allows a construction in which the polyurethane coated sheets need not be particularly aligned prior to the RF sealing steps. Ribs, splines, and other types of texturing which are specially aligned with the maze 25 may provide slightly improved characteristics, but are more difficult to fabricate and require careful alignment of sheets.

After the maze 25 is fabricated, a second sheet of polyurethane coated nylon cloth 50 is then placed, polyurethane side down over the maze 25 structure, and sealed about its periphery to the three other sheets 49, 48, 47 by means of an RF heated die 104 and pressure. This second sheet of polyurethane coated cloth 50 has a discharge valve seat 60, which is formed by a flange 61, formed of a polyurethane or Tygon® tube 24 RF sealed to it in an appropriate location.

EXAMPLE 11

Cryotherapy System Refrigerant Composition

A refrigerant mixture is produced by mixing, by weight 40% 152A (low boiling), 20% 142B (mid boiling) and 40% 123 (high boiling). 8 ounces of this mixture is placed in a 6 ½ inch aerosol canister 1, having a compatible sealing material system.

The refrigerant mixture may also include R-124 instead of R-142B. Alternatively, the proportions may also be one third each of the components by weight. The proportions may also be 20% R-152A, 40% R-142B and 40% R-123.

Aerosol canisters having carbon dioxide filled bladders to propel the contents are available. If such an arrangement is employed, a mixture having around 20% or less of the lowest boiling component may be employed, while still ensuring flow of liquid refrigerant 13 from the canister 1.

EXAMPLE 12

Cryotherapy System High Tensile Strength

A cooling matrix is formed by laminating two sheets of a thin, high tensile strength polymer film, preferably metalized, into a maze structure. This cooling matrix may be a cryotherapy applicator, a seat cushion, a radiator, a footwear component, or an article of clothing. These films are preferably thin and of uniform thickness, so that, in contrast to the polyurethane sheets employed in other embodiments according to the present invention, no surface features or integral turbulators are generally provided. Such turbulators may, however, be provided as a separate element.

The high tensile strength polymer has sufficient strength to resist deformation from the mechanical effects of refrigerant volatilization while maintaining flexibility and the ability to conform around biological structures. Thus, the high tensile strength polymer will not tear or balloon over the vaporizing refrigerant and turbulent refrigerant flow.

The maze structure is defined by an RF sealing pattern, which is preformed prior to metalization. The sheets may also be sealed together by a laser welding process which locally heats the sheets to the fusion temperature. This laser may be a carbon dioxide laser or other type. An overpocket structure may also be provided to control pressure. Layers may be selectively fused by providing, for example, a printed, e.g., silk screened or lithographed, pattern, which masks or localizes a heating effect. The pattern may also be formed of a material having a low fusion temperature, adhesive, or other material which reacts to selectively adhere adjacent laminated layers.

The films may be of any type having the necessary characteristics. The film must have sufficient strength to produce a usable device both for its abstract function of providing cooling and optionally pressure, and also be suitable for application to the human body. Preferred materials include polyester films, including but not limited to Mylar® (du Pont), HostaPhan® (Hoechst-Celanese), Lumirror® (Toray), Melinex® (ICI) and film packaging available from 3M. These films may each be formed of multiple layers, to provide the desired qualities. These films may also be metalized, which may be useful in reducing film permeability and increasing insulation value.

The films must be sealable to form a laminated maze structure which ensures even and complete vaporization of the refrigerant in the cooling matrix. The seal must be strong and remain flexible. The film material must be compatible with the selected refrigerant or refrigerants, meaning that the film is impermeable to the refrigerant, and its properties do not degrade over time. These properties may be available from standard materials employing usual processing, in the system according to the present invention.

Such film devices may be disposable, or usable over a limited time period. The outer surface may be laminated to a foam layer, which will decrease the "crinkle" of the film and give the device "body", and increase the longevity of the device by protecting the surface of the film. This crinkle is caused by a high stiffness of the preferred polymer films.

The film device may also include, integrated into the structure, a reservoir with sufficient refrigerant for a single treatment. The reservoir is separated from the cooling matrix by a valve, which may be a single use, irreversible valve, or a reusable valve. The user affixes the device to the area under treatment, activates the valve, and when the treatment is concluded, the device may be disposed of.

In a limited use device, the pressure relief valve may comprise a mushroom-type valve, which is preset for the desired pressure, i.e., 21 mm Hg. These valves are generally considered less suitable for repeated use because their characteristics may vary over extended use. However, in a disposable device, the relief valve need only be accurate for short periods and a mushroom-type valve may be appropriate. The valve may be formed separately with a film periphery, and heat sealed into an aperture in the overpocket.

The supply tube structure from the reservoir may be formed by a laminated film structure.

EXAMPLE 13

Inflatable Polymer Film Devices

Laminated high tensile strength polymer films may be used to produce heat insulating devices for use by persons subject to adverse environmental conditions. These devices may be very compact, yet provide a high degree of warmth to the user. These devices may be used, for example, in emergency circumstances, and the low manufacturing cost allows disposal after a limited number of uses. These devices may provide effective insulation, especially when a gas space is provided between layers of the devices According to the present invention, this gas layer may be provided by a potential space between laminated layers of polymer film, which is expanded by a gas (e.g., carbon dioxide, nitrous oxide, air, nitrogen cartridge) or volatilization of a fluid which are released into the space and inflate the device. The device may also be inflated by a blow valve, or a pump. These devices may be formed as blankets, sleeping bags, jackets, pants, hats, masks, and other garments.

These devices may also be provided with liquid flow passages for distributing or redistributing heat, such as from a warm midriff section to cold lower extremities. Circulation of this liquid may be by passive or active means. In a sleeping bag embodiment, for example, a pump may be operated from expansion of the chest during respiration.

While refrigerant fluids do initially provide a cooling effect, in a large device, the overall cooling will be negligible. This is due to the fact that gasses in general expand to 22.4 liters per mole of liquid, and therefore only a relatively small amount of liquid is necessary in order to inflate the device. Standard refrigerants absorb about 15–30 cal/gm during vaporization. Therefore, the cooling will not be a major effect.

EXAMPLE 14

Object Cooling System

The cooling system according to the present invention may be used to cool various objects. For example, pharmaceuticals, foods, beverages and other perishables may require mild cooling during transport or for use. In this case, a refrigeration system according to the present invention may be provided to obtain or maintain acceptable temperatures.

It is often desirable to avoid temperatures below freezing in hydrated samples. Thus, a temperature controlled cooling matrix may be employed to maintain a desired level of cooling.

The present invention thus provides a system and method for providing effective portable cooling and pressure for various purposes. These include drug storage and hazardous material transport. For example, insulin dependent diabetics often travel with insulin. This insulin should be cooled to between about 2°–25° C., in order to prevent degradation and ensure potency. However, under hot conditions, the ambient temperature is higher than the recommended storage temperature. While it is known to use a freezer-activated cooling device to cool the insulin, this requires that periodically a freezer be available. The present system, when adapted by miniaturization and the provision of external insulation, may provide a long term cooling solution which does not require access to a freezer. Likewise, where hazardous, heat sensitive materials are to be stored or transported, the present system allows for cooling for a prolonged period, with a simple and inexpensive apparatus.

A system for cooling comestibles, such as consumer and institutional beverages, including soda and beer cans, wine bottles, paper cartons and other potable liquids, e.g., water, milk, baby formula, etc., may also be constructed according to the present principles. A beverage container, e.g. an aluminum can may be inserted in a sleeve, preferably formed of polyurethane or aluminized Mylar® (du Pont), HostaPhan® (Hoechst-Celanese), Lumirror® (Toray), Melinex® (ICI) and film packaging available from 3M, or other high tensile strength polymer film, which includes a refrigerant maze or vaporization channels, from which the refrigerant vaporizes. The sleeve preferably inflates due to the pressurized refrigerant, whose escape is retarded to create a back-pressure, causing close contract between the sleeve and the can. The refrigerant canister preferably includes enough contents to cool a number of cans, e.g., each of six cans from about 28° C. to about 4° C., and cools each can in less than about 1 minute.

EXAMPLE 15

Beverage Container Cooling System

In an embodiment of the invention, an open-circuit refrigeration system is provided for a beverage container, including a reservoir of refrigerant which is expended in the process.

The reservoir according to this embodiment is provided external to the beverage container. This external reservoir preferably has a valve, to selectively allow release of contents, which will be pressurized at normal environmental temperatures. No propellant per se is necessary in the container, although a low boiling component, e.g., R-124, may be included in the mixture to ensure a high vapor pressure at normal environmental temperatures The external reservoir preferably has a safety mechanism to avoid accidental discharge or intentional misuse, while allowing the device to achieve its intended function.

The cooling matrix may be provided as a reusable cooling sleeve, with an external reservoir provided which discharges refrigerant sufficient to cool the beverage.

Figure 15:
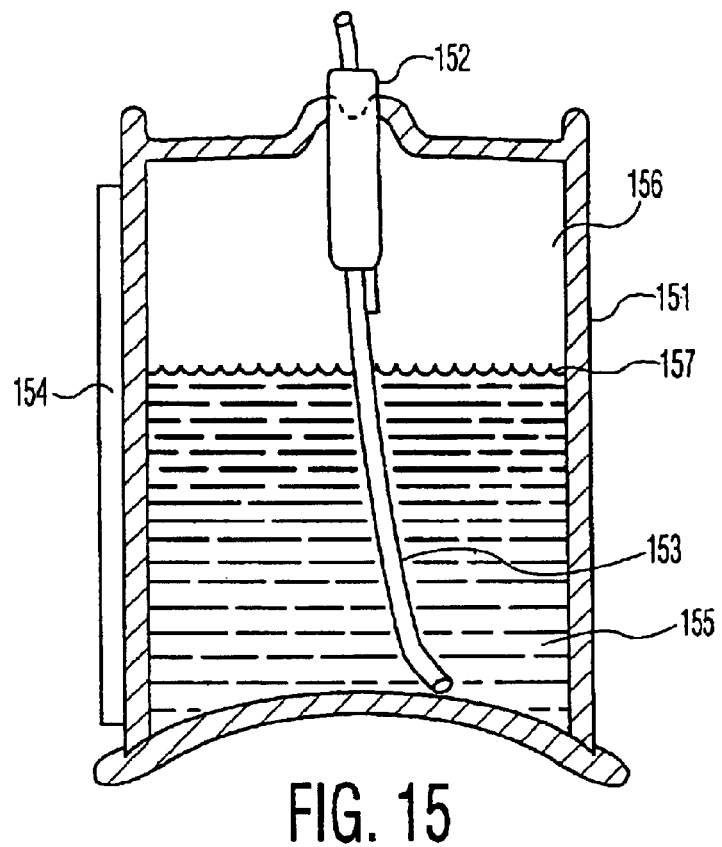
FIG. 15 is a diagrammatic side view of an external refrigerant canister.

As shown in FIG. 15, the external container 151 may be a standard-type aerosol canister with an orientation-independent valve 152, to allow fluid release in the upright or inverted position. This function may be provided by a valve stem having a steel ball which selectively occludes one of two apertures to block gas flow, by employing the Venturi effect, and a dip tube 153, wherein fluid is selectively vented rather than gas from the container.

A special valve system may be provided in the external reservoir as a further safety feature, which blocks flow to a trickle if the back pressure is not above a predetermined threshold, e.g., at least 1.1 atmospheres, thereby limiting flow unless there is backpressure, indicative that external container is filling the internal reservoir.

The external container 151 preferably has a volume of between about 3 and 32 ounces of refrigerant, although larger amounts may be provided in bulk. The external container 151 is preferably formed of steel or coated steel, although aluminum may be used.

In order to determine a fluid level in the external container, a temperature indicator, such as a liquid crystal strip 154, may be provided on the side of the container. The vaporization of liquid in the can will cool the liquid 155, allowing the fluid level to be read by a change in temperature, due to the higher heat capacity of the liquid 155 as compared to the gas 156 in the upper portion of the external container 151. Thus, even a small amount of vaporization will chill the liquid 155 refrigerant to allow a measurable difference at the fluid/gas interface 157.

The external reservoir 201 may be linked to the internal reservoir 202 through a fitting 203 on the cooling sleeve 204, optionally with an extension 205. The extension 205 may be of any kind adapted for the purpose, but preferably is formed of a polymeric tube of a material compatible with the refrigerant composition, such as polyurethane or polyvinyl chloride. The external reservoir 201 preferably does not vent unless an interlock activated valve 206 is engaged with a mating part 207, which preferably has a check valve function to prevent backflow after disconnection. When the interlock activated valve 206 is mated with mating part 207, refrigerant 208 may flow. Interlock activated valve connectors, are available from, e.g., Colder Products Corp., St. Paul, Minn. ("Two way Shutoff Valves") and Qosina Corp., Edgewood, N.Y.

The interlock actuated valve 206 may include a rigid cannula 209, which is inserted in a mating orifice 209, having an integral Bunsen valve 210. This cannula 209 may be, for example, a steel or rigid plastic tubular member having a 1–1.5 mm OD and a 0.1–1.0 mm ID at the tip 215. A check valve is integral to the interlock actuated valve 206, having a ball 213 which is displaced from a valve seat 214 when mated with the mating part 207. The tip 215 is preferably blunt or rounded with apertures 216 near the distal end of the wall 217.

Alternatively, instead of an interlock activated valve 206 associated with the external reservoir 201 or extension 205, the valve may be a twist activated valve. The valve in this case is keyed, so that it transmits a rotational force. The valve tip may be oblong, polygonal or keyed, and is inserted into a form fitting mating element on the cooling device. A twist of the container imparts a relative twist to the valve, releasing the refrigerant 208. Further, the valve tip may form an integral part of the valve, in which a tension releases the container contents, or be an additional component.

A still further alternative includes a retraction activated valve. The valve tip is inserted into an insertion portion of the cooling device, and retracted to release the contents. After filling is complete, a disengagement mechanism is activated to release the valve tip and allow withdrawal.

The filling mechanism, including the external container, valve, extension and the fill valve of the cooling device may cooperate to control the filling process to prevent overfilling or waste of refrigerant. This function may be provided by a special chamber within tine external container which partitions an amount of refrigerant for a filling operation. Alternative methods include a time limit on a fill, a back-pressure limit, a low flow rate limit, a mechanical shutoff or a thermostatic shutoff, provided in either the valve associated with the external reservoir or in the cooling device.

As an alternative to an affixed extension, the external container, especially if it has sufficient contents for multiple uses, may be fitted with a reusable adapter system for connection with an injection valve, as shown in FIGS. 2A, 2B, 2C, 3A and 3B. This injection valve may provide a controlled or controllable flow from the external reservoir and also prevent accidental or dangerous intentional misuse of the contents. An extension is provided which allows the refrigerant fluid to flow, through a fill valve of the cooling device, into the reservoir.

Figure 30:
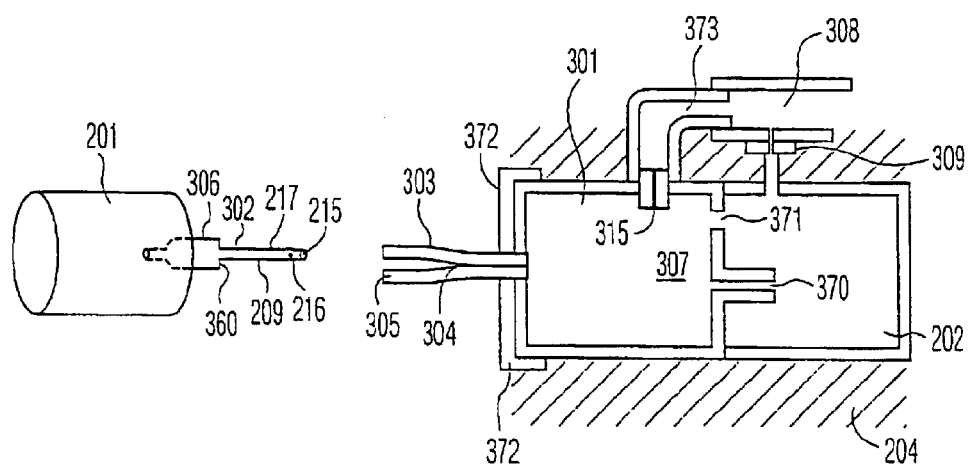
FIG. 30 is a detail view of a second interlocking valve system according to the present invention.
Figure 31:
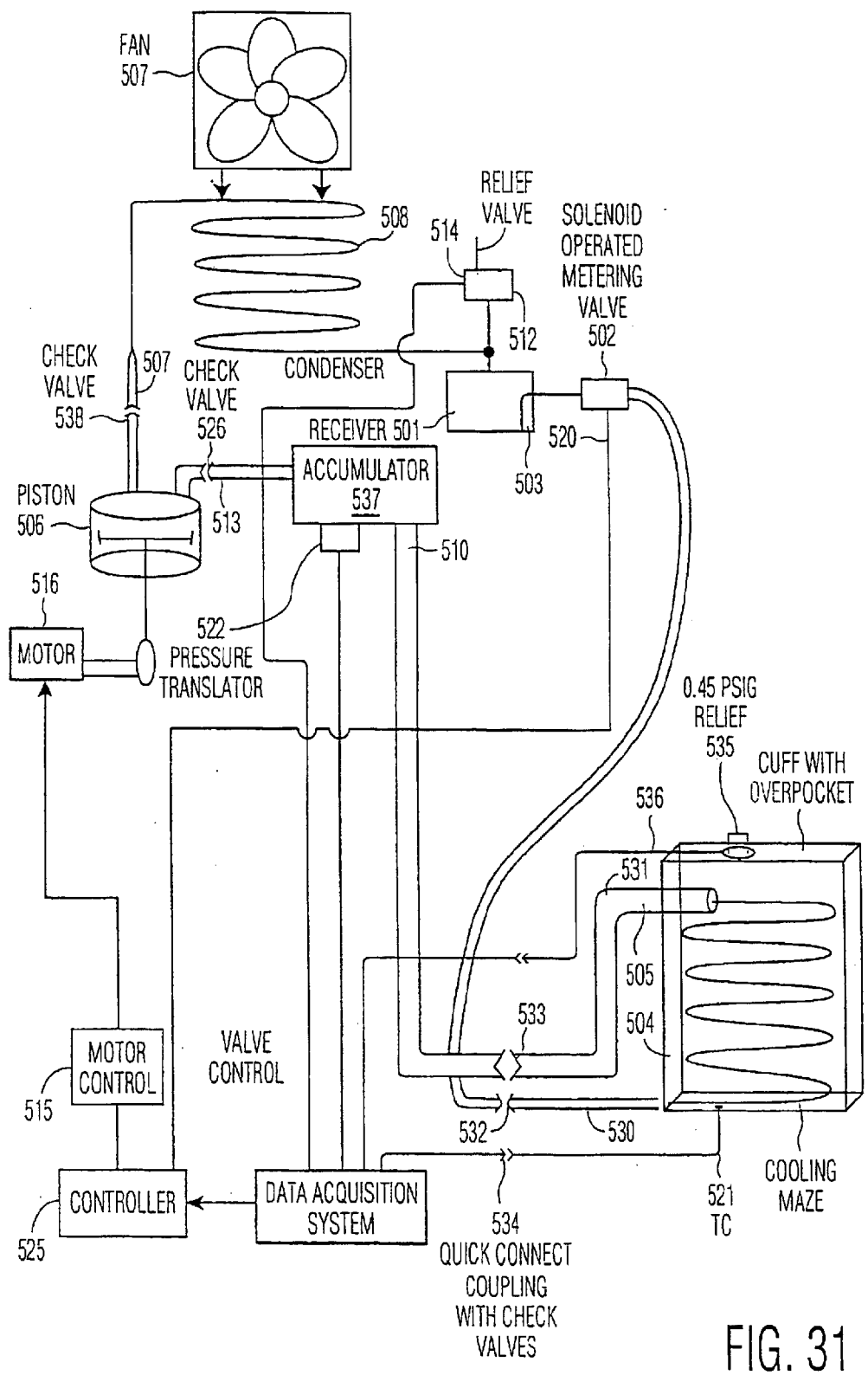
FIG. 31 is a schematic view of a closed cycle cryotherapy system.

As shown in FIG. 30, the refrigerant receiving portion of the cooling device may also include a depression operated valve 301, which is depressed by a stiff cannula 302. In this case, the fill valve of the cooling device is preferably a polymeric cylindrical tube 303 which is self sealing, i.e., a cannula is inserted in the lumen of the rubber tube to pass contents; after removal of the cannula, a seal 304 is formed which prevents flow in either direction. The top neck 305 of the rubber tube presses against the valve member of the external reservoir 201, releasing the refrigerant 208 from the external reservoir 201. The refrigerant flows out of the cannula 302 into a space 307 which leads to the cooling matrix 308 of the cooling device 204. The orientation of the cooling device is such that the liquid refrigerant drops into a dependent portion of the cooling device and accumulates.

A pressure relief valve 309, shown schematically in FIG. 30, may be provided in proximity to the fill valve, to vent an undesirable overpressure and thereafter again form a seal. This pressure relief valve 309 preferably first vents to the cooling matrix, to avoid waste of refrigerant. If the pressure remains high, refrigerant may thereafter be vented to the environment, to avoid risk of permanent damage or catastrophic failure. Overpressure may be due to blockage of the normal flow channels, massive crushing of the reservoir, very high temperatures, or other events. The pressure relief valve 309, and the system as a whole, is designed to operate at pressures induced by physical activity, normal ambient temperatures, possible variances in refrigerant mix, etc.

Figure 22A:
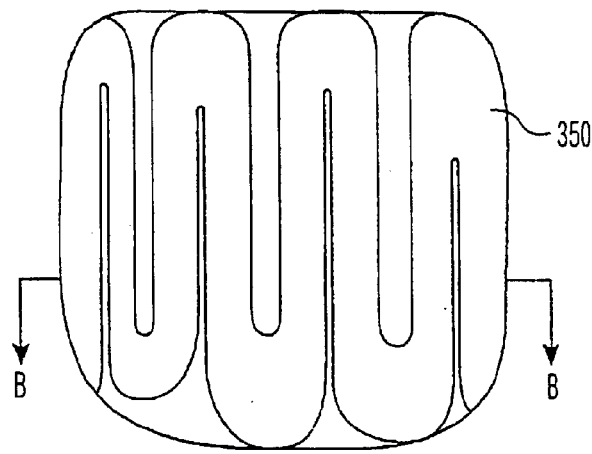
FIGS. 22A and 22B are, respectively, top and cross section views of a local reservoir according to the present invention.
Figure 22B:
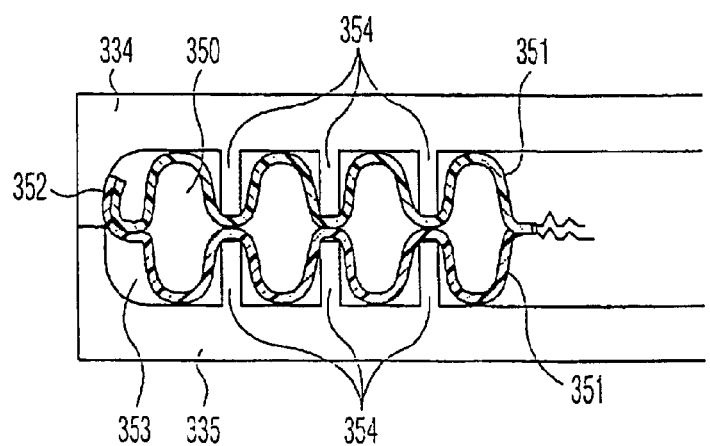

As shown in FIG. 30, the neck 360 of the insertion cannula 215 presses against the neck 305 of the resilient tube 303, causing an activation of the external reservoir valve 306. When the cannula 302 is inserted, refrigerant 208 flows into the coolant matrix 202. A pressure relief valve 372 is formed as an umbrella valve or mushroom valve to vent overpressure The fill valve may also be constructed as shown in FIG. 22. In this figure, a needle may be inserted in an orifice 362 in the resilient tube 361.

EXAMPLE 16

Beverage Container Cooling Matrix

A cooling matrix for a beverage container comprises a plurality of spaces which preferably extend axially with respect to the beverage container, formed as a multilayer laminate of high tensile strength polymer film, such as polyester film. This film may be metalized, for increased insulation properties and refrigerant impermeability. These spaces are formed in accordion fashion, and intercommunicate. The refrigerant-containing spaces are proximate to the beverage container, with a series of gas-containing spaces on the outside of the structure. This gas preferably is derived from the vaporization of the refrigerant. A gravity-separation system is employed to retain the liquid proximate to the beverage container and the gas outside, with the pressure relief valve and gas separator placed to vent the gas containing space.

The refrigerant may also be contained in a pouch or series of pouches bounded by heat sealed high tensile strength polymer film which has been metalized, as shown in FIGS. 17A, 17B, 17C and 17D. For example, the pouch or pouch system has a frangible obstruction which may be broken to allow release of the refrigerant, which will allow vaporization and filling of the gas insulating spaces. This vaporization will cool the beverage.

FIG. 17A shows a tubular polymeric film structure 401, which has been heat sealed at both ends 402, 403 in a conical formation to contain the refrigerant 404. The refrigerant is released by puncturing the polymeric film structure 401. The tubular polymeric film structure is encased in a sealed outer casing, not shown, which captures the refrigerant and channels it to the cooling matrix.

FIG. 17B shows a segmented laminated polymeric film structure 405 which holds a large volume of refrigerant with relatively reduced wall stresses A tube 406 is sealed to the structure 405, having a flow restricter 407 Refrigerant flows from the flow restricter to the cooling matrix.

FIG. 17C shows a rectangular laminated bag 408 having peripheral seals, formed by heat sealing or RF sealing. A puncturable septum 409, into which a pointed cannula is inserted to release the refrigerant. The septum 409 has protrusions 410 which seal around the cannula. A septum 409 may provided both on the inner and outer surfaces of the polymeric film forming the bag 408.

FIG. 17D shows a rectangular laminated bag 411, having a seated port 412 for filling the laminated bag 411, which is sealed after the refrigerant flows into the bag. This port 412 may be heat sealed, adhesive sealed or crimped. Advantageously, a non-heat method is employed to initially seal the laminated bag 411, allowing refrigerant to be evacuated from the port 412 prior to heat sealing, which may provide enhances strength. An exhaust port 413 is provided in the laminated bag 411 prior to filling. This exhaust port 413 includes a frangible structure in a flow restricter 414, for venting of refrigerant to the cooling matrix.

The exit of the cooling matrix is provided with a flow restricter or valve. This exhaust valve serves the function of preventing loss of unevaporated refrigerant and inflating the insulating outer layer. This valve may be a simple pressure relief valve.

As a single beverage container may be provided as a two chamber system. The beverage resides in a single chamber, with the refrigerant in a second chamber. The refrigerant may be above or below the beverage container, or may be distributed around the periphery of the container.

A plurality of such containers may be provided in a multipack distribution package. It is noted that about 33% by volume of the liquid will be refrigerant. Thus, for a 12 ounce can, 16 ounces total fluid will be provided.

Alternatively, a number of beverage containers, either each will its own cooling sleeve, or with a single shared sleeve, with a common reservoir for all of the beverage containers. For example, a "six pack" may be provided with five cans of beverage and an additional canister of refrigerant Likewise, six beverages may be provided in a hexagonal formulation with a seventh canister of refrigerant in the center.

Alternatively, a plurality of beverage containers may be provided in a single cooling matrix system, to simultaneously cool a number of beverage cans

EXAMPLE 17

Refrigerant Reservoir Contents Gage

Figure 16:
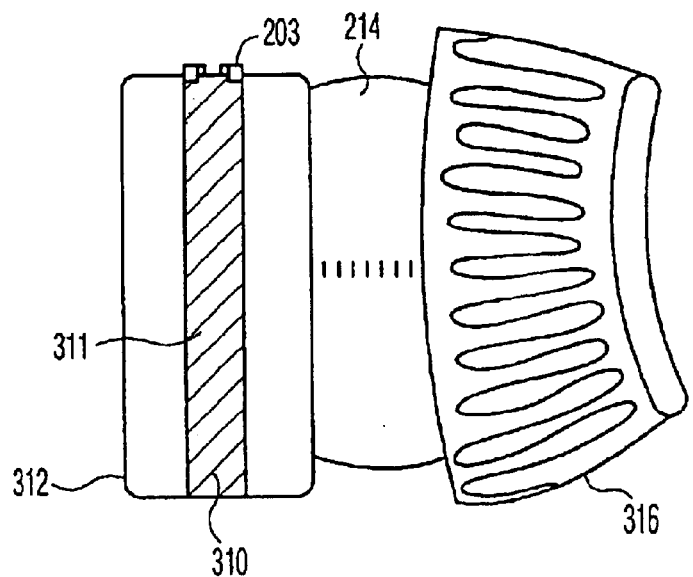
FIG. 16 is a rear view of a liquid to air intercooler according to one embodiment of the present invention, for use in cooling footwear.

A reservoir contents gage 310, as shown in FIG. 16, may be provided by a strip of temperature sensitive liquid crystal 311 or other thermal sensitive optical indicator, which allows a visual indication of the cold liquid level in the reservoir. Further, an indicator may be provided to monitor the initial cooling function, to show the user when the desired temperature is reached. An automatic shutoff may be provided to block further flow from the external reservoir after a minimum target temperature is reached. This may be provided by, e.g., a thermostat or other device which senses the temperature or blocks flow if the temperature drops to low. The container would then continue to bleed slowly to maintain the temperature in the cooling device.

An electronic contents gage may be employed which determined the volume of fluid in the reservoir by measuring a stretch on a wall of the reservoir, thereby indirectly measuring the pressure, by determining the position of a mechanical float, by determining a volume of gas in the reservoir by, e.g., determining a resonant frequency, or by other known means. The output of an electronic gage may be proportional, showing a level, or binary, showing when the reservoir is depleted or full.

EXAMPLE 18

Recharge Valve

A valve system may be provided in the cooling device if a detachable external reservoir is employed. The valve is preferably a three port device, having the following functions:

1. Provides a sealed port which may be selectively opened to allow refrigerant to flow into the cooling device from an external container.

2. Provides a pressure relief function to selectively vent gaseous refrigerant to the atmosphere in case of overpressure 3. Allows refrigerant to enter the cooling device.

Figure 23:
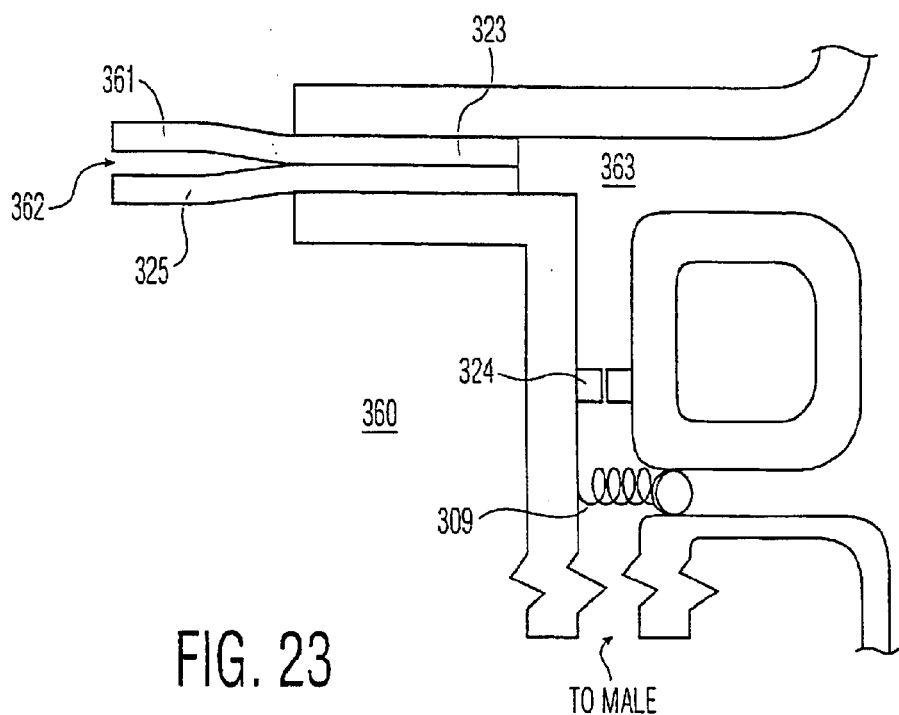
FIG. 23 is a schematic cross section of a valve system according to the present invention.
Figure 24:
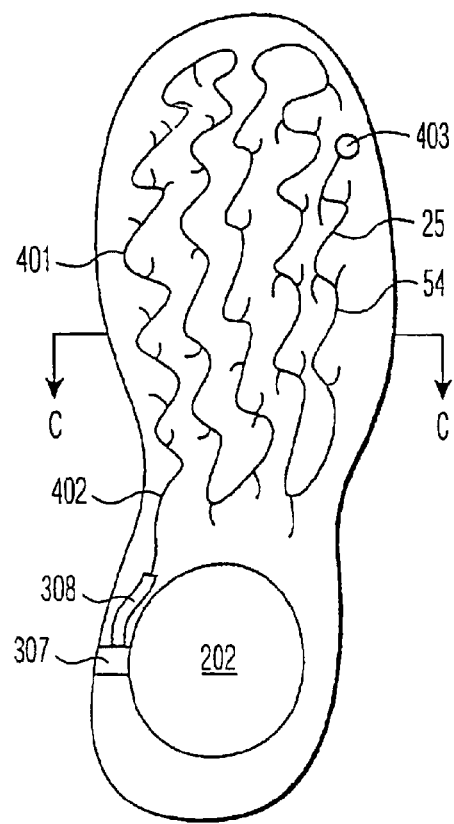
FIGS. 24 and 25 are top and cross section views, respectively, of a footwear embodiment cooling matrix according to the present invention.
Figure 25:
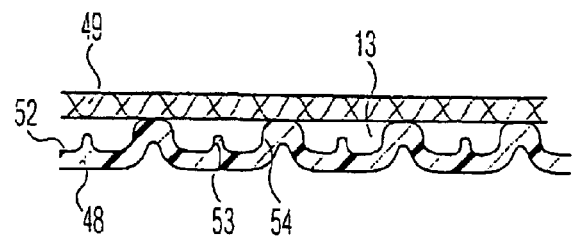
Figure 26:
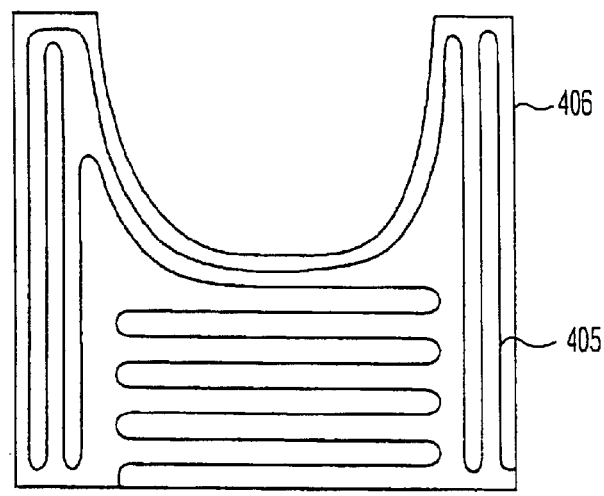
FIG. 26 is an unfolded view of a footwear upper cooling matrix according to the present invention.
Figure 27:
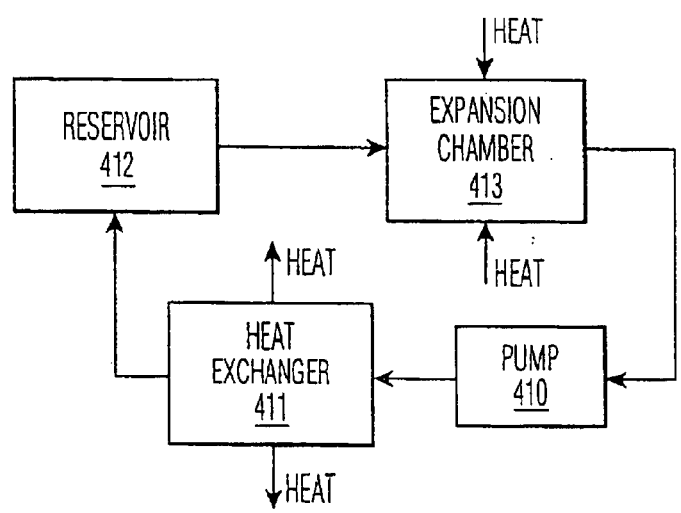
FIG. 27 is a block diagram of a closed circuit cooling system according to the present invention.
Figure 28:
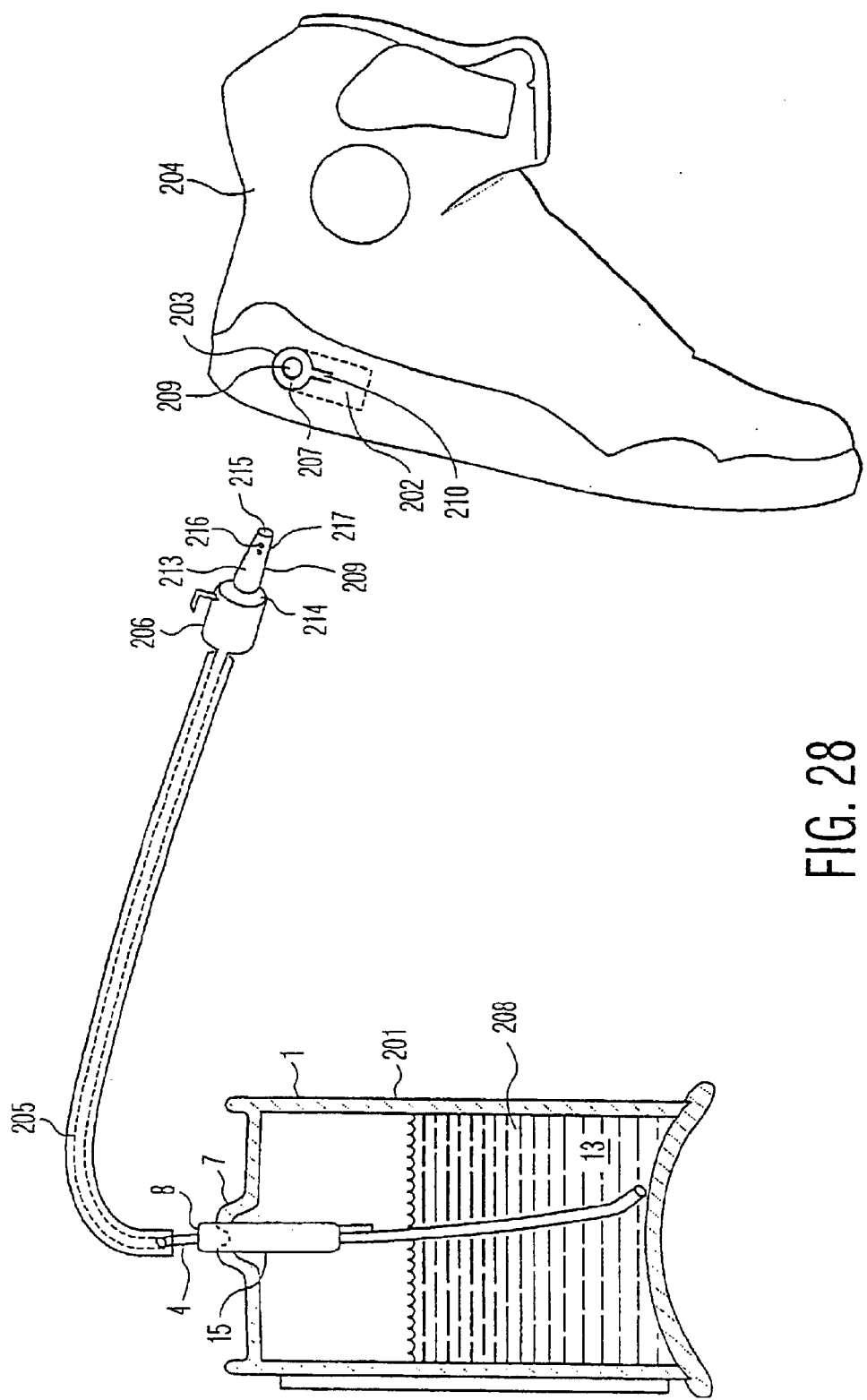
FIG. 28 is a schematic view of a footwear cooling system according to the present invention.
Figure 29:
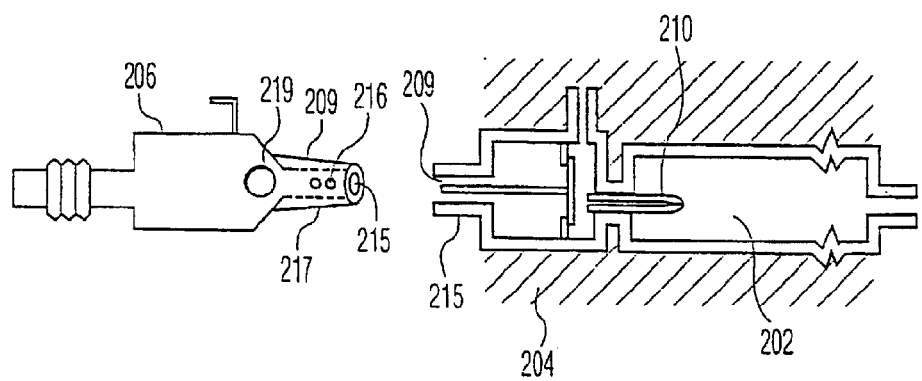
FIG. 29 is a detail view of a first interlocking valve system according to the present invention.

As shown in FIG. 23, the valve structure 360 preferably is encased in a material which is compatible with the refrigerant, and which may be sealed to prevent unwanted leakage of refrigerant. For example, the valve structure 360 may placed in a tube be formed of polyurethane, or may be inserted and sealed in a portion of a preformed chamber or chamber liner.

EXAMPLE 19

Recharge Port

As shown in FIG. 23, an external container fill port may be provided as a resilient tube 361, in which the lumen is collapsed, preventing flow in either direction. A stiff cannula, attached to the external container, passes through the lumen 362 to a space 363, where refrigerant may be injected into the cooling device. This resilient tube 361 may also include an integral pressure relief function 309, so that when the pressure in the space beyond the lumen is above a threshold, which may be predetermined or dynamically alterable, refrigerant will vent from the reservoir. A membrane is provided which selectively passes gaseous refrigerant from the device, while retaining fluid.

A further control may be provided which is manually or automatically adjusted to limit the refrigerant flow rate from an external reservoir into the cooling device. Thus, a thermostat may be included which allows or increases flow of refrigerant when the cooling device temperature is above a certain level, and blocks or restricts flow when the temperature is below a certain level. The thermostatic control may also be responsive to a relative temperature rather than absolute. A sensing element, which may be, e.g., a bimetallic element, senses the temperature of the cooling matrix. For example, a bimetallic element flexes in one direction when heated and in the other when cooled. The bimetallic element rests against a needle valve, at a distal portion of the controlled flow path. The activation temperature may be preset or adjusted by, e.g., a helically threaded screw.

In another embodiment, a device is provided by a water-filled valve which freezes and shuts off flow when the temperature falls below 0° C. Such a device is located between the external reservoir and the cooling matrix. Thus, if the flow is too great, the water freezes, stopping refrigerant flow due to expansion, and preventing freezing

EXAMPLE 20

Cooled Footwear

In garments or footwear, the operating temperatures are generally about 30°–45° C. on the body side and about −20°–+40° C. on the external side. In general, cooling may be desired when the body temperature is above 37° C. and the external temperature is above 10° C. Below these temperatures, cooling by active or facilitated means may not be necessary or desirable It should also be noted that after a short period, footwear reaches a temperature steady state, with the metabolic heat from the foot transferred to the environment, so that the rate of production equals the rate of withdrawal. Therefore, in an active or facilitated heat removal system, the amount of heat to be radiated is of the same order of magnitude of heat shedding as a normal shoe. Thus, the radiator need not be very large in comparison to the shoe, nor operate at substantially elevated temperatures over that normally achieved in a shoe under normal circumstances.

Under circumstances where the environmental temperatures are very low, it may be desirable to provide heat to the body, instead of removing it. In such a case, many of the principles discussed herein may be used to provide active or facilitated heating, albeit with a modified arrangement. Thus, for example, heat may be supplied from the environment or from other body parts to a cold extremity through a heat exchanger. For example, a heat exchanger integrated in a sock may be used to draw heat to the foot.

In a preferred embodiment, a closed cycle refrigeration system is provided within a shoe, having a compressor, condenser, evaporator and metering valve, as more fully described below.

The present invention may also be implemented as an electrically operated pump, which serves to operate a heat pump. Refrigerant is compressed by an electrically operated pump, which heats the refrigerant. The pump may be a turbine or positive displacement type. Preferably, the electrical system is supplemented by mechanical energy from the use of the footwear, or the electrical power source is recharged by use of the footwear. In a turbine pump, the pumping element rotor may be magnetically coupled to the stator through a diaphragm. The rotor spins at high speed to compress the vaporized refrigerant. The hot compressed refrigerant flows through a radiator, which cools and condenses the refrigerant. The condensed refrigerant is stored in a reservoir, and released to a cooling matrix in proximity to the foot where it vaporizes and cools the foot. Vaporized refrigerant is returned to the pump. The pump may also be a positive displacement type, where a piston or variable volume chamber is provided which pressurizes the refrigerant. The piston and cylinder are preferably hard materials, such as metal, glass, ceramic or certain plastics. A variable volume chamber may be provided as a diaphragm pump.

An electrically powered embodiment according to the present invention is preferably powered by lithium ion rechargeable, lithium polymer, nickel metal hydride rechargeable or alkaline (disposable or rechargeable, available from Rayovac). Alternatively, zinc-air batteries may be employed, as either primary cells or as rechargeable cells.

Rechargeable batteries may be recharged by an inductive coupling charger, with appropriate circuitry embedded in the footwear, or by direct electrical contacts. For example, two AA size primary alkaline cells may be provided in the heel of the footwear, which are replaceable through the side or rear of the heel. An electronic controller may be provided to control or modulate the motor, based on an open loop or closed loop control program. In a closed loop program, a temperature or temperature differential may be maintained. In an open loop control, a constant or time varying activity of the motor may be provided.

As a further embodiment, an electrochemical cell or cells having an intrinsic Peltier thermoelectric junction may be employed. In such a system, the cell is activated, and allows a current to flow. This current cools one thermoelectric junction and heats another. Advantageously, these thermoelectric junctions are integral to the battery and form part of the electrochemical structure as well. Thus, a self-contained, high energy density unit may be provided for one time use. It is also possible that such an integral thermoelectric-electrochemical cell may be rechargeable. The cooling cell, in this case, is likely formed as a heel insert. The high temperature junction dissipates heat preferably on the sides and rear of the footwear.

When a motor is provided, the external heat exchanger for shedding heat energy may be on an external portion of the footwear, or internal and provided with an air flow system Thus, the external heat exchanger may be provided internally to the footwear, with a blower driven by the same motor as the pump. It is preferable that the air flow from front to rear of the footwear, so that normal movements of the wearer assist in heat removal. However, the air may move laterally, or be drawn from within the footwear, withdrawing additional heat. The blower may be a turbine or propeller type, having a large flow volume and lower pressure operating characteristic. The air flow may also be derived entirely from movements of the wearer, such as by providing a mechanically operated air pump driven by each footstep.

The independence from conditions of use is particularly important for footwear, which may be subjected to significant stresses or shocks. For example, the cooling matrix may be provided in or as a part of a cushion below the foot. In such instance, the external pressure on portions of the matrix may vary from zero to about 2000 psi in short periods, such as during sports use, e.g., walking, jogging, running, hiking, technical climbing, basketball, football, baseball, soccer, lacrosse, tennis, badminton, racquetball, squash, handball, field and track sports, aerobics, dance, weightlifting, cross training, cycling, equestrian sports, boxing, martial arts, golf, bowling, hockey, skiing, ice hockey, roller skates, in-line skates, bowling, boating and rowing. Business or occupational use will also subject the footwear to pressure transients, such use including industrial use, carrying, lifting, office use and the like.

It is understood that footwear is available in various sizes, and that the cooling requirements may vary for shoes of differing sizes and for differing purposes. It is also possible to determine for each individual an optimized flow path and/or flow characteristics, by using a sensor to determine the shape, perfusion and heat transfer characteristics of the foot, and creating a flow path in the footwear, i.e., in the sole portion, or the upper portion, or both, corresponding to the cooling requirements. Thus, the footwear may be custom designed for the wearer. Advantageously, the customization occurs by way of a module which is selected or fabricated for the wearer, which is inserted into footwear of the correct size and style.

External Container

In a one embodiment of the invention, an closed cycle refrigeration system is provided for the footwear, which may be recharged from an external reservoir of refrigerant, in the case of leakage. Various types of footwear may be cooled, including athletic and vocational footwear, as well as casual and formal shoes. The cooling system, or portions thereof, may also be provided extending to up the ankle, for example in socks, shin guards, leg splints, casts, bandages, innersoles, knee pads, and "leg warmers".

The external reservoir preferably has a valve, to selectively allow release of contents, which will be pressurized at normal environmental temperatures due to the vapor pressure of the refrigerant. The refrigerant is, for example, 1,1,1,3,3,3,-hexafluoropropane [R-236fa; [CF$_3$—CH$_2$—CF$_3$; C.A.S. No. 690-9-1] or octafluorotetrahydrofuran [c-(CF$_2$)$_4$O; C.A.S. No. 773-14-8]

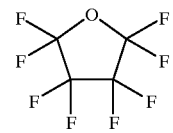

each of which has a boiling point around 0 to −1° C.

The external container preferably has a safety mechanism to avoid accidental waste or intentional misuse, while allowing the internal reservoir to fill rapidly. Thus, a back pressure sensing valve may be employed to limit release to the environment.

As shown in FIG. 1, the external container 101 may be a standard-type aerosol canister with an orientation-independent valve 102, to allow fluid release in the upright or inverted position. This function may be provided by a valve stem having a steel ball which selectively occludes one of two apertures to block gas flow, by employing the Venturi effect, and a dip tube 103, wherein fluid is selectively vented rather than gas from the container.

A special valve system may be provided as a further safety feature, which blocks flow to a trickle if the back pressure is not above a predetermined threshold, e.g., at least 1.1 atmospheres, thereby limiting flow unless there is backpressure, indicative that external container is filling the internal reservoir.

The external container 101 preferably has a volume of between about 1 and 32 ounces of refrigerant, although larger amounts may be provided in bulk The external container 101 is preferably formed of steel or coated steel, although aluminum may be used.

In order to determine a fluid level in the external container, a temperature indicator, such as a liquid crystal strip 104, may be provided on the side of the container. The vaporization of liquid in the can will cool the liquid 105, allowing the fluid level to be read by a change in temperature, due to the higher heat capacity of the liquid 105 as compared to the gas 106 in the upper portion of the external container 101. Thus, even a small amount of vaporization will chill the liquid 105 refrigerant to allow a measurable difference at the fluid/gas interface 107.

Extension

The external reservoir 201 may be linked to the internal reservoir 202 through a fitting 203 on the garment or footwear 204, optionally with an extension 205. The extension 205 may be of any kind adapted for the purpose, but preferably is formed of a polymeric tube of a material compatible with the refrigerant composition, such as polyurethane or polyvinyl chloride. The external reservoir 201 preferably does not vent unless an interlock activated valve 206 is engaged with a mating part 207, which preferably has a check valve function to prevent backflow after disconnection. When the interlock activated valve 206 is mated with mating part 207, refrigerant 208 may flow. Interlock activated valve connectors, are available from, e.g., Colder Products Corp., St. Paul, Minn. ("Two way Shutoff Valves") and Qosina Corp., Edgewood, N.Y. The mating part 207 is integrated into the footwear 204, allowing flow of refrigerant 208 into the footwear.

The interlock actuated valve 206 may include a rigid cannula 209, which is inserted in a mating orifice 211, having an integral Bunsen-type valve 210. This cannula 209 may be, for example, a steel or rigid plastic tubular member having a 1 to 1.5 mm OD and a 0.1 to 1.0 mm ID at the tip 215. A check valve is integral to the interlock actuated valve 206, having a ball 213 which is displaced from a valve seat 214 when mated with the mating part 207. The tip 215 is preferably blunt or rounded with apertures 216 near the distal end of the wall 217.

Alternatively, instead of an interlock activated valve 206 associated with the external reservoir 201 or extension 205, the valve may be a twist activated valve The valve in this case is keyed, so that it transmits a rotational force. The valve tip may be oblong, polygonal or keyed, and is inserted into a form fitting mating element on the garment or footwear. A twist of the container imparts a relative twist to the valve with respect to the footwear, releasing the refrigerant 208. Further, the valve tip may form an integral part of the valve, in which a tension releases the container contents, or be an additional component.

A still further alternative includes a retraction activated valve. The valve tip is inserted into an insertion portion of the garment or footwear, and retracted to release the contents. After filling is complete, a disengagement mechanism is activated to release the valve tip and allow withdrawal.

The filling mechanism, including the external container, valve, extension and the fill valve of the garment or footwear may cooperate to control the filling process to prevent overfilling or waste of refrigerant. This function may be provided by a special chamber within the external container which partitions an amount of refrigerant for a filling operation. Alternative methods include a time limit on a fill, a back-pressure limit, a low flow rate limit, a mechanical shutoff or a thermostatic shutoff, provided in either the valve associated with the external reservoir or in the footwear.

Figure 6:
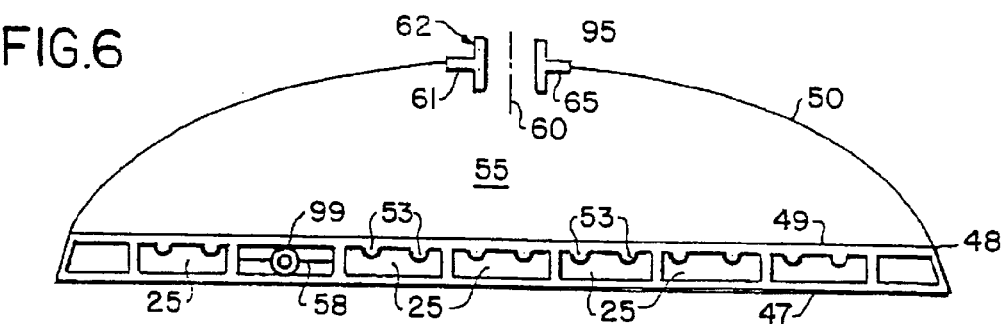
FIG. 6 is a diagrammatic, cross-sectional view of the cryotherapy device according to the present invention.
Figure 8B:
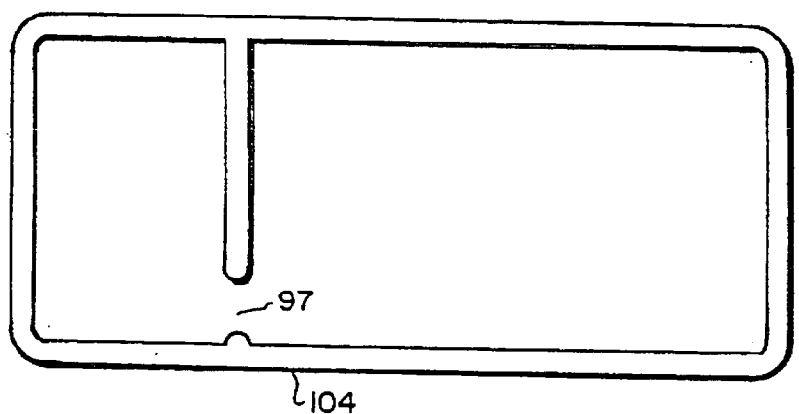
FIG. 8B is a perimeter die for forming the pressure pocket over the maze set forth in FIG. 7.
Figure 8A:
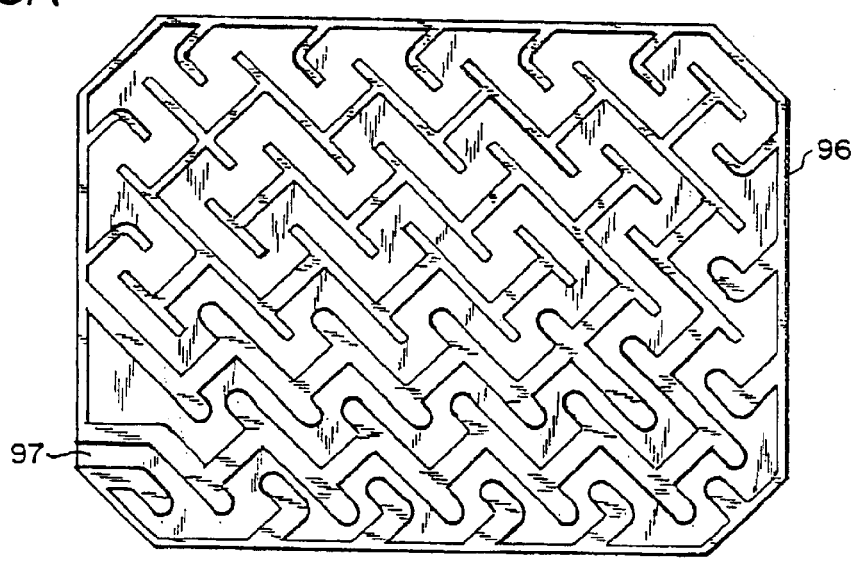
FIG. 8A is a RF-sealing die for forming the maze set forth in FIG. 7.
Figure 7:
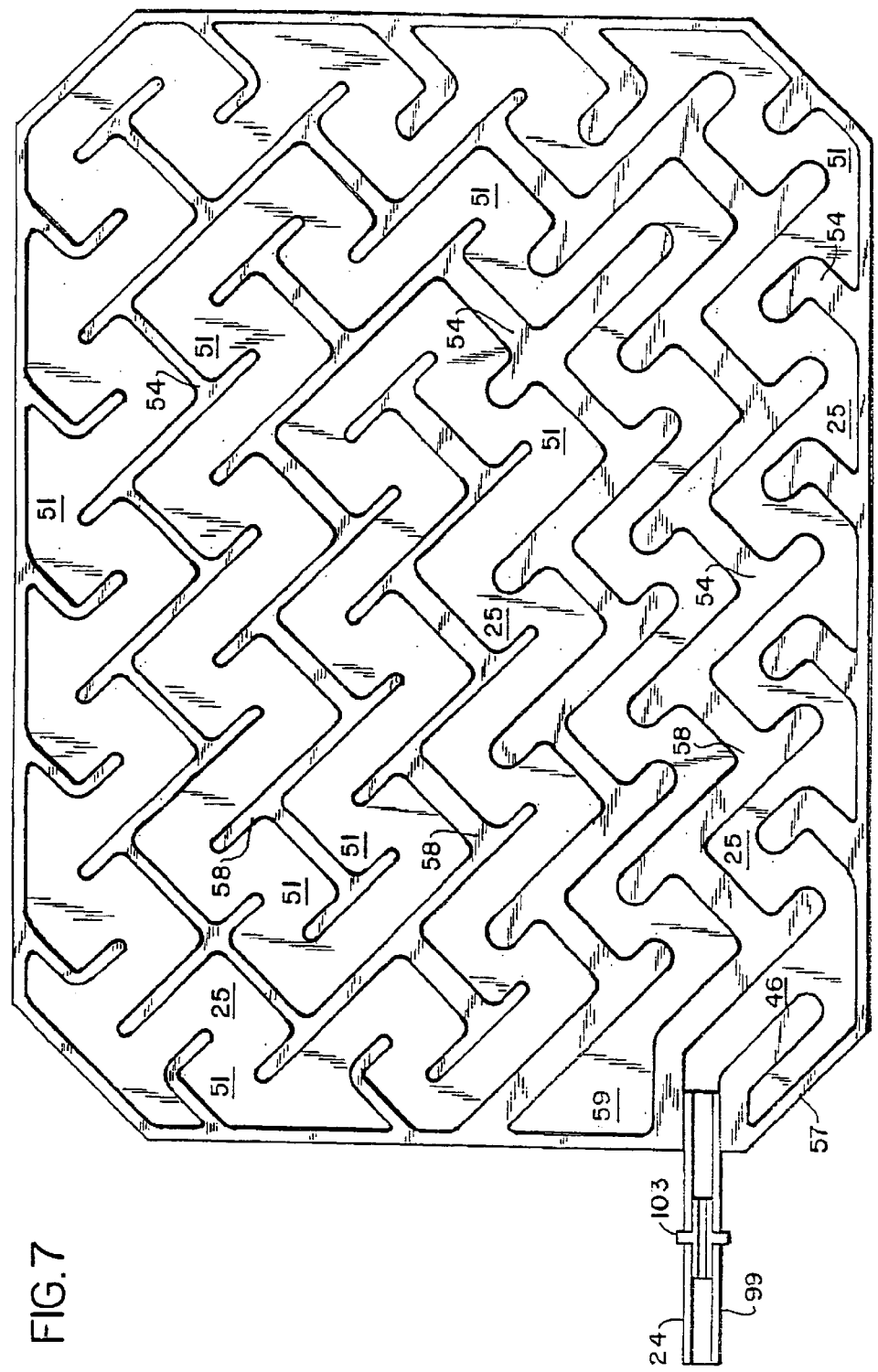
FIG. 7 is a top view of a preferred embodiment of the maze pattern in accordance with the present invention.
Figure 8C:
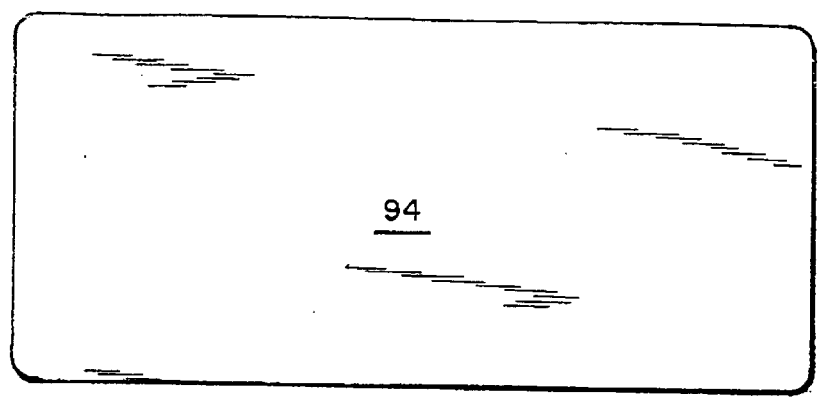
FIG. 8C is die table for forming the maze and pressure pocket of FIGS. 8A and 8B

As shown in FIG. 6, the refrigerant receiving portion of the footwear may also include a depression operated valve 301, which is depressed by a stiff cannula 302. In this case, the fill valve of the garment or footwear is preferably a polymeric cylindrical tube 303 which is self sealing, i.e., a cannula is inserted in the lumen of the rubber tube to pass contents; after removal of the cannula, a seal 304 is formed which prevents flow in either direction. The top neck 305 of the rubber tube presses against the valve member of the external reservoir 201, releasing the refrigerant 208 from the external reservoir 201. The refrigerant flows out of the cannula 302 into a space 307 which leads to an internal reservoir 202 as well as the cooling matrix 308 of the garment or footwear 204. The orientation of the garment is such that the liquid refrigerant drops into the reservoir and accumulates.

Pressure Relief Function

A pressure relief valve 309, shown schematically in FIG. 6, may be provided in proximity to the fill valve, to vent an undesirable overpressure and thereafter again form a seal. If the pressure of the refrigerant exceeds a relief pressure, gas is vented to the environment. This gas will include refrigerant and also non-condensable components, such as air. Overpressure may be due to blockage of the normal flow channels, massive crushing of the reservoir, very high temperatures, buildup of non-condensables, or other events. The pressure relief valve 309, and the system as a whole, is designed to operate at pressures induced by physical activity, normal ambient temperatures, possible variances in refrigerant mix, etc.

Internal Reservoir

In the case of footwear, an internal reservoir 313, is preferably provided, preferably located and constructed to be insulated from undue effects of the mass of the wearer and various activities, such as walking, jumping and running and other activities as known in the art. The pressure relief valve 309 may also be set at a relatively high pressure, above that which would be seen under such conditions, or provide dynamic suppression so that an high pressure impulse duration would be required for relief. The reservoir is preferably located in the heel 312 of the footwear 204 so that the characteristics of the footwear 204, other than a weight change, should not be substantially altered when the reservoir is in various states of fill Thus, a relatively stiff wall structure is preferred, with the mechanical properties determined primarily by other structures and elements of the shoe. Alternatively, the reservoir may be located in proximity to the upper portion of the footwear, e.g., a canister located behind the heel of the footwear or in the ankle padding.

The internal reservoir 313 of the footwear 204 preferably has one or more outlets 314, which are controlled by a primary flow control system 315. This system may optionally block flow when there is no foot in the footwear 204 by detecting whether the footwear 204 is being worn. If there is no foot in the footwear 204, release of refrigerant 208 from the internal reservoir 313 is blocked. A manual override may also be provided. Thus, if the internal reservoir 313 contains compressed refrigerant, an immediate precool will result from putting on the footwear.

The flow of refrigerant 208 from the internal reservoir 313 is caused by a pressure gradient, which is induced by a pump and vapor pressure of liquid refrigerant. The pump compresses refrigerant vapors above a critical point, heating and pressurizing the refrigerant. A condenser structure is provided, which sheds heat to the environment, leaving a pressurized, cooled refrigerant liquid. A heat exchanger 316, acting as the condenser, is preferably provided distal from the foot and the cooling matrix so that the heat released by compression and/or condensation does not counteract the cooling function of the system. For example, the heat exchanger may be provided behind the heel or on top of the foot above an insulating layer.

The pump generates a pressure of at least 50–85 psig. Thus, a 150 pound person would exert (static) 150 pounds over a one square inch compressor "piston". Dynamic pressure during activity will be higher, e.g., over 300 psi, but of shorter duration. The optimal location for the pump is near the ball of the foot, behind the big toe. Using the aforementioned preferred refrigerants, the volume, at standard temperature and pressure, of gaseous refrigerant to be processed is about 15 ml/min per Watt heat energy to be transferred. Thus, each shoe, assuming 30 compression cycles per minute, would have to compress 0.5 ml per compression cycle per Watt, or about 2.5 ml per compression cycle for 5 Watts cooling capacity. This 2.5 ml capacity is achieved, for example, with a compressor having a diameter of about 2.5 cm and a stroke of about 0.5 cm. These parameters are achievable.

Internal Reservoir—Fabrication

A reservoir may be formed in the heel portion of footwear, especially athletic footwear, in the form of a balloon or bubble. This reservoir may be formed in four different ways.

Ellipsoidal Chamber

Figure 9:
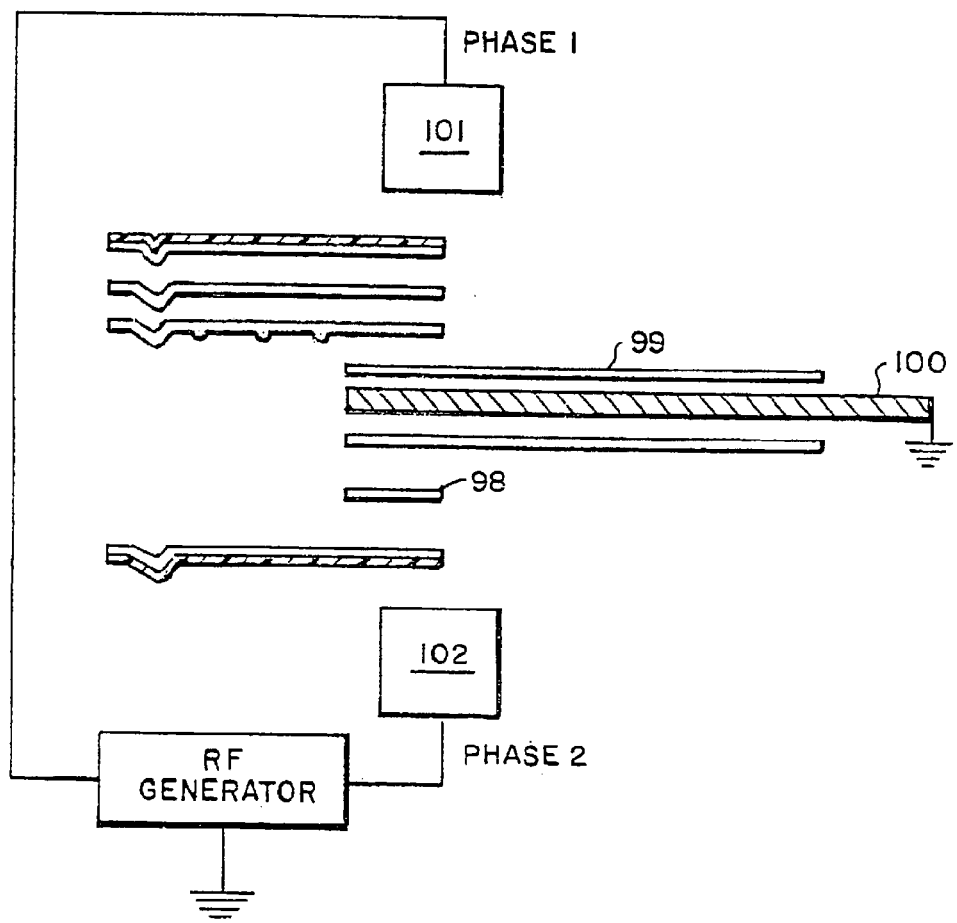
FIG. 9 is a diagrammatic, semi-schematic representation of a dual-sided sealing technique for the inject location in accordance with the invention.

According to one embodiment, shown in FIG. 9, the reservoir is an ellipsoidal chamber 320, formed of a high tensile strength polymer, which may be polyurethane, polyvinyl chloride, PET, polystyrene, nylon, or other known polymers. Further, the wall 321 of the ellipsoidal chamber 320 may be reinforced with fibrous material, such as Kevlar®, nylon, fiberglass, ceramic fiber, glass fiber, carbon fiber, steel wire, stainless steel or other metallic (ferrous or nonferrous) or other known high tensile strength material fibers. In a preferred embodiment, the chamber is preformed with an aperture 322, which may include a valve structure 323, flow restricter 324 and coupling 325. The ellipsoidal chamber 320 chamber is placed in a heel portion 312 of the footwear 214 at a central portion thereof, with a surrounding structure which has a high stiffness and low compliance. This surrounding structure preferably provides a mechanical support for the wall of the ellipsoidal chamber, preventing activity induced crushing of the chamber and equalizing the tension on portions of the wall 321. Forces are transmitted through the surrounding structure, bypassing the ellipsoidal chamber 320. Of course, the ellipsoidal chamber 320 may be employed to absorb certain shocks, so long as these so not exceed a rated (or derated) pressure or shock capacity of the ellipsoidal chamber 320.

Internally Supported Chamber

Figure 10:
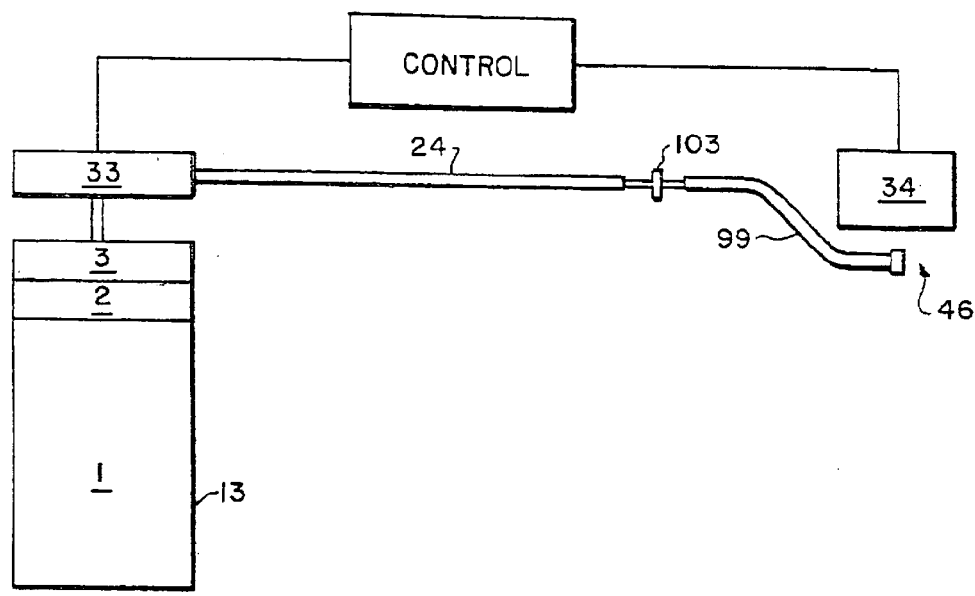
FIG. 10 is a diagrammatic, semi-schematic representation of a temperature feedback control system in accordance with the invention.

According to this embodiment, shown in FIGS. 10A and 10B, the flattened ellipsoidal chamber 330 is sandwiched between an upper 334 and lower 335 portions of the heel 312 of the footwear 214. These upper 334 and lower 335 portions include supports 336, which extend inward toward the flattened ellipsoidal chamber. During assembly, a support 336 extending from the upper 334 portion, a first optional layer 332, the flattened ellipsoidal chamber 330, a second optional layer 333, and a support 336 extending from the lower 335 portion are sealed together. The walls 331 of the flattened ellipsoidal chamber 330 corresponding to the supports 336 of the upper 334 and lower 335 portions of the heel 312 are sealed together, so that the resulting structure includes solid supports 336 which transmit forces through the heel 312, bypassing the flattened ellipsoidal chamber void space. These supports should provide stiffness along a vertical axis, although they may physically be oriented at an angle to provide lateral stability to the footwear. The optional layers 332, 333 may be heat sealed to form a four layer structure, which is not heat sealed at the supports to the upper 334 and lower 335 portions of the heel 312. The supports 336 in the upper 334 and lower 335 portions of the heel 312 may include a gas-filled space 337, filled with, e.g , air or nitrogen, to absorb shocks. These supports 336 allow externally applied forces and shocks to bypass the flattened ellipsoidal chamber 330; however, as noted below, the flattened ellipsoidal chamber 330 may also be involved in shock absorption to a limited extent. The upper 334 and lower 335 heel portions are formed to surround the flattened ellipsoidal chamber 330 with a high stiffness and low compliance frame, to provide a mechanical support for the wall 33 1 of the flattened ellipsoidal chamber 330, preventing activity induced crushing and equalizing the tension on portions of the wall 331, while directing forces through the surrounding structure. Of course, the flattened ellipsoidal chamber 330 may be employed to absorb certain shocks, so long as these so not exceed a rated (or derated) pressure or shock capacity of the system. The optional sheets 332, 333 may be of a reinforced material, preferably a heat sealable polymer, which conforms to the upper and lower surfaces of the chamber, providing support to the wall 331.

Integral Chamber

Figure 11B:
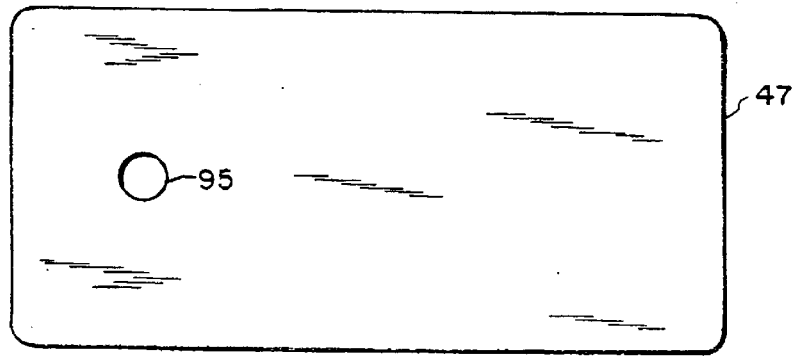
FIG. 11B is a plan view of the center, non-turbulator sheet in accordance with the invention which can be used as a backer sheet for the sheet shown in FIG. 11A.
Figure 11A:
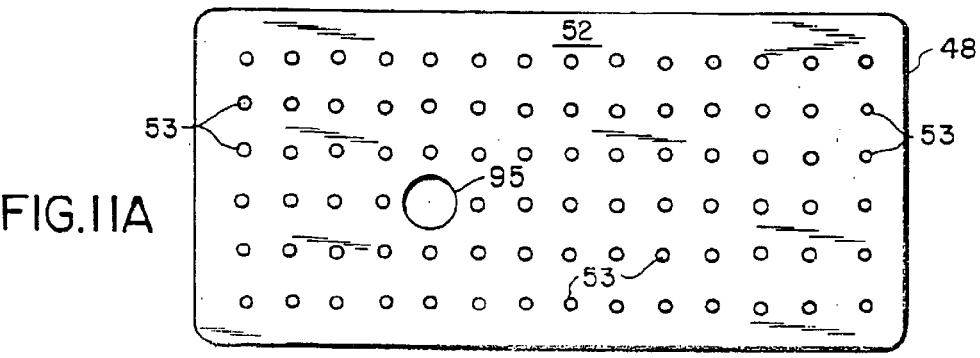
FIG. 11A is a plan view of a sample turbulator sheet in accordance with the invention.
Figure 12:
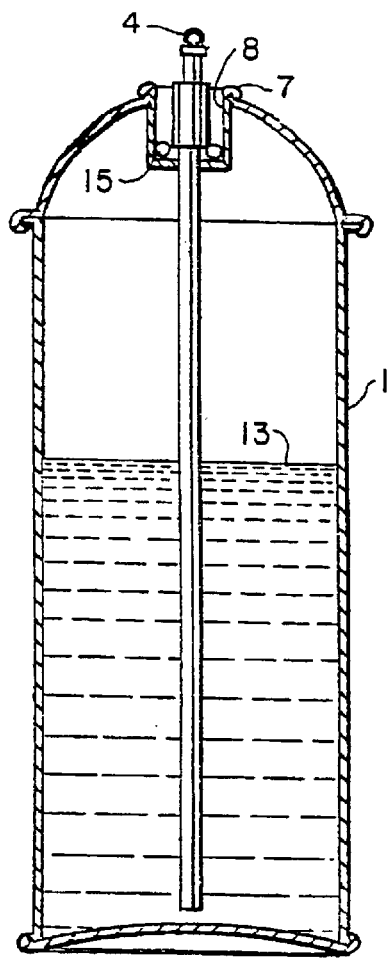
FIG. 12 is a cross-sectional view of a typical canister.
Figure 13A:
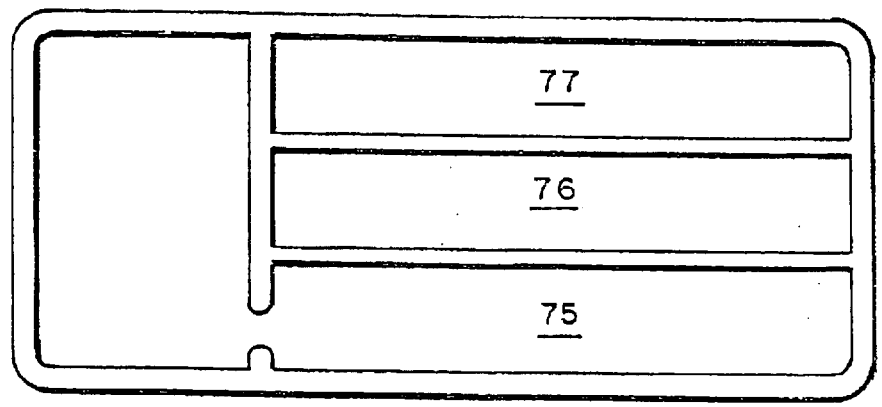
FIG. 13A is a plan view of a perimeter die for a peristaltic pump version for forming the pressure pocket over the maze set forth in FIG. 7.
Figure 13B:
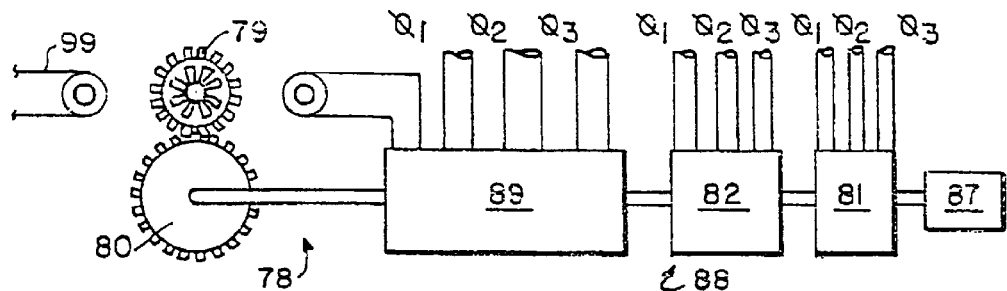
FIG. 13B is a diagrammatic view of a turbine driven, rotary valve system for a peristaltic pump in accordance with the invention.
Figure 13C:
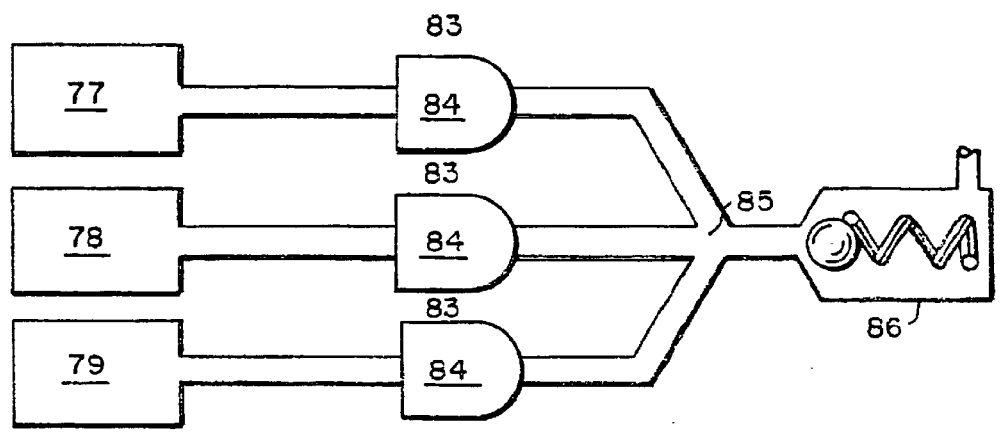
FIG. 13C is a diagrammatic view of a distribution system for bladders of a peristaltic embodiment emptying through check-valves to a single pressure controlling device.
Figure 14:
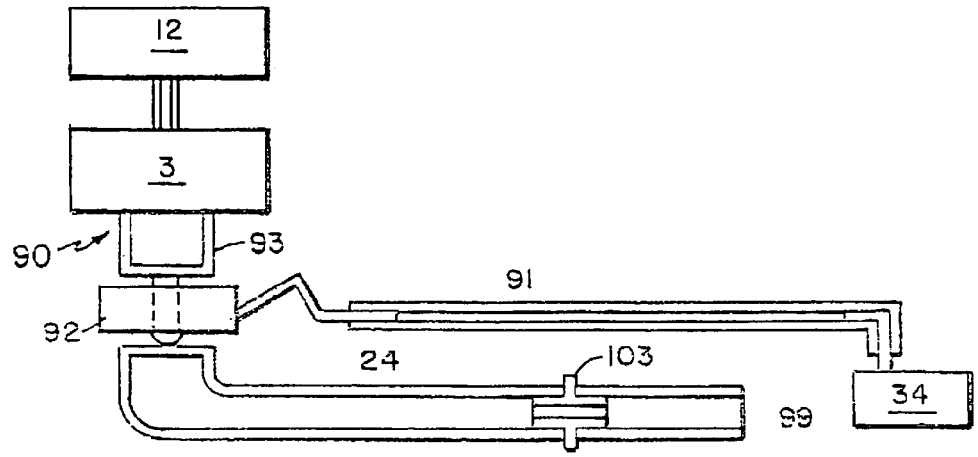
FIG. 14 is a diagrammatic, semi-schematic view of a hydraulic feedback, temperature control system in accordance with the present invention.

According to this embodiment, as shown in FIG. 11, the reservoir 340 is formed as a space in a heel 312 structure of footwear 214, optionally with a sealing liner 341. The space may further contain or be filled with a supporting structure, which may be vertical or tilted supports or an open cell foam. The heel 312 may be formed by molding, lamination, heat sealing, adhesives, or other known methods. The space preferably has a wall which is smooth, without gaps where layers are joined. The heel structure is preferably formed of polyurethane, optionally with fillers and layers to provide additional strength. Thus, a chamber which is capable of withstanding high pressures is integrally formed in the heel. Known materials for providing high tensile strength walls include various reinforcing fibrous materials, such as Kevlar®, nylon, fiberglass, ceramic fiber, and steel mesh.

In the case where a sealing liner 341 is placed within the integral chamber, the sealing liner 341 preferably opens into a valve structure which includes a filling valve 323, an outward flow restricter 324 and optionally a pressure relief valve 309.

When no sealing liner 341 is present, the outward flow restricter 324 may be separate from the fill valve 323 and optional pressure relief valve 309 Therefore, a small aperture, which may be a molded, machined or formed tube or passage, is provided extending through a wall of the chamber, which allows a controlled flow or refrigerant out of the chamber. Of course, an integral multifunction valve may also be provided which includes a filling valve 323, an optional pressure relief valve 309 as well as a controlled flow system to bleed refrigerant to the cooling matrix.

In one embodiment, the chamber is formed between an upper and lower portion of the heel of the footwear. These upper and lower portions include supports, which extend inward toward the chamber, and may be vertical or inclined in order to provide stability, in the manner according to FIGS. 10A and 10B. For example, when inclined laterally, these supports may provide desired lateral stability. During assembly, the upper 334 portion and the lower 335 portion are sealed together, preferably by RF heat sealing. A valve structure is also sealed in place near the instep region, which communicates with the space of the chamber. The upper 334 and lower 335 portions of the heel 312 may each be composite structures, to provide desired mechanical and sealing properties.

Heat Sealed Laminate Chamber

According to this embodiment, the reservoir is a chamber 350 formed from two sheets 351 of flexible heat sealable polymer, preferably polyurethane. The sheets are preferably RF heat sealed together. A potential space exists between the two layers 351, which may be pretested for leaks. The sheets forming the chamber 350 may be reinforced with fibrous material, such as Kevlar®, nylon, fiberglass, ceramic fiber, or other known high tensile strength fibrous materials. In a preferred embodiment, the sealed chamber 350 is preformed with an aperture, which may include a valve structure 323, flow restricter 324 and coupling 325.

The chamber 350 is placed during assembly of the heel structure of the footwear between upper 334 and lower 335 portions of the heel 312. The outwardly extending heat-sealed seam 352 of the sealed chamber is flexed and pressed against the wall 351 of the sealed chamber, which in turn is supported by a recess 353 formed between the upper 334 and lower 335 portion of the heel 312. Thus, when the sealed chamber is pressurized, the forces on the wall are transmitted to the heel structure, strengthening the sealed chamber 350.

These upper 334 and lower 335 portions may include supports 354, which extend inward toward the chamber, in like manner to FIGS. 10A and 10B. These supports 354 may be mechanically linked to the chamber during assembly to provide additional strength and support. Further, conforming layers may be affixed adjacent to the walls of the sealed chamber to provide additional support 354. The sealed chamber 350 is supported be the outer walls formed by the upper 334 and lower 335 portions of the heel 312. Further, internal supports 354 may be formed which maintain the patency of the space. These supports 354 may be pressed against the sealed chamber, or may be sealed through the walls of the sealed chamber to form a solid support. By sealing these supports, internal pressure in the sealed chamber does not cause a spreading of the upper 334 and lower 335 portions of the heel 312. Forces applied to the heel 312 therefore bypass the sealed chamber 350. These supports 354 should provide stiffness along a vertical axis, although they may physically be oriented at an angle to provide lateral stability to the footwear. The conforming layers may be heat sealed to form a six (or more) layer structure. The supports 354 in the upper 334 and lower 335 portions of the heel 312 may include a gas-filled space, filled with, e.g., air or nitrogen, to absorb shocks.

The Valve

A valve system is provided in the footwear, preferably a three port device, having the following functions:

1. Provides a pressure relief function to vent refrigerant to the atmosphere in case of overpressure (optional).

2. Allows the footwear to be recharged with refrigerant from an external source.

3. Allows a controlled flow of refrigerant to flow from the internal reservoir at a high pressure to the cooling matrix at a lower pressure.

The valve structure 360 preferably is encased in a material which is compatible with the refrigerant, and which may be sealed to prevent unwanted leakage of refrigerant. For example, the valve structure 360 may placed in a tube be formed of polyurethane, or may be inserted and sealed in a portion of a preformed chamber or chamber liner.

Fill Port

The external container fill port is preferably a resilient tube 361, in which the lumen is collapsed, preventing flow in either direction. A stiff cannula, attached to the external container, passes through the lumen 362 to a space 363, where refrigerant may be injected into the footwear. This resilient tube 361 may also include an integral pressure relief function 309, so that when the pressure in the space beyond the lumen is above a threshold, which may be predetermined or dynamically alterable, refrigerant will vent from the reservoir.

Fill Valve

As shown in FIG. 6, the neck 360 of the insertion cannula 215 presses against the neck 305 of the resilient tube 303, causing an activation of the external reservoir valve 306. When the cannula 302 is inserted, refrigerant 208 flows into the internal reservoir 202. Preferably, a pair of orifices are present, with a longer tube 370 attached to one than the other 371. Thus, liquid refrigerant 208, which is more dense than gaseous refrigerant, will flow through the longer tube 370 into the reservoir 202 while gaseous refrigerant will flow upward, out of the reservoir 202 from the other orifice 371. A pressure relief valve 372 is formed as an umbrella valve or mushroom valve to vent overpressure.

The fill valve may also be constructed as shown in FIG. 22. In this figure, a needle may be inserted in an orifice 362 in the resilient tube 361. The needle displaces a ball 364 from a ball seat 365, forming a pressure relief valve. A spring 366 is provided to control the relief pressure and center the ball 364. The needle preferably is inserted through the valve orifice 376, to preferentially fill the internal reservoir 202 with liquid refrigerant 208. A bypass path 324 is provided to allow normal release of refrigerant to the cooling matrix 368.

Controlled Flow Path

A separate controlled flow path is provided from the internal reservoir 202 to the space beyond the member This flow path has a flow restricter 315 having small aperture, and is designed to be the limiting factor in the flow of refrigerant from the internal reservoir 202 to the cooling matrix 308. This aperture may be formed of a tube of any type, for example a ceramic, glass or metal tube which is approximately 3 to 10 mm in length and has an internal diameter of between about 0.002 and 0.008 inches. This tube diameter is selected to provide an unrestricted flow rate of between about 2 to 10 ml per minute of refrigerant, which allows extended and controlled cooling of the footwear 214.

Flow Control System, Temperature Sensitive

A further control may be provided which is manually or automatically adjusted to limit the refrigerant flow rate. Thus, a thermostat may be included which allows or increases flow of refrigerant when the footwear temperature is above a certain level, and blocks or restricts flow when the temperature is below a certain level. The thermostatic control may also be responsive to a relative temperature rather than absolute. A sensing element, which may be, e.g., a bimetallic element, senses the temperature of the cooling matrix at a portion of the refrigerant flow path near the proximal portion and distal to a constriction. For example, a bimetallic element flexes in one direction when heated and in the other when cooled. The bimetallic element rests against a needle valve, at a proximal portion of the controlled flow path. The activation temperature may be preset or adjusted by a helically threaded screw.

The temperature sensitive flow control element may optionally be integral with or separate from the primary flow control system. Further, this flow control element may be provided as a single control or a series of parallel control elements for a plurality of flow paths in the cooling matrix, to control the temperature of the heat transfer system. The temperature achieved at the body, in the case of footwear being the foot, is preferably above 2° C. in order to prevent tissue freezing, and more preferably above 4° C. to provide extended comfort and prolong the life of the reservoir. A temperature drop of at least 5° C., e.g., to a temperature between about 15°–30° C., is preferred.

An example thermostatic element is a bimetallic element which selectively obscures an orifice. A more complex arrangement includes a proportionally controlled thermosensitive valve structure, which may be provided by a valve having a variable effective aperture due to a pressure exerted on a ball in a valve seat, or a deformation with concomitant variable occlusion of a flow tube. A stepwise continuous control valve may also be provided by multiple occlusion events. In a thermostatic embodiment, it is generally preferred that the thermostatic element measure a critical temperature in the cooling matrix, i.e., a lowest temperature in proximity to tissue, rather than a temperature in proximity to the thermostatic regulator itself. Therefore, the thermostatic element may require a linkage between the temperature measurement site and flow regulation site. In the case of a bimetallic strip, this linkage may be inherent in the design. Otherwise, a mechanical, hydraulic or pneumatic link may be provided.

An electronically controlled embodiment may include a solenoid, piezoelectric or micromachined valve which may be proportionally acting or pulse modulated, by width, frequency and/or amplitude, to establish the steady state conditions. This pulsatile flow may be purely time based, or may be regulated by a sensor to assist in temperature regulation in the maze. Such a temperature regulated device provides a temperature sensor near the proximal portion of the cooling matrix, which is presumed to the coldest portion. The coldest portion of the cooling matrix preferably remains at or above 2° C.

In another embodiment, a safety device is provided by a water-filled valve which freezes and shuts off flow when the temperature falls below 0° C. Such a safety device is located between the internal reservoir and the cooling matrix and is configured to be approximately 2°–5° C. below the coolest portion of the cooling maze, with a faster thermal response time. Thus, if the flow is too great, the water freezes, stopping refrigerant flow due to expansion, and preventing tissue freezing. Such a device may be located distal to a significant pressure drop, so that the temperature drop due to refrigerant expansion is maximized.

The thermostatic control is provided to regulate temperature in the cooling matrix. The thermostat preferably controls flow from the internal reservoir distal to the flow control element to the cooling matrix, based on an average temperature from one or more critical areas. It is also possible to have a number of individually thermostatically controlled paths, although a single flow path is preferred. The thermostat may have a fixed or variable setpoint, and where a plurality of thermostatic control points are provided, each may be set at a different temperature or have other differing characteristics. Where a plurality thermostatic elements are provided, the temperature setpoints are preferably set by design and not individually adjustable, however an external adjustment may be provided to influence these elements together. The thermostatic element may be mechanical, hydraulic or electronic in nature.

If a plurality of flow paths are provided in the cooling matrix, each flow path may be individually temperature or flow regulated at a proximal flow portion thereof by self regulating elements. These self regulating elements may control absolute flow through each path or a relative distribution of flow as compared to the other flow paths.

Cooling Matrix

The cooling matrix 308 comprises one serpentine path 401 or a plurality of parallel flow paths. These paths are provided such that the refrigerant vaporization extends through the entirety of the path, in order to avoid cold spots due to pooled liquid refrigerant vaporization. This vaporization causes a liquid to gas volume increase which causes a net flow from proximal to distal portion of the matrix, the distal portion being lower in pressure and closer to atmospheric pressure than the distal portion. Thus, gas vaporization, and hence cooling, is spread over essentially the entirety of the cooling matrix 308.

The flow rate through the cooling matrix 308 should be low enough that no liquid refrigerant is present at the exit portion, yet the cooling function is effective throughout the cooling matrix. One exception to this design parameter is if a recycling system is provided, which would allow liquid refrigerant to be reinfused into the cooling matrix. In such a system, a high temperature boiling component of the refrigerant may advantageously be provided to act as a heat transfer agent, which may be provided in excess quantities. This agent may accumulate at various portions of the flow circuit, and will generally not interfere with effective cooling and the maintenance of a steady state condition. The volume of this component, if liquid, must be accounted for in the operation of the compressor.

The cooling matrix 308 preferably is provided with catch-pockets 402, i.e., blind paths, in order to prevent gravitational flow of the liquid refrigerant from proximal to distal portions of the cooling matrix. Further, the configuration of the catch-pockets 402, in conjunction with surface irregularities, should be such as to create turbulence in the flow of refrigerant to assist in nucleation for evaporation of refrigerant. The cross sectional area of each flow path preferably increases with increasing distance from the reservoir, to control the increase in velocity of the contents, which would otherwise tend to expel liquid refrigerant from the end of the maze. On the other hand, a portion of the refrigerant should remain as a liquid near the end of the maze in order to provide effective cooling in this area. The terminus of the flow path preferably has a larger cross sectional area than the proximal portion, to further reduce the velocity and allow any remaining refrigerant to vaporize. High surface area elements, e.g., boiling rocks made of marble, may also be provided in the cooling matrix is assist in vaporization at spots where turbulence alone is insufficient to assure complete vaporization. If is preferred, however, that flow turbulence be controlled in order to control vaporization. Turbulence in the maze may be controlled by the placement of members into the flow path, by angulations of the flow path, and by focused restrictions in the flow path.

The cooling matrix may be formed by providing stiff flow paths embedded in the insole, which is flexible and compliant, which are supported against collapse from pressure in the surrounding material. Flow paths may also be provided in the footwear upper. The flow paths may be hot pressed, molded, machined or heat, adhesive, or RF-sealed in place.

The sole structure may be a two layer structure, with the flow path formed integrally between two layers, or a multilayer structure in which the flow path is formed as a separate structure and assembled within the sole. For example, a preformed cooling matrix having a maze design may be formed from two polyurethane sheets which are heat sealed together in a maze pattern. This cooling matrix may be sandwiched between an upper and lower laminate of a sole, having recesses adapted for receiving the cooling matrix, or placed above the sole and under an insole pad, formed of, e.g., Sorbothane® (FIG. 16 shows a refrigerant flow path 405 in an unfolded footwear upper 406.

Terminus of Cooling Matrix

Footwear in active use is subject to large pressures and pressure gradients Therefore, it is possible in certain circumstances to reliquify at least a portion of the gaseous refrigerant for reuse. In such a case, a compression chamber or pump with significant associated external heat exchange area is provided in the heel and/or ball of the foot. When the wearer steps or jumps, the contents of the chamber will be pressurized. This pressurization will cause an increase in temperature. Depending on design, the compressor structure may be distributed, having multiple segments, each having a pair of check valves, which will allow the system to operate even if the wearers gait is abnormal or the activity nonstandard. The increased temperature will result in a localized temperature gradient, allowing heat to be lost to the environment by means of a radiator system, and the refrigerant will be reliquified. This reliquified refrigerant may be returned to the internal reservoir. A separate channel may also be provided for this reliquified refrigerant. The radiator element is provided on the outside of the footwear. A closed circuit system is shown in block format in FIG. 17, in which refrigerant is compressed in a pump 410, where the compression causes a heating of the refrigerant. The hot refrigerant loses excess heat to the environment in a heat exchanger 411. The cooled refrigerant is stored in a reservoir 412, from which it is released into an expansion chamber 413, which corresponds to the present cooling matrix. Vaporized refrigerant is the drawn into the pump 410 where it is repressurized.

The compression chamber may also be used to provide a pressure source for the reservoir, as stated above. In one embodiment, in order to avoid the effects of the large dynamic variations in pressure, the entire cooling matrix operates as a closed cycle system at a pressure equalized with or above the average pressure exerted by the wearer on the matrix.

Cooling Matrix in Footwear Upper

Figures 18, 19:
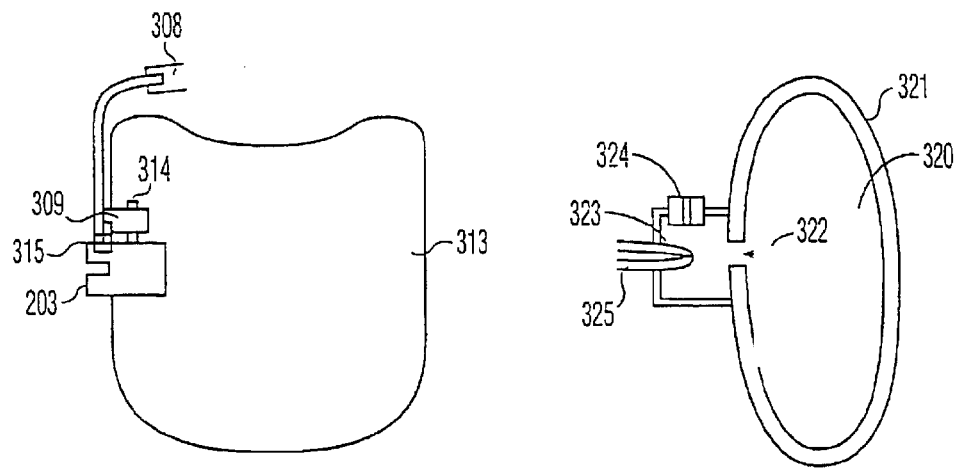
FIGS. 18 and 19 are top schematic views of local reservoirs for refrigerant according to the present invention.
Figure 20A:
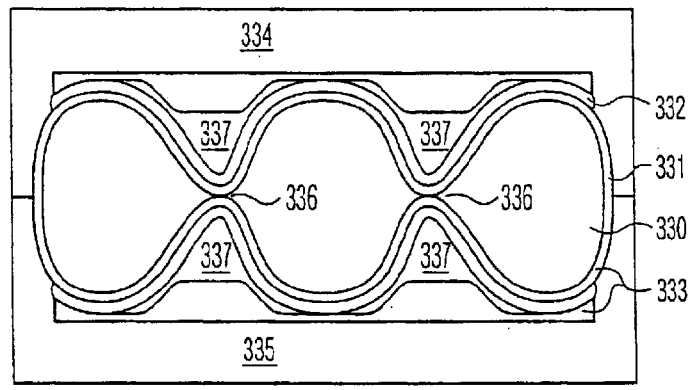
FIG. 20A and 20B are, respectively cross section and top views of a local reservoir for refrigerant according to the present invention.
Figure 20B:
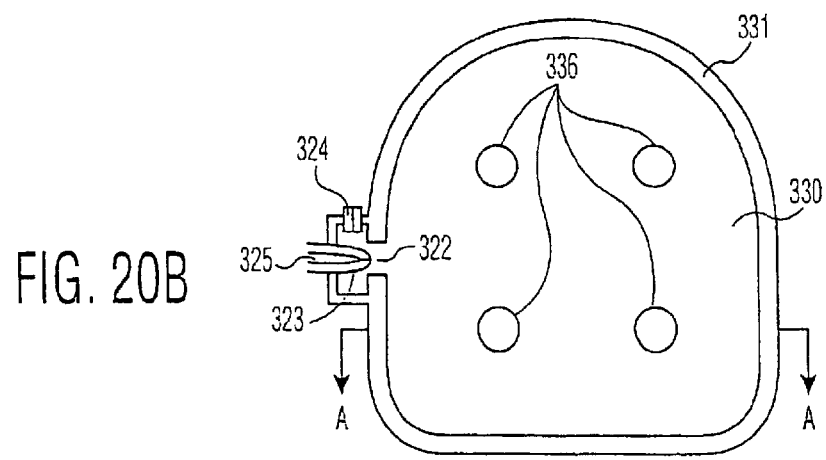
Figure 21:
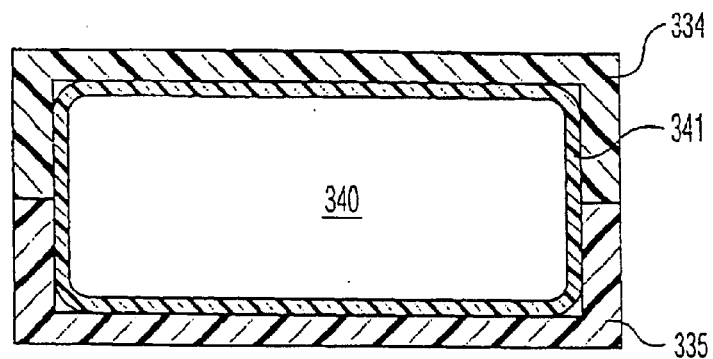
FIG. 21 is a cross section view of a local reservoir for refrigerant according to the present invention.

In yet another embodiment, a cooling matrix is provided primarily in the shoe upper rather than sole, as shown in FIG. 16 in principal, the operation is similar to that described above; however, the shoe upper 406 will generally not be subject to forces of the same magnitude as the sole, so that the refrigerant vaporization channels may be flexible, laminated sheets. The present cooling system may also be included in footwear which has inflatable bladders according to the prior art. As shown in FIG. 18, the cooling maze may have a regular pattern, or be somewhat more randomly organized As shown in FIG. 19, the sheets which make up the shoe upper may be RF heat sealed together, possibly in multiple operations. Further, the vaporized refrigerant may be used to inflate bladders in the shoe upper or insole. When applied to the footwear upper, cooling may also be applied to the ankle and Achilles' tendon area, especially in high top sneakers or boots.

The cooling matrix system in the footwear upper is preferably formed of sealed layers of urethane having a potential space formed therebetween. The urethane may be coated with a nylon cloth. The cooling matrix is formed into a maze, having a plurality of blind pockets that form traps of varying orientation, by the use of radio frequency sealing, into specific patterns that allow for contour placement of the cooling effect device around the foot. The Nylon cloth reinforcement, if provided, is preferably between 100–1000 denier. The nylon is most preferably 200 denier, with a water repellent outer finish. The refrigerant paths are preferably separated by spaces, which are perforated to allow air flow and moisture evaporation.

The radio-frequency sealing process joins two or more sheets in parallel planes by passing a radio-frequency or microwave signal through the layers, causing localized heating in the layers in a pattern conforming to the antenna-applicators. If materials other than urethane are used, then other known sealing or fusing the layers may be applicable. These methods include heat sealing, adhesives, pressure sealing, sewing and the like. This localized, patterned heating from an RF sealing process causes the polyurethane coating of the nylon mesh to fuse with adjacent layers. On cooling, the fused portions form a hermetic-type seal, which is adequate to contain the refrigerant as a liquid and as a pressurized gas. The polyurethane coated nylon material has a low compliance, so that once the device is filled with refrigerant, further input of refrigerant will expel substantially the same amount of refrigerant from the exit port of the cooling matrix. The exit port may be connected to a bladder, which provides improved fit and support to the foot.

Cooling Matrix—Secondary Heat Exchanger

The refrigerant may also be used to indirectly cool the foot of the wearer through a heat exchange system. In this system, the refrigerant is used to cool a heat exchange liquid, which may be water, polyethylene glycol solution, glycerol, mineral oil, or another liquid. A thixotrophic composition may also be used to provide both cooling and shock absorbing properties. Advantageously, if water is used, it will self regulate to a temperature above 0° C. (thereby allowing flow) and prevent freezing of the foot in case of misregulation.

In a heat exchanger system, the refrigerant is released from the reservoir to cool a heat exchange fluid contained in a pressurized channel. The fluid in the channel is induced to flow in one of three ways. First, the refrigerant volatilization may be used to run a miniature turbine, gear pump or peristaltic pump; second, a small electric motor may run a pump; and third, movements by the wearer may be used to propel the fluid. Of course, other circulating systems are known. The flow rate of fluid in the channel should be rapid, in order to provide even temperature distribution. In the area of the heat exchanger, refrigerant contacts the outside of the fluid flow tube, and cools the liquid therein. Since the heat exchange fluid is contained in a closed system, high pressures and transients will have little effect on it. Since the heat exchanger is not subjected to large pressure changes, the system may be optimized to operate under ambient environmental conditions. Further, a single fluid flow path and cooling regulating system may be provided. This heat exchanger is preferably provided behind the heel of the wearer or in the shoe sole or heel in a protected area.

Closed Circuit Facilitated Heat Exchange

In a facilitated cooling arrangement, a refrigerant is used in a heat pipe arrangement. Fluid near the heat source vaporizes, absorbing heat. The increase in volume causes a convective flow through a conduit to a radiator, where the vaporized refrigerant is condensed, giving off heat to the environment. The refrigerant thus circulates, siphoning off heat to the environment. This system may also include an active pump to assist in fluid circulation, as well as a compressor, to facilitate condensation of the refrigerant. This system has a constant volume, and will be above atmospheric pressure during use. This pressure will be such that a steady state is maintained in the system. For example, if R-123 refrigerant is employed, the portion of the system in contact with the body will be about 32°–36° C., while the external cooling radiator will be several degrees cooler. The pressure will rise, from a room temperature condition, so that the boiling point will be somewhat elevated from 28° C., and therefore the existing temperature gradients will drive the system. This facilitated heat transport system will not operate if the ambient temperature is above the body temperature. Of course, other refrigerant systems may be used to provide different boiling points or characteristics. The radiator preferably has a high surface area, and may be moistened, to allow evaporative heat loss or withdrawal.

Under high ambient temperature conditions, it may be necessary to cool the body below ambient temperatures. In this instance, an active refrigeration or evaporation system must be employed. Such a system may employ an open circuit refrigeration system, a closed circuit refrigeration system with an active energy source, e.g. a foot operated pump, or a water source for evaporative cooling. These systems are generally described above.

EXAMPLE 21

Temperature Controlled Seating Surface

Typical temperature control systems for seating surfaces use electric heaters or forced air to heat or cool the seat seats. In contrast, the present invention employs a circulating fluid, which may be the refrigerant or secondary heat exchange fluid, below the surface of the seat.

Using the principles according to the present invention, it is possible to produce beneficial cooling in other than garments and footwear. In particular, a seat cushion may be provided which withdraws heat, thus making sitting for extended period more comfortable. This cushion may be embedded in the seat or be removable. A removable cushion may be used anywhere heat removal is desired, such as in or on a vehicle, to treat a feverish child, to anesthetize a burn victim, etc.

In design, the cushion includes a cooling matrix, which will normally be fed directly from an external reservoir connected by an umbilical tube to a source of refrigerant, or a refrigerant recycling system. The cushion may also be fed by a secondary cooling system, i.e., where water or antifreeze is chilled by a primary refrigeration system, which is then cycled through the cooling matrix. An internal reservoir will normally not be necessary for a seat cushion, and an external reservoir is preferably used to store liquid refrigerant.

The flow rate of refrigerant into the cushion will be controlled by the flow control element, optionally with a thermostatic control element. A pressure relief function is also preferably included at the proximal portion of the cushion.

In an open circuit cooling cushion, the refrigerant will be vented at a distal portion of the maze of the cooling matrix, to the atmosphere. In a closed circuit cooling cushion, the gaseous refrigerant will be collected at the distal terminus of the maze and recompressed to a fluid by a compressor, which will normally be an electric pump or a compressor run by a motor provided for other purposes. Associated with the compressor pump is a radiator, which removes heat from the system. A closed circuit facilitated heat removal system may also be used, employing a radiator as well to remove excess heat. The radiator may be cooled by air, water, and/or Peltier junction, i.e., a thermoelectric cooler.

In an automotive application, the cooling matrix may obtain refrigerant from a tap off the automobile air conditioning system, returning vaporized refrigerant to the low pressure side of the compressor. Advantageously, in order to reduce refrigerant loss from leaks, a secondary cooling system is provided which cycles a cooled liquid from an under-hood refrigeration system to the seat cushions. In this case, any temperature control should preferably control the cooling of the secondary cooling system, rather than the flow through the secondary cooling system itself. The cooling pads may be integral to the seat, or removable. If the cushion is removable, it is preferred that check valves be provided in the fluid flow lines to prevent coolant leakage upon disconnection.

In a facilitated heat removal system, the radiator may be immersed in ice water or another secondary heat removal system While such an ice bath is generally impractical for footwear or other garments, a stationary seat cushion or blanket may be used where ice or other cold source is available.

EXAMPLE 22

Air Dehumidification

The cooling matrix may be used to locally cool air, which will condense water vapor if the air is saturated with humidity. Thus, where localized dehumidification is desired, e.g., a bathroom mirror, the cooling matrix may be helpful. Such a dehumidification system may be an open circuit, closed circuit run by, e.g., an electric compressor, or a facilitated heat removal system. A facilitated heat removal system may derive a cool source from, e.g., flowing cold water, which may be available near a bathroom mirror. In order to defog a mirror, the dehumidified air is flowed past the surface of the mirror, preventing condensation and evaporating any condensed moisture.

EXAMPLE 23

Object Cooling

The cooling system according to the present invention may be used to cool various objects. For example, pharmaceuticals, foods, beverages and other perishables may require mild cooling during transport or for use. In this case, a refrigeration system according to the present invention may be provided to obtain or maintain acceptable temperatures.

It is often desirable to avoid temperatures below freezing in hydrated samples. Thus, a temperature controlled cooling matrix may be employed to maintain a desired level of cooling.

The present invention thus provides a system and method for providing effective portable cooling and pressure for various purposes. These include drug storage and hazardous material transport. For example, insulin dependent diabetics often travel with insulin. This insulin should be cooled to between about 2°–25° C., in order to prevent degradation and ensure potency. However, under hot conditions, the ambient temperature is higher than the recommended storage temperature. While it is known to use a freezer-activated cooling device to cool the insulin, this requires that periodically a freezer be available. The present system, when adapted by miniaturization and the provision of external insulation, may provide a long term cooling solution which does not require access to a freezer. Likewise, where hazardous, heat sensitive materials are to be stored or transported, the present system allows for cooling for a prolonged period, with a simple and inexpensive apparatus.

A system for cooling comestibles, such as consumer and institutional beverages, including soda and beer cans, wine bottles, paper cartons and other potable liquids, e g, water, milk, baby formula, etc., may also be constructed according to the present principles. A beverage container, e.g. an aluminum can may be inserted in a sleeve, preferably formed of polyurethane or aluminized Mylar® (du Pont), HostaPhan® (Hoechst-Celanese), Lumirror® (Toray), Melinex® (ICI) and film packaging available from 3M, which includes a refrigerant maze or vaporization channels, from which the refrigerant vaporizes. The sleeve preferably inflates due to the pressurized refrigerant, whose escape is retarded to create a back-pressure, causing close contract between the sleeve and the can. The refrigerant canister preferably includes enough contents to cool a number of cans, e.g. each of six cans from about 28° C. to about 4° C., and cools each can in less than about 1 minute.

EXAMPLE 24

Closed Cycle Cryotherapy Apparatus

A refrigerant having a boiling point of about −1°–0° C. at 14.7 psia, e.g., octafluorotetrahydrofuran, is provided in a receiver 501. The refrigerant is metered through a metering valve 502 from a dip tube 503 in the receiver 501, to provide a coldest temperature in the evaporator 504 of about 0°–1° C. The back pressure in the evaporator 504 exit 505 is held at about 0.3–0.8 psig, to provide a positive pressure and compression The efflux gas is compressed by a compressor 506 to about 80–120 psig, and accompanying heating to 50°–75° C. The compressed refrigerant 506 is cooled, for example to below 30°–40° C., in a fan 507 cooled condenser 508, and accumulates in the receiver 501.

In this system, a number of potential errors may exist, including disconnect of evaporator during operation, blockage of connection, buildup of non-condensables, high condenser pressure, low temperature in evaporator, or the like. A control system is preferably provided, which initially stops flow from the metering valve, which will hopefully allow a return to normal operation. As the compressor continues to operate, the refrigerant in the evaporator is exhausted, and eventually the positive pressure begins to drop. At that point, the compressor is also stopped, to avoid vacuum and potential draw of air into the system. A relief valve is provided near the receiver, which allows the venting of gas from the condenser, which will include both non-condensables and some refrigerant vapor, also allowing correction of an abnormal condition. The refrigerant in the receiver is provided in excess, to accommodate losses over time. The receiver may also be recharged.

In an embodiment of the present invention, the back pressure from the cuff, e.g., 0.4 psig, is important, and must be tightly regulated, more so than the refrigerant flow into the device. Therefore, the primary control to the compressor must be the inlet flow of refrigerant vapors, maintaining a pressure in the return hose 510 of between 0–0.35 psig. Since the compressor 506 is not a variable volume device, it cannot also control the output pressure or flow. Thus, if the compressor 506 outlet pressure rises too high, the only option is to shut off the metering valve (to block further flow to the device) and vent refrigerant from the condenser through a relief valve 512, set to about 120 psia. The conditions which would typically lead to increased pressures in the compressor are buildup of non-condensables, abnormal heat load, or transients. In the former two cases, venting is an appropriate response, while for the third, some compliance in the system is preferred.

Therefore, if the operating conditions at the compressor 506 outlet 513 are normally 100 psia, a pressure relief valve 512 set at 110–130 psi might be appropriate. Note that this would vent non-condensables only after startup. A sensor 514 is preferably provided to detect relief, for example to initiate a shutdown if the condition is not corrected quickly.

In order to control the compressor 506 speed, a motor control 515 is preferably provided, such as a PWM controller (pulse on/pulse off with varying duty cycle). Given the high current loads of the compressor motor 516, such as a 12 VDC motor, which draws up to about 16 amps at stall, a high efficiency system should be employed, for example using low loss power semiconductors. A preferred compressor is based on designed from Thomas Industries, Sheboygan Wis., which may employ a wobble piston and Teflon® cup seal The metering valve 502 preferably includes an automated shutoff for shutdown and "emergency" regulation. A piezoelectric or electromagnetic device 520 may be employed which pulses quantities, e.g., 50–100 microliters, of refrigerant. This metering valve 502, may use cooling device temperature, as measured by a temperature sensor 521 as a primary control variable, subject to override by the compressor 506 inlet pressure as measured by a pressure transducer 522.

To shut down the system, the metering valve 502 is closed. The compressor 506 then operates to draw refrigerant from the cooling device 504, until about 0 psig is achieved in the accumulator 523. A control 525 is provided to draw the cuff pressure to the desired level, which will avoid vacuum and therefore possible influx of non-condensables, at which time the compressor is shut off. The check valve 526 in the compressor head may be sufficient to prevent back-leakage. Otherwise, a secondary shutoff valve (not shown) may be provided.

The hoses to 530 and from 531 the device are provided with interlock activated valve connectors 532, 533, available from, e.g., Colder Products Corp., St. Paul, Minn. ("Two way Shutoff Valves") and Qosina Corp., Edgewood, N.Y. The refrigerant supply tube 531 is, for example, a ⅛" ID tube, and the vapor return tube 532 a__" flexible hose. An electrical continuity connector 534 may also be provided to sense disconnect, which may also carry another sensor signal. In case of disconnect, the metering valve 502 closes and the compressor 506 stops immediately, to avoid draw of non-condensables. A pressure relief valve 535 is provided on the cooling device to prevent inflation (due to evaporating refrigerant) over 0.4–0.45 psig. This relief valve 535 is also present during normal device usage, to prevent overpressure A sensor 536 preferably detects relief valve 535 operation to shut down the metering valve 502. The electrical connections to this sensor 536 may also sense connector disengagement.

The temperature controller 525 for the metering valve may be a simple semiconductor temperature sensor 521 having a low and high setpoint, low being 1° C. and high being 6° C., such as a three wire temperature controller available from Dallas Semiconductors. The sensor for the relief valves 536, 514 may be electrical continuity sensors which detect relief valve ball unseating.

The compressor 506 is preferably driven from a 12 VDC motor 516, driven by a motor control 515. The motor control 515 of the prototype may be a PWM modulated MOSFET, IGBT or bipolar device, controlled to maintain the back pressure in the accumulator 537 at less than 0.4 psig. The accumulator 537 preferably includes a compliant bag, capable of handling up to about 2 psig.

The controller 525 controls the following actions of the device:

(a) normal operation: (i) compressor drawing refrigerant vapor to keep accumulator less than 0.4 psig; (ii) metering valve to supply sufficient refrigerant to keep device at between +1° and +6° C.

(b) overpressure in condenser: (i) shut down metering valve; (ii) vent gas until pressure less than 110–120 psig; (iii) if venting too often, initiate shutdown procedure.

(c) overpressure in cuff: (i) shut down metering valve; (ii) increase motor speed; (iii) if persistent, run compressor until accumulator reaches about 0 psig.

(d) Coupling disconnect during operation: (i) shut down metering valve; (ii) immediately stop compressor.

(e) Normal shutdown: (i) shut down metering valve; (ii) run compressor until accumulator reaches about 0 psig.

EXAMPLE 24

Ergonomic Seating System

Vehicular heating, ventilation and air conditioning systems include systems for heating and for cooling air within a vehicle. These systems are often integrated into a single control system, and under certain circumstances may be simultaneously operational. Known vehicles with climate control systems include automotive, truck, bus, airplane, train, monorail or other individual or mass transportation systems.

An automotive air conditioning device generally includes a compressor, operated by a belt from the engine, which compresses vaporized refrigerant The refrigerant is heated by this compression. The heat is released to the atmosphere through a high surface area refrigerant to air heat exchanger or radiator, which has a stream of air flowing over it by means of a fan motor or induced by the movement of the vehicle. Upon cooling in the heat exchanger, the refrigerant is liquified, giving up the heat of vaporization, and stored in a reservoir Refrigerant from the reservoir is allowed to expand and vaporize in an expansion chamber, absorbing the heat of vaporization and thus cooling. The expansion chamber includes a second heat exchanger, with air flowing over the heat exchanger into the passenger compartment. Vaporized refrigerant from the expansion chamber is recycled through the compressor, thus forming a closed cycle system. Heat absorbed from air entering the passenger compartment is thus lost to the atmosphere through a radiator.

An automotive heating device takes one of three forms, A primary heater generally consists of a heat exchanger with hot engine coolant flowing in a fluid to air heat exchanger with air flowing over the heat exchanger being blown into the passenger compartment. The engine coolant flows through the engine by means of a water pump, and generally also is cooled by a separate radiator. A control may be used to selectively allow flow of engine coolant to the heat exchange system, or may modulate the flow of air, e.g., the ratio of heated air to bypass air, over the heat exchanger. The heater may also be an electrical heating device or a combustion heater. These alternative heating devices are used where the primary heater is insufficient or where the engine is air cooled, and thus no hot coolant is available.

Peltier junctions are known thermoelectric devices which transfer heat from one junction to another, allowing both heating and cooling. Peltier junctions are known in automobiles for use in heating or cooling containers, beverages, and the like. Heated seats in a vehicle are known. These devices are generally resistive electrical components controlled by either a variable power level switch or a thermostat Treated seats are generally employed in winter months to raise the seat temperature to about body temperature for comfort According to one embodiment of the present invention, a seat cushion is be provided which controls temperature, thus making sitting for extended periods more comfortable. In particular, a cooling function is provided, to remove heat from the local environment. This cushion may be embedded in the seat or other furniture or be removable. A removable cushion may be used anywhere heat removal is desired, such as in or on a vehicle, to treat a feverish child, to anesthetize a burn victim, etc.

In addition to standard vehicles having climate control systems, which include, but are not limited to automobiles, busses, trains, airplanes, monorails, trucks, the present system is also applicable to other vehicles, such as bicycles, golf carts and motorcycles, which do not generally have climate control systems.

In design, the cushion includes a cooling matrix, which will normally be fed directly from a reservoir connected by a tube to a source of refrigerant, or a refrigerant recycling system. The cushion may also be fed by a secondary cooling system, i.e., where water or antifreeze is chilled by a primary refrigeration system, which is then cycled through the cooling matrix. An internal reservoir, i.e., a reservoir intimately associated with the cooling matrix, will normally not be necessary for a seat cushion, and an external reservoir is preferably used to store liquid refrigerant.

The present system therefore provides a temperature control system for a vehicular human support device, comprising a support surface, adapted for supporting a human in the vehicle and transmitting forces between the human and the vehicle, a thermally conductive cushion element for transmitting forces between said support surface and the vehicle, having sufficient compliance to distribute uneven forces transmitted between the vehicle and the human, and having sufficient rigidity to support the human, and a heat exchange device having a conduit in which a heat exchange fluid circulates, said heat exchange device being in contact with said thermally conductive cushion to actively alter a temperature of said support surface. An external heat exchange device for altering a heat content of said heat exchange fluid may be provided. A closed circuit system preferably includes a pump for generating a pressure gradient in said heat exchange fluid.

A support surface temperature control system is provided including a refrigeration system in thermal communication with said external heat exchange device. Further, a heating system, or both a cooling and heating system may be provided in thermal communication with said external heat exchange device. The temperature control system, according to one embodiment of the present invention, provides said heat exchange fluid which undergoes a change in phase from a liquid to a gas. In a closed system, a condensing system for cooling said gas and converting said gas to a liquid phase is provided.

The temperature control condensing system may, for example, comprise a thermoelectric junction. Alternatively, said condensing system comprises a compressor and an external heat exchanger. The volatile refrigerant preferably has a boiling point between about −20 to +35 C. A liquid phase system may also be used with an aqueous, organic or refrigerant miscible liquid circulates.

The temperature control system control may include an input for modulating an operation of the temperature control system. A sensor, preferably a temperature sensor associated with the support surface, is provided as said input for detecting a status of the temperature control system, and a control for varying said input in accordance with said status. The system preferably includes a control for selectively heating or cooling said support surface.

A dual system may be provided in which an aqueous medium is provided in thermal communication with said heating system and a volatile refrigerant fluid is provided in thermal communication with said cooling system. The heating system for said support surface may also be electrical.

The present invention also provides an active or facilitated cooling system for a seat cushion, which reduces a temperature of at least a portion of the seat cushion below the ambient temperature, by circulating a cooling medium through a flow path. The system preferably reduces the seat cushion temperature by at least about 5° C., and preferably obtains a minimum seat cushion temperature no less than about 15° C. This temperature reduction is preferably effected by heat absorption caused by evaporation of a volatile composition, or by way of a liquid or gaseous heat transfer medium in a flow channel, which in turn is cooled by an active cooling system. The temperature reduction may also occur by means of a Peltier junction thermoelectric cooling system.

The present invention includes a number of technologies, comprising an entire system of specially designed components which work together. The system is environmentally friendly, and preferably uses a refrigerant composition which is preferably free of chlorofluorocarbons (CFC). The preferred refrigerant has low toxicity and low flammability. The system is therefore adapted to effectively make use non-ozone depleting and low global warming potential refrigerants, as well as to drastically improve on the reliability of prior designs as applied to the novel application. The refrigerants selected for use in accordance with the present invention may boil at a temperature below freezing, without posing a substantial risk of frostbite injury, due to the configuration and operation of the cooling matrix.

The cooling system generally takes one of six forms.

1. First, an open refrigeration system is provided in which a liquid refrigerant is supplied to an evaporation matrix and allowed to vaporize, withdrawing heat, with the gaseous refrigerant vented to the atmosphere.

2. Second, a closed refrigeration system is provided in which a liquid refrigerant is allowed to vaporize in an evaporation matrix, withdrawing heat, with the vaporized refrigerant compressed by a pump. An external heat exchanger or radiator is provided to dissipate the heat of vaporization and condense the refrigerant.

3. Third, a liquid refrigerant is provided which has the characteristic that, under the conditions of containment, vaporizes when in contact with a heat absorption matrix, and condenses in an external heat exchanger under ambient conditions, without an external pump. This facilitated heat removal system may operate without a pump due to the flow induced by a change in density, e.g., the phase change cycle when the refrigerant is vaporized.

4. Fourth, a relatively cool liquid or gas is allowed to flow through a cooling system in the device, withdrawing heat due to the temperature differential and/or from expansion of a gas of vaporization of the liquid. This liquid or gas may be recycled or expelled after passing through the heat absorption matrix. An external heat exchanger may be provided to cool recycled liquid or gas.

5. Fifth, a Peltier junction array is provided to heat and/or cool the seat by means of an electric current passing through the junction.

6. Sixth, another endothermic reaction may be employed, which may be reversible (reusable) or irreversible (one time use). For example, the dissolution of certain salts in solvents, such as sodium thiosulfate in water, is an endothermic process.

The various cooling methods may be combined, as is known in the art, to achieve enhanced functionality. For example, a refrigeration cycle may be hybrid, operating in various phases, or be related to a number of the above mentioned methods.

It is noted that in automobiles, the stable operating temperatures are generally about 18° to 32° C. in the interior and about −40° to +50° C. on the exterior.

Under circumstances where the environmental temperatures are very low, it may be desirable to provide heat to the body, instead of removing it. In such a case, many of the principles discussed herein may be used to provide active or facilitated heating, albeit with a modified arrangement. Thus, for example, heat may be supplied from the engine, engine coolant, environment or from other body parts to a cold extremity through a heat exchanger. An electrical heater, including a Peltier junction operating as a heater, may also be used in conjunction with a heat exchange cooling system.

In one embodiment, the automotive air conditioner and heating system are used to alter the temperature of a heat transfer fluid, such as an antifreeze solution, which circulates in a secondary system. This antifreeze solution is actively pumped through a circuit which includes cushions in the car seats, without a phase change. The temperature is preferably controlled by thermostatically controlling the temperature of the circulating fluid at the interface with the primary system, and modulating the primary system, while maintaining flow through the secondary cooling system which includes the seats.

Another embodiment provides a volatile refrigerant in a local closed circuit which includes the car seat, which vaporizes in a cooling matrix in the seat. A secondary heat exchange system transfers the heat from the closed system in the seat to a remote radiator, which may be cooled directly by air, e.g. in a radiator, or by the automobile air conditioner. The closed system includes a compressor, a reservoir, the cooling matrix and a heat exchanger. In this case, the temperature of the cushion may be regulated, at least in part, by controlling the flow of refrigerant from the reservoir into the cooling matrix When a source of compressed air is available or is made available, a vortex cooling system may be used. This system separates air molecules of differing temperatures, i.e., velocities, by centrifugal effect, allowing the colder air molecules to be drawn off and used for cooling This cold air may be used directly or provided to a heat exchanger.

In order to control the resulting temperature, a number of possibilities are available:

1. First, in the case of cooling, the refrigerant composition may be specifically selected for appropriate volatilization characteristics. For example, the boiling temperature at the containment pressure, which will normally be superatmospheric, may be selected so that the boiling temperature is approximately the same as the desired temperature. If cooling alone is desired, the boiling temperature should be somewhat below the desired temperature. If heating is desired, then the boiling temperature should be above the desired temperature. Thus, in the case of heating, it is desired that the heat transfer liquid not be volatile at the working temperatures and pressures, while in the case of cooling, it is desired that the refrigerant volatilize to withdraw heat. The refrigerant may therefore be used for both heating and cooling if the operating conditions change so that the refrigerant volatilizes during cooling and does not volatilize during heating, by, e.g., increasing the pressure or by temporarily altering the composition of the refrigerant. Of course, if the refrigerant volatilizes at the desired temperature, it will tend to buffer the cooling matrix around this desired temperature, assuming the heat exchanger is controlled to supply or withdraw heat appropriately, According to an embodiment of the invention, a variable mix or refrigerants may be provided which are separated by condensation properties and are selectively fed in mixed form to the cooling matrix to control the temperature.

2. Second, the containment pressure in the cooling zone may be altered to control the boiling temperature. This pressure will normally be controlled by the pump, which will draw a variable vacuum in at least the terminal portion of the cooling matrix This pressure may also be altered by varying a volume of an accumulator. Local pressures may also be varied by controlling flow rates or geometry.

3. Third, the rate of supply of volatile refrigerant to the evaporation zone may be tightly controlled to regulate the heat absorption to a desired level This method must also ensure that localized cooling capacity does not exceed localized heat production for extended periods. Thus, the average cooling under sustained operating conditions should not exceed the heat transfer into the system, or temperatures will decline. Further, while steps may be taken to accelerate achieval of desired operating conditions, at steady state the supply of a refrigerant with a boiling point significantly below the desired temperature should be tightly controlled in order to ensure comfort.

4. Fourth, heat may be provided, i.e., through a generator or transfer mechanism, to counterbalance the heat absorption of the refrigerant, especially at a localized cold spot, so that surrounding areas achieve a desired temperature. In an automobile, the thermodynamic inefficiency of this method may be compensated by the simplicity of control and the ability to operate the cooling system under constant conditions.

5. A combination of the above measures may be employed in a control system, which may be, e.g, active or passive, mechanical, hydraulic, pneumatic or electronic systems or methods.

6. An intermediate heat exchanger system may be provided to insulate the tissue from close contact with the refrigerant. In addition, a high heat conductivity layer may be used to help evenly distribute the cooling.

Obviously, if an optimal flow rate of a particular refrigerant for a given cooling effect may be determined, a system for providing a controlled flow rate provides a simple solution for controlling the system However, the effect of the evaporation of the refrigerant on the system as a whole is very dependent on environmental factors, so that it is difficult to execute an open loop temperature control based on flow rate alone. Thus, for an accurate control, a feedback system may be employed, which may alter the refrigerant flow rate or alter some other variable of the system. For example, a small heater may be provided to adaptively balance the system to achieve a desired temperature. An unregulated control system, i.e., one which has a constant flow of refrigerant or is otherwise not controlled for alteration in environmental factors, may be used, however, if the user can tolerate these variations or can manually adjust the system to his desires.

When an open refrigeration system is employed, the preferred refrigerant is a volatile liquid comprising a mixture of second generation non-CFC refrigerants consisting of, e.g., about 50 to 90% 123 (BP 28° C.) and about 10 to 50% 124 (BP −11° C.). Such a mixture of components provide a number of advantageous characteristics in the present system. These refrigerants are miscible, and may form, at least in part, an azeotropic mixture. The low boiling component 124 ensures a high vapor pressure at room temperature, which facilitates transfer of the refrigerant from a storage container or reservoir and generally ensures a state of active vaporization. The high boiling component 123 promotes heat transfer through the walls of the evaporation system, and has a sufficient heat of vaporization to provide effective cooling. This high boiling component stabilizes the cooling function with respect to environmental effects and distributes the cooling effect over the entire area of the cooling matrix, being substantially vaporized before expulsion from the cooling matrix. The high boiling component 123 promotes heat transfer through the walls of the evaporation system, and also has sufficient heat of vaporization to provide effective cooling.

The preferred refrigerants include second generation hydrofluorocarbon, hydrochlorofluorocarbon, fluorocarbon and hydrocarbon refrigerant fluids such as the mid-boiling components R-142B (BP around −9° C.) and R-124 (BP around −11° C.), the low boiling components R-152A (BP around −24° C.), R-143A, R-125, R-23, OZ-12 and R-134A and the high boiling component 123 (BP around 28° C.). See Du Pont Fluorochemicals, AG-2 ENG (10/92).

In order to control temperature with a refrigerant based cooling system, the flow of refrigerant may be modulated. The control may be manual or automatic, with a thermostatic or other feedback mechanism.

The automobile seat is designed to provide comfortable support for the passenger or driver of the automobile. The seat normally includes a seat material, which may be leather, cloth, vinyl, or other durable material. The seat material is a thin layer over a cushion element. While stiff seats are known, such as in racing vehicles, generally it is believed that the padding allows extended use of the seat without discomfort. According to the present invention, a heat exchanger is embedded in the seat. The cushion element must be sufficiently thermally conductive to allow the heat exchanger to operate effectively. Since normally used cushioning elements are somewhat insulating, the layer of cushioning between the heat exchanger and the surface should be thin enough to effectively transfer heat. The layer above the heat exchanger may also be fabricated of a padding or cushioning material which has a high heat conductivity. The cushioning layer also is effective transmits forces between the support surface and the vehicle. The cushioning element has sufficient compliance to distribute uneven forces transmitted between the vehicle and the human, in order to provide comfort. The cushioning element also provides sufficient rigidity to support the human in the seat.

The cooling pads may be integral to the seat, or removable. If the cushion is removable, it is preferred that check valves be provided in the fluid flow lines to prevent coolant leakage upon disconnection.

Since most padding materials tend to be heat insulating, the heat exchanger should be located as close to the seat surface as possible, but with sufficient padding so that the heat exchanger is not perceptible to touch. The heat exchanger is pressurized, so that, without padding, the heat exchanger might produce an objectionable tactile sensation This padding may be a closed cell foam or the like.

In another embodiment of a cooled seat cushion, an air flow system is provided to pump air through one or more channels in the seat cushion. The flow is induced by an air pump driven by an electric motor. The walls of the channels are stiff and support the channels against collapse. The cold air may be provided by the air conditioning system.

Nonvolatile Refrigerant

According to one embodiment, in a cooling heat exchanger system, a nonvolatile refrigerant is released from the reservoir to cool a heat exchange fluid contained is a pressurized channel. The nonvolatile refrigerant may be, for example, water, antifreeze solution, or an oil. The fluid in the channel is induced to flow by a pump, which is preferably driven by an electric motor. The flow rate of fluid in the channel is rapid, in order to provide even temperature distribution. In the area of an external heat exchanger, the heat exchange fluid is cooled, e.g., by a vaporizing refrigerant, water evaporation, a Peltier junction, or other known means. The heat exchange fluid is preferably contained in a closed system, so that high pressures and transients will have little effect. Since the heat exchanger is not subjected to large pressure changes, the system may be optimized to operate under ambient environmental conditions.

Volatile Refrigerant

According to one embodiment of an automotive seat cooling system, the cooling matrix in the seat holds a volatile coolant comprising a non-CFC refrigerant or refrigerant mixture. Volatile refrigerants are characterized in that they have a high vapor pressure These refrigerants cool by absorbing the heat of vaporization. In a cooling system embodiment employing a volatile refrigerant, the flow rate of refrigerant into the cushion will preferably be controlled by modulating a pump or controlling a flow control element, optionally with a thermostatic control element or another type of control.

In an open circuit cooling cushion, i.e., one which does not recycle refrigerant, the refrigerant will be vented at a distal portion of the maze of the heat exchanger to the atmosphere or environment. Open circuit applications in automotive applications are not preferred, however, due to the volume of refrigerant required, and the ready availability of a power source for recycling refrigerant.

Figure 46A:
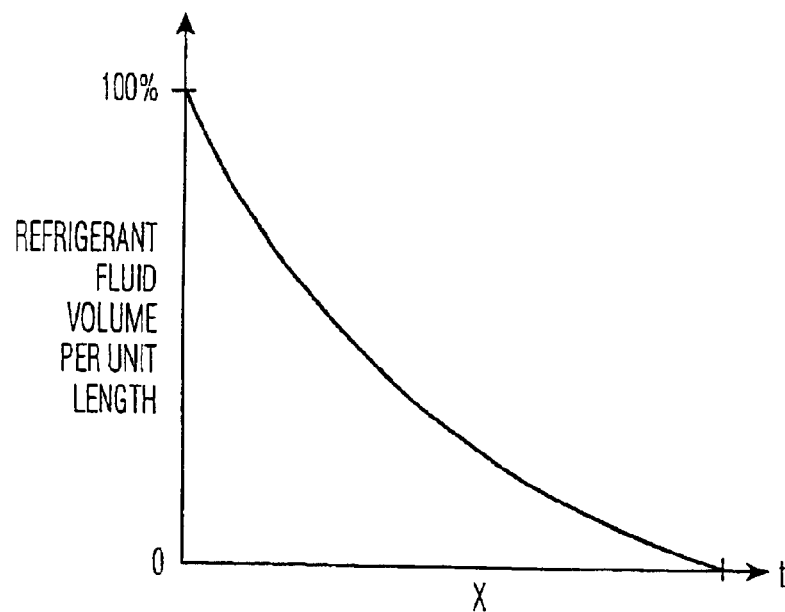
FIGS. 46A and 46B are two graphs of the fluid volume per unit area and proportion of high boiling component in the remaining volatile refrigerant fluid in an embodiment according to the present invention.
Figure 46B:
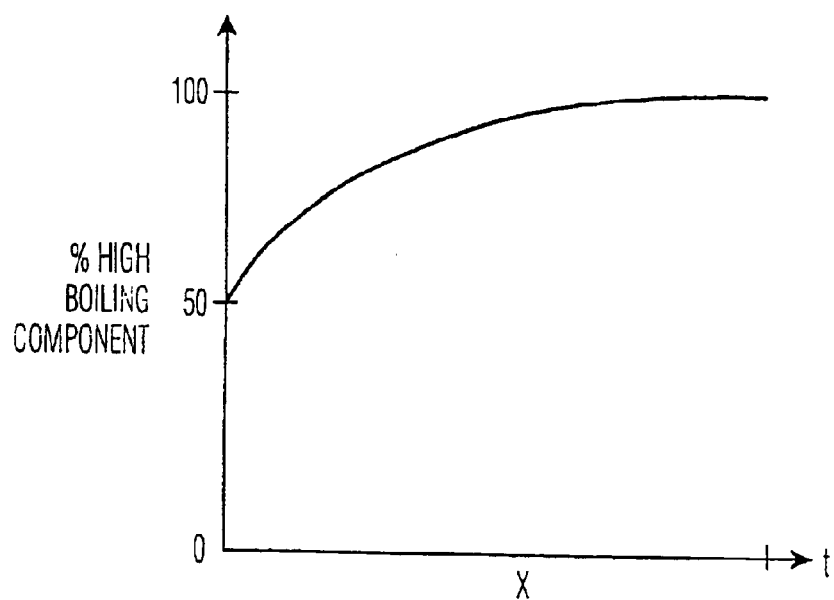

The refrigerant may be, for example, a binary mixture of a medium temperature boiling component and a high temperature boiling component. In a binary mixture, the lower temperature boiling component will volatilize first, providing substantial cooling. However, in order to cool the entire area of the cooling matrix, the higher boiling component is provided, which acts to assist in heat transfer, cools the distal portion of the matrix, and buffers the cooling matrix at a higher temperature than the lower temperature component alone. As shown in FIG. 46B, the proportion of high boiling component per unit volume increases with increasing distance from the inlet port of the cooling matrix. The total volume of total fluid per unit length of the cooling matrix is shown in FIG. 46A. As shown in FIG. 46A, the high boiling point component is carried to a further point in the cooling matrix than the lower boiling point component.

A ternary mixture may be provided to allow small variations in the operating temperature of the cooling matrix, e.g., the heat exchanger. The lowest boiling component is provided, as described with respect to a binary mixture, to ensure high vapor pressure Two or more higher boiling point refrigerants are provided, one which boils at a temperature which is lower than the lowest temperature desired, and one which boils at a higher temperature. In the compressor/condenser portion of the device, the three fractions may be separated by their ease of condensation. The lowest boiling component may be continuously provided, while the other two components may be mixed in various proportions to control the cooling of the cooling matrix. If the boiling point of these fractions is high enough, i.e., significantly above the desired temperature, they may also be used to transfer heat to the cooling matrix.

In a facilitated heat removal system embodiment according to the present invention, i.e., one in which substantial external energy is not added to the system to effect recycling, other than the heat transferred from the heat exchanger, the external radiator may be immersed in ice water or another secondary heat removal system. While such an ice bath is generally impractical for garments, a stationary seat cushion or blanket may be used where ice or other cold source is available.

In a closed circuit cooling cushion, employing a volatile refrigerant, the vaporized refrigerant will be collected at the distal terminus of the maze and recompressed to a fluid by a compressor, which will normally be an electric pump or a compressor run by the motor provided for vehicular propulsion, e.g., by a belt off the engine. Associated with the compressor pump is a radiator, which removes heat from the system. The gas compression causes an increase in temperature, allowing heat to be lost to the relatively lower temperature atmosphere. The radiator may be cooled by air, water, and/or a Peltier junction, i.e., a thermoelectric cooler. The air may be provided by the automotive air conditioning system, or the environment.

The cooling system may obtain refrigerant from a tap off an automobile air conditioning system liquid refrigerant flow line, returning vaporized refrigerant to the low pressure side of the compressor. This requires the automobile refrigerant to flow into the passenger compartment, into a relatively complex arrangement. Advantageously, however, in order to avoid this complexity with risk of loss of refrigerant from leaks, a secondary cooling system is provided which uses the automobile air conditioning system to withdraw heat from a local loop which includes the seat cushions. This system may thus cycle a liquid cooled by an under-hood refrigeration system to the seat cushions This cooled liquid may be a volatile or non-volatile refrigerant. In the case of a nonvolatile refrigerant, any temperature control should preferably control the cooling of the secondary cooling system, rather than the flow through the secondary cooling system itself. In the case of a volatile refrigerant, a control may be provided in both the primary and secondary cooling loops, with a control in the loop including the automobile seat preferably present.

Temperature Control

A temperature sensitive flow control element may be provided as a single control or a series of parallel control elements for a plurality of flow paths of coolant in the cooling matrix, to control the temperature of the heat transfer system. The temperature achieved at the body is preferably above 4° C. in order to prevent tissue freezing, and more preferably above 15° C. to provide extended comfort. A temperature drop of at least 5° C. is preferred, although smaller drops may be desired for comfort.

When a volatile refrigerant is provided, a control system for a refrigerant coolant is preferably provided to be manually or automatically adjusted to limit the refrigerant flow rate. A thermostat may be included which allows or increases flow of refrigerant when the temperature is above a certain level, and blocks or restricts flow when the temperature is below a certain level. The thermostatic control may also be responsive to a relative temperature rather than absolute. A sensing element, which may be, e.g, a bimetallic element, senses the temperature of the cooling matrix at a portion of the refrigerant flow path near the proximal portion and distal to a constriction. This sensing element acts to control the modulation of coolant flow. For example, a bimetallic element flexes in one direction when heated and in the other when cooled. The bimetallic element rests against a needle valve, or activates a piston valve, at a proximal portion of the controlled flow path. The activation temperature may be preset or adjusted by a helically threaded screw.

The temperature control arrangement may include a proportionally controlled thermosensitive valve structure, which may be provided by a valve having a variable effective aperture due to a pressure exerted on a ball in a valve seat, or a deformation with concomitant variable occlusion of a flow tube. A stepwise continuous control valve may also be provided by multiple occlusion events. In a thermostatic embodiment, it is generally preferred that the thermostatic element measure a critical temperature in the cooling matrix, i.e., a lowest temperature in proximity to tissue, rather than a temperature in proximity to the thermostatic regulator itself. Therefore, the thermostatic element may require a linkage between the temperature measurement site and flow regulation site. In the case of a bimetallic strip, this linkage may be inherent in the design. Otherwise, a mechanical, hydraulic or pneumatic link may be provided.

An electronically controlled embodiment may include a solenoid or piezoelectric valve which may be proportionally acting or pulse modulated, by width, frequency and/or amplitude, to establish the steady state conditions. This pulsatile flow may be purely time based, or may be regulated by a sensor to assist in temperature regulation in the maze. Such a temperature regulated device provides a temperature sensor near the proximal portion of the cooling matrix, which is presumed to the coldest portion. The coldest portion of the cooling matrix preferably remains at or above 2° C., and more preferably above 15° C.

In another embodiment, a safety device is provided by a water-filled valve which freezes and shuts off refrigerant flow when the temperature falls below 0° C. Such a safety device is located between the reservoir and the cooling matrix at a refrigerant expansion point, and is configured to be approximately 2°–5° C. below the coolest portion of the cooling maze, with a faster thermal response time. Thus, if the refrigerant flow is too great, the water freezes, stopping refrigerant flow due to expansion, and preventing tissue freezing Such a device may be located distal to a significant pressure drop, so that the temperature drop due to refrigerant expansion is maximized.

The thermostatic control is provided to regulate temperature in the cooling matrix. The thermostat preferably controls flow from the internal reservoir distal to the flow control element to the cooling matrix, based on an average or nadir temperature from one or more critical areas. It is also possible to have a number of individually thermostatically controlled paths, although a single flow path through the cushion is preferred. The thermostat may have a fixed or variable setpoint, and where a plurality of thermostatic control points are provided, each may be set at a different temperature or have other differing characteristics, such as time constant. The thermostatic element(s) may be mechanical, hydraulic or electronic in nature If a plurality of flow paths are provided in the cooling matrix, each flow path may be individually temperature or flow regulated at a proximal flow portion thereof by self regulating elements. These self regulating elements may control absolute flow through each path or a relative distribution of flow as compared to the other flow paths.

Volatile Refrigerant Cooling Matrix

Figure 49:
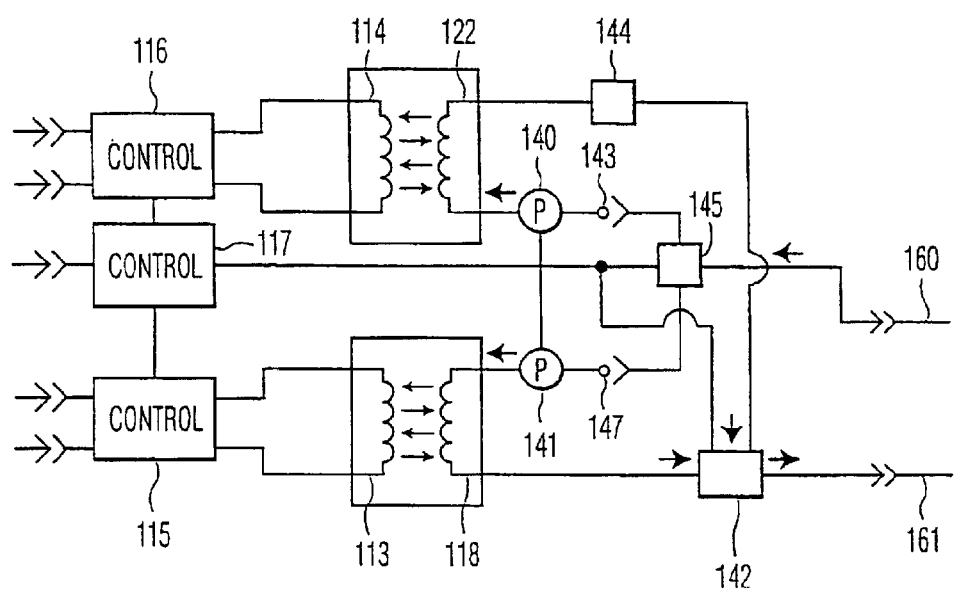
FIG. 49 is a schematic view of a heating and cooling system interfaced to automotive heating and cooling systems according to the present invention.

As shown in FIG. 49, the cooling matrix comprises one serpentine path 25, although a plurality of flow paths may be provided if a flow distribution system is provided to ensure equal flow even if one path is partially obstructed. These paths are provided such that the refrigerant vaporization extends through the entirety of the path, in order to avoid cold spots due to pooled liquid refrigerant vaporization. This vaporization causes a liquid to (,as volume increase which causes a net flow from proximal to distal portion of the matrix, the distal portion being lower in pressure and closer to atmospheric pressure than the distal portion. Thus, gas vaporization, and hence cooling, is spread over essentially the entirety of the cooling matrix.

The flow rate through the cooling matrix should be low enough such that no actively vaporizing liquid refrigerant is present at the exit portion 59, yet the cooling function is effective throughout the cooling matrix. A lubricant or oil component may flow with the refrigerant in the maze 59. A high temperature boiling component of the refrigerant may advantageously be provided to act as a heat transfer agent, which may be provided in excess quantities. This agent may accumulate at various portions of the flow circuit, and will generally not interfere with effective cooling and the maintenance of a steady state condition. Advantageously, where the maze is used for both heating and cooling the seat, the proportion of high boiling component or oil may increase for heating and decrease for cooling, through the same flow path. Thus, by altering the operating conditions, the net effect of the heat exchanger may vary.

The cooling matrix preferably is provided with catch-pockets 51, i e., blind paths, in order to prevent gravitational or inertial flow of the liquid refrigerant from proximal to distal portions of the cooling matrix. Further, the configuration of the catch-pockets 51, in conjunction with surface irregularities should be such as to create turbulence in the flow of refrigerant to assist in nucleation for evaporation of refrigerant. The cross sectional area of each flow path preferably increases with increasing distance from the reservoir, to control the increase in velocity of the contents, which would otherwise tend to expel liquid refrigerant from the end of the maze. On the other hand, a portion of the refrigerant should remain as a liquid near the end of the maze in order to provide effective cooling in this area. The terminus of the flow path preferably has a larger cross sectional area than the proximal portion, to further reduce the velocity and allow any remaining refrigerant to vaporize. High surface area elements, e.g. boiling rocks made of marble, may also be provided in the cooling matrix is assist in vaporization at spots where turbulence alone is insufficient to assure complete vaporization. If is preferred, however, that flow turbulence be controlled in order to control vaporization. Turbulence in the maze may be controlled by the placement of members into the flow path, by angulations of the flow path, and by focused restrictions in the flow path.

Cooling Matrix

The preferred cooling matrix is formed of two laminated sheets of polyurethane, having a maze pattern formed by RF sealing. The polyurethane sheets may be reinforced by a stiff fabric, such as ballistic nylon. Other embodiments provide a high modulus polymer film, such as polyester (polyethylene phthalate polymer) (e.g., Mylar), which is heat sealed to form a defined fluid flow path. Essentially, the polyurethane is relatively compliant, and thus is more comfortable near the skin, absorbs vibration, does not "crinkle", and is durable though various flexion and use. The polyester film, on the other hand, is relatively incompliant, and, without reinforcement, such as by lamination with a fibrous sheet, e.g., Nylon, will withstand the forces generated by the boiling refrigerant. The polyester film is also thinner, typically lower ion cost, especially when a lamination is deemed unnecessary, and potentially presents a better diffusion barrier for a given sheet thickness for refrigerant, especially when coated, for example with an aluminized layer. Therefore, a polyester film may be subject to lower buildup of condensables and lower loss of refrigerant. It is noted that, since the high modulus polymer film will typically be thinner, different technologies must be employed to texture the surface and polyurethane, which may be heated and plastically deformed with a surface pattern.

The inner surface of a first polyurethane sheet faces a second polyurethane sheet. Inner surface of first sheet has surface feature, being small cylindrical protrusions, ribs or an interrupted spline longitudinally placed. i.e. with a long dimension parallel to the expected flow with respect to the maze 25, which protrude into the refrigerant flow path. These surface features may be formed by heating the sheet while it is placed under pressure in a die, having a corresponding pattern formed on its face.

The surface features are herein referred to as turbulators. While these turbulators are not necessary in all circumstances, and indeed their function may be accomplished by the convolutions of the walls 54 of the maze pattern, where the maze 25 is large and the maze pattern includes relatively long runs, the inclusion of turbulators is preferred. As stated above, the turbulators are preferably provided on the first polyurethane sheet wall of the maze 25, and serve to decrease laminar flow and increase turbulent flow in the maze 25. Turbulent flow promotes vaporization, and by providing dispersed turbulators throughout the flow path, temperature variations in the maze 25 are minimized. In addition, these surface features have a second function, that of maintaining a flow passage in the maze 25 even if it is flexed or folded, thereby preventing a backpressure buildup and possible device failure.

The protrusions, ribs or interrupted spline provided as the surface features are preferably provided such that flow will be maintained even if the maze 25 is bent 90 degrees over a 1 cm diameter rod. It is noted that, in a seating arrangement, such maintenance of patency of the flow path when subjected to flexion is less critical than in cryotherapy devices, as discussed above; therefore, this design consideration is somewhat optional in this embodiment. Therefore, a high modulus polymer film without surface texturing may be acceptable.

The protrusions of the surface features should protrude about one quarter to about one half the apparent diameter of the lumen of the maze 25 Ribs, if provided, preferably run parallel to the maze 25 pattern, and are about 1 to 3 mm long with an interruption of about 5 to 15 mm.

The turbulator elements are preferably located no further apart than about the apparent diameter of the lumen of the maze 25 at that point. Sharp turns, e.g. about 90 degrees or greater, may be used or applied instead of protrusions as the turbulators for generating turbulence. The longest straight path of the maze 25 should be no longer than about ten times the apparent diameter. The path layout is designed to be such that the maze 25 will allows removal of up to about 2 cal/min per 10 square centimeters of maze 25, depending on the refrigerant employed. The optimal heat removal rate, however, will depend on a number of factors, such as ambient temperature, external insulation, tissue temperature, heat production and heat capacity, humidity, and other factors.

The refrigerant path is thus defined by the maze 25, with the walls maintained separated by the protrusions or ribs to help maintain patency of the lumen. The maze 25 has a cross sectional area which increases in tapered fashion as the refrigerant progresses through the maze 25. The velocity of the refrigerant will tend to remain constant or increase slightly due to vaporization of the refrigerant and the pressure necessarily decrease, thus causing or allowing flow through the maze 25. The maze 25 is preferably formed by a flow path having a width of about 1 to 10 mm minimum between sealed portions 58, with a gradually enlarging taper along the flow path to a size having an inflated cross section. Depending on circumstances, the terminus 59 of the maze 25 may be at least one and one-half times larger than that of the inlet portion cross section. The maze 25 has a series of pockets, blocking any straight path, which serves to distribute the volatilizing refrigerant throughout the maze 25 and prevent liquid refrigerant from discharging directly to the exit of the maze 25, by means of gravity (orientation), vibration inertia or by means of a sudden increase in pressure The maze 25 includes a single flow path which leads from the origin 46 to the terminus 59. The maze 25 follows a serpentine path which provides a plurality of spaces, the blind pockets 51, for the accumulation of refrigerant fluid, having orientations so that fluid will be trapped, regardless of the orientation of the footwear. The sealed portions 58 of the walls of the maze 25 preferably have a width of about from 1 to 10 mm, with any ends having a curved edge. The path is designed so that cooling is evenly distributed over the maze 25.

A serial flow path is preferred to ensure patency of the lumen. If a plurality of paths are provided, the paths preferably should not have parallel flow, because the proximal portion of each flow path will likely have a lower temperature than the distal portion, causing significant temperature gradients when these paths are parallel. Rather, the paths should be antiparallel or convoluted to provide an even temperature across the cooling matrix.

The cooling matrix system is preferably formed of a urethane coated nylon cloth which is formed into a maze, having a plurality of blind pockets that form traps of varying orientation, by the use of radio frequency sealing, into specific patterns that allow for contour placement of the cooling effect device in the seat. The Nylon cloth is preferably between 100–1000 denier. The nylon is most preferably 200 denier. The cooling matrix may be formed below the seating material, possibly with a padding material between the cooling matrix and the seating surface. The refrigerant paths are preferably separated by spaces, which are perforated to allow air flow and moisture evaporation. Of course, the normal seating material may be used as an overlayer to protect the cooling matrix.

The radio-frequency sealing process joins two or more sheets in parallel planes by passing a radio-frequency or microwave signal through the layers, causing localized heating in the layers in a pattern conforming to the antenna-applicators If materials other than urethane are used, then other known sealing or fusing the layers may be applicable. These methods include heat sealing, adhesives, pressure sealing, sewing and the like. This localized, patterned heating from an RF sealing process causes the polyurethane coating of the nylon mesh to fuse with adjacent layers. On cooling, the fused portions form a hermetic-type seal, which is adequate to contain the refrigerant as a liquid and as a pressurized gas. The polyurethane coated nylon material has a low compliance, so that once the device is filled with refrigerant, further input of refrigerant will expel substantially the same amount of refrigerant from the exit port of the cooling matrix. The exit port 60 is connected to a recycling system, which leads to the compressor.

Cooling Matrix—Secondary Heat Exchanger

Figure 45:
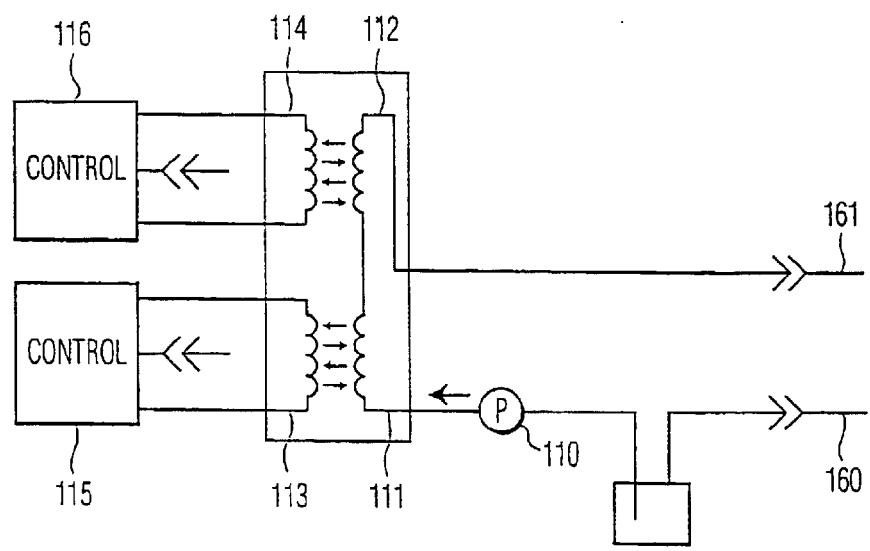

The refrigerant may also be used to indirectly cool the seat through a heat exchange system. In this system, the refrigerant is used to cool a heat exchange liquid, which may be an aqueous liquid, such as water, polyethylene glycol solution, glycerol, or an oil, such as mineral oil, or another liquid. A thixotropic composition may also be used to provide both cooling and shock absorbing properties. Advantageously, if water is used, it will self regulate to a temperature above 0° C. (thereby allowing flow) and prevent freezing or frostbite in case of misregulation. FIG. 45 shows a secondary heat exchanger temperature control system in which a supply line 161 supplies a heat exchanger in the seat 164 with a temperature altering medium, which in this case is non-volatile. A pump 110 causes the liquid to flow through an external heat exchanger 111, 112, which in turn is heated by heater coil 113 or cooled by refrigeration coil 114 The temperature of the fluid in the external heat exchanger 111, 112 coils is regulated by controls 115 and 116, which control the flow of heated media or air conditioner refrigerant to the external heat exchanger, respectively. The heating and cooling functions are preferably not active simultaneously. The external heat exchanger may be associated with the automotive air plenum.

Figure 44:
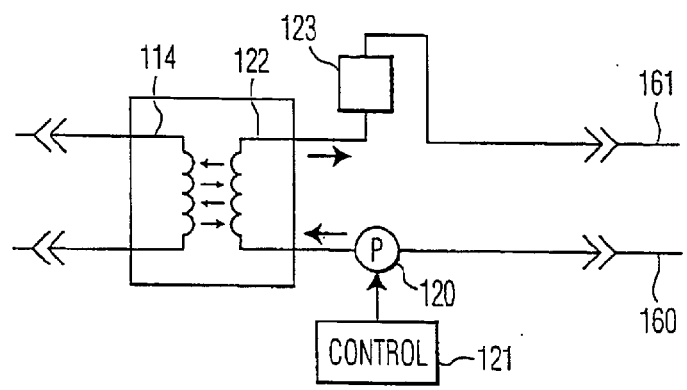
FIGS. 44 and 45 are schematic views of external heat exchanger for providing cooling, and heating and cooling, respectively, according to the present invention.

FIG. 44 shows a cooling system which employs a volatile refrigerant in the fluid flow path. Vaporized refrigerant is received from exhaust line 160 to a compressor pump 120, which is controlled by a control 121. The compressor pump 120 compresses the refrigerant, which is then cooled in external heat exchanger 122 by refrigerant from the automotive air conditioner in refrigerant coil 114. The condensed refrigerant is stored in condenser 123, from which it is released to supply line 161 to the cooling maze 164.

Figure 47:
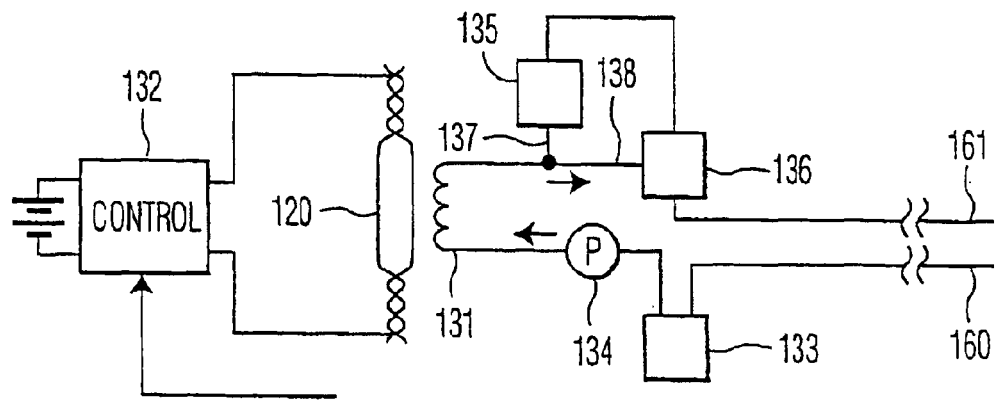
FIG. 47 is a schematic view of a first embodiment of a thermoelectrically controlled heating and/or cooling system according to the present invention.

FIG. 47 shows a thermoelectric embodiment according to the present invention. A Peltier junction 130 provides cooling or heating to the fluid in the external heat exchange coil 131 based on the polarity of applied current. A control 132 controls the polarity and amount of current which flows in the Peltier junction 132, which in turn supplies or withdraws heat relating to the polarity and amount of electrical current. A sensor 165 in the seat 168 provides feedback to the control 132. This sensor is preferably a temperature sensor, producing a monotonic signal with respect to temperature, to allow control over the temperature of the seating surface. In order to coot the seat 168, an oil, e.g., a compressor lubricating oil, which is miscible with the refrigerant, is accumulated in a reservoir 133. Since the return line 160 returns the volatilized refrigerant and any nonvolatilized component, a simple gravity trap may be employed to separate the oil. The compressor pump 134 compresses the vaporized refrigerant, which is cooled in the external heat exchanger 131 by the Peltier junction 130. Liquid refrigerant accumulates in a refrigerant reservoir 135, where it may be further cooled. The refrigerant is released from the refrigerant reservoir 135 through valve 136 to the supply line 161, in order to cool the seat 168, shown in FIG. 43. The valve 136 does not allow refrigerant to bypass the reservoir 135 through shunt 138 in the cooling mode. Further, the flow path from the reservoir 135 through the valve 136 is restricted, causing a buildup of backpressure, allowing the pump 134 to act as a compressor for liquefying the refrigerant.

When the seat is desired to be heated, the oil received from exhaust line 160 is ported through reservoir 133 and through the pump 134, and passes through the external heat exchanger 131. The oil is then heated by the Peltier junction controlled to supply heat to the external heat exchanger. Any refrigerant in the line remains as a gas, because it is not cooled. In addition, as will be discussed later, in the heating mode, a low back pressure is maintained so that the pump 134 does not act as a compressor to condense the refrigerant. The heated oil is then directed through shunt 138 by valve 136 to supply line 161. The reservoir 135 has a check valve at its inlet port 137 from the external heat exchanger 131. When the valve 136 is operated in heating mode, the refrigerant remains in the reservoir 135, and is blocked by valve 136 from being released. The flow restriction from the heat exchanger 131 through the valve 136 to the supply line 161 is low, so that no undesirable back pressure is generated. It should be noted that the embodiment according to FIG. 47 may be operated as a heating system or as a cooling system only, and need not include both functions. In this case, the valve 136, and either the reservoir 133 or the reservoir 135 are unnecessary.

Figure 43:
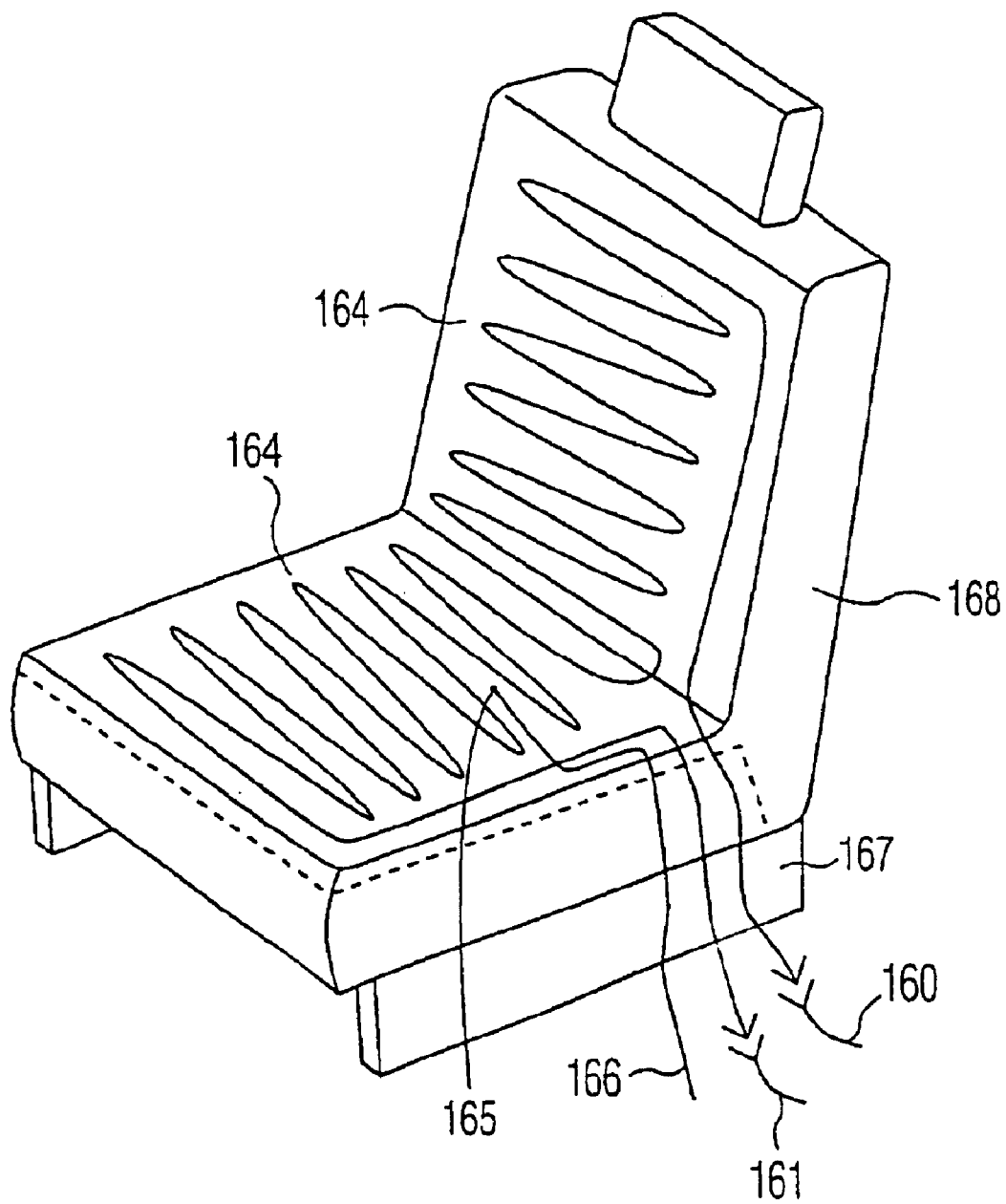
FIG. 43 is a perspective view of an automobile seat having a heat exchange matrix embedded therein according to the present invention.
Figure 48:
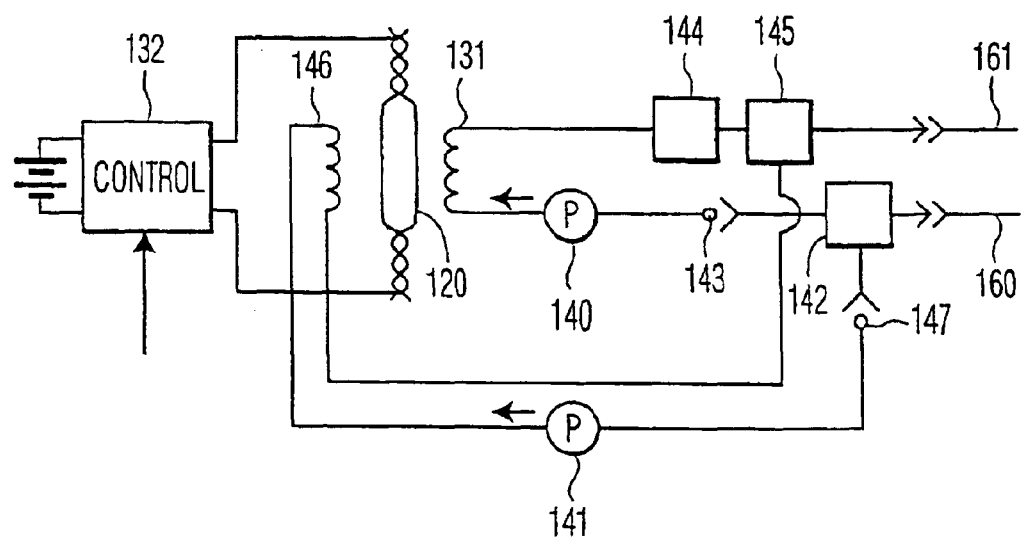
FIG. 48 is a schematic view of a second embodiment of a thermoelectrically controlled heating and cooling system according to the present invention.

FIG. 48 shows an alternate arrangement for heating and cooling the automobile seat 168, shown in FIG. 43. It should be noted that in a thermoelectric system, as shown in FIGS. 47 and 48, the system may be used an any environment where electrical power is available, and need not be limited to automotive environments. In FIG. 48, two pumps, are provided. A cooling pump 140 acts as a compressor, while a heating pump 141 operates at low pressure. The two pumps 140, 141 are linked in a common system, having supply line 161 and exhaust line 160.

In a cooling mode, gaseous refrigerant is returned by exhaust line 160. A separator 142 is provided to separate a lubricating heat transfer agent, which may be an oil, from the refrigerant. Refrigerant gas is supplied through check valve 143 to the cooling pump 140. The cooling pump 140 compresses the refrigerant, which is cooled in external heat exchanger 131 by the Peltier junction. The compressed, cooled refrigerant condenses in condenser 144, and is ported through valve 145 to the supply line 161. In the cooling mode, pump 141 is inoperative and flow from the heating external heat exchanger 146 through the valve 145 is blocked Backflow of fluid from the heating circuit is prevented by check valve 147.

In a heating mode, a heating heat transfer fluid, which is miscible with the volatile refrigerant, is received from exhaust line 160. The oil and gas are separated in separator 142, and the oil flows through check valve 147 to low pressure pump 141. Pump 141 causes the oil to flow through heating external heat exchanger 146, to the valve 145. Valve 145 allows the oil to flow with low back pressure to the supply tube 161. Check valve 143 prevents backflow of refrigerant from the cooling circuit, while valve 145 blocks flow from the condenser 144.

In the embodiments of FIGS. 47, 48, and 49, the transition from heating to cooling may be effected gradually, building up pressure in the cooling circuit and cooling the refrigerant as much as possible to trap as much refrigerant as possible in the cooling circuit before commencing heating. Likewise, the transition from heating to cooling may be effected gradually, by accumulating as much oil as possible in the reservoir 133, 142 before isolating the heating circuit. Withdrawn oil volume may be replaced refrigerant, and vice versa.

FIG. 49 shows an embodiment similar to FIG. 48, except the heating and cooling of the external heat exchangers is effected by the automotive air heating and cooling systems. Corresponding numbers perform similar functions in a similar fashion. These systems differ in that the cooling in the embodiment according to FIG. 49 comprises a refrigerant to refrigerant external heat exchanger 122 rather than the thermoelectric junction to refrigerant external heat exchanger 131 of FIG. 48, and an aqueous solution (engine coolant) to oil external heat exchanger 118 instead of the thermoelectric junction to oil external heat exchanger 146. The system according to FIG. 49 is controlled by a control 117 which ensures that the heating and cooling functions are not simultaneously active. The automotive heating system is controlled by control 115 and the cooling is controlled by control 116. The control 117 communicates with these controls to ensure consistent results. Control 117 also receives a sensor input from sensor cable 166, which is connected to sensor 165.

EXAMPLE 26

Adaptive Seating Surface

An adaptive seating surface is provided having a controllable surface contour, optional controllable temperature, and optional controllable dynamic response. The seat provides ergonomic advantages and improved performance.

The contour of the seating surface is adjusted by pneumatic actuators beneath the seating surface. These actuators are provided to correspond to anatomic regions, and are controlled on the basis of a physiological model of the seated body, a comfort model, and a sensor array near the seating surface. A single control system manages the sensors and actuators, although multiple cellular processors, each controlling an actuator and receiving inputs from neighboring sensors and other cells, may also be implemented.

Figure 32A:
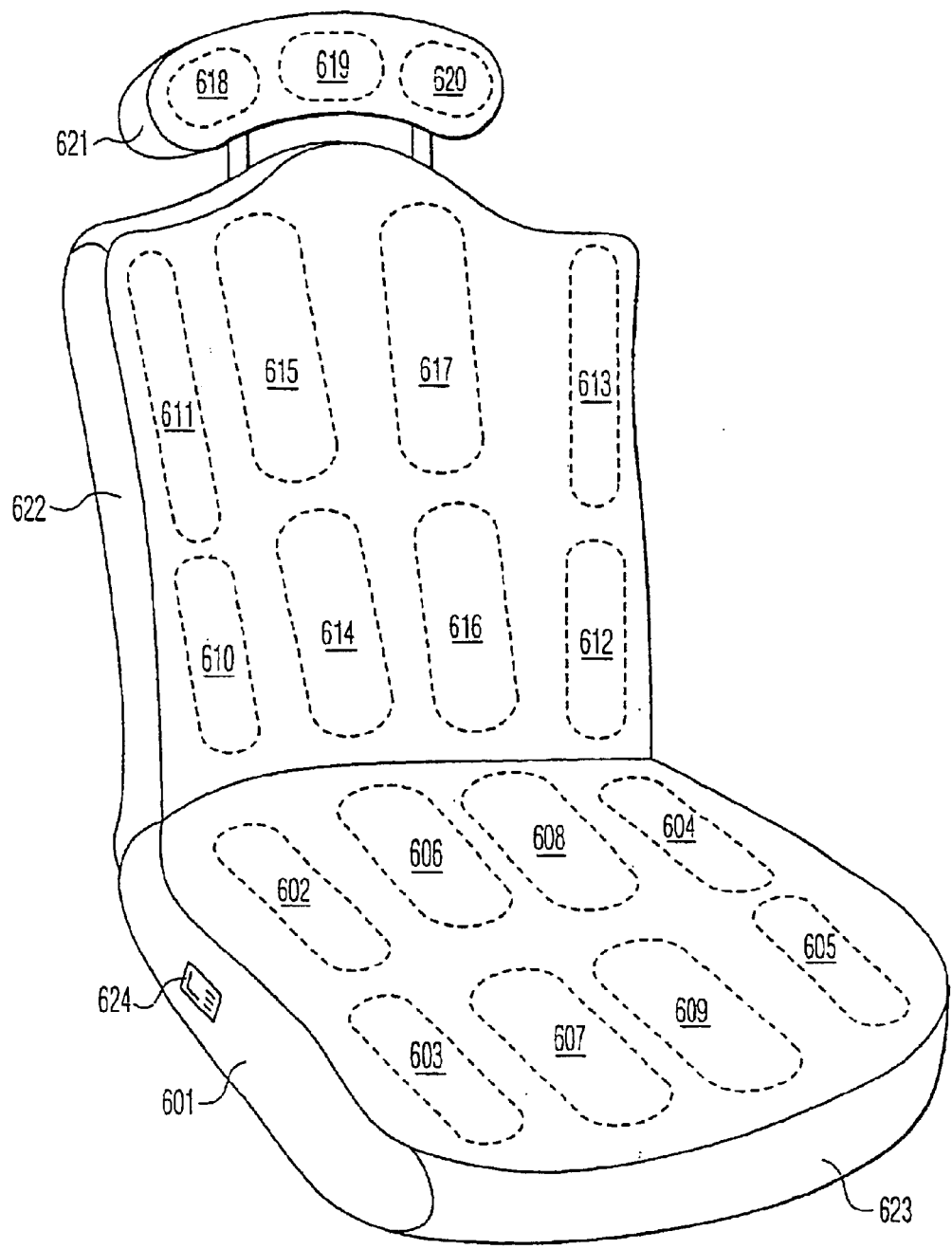
FIGS. 32A, 32B, 33A and 33B are perspective and cross sectional view of an ergonomic seat and schematics of a control system therefore, respectively.

As shown in FIG. 32A, a seat 601, for example an automobile seat, is provided with a set of actuators 602–620, each within a specified region. An air compressor 680, for example operating at 5–25 psi, supplies a separate valve 666 for each actuator 602–620, which is a bladder 663. The valve 666 may be, for example, a micromachined valve or miniature electromagnetic valve. The seating surface 650 itself is, for example, leather or fabric.

The valve 666 has two distinct functions; it controls the volume of air or gas in the bladder 663, from compressor 680 through pneumatic feed line 668, and separately controls the restriction of gas flow between the bladder 663 and a reservoir bladder 669 which serves to control dynamic response of the system. As the restriction imposed by the valve 666 decreases, the effective compliance of the bladder 663 increases, asymptotically reaching the compliance of the combined bladder 663 and the reservoir bladder 669. When the valve 666 effectively blocks gas flow between the reservoir bladder 669 and the bladder 663, the bladder 663 is relatively incompliant, and further is more elastic. The valve 666 equalized the pressure between the bladder 663 and the reservoir bladder 669, with a lengthy time constant.

Figure 33A:
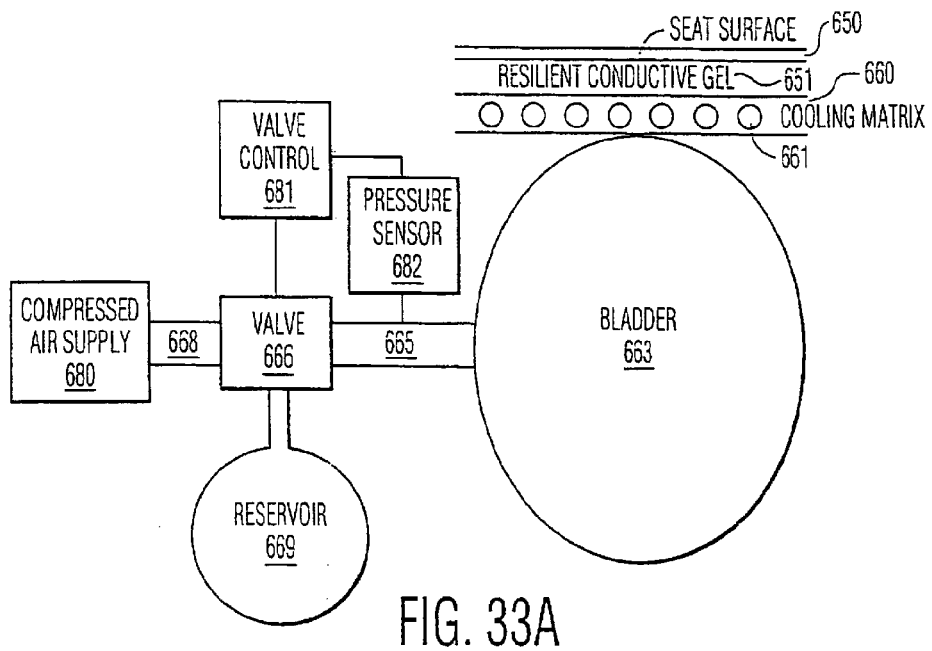

A pressure sensor 682 may be provided in the bladder 663 or in the pneumatic line 665 feeding the bladder 663, to measure the pressure within the bladder 663. A valve control 681 is provided to control the valve, and, as shown in FIG. 33A, may be used to effect a closed loop control over the pressure within the bladder 663.

Figure 33B:
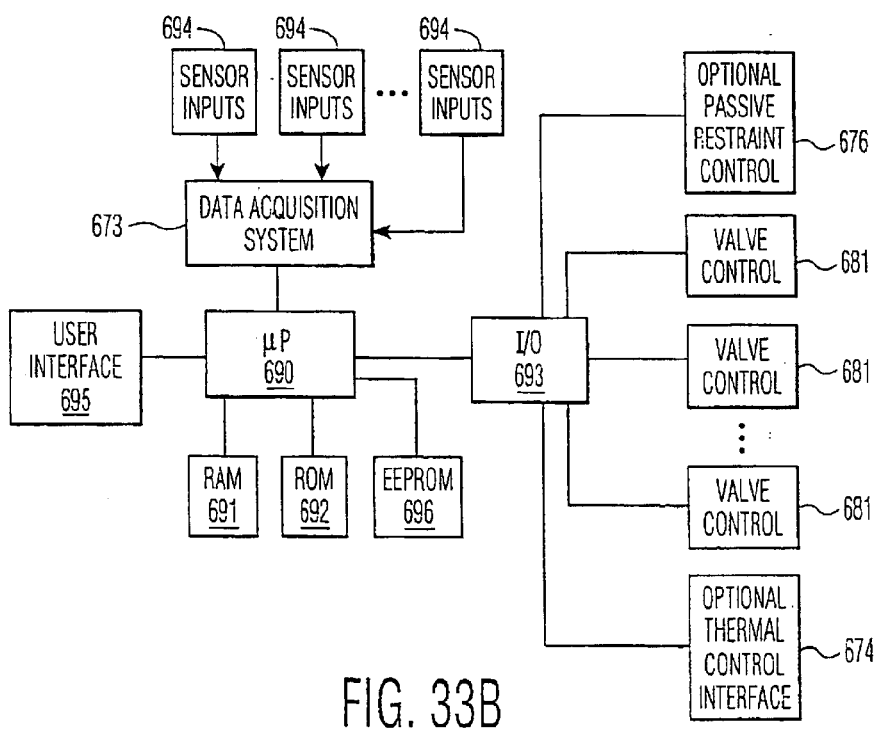
Figure 34A:
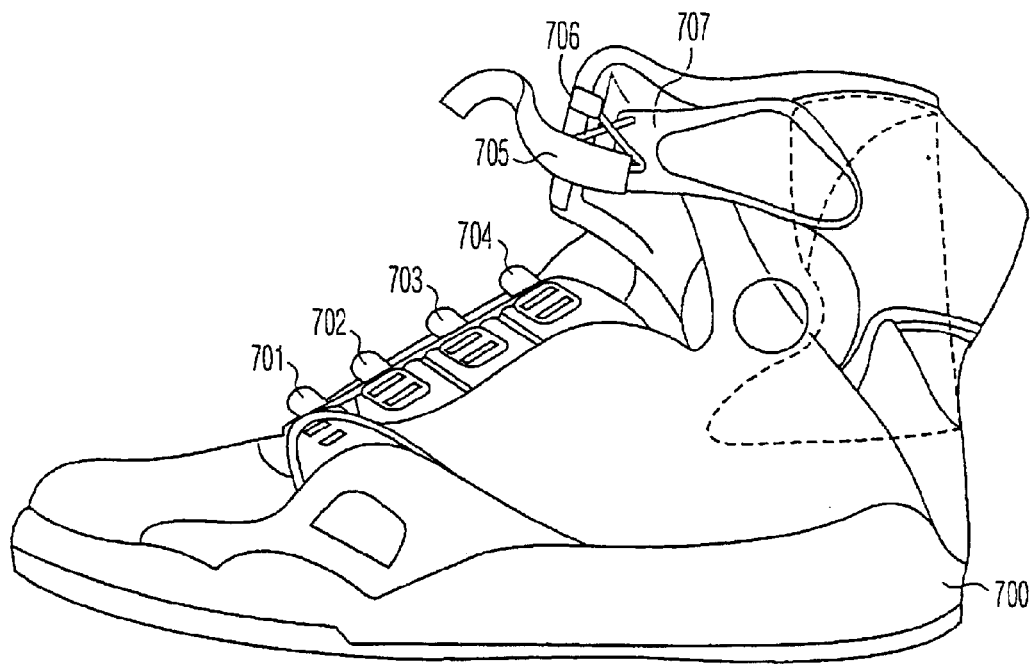
FIGS. 34A, 34B show a side and top view, respectively of an ergonomic footwear system having actuators to control fit.
Figure 34B:
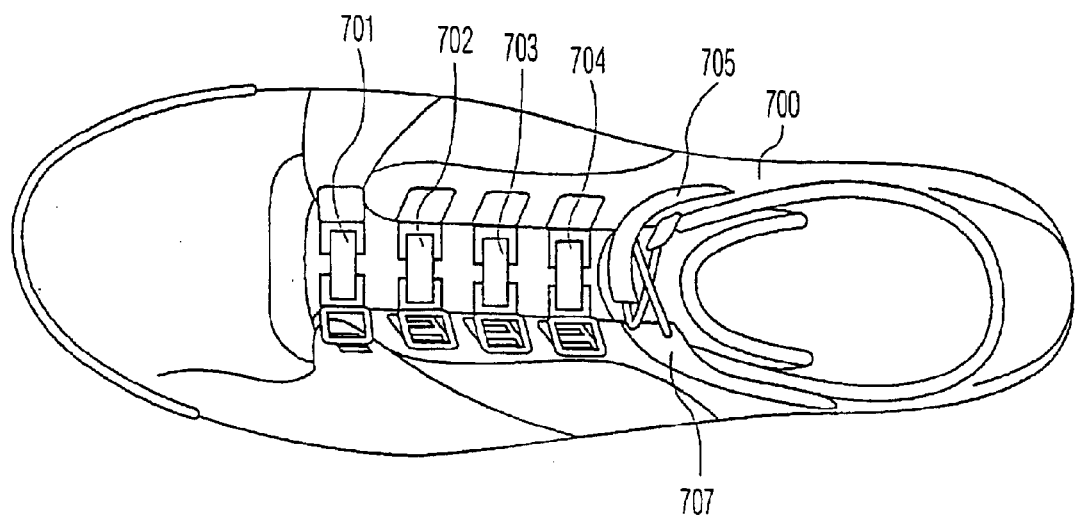

As shown in FIG. 33B, a distributed control system may be implemented, having a central processor 690, interfacing with valve controls 681. Alternately, a central control may be implemented. The central processor 690 receives inputs from sensor inputs 694, which include pressure sensors 682 or force sensors 561, 562, 563, and optionally other types of sensors, such as temperature sensors 656. A data acquisition system 673 receives input from the sensor inputs 694 and interfaces with the central processor 690. The central processor 690, which is, for example, an Intel 80486, Intel 80196, Microchip PIC series, or other processor type, interfaces with random access memory (RAM) 691 for storing process variables and other data, and read only memory (ROM) 692 which stores program information. Nonvolatile data storage memory, for example electrically erasable programmable read only memory 696 (EEPROM) or flash memory, may be used to persistently store data, for example user preferences, environmental characteristics, and adaptive parameters.

Figure 32B:
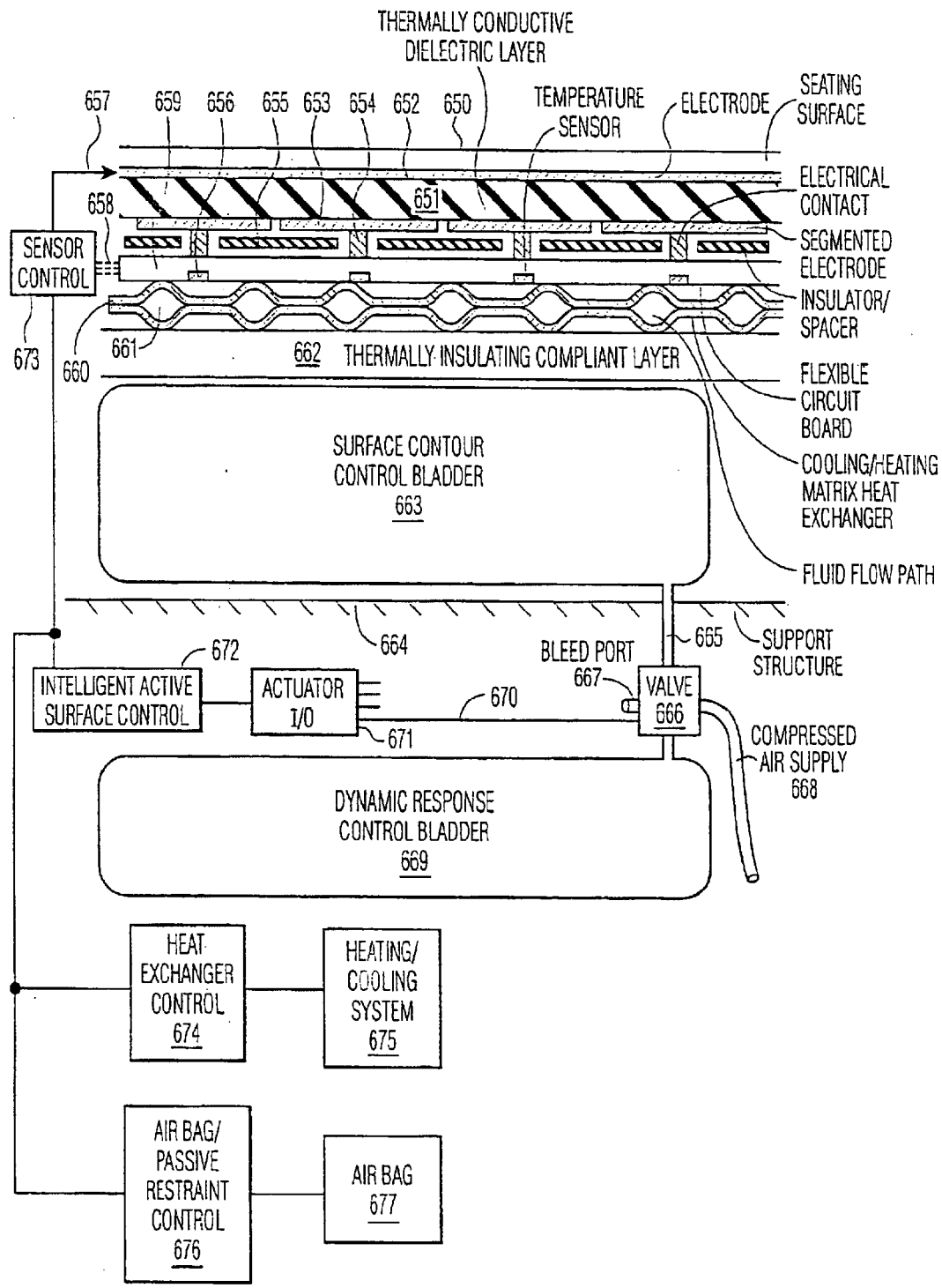

As shown in the embodiment of FIG. 32B, a force sensor 651, 652, 653 is provided for measuring the pressure exerted by an occupant of the seat. This sensor provides a polyurethane layer 651, which is metalized 652 on one side, preferably the upper side, and formed as an array of separate conductive zones 653 on the other side. The polyurethane may be, for example, a Sorbothane type mechanical shock absorbing polymer The separately conducting zones 653 are used, with the polyurethane layer 651 and metalized 652 side as a capacitive sensor, responsive to an applied pressure. In place of the polyurethane layer, other specially thermally conductive dielectric layers, such as Raychem HeatPath thermally conductive gel CTQ 3000 may be used. The conductive zones are each contacted by a conductive pad 654, through an apertured insulator sheet 655, to a planar flexible circuit 659. The planar flexible circuit 659 may have thermal sensors, for example thermistors or semiconductor junction sensors. The planar flexible circuit 659 interfaces through cable 658 to a sensor control 673, whose primary function is to control the data acquisition from the multiple force sensor zones.

Beneath the planar flexible circuit 659 is an optional heat exchanger 660, which has an integral fluid flow path 661, which is suitable, for example, for circulating an antifreeze solution, oil or a volatile refrigerant. The heat exchanger 660 system is controlled by a heat exchanger control 674, which in turn controls a heating/cooling system 675. The heat exchanger control 674 receives input from the temperature sensors 654.

Advantageously, the force 651, 652, 653 and temperature sensors 654 in the seating surface may also be used as inputs to an automotive air bag/passive restraint control 674, which controls one or more air bags 677. By measuring the force distribution profile and temperature, the system can distinguish inanimate objects (cold), large and small persons, and various seating positions.

Below the heat exchanger 660 is a thermally insulating compliant layer 662, which rests on top of a surface contour control bladder 663. The bladder 663 communicates, through line 665, to a valve 666, which receives compressed air through compressed air supply line 668. A bleed port 667 allows the valve 666 to deflate the bladder 663. The valve 666 also serves to selectively and proportionally provide a path to a dynamic response control bladder 669, to effectively control an air volume within the bladder 663 system, and to control damping of transient forces The valve 666 is controlled through a cable 670 from an actuator input/output interface 671, to the intelligent active surface control 672.

The intelligent active surface control 672 seeks to adjust the pressures within the various bladders 663 to achieve uniform forces over analogous anatomical parts, although a cycling of pressures or other asymmetry may also be provided For weight bearing portions, such as the buttocks, the system evenly distributes the forces and damps significant transients. For the back, lumbar support is provided, though the forces are not equalized with the buttocks. The thighs are supported, and the pressure exerted is based on user preference, seating position, a history of movements, and dynamic forces. The headrest optionally includes actuators as well, and is preferably resilient, but absorbs shocks in the event of a high intensity transient. The seating position is controlled by user control 624, which also receives user preferences for adaptive seating system control.

In particular contexts, the system may be even more sophisticated. For example, in a seating surface, the pressure along the back should not equal the pressure along the seat. However, the optimal conformation of the surface may be more related to the compliance of the surface at any controlled area than on the pressure per se. Thus, a sensed highly compliant region is likely not in contact with flesh. Repositioning the surface will have little effect. A somewhat compliant region may be proximate to an identifiable anatomical feature, such as the scapula in the back. In this case, the actuator associated with that region may be adjusted to a desired compliance, rather than pressure per se. This provides even support, comparatively relieving other regions. Low compliance regions, such as the buttocks, are adjusted to achieve an equalized pressure, and to conform to the contour of the body to provide an increased contact patch. This is achieved by deforming the edges of the contact region upwardly until contact is detected The thigh region employs a hybrid algorithm, based on both compliance and pressure.

An adaptive intelligent surface need not be limited to the control of surface contour. Thus, the surface contour, local compliance and local damping may all be controlled. Thus, for example, the dynamic aspects of the control may all be subject to closed loop electronic control.

EXAMPLE 27

Adaptive Footwear

As shown in FIGS. 34–40, footwear is provided with an upper fit controlled by a set of hydraulic actuators 701–705. These actuators 701–705 control the tension on a set of straps 707–711 on the upper, which assure a proper fit. The pressure in each actuator 701–705 is measured by a pressure sensor 767. A set of strain gages (not shown) integrated into the upper or straps 707–711 may also be used to determine the fit of the shoe 700.

The actuators 701–705 receive pressurized fluid from a hydraulic compressor 755, which selectively communicates to each actuator 701–705 through check valve 759, line 760 and rotary valve 761. The rotary valve 761 is driven by an electrical actuator, for example a shape memory actuator, controlled by the control module 754. A reservoir 756 is provided for hydraulic fluid, which is, for example, an ethylene glycol antifreeze or mineral oil. The strap 764, is noncompliant, and driven by the stretch of the lower surface of the sole during dorsiflexion to power the hydraulic compressor 755.

Optionally, each actuator may be associated with a dynamic response chamber, allowing control over damping and dynamic response. This dynamic response is, in turn, controlled by a microvalve array, which employs a set of proportional shape memory alloy valve elements.

The control module 754 is powered by a rechargeable lithium battery 753 within the sole, and further by an electrical generator 763 driven off sole dorsiflexion, through strap 764, to move magnet 780 with respect to coil 781.

The sole shoe 700 has integrated in it an adaptive fit system, including fluid filled chambers 722, 723, 724, 725, 728 and 729. These chambers are disposed to control the fit with respect to particular anatomical regions, i.e., chamber 722 hallucis, chamber 728 metatarsals, chamber 723 instep, chamber 729 lateral aspect of foot, and chambers 724 and 725, heel. The heel is provided with a concentric toroidal set of chambers to assist in obtaining dynamic stability.

Figure 35A:
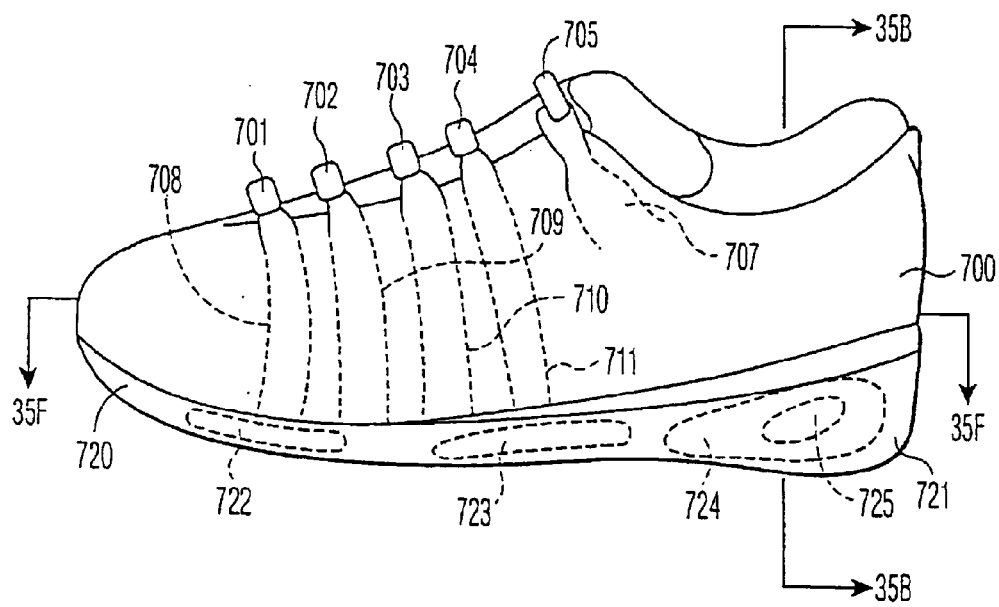
FIGS. 35A–35F show a perspective view, and cross section of ergonomic footwear, sole actuator zone layout, sole sensor zone layout, schematic and cross section of an ergonomic footwear embodiment.
Figure 35B:
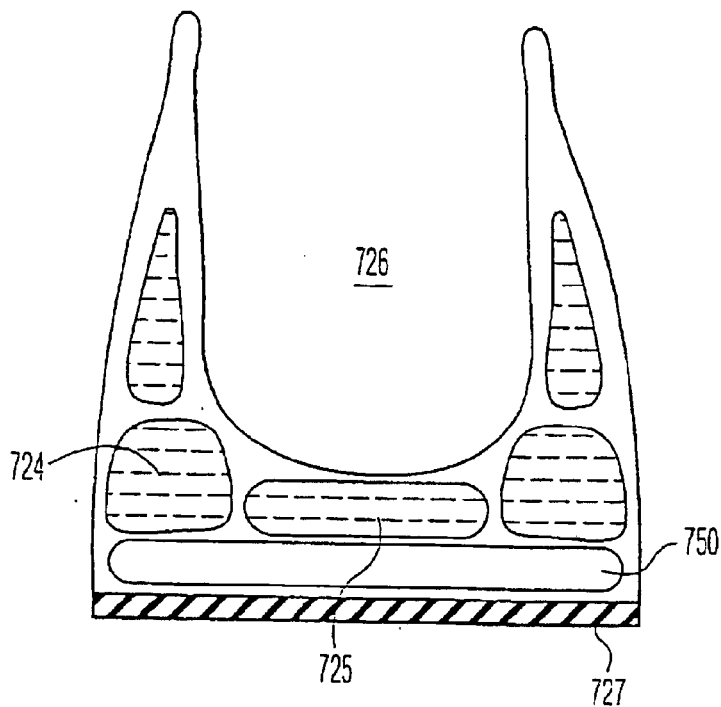
Figure 35C:
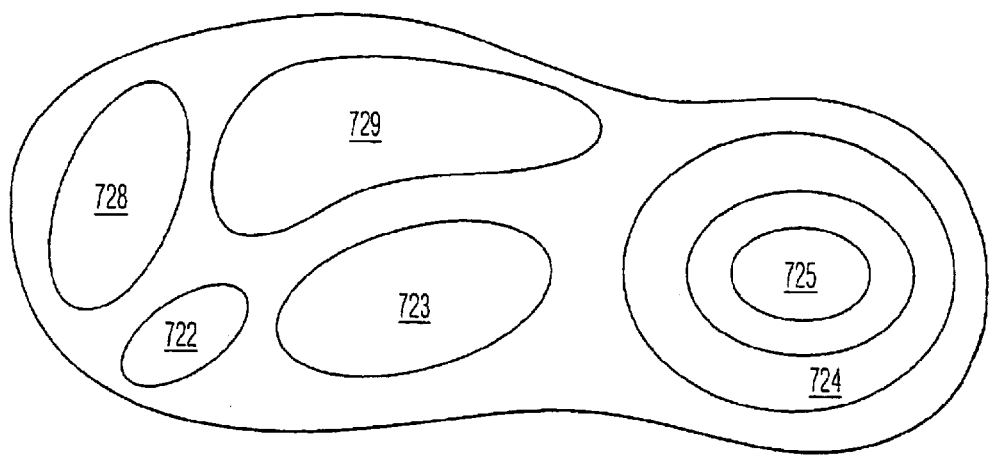
Figure 35D:
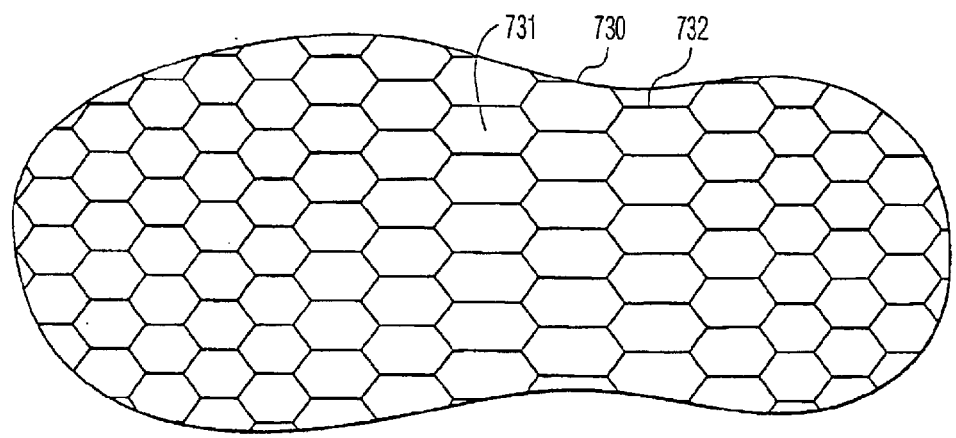
Figure 35E:
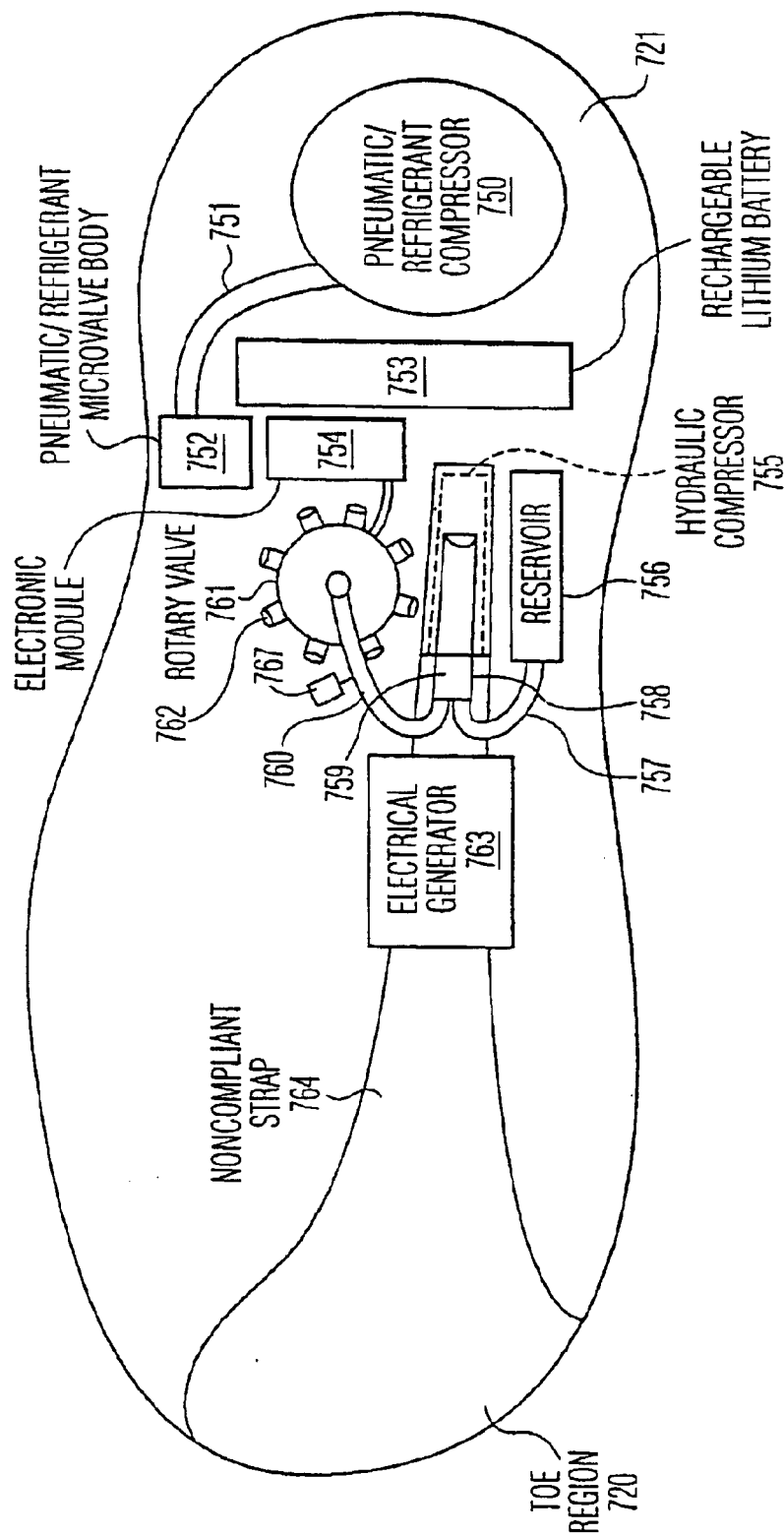
Figure 35F:
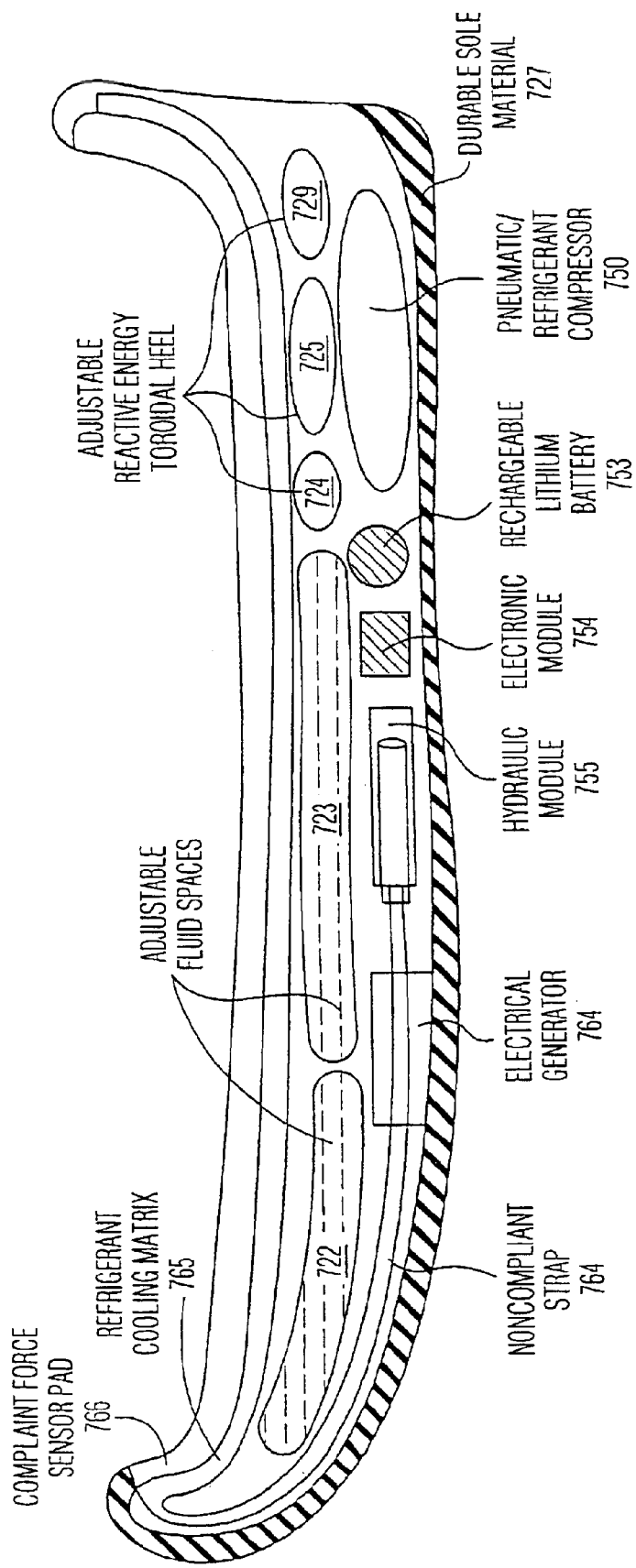

FIG. 35D shows a hexagonal tiled array of a sole pressure sensor, for determining forces applied on the foot. Each hexagonal the forms a capacitive sensor segment, read by the electronic module 754. Preferably, the sensor segments 731 are addressable by respective ground plane, reducing the number of interface lines necessary. The dielectric layer of the force sensor 730 is preferably Sorbothane, thus allowing the pressure sensor to effectively function to absorb shock.

Beneath the force sensor 730 and above the adaptive fit system lies a refrigerant cooling matrix 765. This refrigerant cooling matrix 765 receives a compressed and cooled refrigerant from compressor 822, through external heat exchanger 825 and flow restriction orifice 826. A refrigerant reservoir 823 receives warmed refrigerant for recycling. The compressor 822, which corresponds to the pneumatic refrigerant compressor 750, is situated under the heel and is operated under the forces exerted during locomotion. The compressor 750, through line 752, leads to pneumatic refrigerant microvalve body 752, which is employed to control the static and dynamic properties according to the present invention, in pneumatic bladders of the footwear, which are similar to those conventional in the art, although filled with refrigerant instead of air in a closed system and further optionally provided with dynamic response control chambers, which are, for example, in the sole. Thus, microvalve 810 controls the fluid amount in actuator expansion space 814 from the pressurized hydraulic fluid source 812, provided by the hydraulic compressor 829, and also the dynamic flow of fluid between the actuator expansion space 814 and the pressure equalized damping space 813, under the control of control 811.

The electronic module 754 may include a user input, such as speech recognition, e.g., using a device available from Sensory Inc. For example, this user input allows the user to instruct the footwear to anticipate a particular condition, in advance, so that the operational characteristics conform to the environmental conditions. Thus, for example, before a sporting event, a user may override an adaptive algorithm with a voice command in anticipation of a new set of conditions. These conditions may be, for example, the start of an event, turns, jumps, stairs, slippery conditions, or the like. The electronic module 754 receives the voice command through a microphone, and processes the command to provide a defined or changed set of operational parameters, stored in memory. Of course, other user inputs may be employed, for example radio frequency, infrared or ultrasonic communications from a remote control, for example in a wristwatch or bracelet, or even a miniature keypad.

Figure 40:
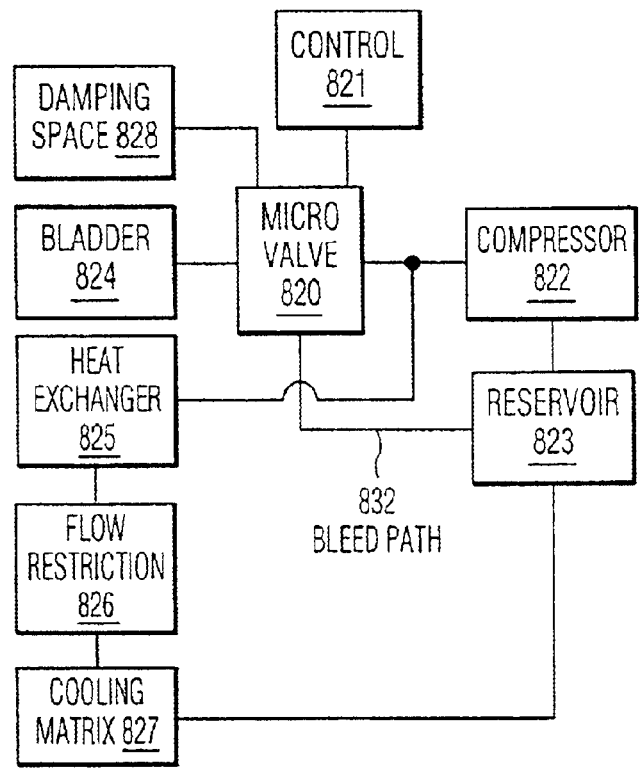

As shown in FIG. 40, the pneumatic system is dual function, having a refrigeration function, as discussed above, and a dynamic response function, by selectively controlling flow between each bladder 824 and a respective damping space 828.

In order to bleed a respective bladder or actuator, the microvalve 810, 820 provides a bleed path 831, 832 to a respective hydraulic 830 or pneumatic 823 reservoir.

The bottom of the sole is laminated with a durable sole material 727. Other features conventional in footwear may be used in conjunction with the present embodiment.

Figure 36:
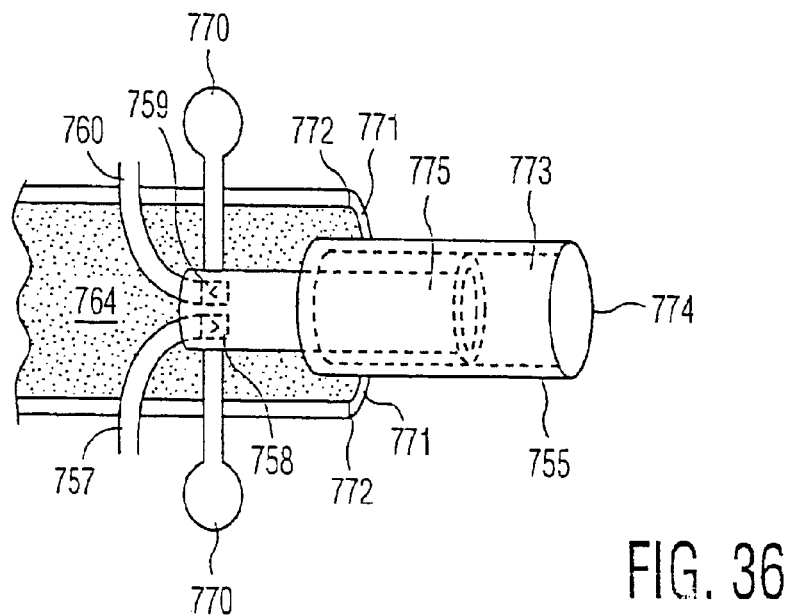
FIGS. 36–38 are details of a compressor, electrical generator and actuator, respectively.
Figure 37:
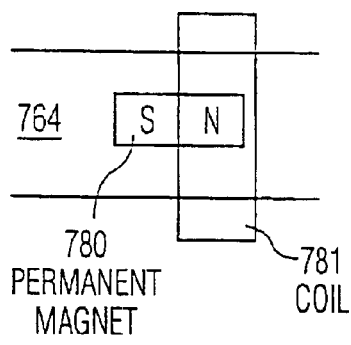

FIG. 36 shows a detail of the hydraulic compressor 755. The strap 764 provides tension on connection rings 771, adhered with adhesive 772 to the outer shell 774 of the cylinder 773. Within the cylinder 773 rides a hollow piston 775, which is closed on the end opposite the cylinder 773. The space inside cylinder 773 and hollow piston 775 is filled with a hydraulic fluid, which is an ethylene glycol antifreeze or mineral oil. Two check valves are provided, one 758 to draw fluid from reservoir 756 through line 757, and one 759 to expel compressed hydraulic fluid to rotary valve 761. Arms 770 hold the hollow piston in fixed position with respect to the moving strap 764 and cylinder 773.

Figure 38:
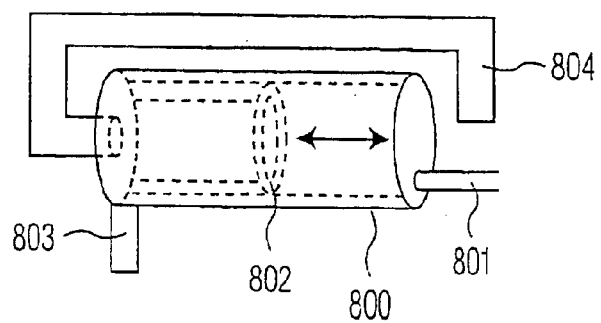
Figure 39:
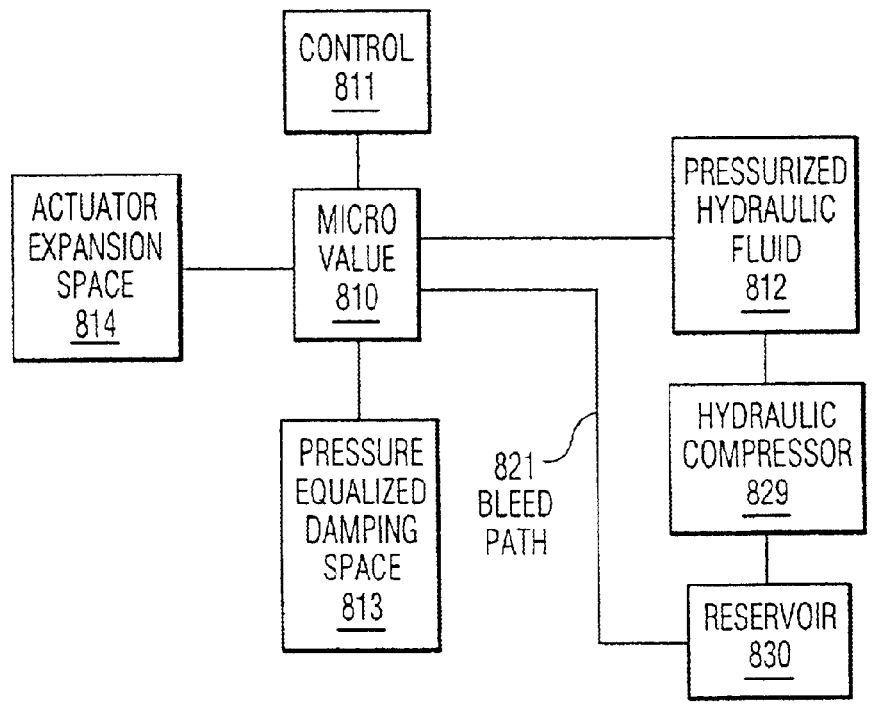
FIGS. 39–40 show schematic diagrams of an ergonomic damped footwear system, and an ergonomic cooled and damped footwear system embodiment, respectively.

FIG. 38 shows a detail of each actuator 701–705 which control fit in the upper A cylinder 802 is displaceable within cylinder 800. Hydraulic fluid, through line 801, enters the cylinder and displaces the piston 802, causing arm 803 and 804 to move with respect to each other. The arrangement allows increasing pressure within the cylinder 800 to tighten respective straps 707–711.

EXAMPLE 28

Inflatable Bladders in Upper

According to another embodiment of the invention, a set of inflatable bladders are formed in the footwear upper. These bladders may be inflated with air, refrigerant, or liquid. The bladders are formed of two layers of a modulus polymer film, for example polyester film (e.g., Mylar) with conduits formed integral to the heat sealing pattern to az control system, which is, for example, embedded in the sole. Advantageously, a cooling system is provided which removes heat from below the bladder system. Thus, according to one embodiment, a volatile refrigerant flows through a maze pattern segment formed between a first and second layer of heat-sealed film. The terminus of the maze pattern segment is an aperture formed through one of the film layers, leading to a bladder segment formed between a second and third layer of heat sealed film. The bladder segment has a conduit formed by an elongated potential space between the second and third layers to a controllable pressure relief valve system, for example in the sole. Since the pressure resulting from volatilization of refrigerant is relatively high, individual bladder segments may be selective pressurized from 0 psig to 50 psig.

It is noted that, while the layers are planar, they may be overlaid, and indeed the pressure fluid need not be the same in each bladder Thus, low pressure, refrigerant filled cushioning bladders may overlie high pressure liquid filled contour control bladders, to provide both comfort and fit.

Figure 41:
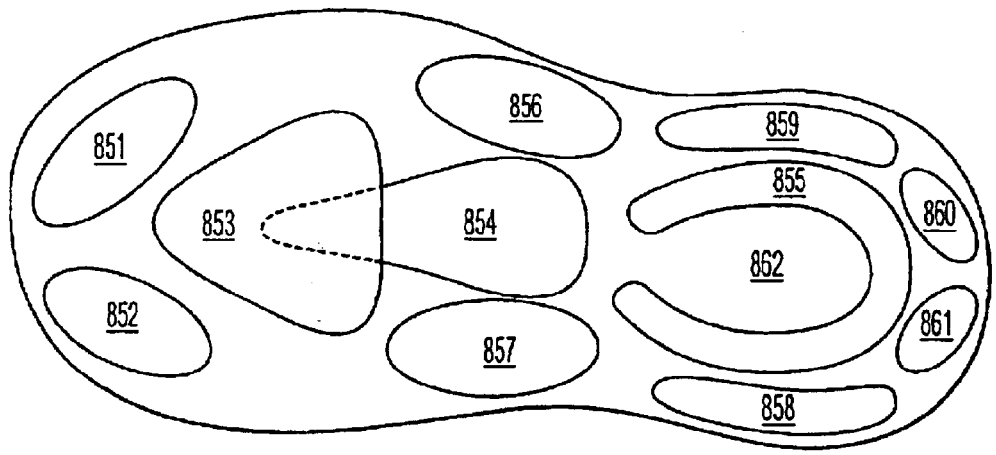
FIGS. 41 and 42 show a bladder zone layout and semischematic diagram of a footwear upper control system.

As shown in FIG. 41, the upper 850, with ankle region 862, may be divided into a plurality of segments, including hallucis 852, toes 851, central 853, tongue 854, lateral 856, medial 857, ankle 855, rear lateral 859, rear medial 858, and Achilles 860, 861.

Figure 42:
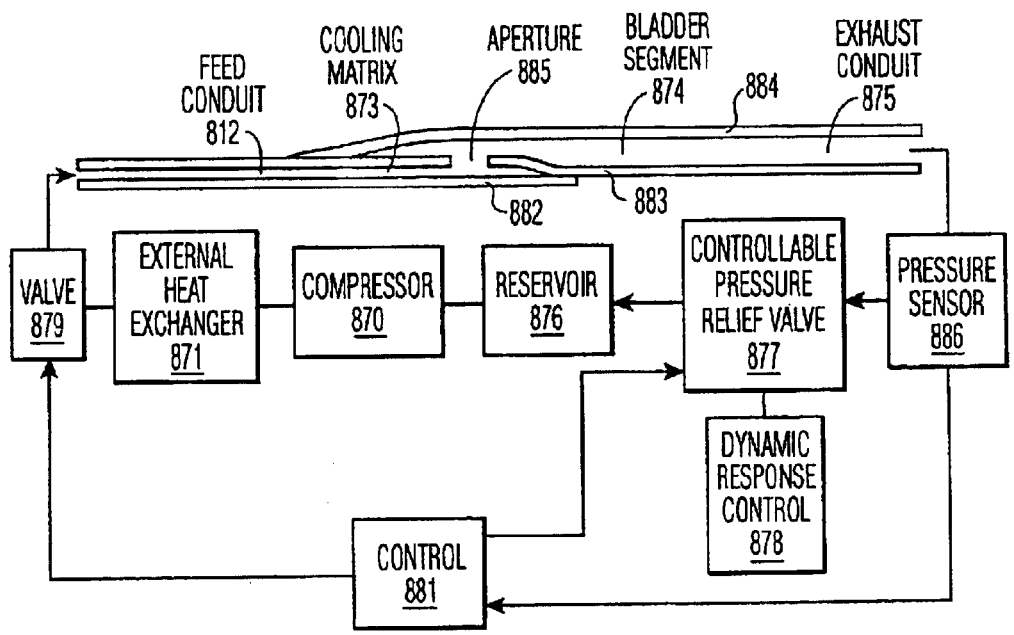

As shown in FIG. 42, a three layer structure is formed of layers 882, 883 and 884. Layers 882 and 883 form a conduit 872 from a control valve 879, leading to a cooling matrix 873. The cooling matrix 873 terminates in an aperture 885 leading to a bladder segment 874. The bladder segment 874, in turn, leads through an exhaust conduit region 875 to a pressure sensor 880 and a controllable pressure relief valve system 877. The pressure relief valve system 877 leads to a compliant reservoir 876, which feeds a compressor 870. The compressor 870 empties into an external heat exchanger 871, which may also be formed of heat sealed films, to form an elongated flow path adjacent to the air external to the footwear. The external heat exchanger 871 leads to the control valve 879, which leads to the feed conduit 872. The controllable pressure relief valve 877 and control valve 879 are each controlled by a control 881, which may either operate in open loop mode or receive and process the input from pressure sensor 880. The control 881 may also provide active damping, in conjunction with the controllable pressure relief valve system 877 and the dynamic response control chamber 878, which is preferably embedded within the sole.

The system therefore integrates both cooling and adaptive fit. The compressor 870 is preferably driven by gait induced pressure variations in the sole. The control is preferably a microprocessor, although a simple mechanical device may be sufficient. By employing high modulus polymer film, a large transient dynamic pressure range is supported facilitating high performance footwear design without sacrificing comfort.

Attached hereto as appendices are two disclosures, "Cryconditioning Footwear System and Method for Making and Using" and "Ergonomically Adapted Thermal Transfer Device", expressly incorporated herein by reference.

It should be understood that the preferred embodiments and examples described herein are for illustrative purposes only and are not to be construed as limiting the scope of the present invention, which is properly delineated only in the appended claims.

What is claimed is:

1. An article of footwear, comprising a bladder having a pressurized fluid therein, a dynamic response chamber, and a control for controlling a dynamic flow of pressurized fluid between said bladder and said dynamic response chamber caused by transient forces, wherein said flow of pressurized fluid is dependent on a state of said dynamic response chamber.

2. The article according to claim 1, wherein said control comprises an electrically controllable valve.

3. The article according to claim 1, wherein said dynamic response chamber is embedded within the sole.

4. The article according to claim 1, wherein said article of footwear further comprises an upper having an inelastic portion, wherein said pressurized fluid in said bladder is internal to said inelastic portion and pressurize fluid in said dynamic response chamber is external said inelastic portion.

5. The article according to claim 1, wherein said bladder is controllably pressurized.

6. The article according to claim 5, wherein a source of compressed fluid for said bladder comprises a gait operated compressor.

7. The article according to claim 1, further comprising a pressure sensor for sensing a pressure within said bladder.

8. The article according to claim 7, wherein said control is responsive to said pressure sensor.

9. The article according to claim 1, wherein said control is adaptive to conditions of operation.

10. The article according to claim 1, wherein said bladder is formed of a polymer film having a modulus of greater than about 400 kpsi per ASTM D882.

11. The article according to claim 1, further comprising a heat exchanger for altering a temperature of at least a portion of the article.

12. The article according to claim 11, wherein said heat exchanger selectively cools a portion of a foot within the article of footwear.

13. A dynamically controlled footwear system, comprising:
(a) an enclosed space having a wall, said wall communicating forces with a wearer's foot; and
(b) a control system for separately controlling a static and dynamic characteristic of said enclosed space.

14. The system according to claim 13, further comprising a sensor, for sensing a wearer activity.

15. The system according to claim 13, wherein said static characteristic corresponds to a tension of the enclosed space wall and said dynamic characteristic corresponds to an effective damping of forces in the wall of the enclosed space.

16. The system according to claim 13, wherein the control adjusts a pressure of a working fluid.

17. The system according to claim 13, wherein the enclosed space is filled with a working fluid which changes phase within a range of normal operating conditions.

18. The system according to claim 13, wherein the control comprises a hydraulic fluid.

19. The system according to claim 13, wherein the control is an active control which operates from pedal energy.

20. The system according to claim 13, wherein a static fit of the footwear tightens with increased levels if user activity.

21. The system according to claim 13, wherein said wall has low mechanical compliance, said control acting to control a perceived compliance of said enclosed space.

22. The system according to claim 13, further comprising at least one additional enclosed space having a wall, said wall communicating forces with a wearer's foot, and being controlled by said control system to separately control a static and dynamic characteristic of said additional enclosed space.

23. The system according to claim 13, wherein said control comprises a selectively operable valve for adjustably controlling a dynamic flow of a working fluid within said enclosed space in response to a transient force.

24. The system according to claim 13, further comprising means for determining an activity type, said control system being dependent on said determined activity type.

25. An article of footwear, comprising a bladder having a pressurized fluid therein, a dynamic response chamber, and a control for controlling a dynamic flow of pressurized fluid between said bladder and said dynamic response chamber caused by transient forces, wherein said flow of pressurized fluid is dependent on a state of said dynamic response chamber, wherein said bladder is formed of a polymer film having a modulus of greater than about 400 kpsi per ASTM D882.

26. The article according to claim 25, wherein said control comprises an electrically controllable valve.

27. The article according to claim 25, wherein said dynamic response chamber is embedded within the sole.

28. The article according to claim 25, wherein said article of footwear further comprises an upper having an inelastic portion, wherein said pressurized fluid in said bladder is internal to said inelastic portion and pressurized fluid in said dynamic response chamber is external said inelastic portion.

29. The article according to claim 25, wherein said bladder is controllably pressurized.

30. The article according to claim 29, wherein a source of compressed fluid for said bladder comprises a gait operated compressor.

31. The article according to claim 25, further comprising a pressure sensor for sensing a pressure within said bladder.

32. The article according to claim 31, wherein said control is responsive to said pressure sensor.

33. The article according to claim 25, wherein said control is adaptive to conditions of operation.

34. The article according to claim 25, further comprising a heat exchanger for altering a temperature of at least a portion of the article.

35. The article according to claim 34, wherein said heat exchanger selectively cools a portion of a foot within the article of footwear.

36. An article of footwear, comprising a bladder having a pressurized fluid therein, a dynamic response chamber, and control for controlling a dynamic flow of pressurized fluid between said bladder and said dynamic response chamber caused by transient forces, herein said flow of pressurized fluid is dependent on a state of said dynamic response chamber, wherein said bladder is controllably pressurized, and a source of compressed fluid for said bladder comprises a gait operated compressor.

37. The article according to claim 36, wherein said control comprises an electrically controllable valve.

38. The article according to claim 36, wherein said dynamic response chamber is embedded within the sole.

39. The article according to claim 36, wherein said article of footwear further comprises an upper having an inelastic portion, wherein said pressurized fluid in said bladder is internal to said inelastic portion and pressurized fluid in said dynamic response chamber is external said inelastic portion.

40. The article according to claim 36, further comprising a pressure sensor for sensing a pressure within said bladder.

41. The article according to claim 40, wherein said control is responsive to said pressure sensor.

42. The article according to claim 36, wherein said control is adaptive to conditions of operation.

43. The article according to claim 36, wherein said bladder is formed of a polymer film having a modulus of greater than about 400 kpsi per ASTM D882.

44. The article according to claim 36, further comprising a heat exchanger for altering a temperature of at least a portion of the article.

45. The article according to claim 44, wherein said heat exchanger selectively cools a portion of a foot within the article of footwear.

46. A dynamically controlled footwear system, comprising:
(a) an enclosed space having a wall, said wall communicating forces with a wearer's foot, wherein said wall has low mechanical compliance, said control acting to control a perceived compliance of said enclosed space; and
(b) a control system for separately controlling a static and dynamic characteristic of said enclosed space.

47. The system according to claim 46, further comprising a sensor, for sensing a wearer activity.

48. The system according to claim 46, wherein said static characteristic corresponds to a tension of the enclose space wall and said dynamic characteristic corresponds to an effective damping of forces in the wall of the enclosed space.

49. The system according to claim 46, wherein the control adjusts a pressure of a working fluid.

50. The system according to claim 40, wherein the enclosed space is filled with a working fluid which changes phase within a range of normal operating conditions.

51. The system according to claim 40, wherein the control comprises a hydraulic fluid.

52. The system according to claim 40, wherein the control is an active control which operates from pedal energy.

53. The system according to claim 40, wherein a static fit of the footwear tightens with increased levels if user activity.

54. The system according to claim 40, further comprising at least one additional enclosed space having a wall, said wall communicating forces with a wearer's foot, and being controlled by said control system to separately control a static and dynamic characteristic of said additional enclosed space.

55. The system according to claim 40, wherein said control comprises a selectively operable valve for adjustably controlling a dynamic flow of a working fluid within said enclosed space in response to a transient force.

56. The system according to claim 40, further comprising means for determining an activity type, said control system being dependent on said determined activity type.

* * * * *